(12) United States Patent
Kassis et al.

(10) Patent No.: US 12,146,869 B2
(45) Date of Patent: Nov. 19, 2024

(54) METHODS AND COMPOSITIONS FOR ANALYTE QUANTIFICATION

(71) Applicant: MATTERWORKS INC, Somerville, MA (US)

(72) Inventors: Timothy Kassis, Saugus, MA (US); Jefferson Pruyne, Somerville, MA (US); Mark D. Simon, Somerville, MA (US); Mimoun Cadosch Delmar Akerman, Brookline, MA (US); Jennifer Campbell, Arlington, MA (US); Ana Henriques Da Costa, Cambridge, MA (US); Laura Kolinsky, Boston, MA (US); John M. Geremia, Wayland, MA (US)

(73) Assignee: MATTERWORKS INC, Somerville, MA (US)

( * ) Notice: Subject to any disclaimer, the term of this patent is extended or adjusted under 35 U.S.C. 154(b) by 0 days.

(21) Appl. No.: 18/352,610

(22) Filed: Jul. 14, 2023

(65) Prior Publication Data

US 2024/0167986 A1  May 23, 2024

Related U.S. Application Data

(63) Continuation of application No. 17/930,338, filed on Sep. 7, 2022, now Pat. No. 11,754,536.
(Continued)

(51) Int. Cl.
*G01N 30/72* (2006.01)
*C12M 1/34* (2006.01)
(Continued)

(52) U.S. Cl.
CPC ............. *G01N 30/72* (2013.01); *C12M 41/30* (2013.01); *G01N 30/7233* (2013.01);
(Continued)

(58) Field of Classification Search
CPC .............. G01N 30/72; G01N 30/8665; G01N 2030/045
(Continued)

(56) References Cited

U.S. PATENT DOCUMENTS

| | | |
|---|---|---|
| 7,151,976 B2 | 12/2006 | Lin |
| 7,451,052 B2 | 11/2008 | Wang et al. |

(Continued)

FOREIGN PATENT DOCUMENTS

| | | |
|---|---|---|
| CN | 107703243 B | 6/2021 |
| EP | 3945314 A1 | 2/2022 |

(Continued)

OTHER PUBLICATIONS

Abrahamsson et al. Applications of Machine Learning to In Silico Quantification of Chemicals without Analytical Standards. J. Chem. Inf. Model. 2020, 60, 2718-2727.
(Continued)

*Primary Examiner* — Michael Maskell
(74) *Attorney, Agent, or Firm* — Wilson Sonsini Goodrich & Rosati

(57) ABSTRACT

Disclosed are methods, libraries, and samples for quantifying a target analyte in a laboratory sample including the target analyte. The methods typically include the step of estimating the amount of the target analyte in the laboratory sample from mass spectrometric data including signal intensities for the target analyte and one or more internal standards, where the mass spectrometric data are an output of a mass spectrometric analysis of a target sample produced from the laboratory sample and a predetermined amount of the one or more internal standards. The present disclosure also provides a method for analyte quantification. The method comprises adding one or more calibrators to a sample comprising one or more analytes; applying mass
(Continued)

Exemplary method for sample processing spectrometry (MS) to the sample; and using a trained machine learning model to determine an absolute concentration of the one or more analytes.

1 Claim, 44 Drawing Sheets

Related U.S. Application Data

(60) Provisional application No. 63/371,978, filed on Aug. 19, 2022, provisional application No. 63/274,513, filed on Nov. 1, 2021.

(51) Int. Cl.
*G01N 30/86* (2006.01)
*G01N 30/02* (2006.01)
*G01N 30/04* (2006.01)

(52) U.S. Cl.
CPC ... *G01N 30/8665* (2013.01); *G01N 2030/027* (2013.01); *G01N 2030/045* (2013.01)

(58) Field of Classification Search
USPC .................................. 250/281, 282
See application file for complete search history.

(56) References Cited

U.S. PATENT DOCUMENTS

| | | | |
|---|---|---|---|
| 7,550,260 B2 | 6/2009 | Kaddurah-Daouk et al. | |
| 7,561,975 B2 | 7/2009 | Young et al. | |
| 7,635,556 B2 | 12/2009 | Kaddurah-Daouk et al. | |
| 7,809,450 B2 | 10/2010 | Lev-Ami et al. | |
| 8,131,473 B1 | 3/2012 | Coffin et al. | |
| 8,265,877 B2 | 9/2012 | Ramsay et al. | |
| 8,271,103 B2 | 9/2012 | Hendler et al. | |
| 8,577,480 B2 | 11/2013 | Vikstroem et al. | |
| 8,846,383 B2 | 9/2014 | Luttmann et al. | |
| 8,849,577 B2 * | 9/2014 | Ryals ............... | G01N 33/5008 702/19 |
| 8,927,221 B2 | 1/2015 | Sato et al. | |
| 8,980,548 B2 | 3/2015 | Shuster et al. | |
| 9,111,026 B1 | 8/2015 | Fernandez | |
| 9,429,939 B2 | 8/2016 | McCready | |
| 9,442,121 B2 | 9/2016 | Kawamura et al. | |
| 9,646,139 B1 | 5/2017 | Zhu et al. | |
| 9,885,727 B2 | 2/2018 | Turino et al. | |
| 9,977,034 B2 | 5/2018 | McCreedy et al. | |
| 10,294,509 B2 | 5/2019 | Ohga et al. | |
| 10,755,905 B2 | 8/2020 | Wang et al. | |
| 10,890,592 B2 | 1/2021 | Kennedy et al. | |
| 10,937,525 B2 | 3/2021 | Williams | |
| 11,060,149 B2 | 7/2021 | Steelman | |
| 11,061,005 B2 | 7/2021 | Adam et al. | |
| 11,181,530 B2 | 11/2021 | Ford et al. | |
| 11,232,936 B2 | 1/2022 | Gajadhar et al. | |
| 11,754,536 B2 | 9/2023 | Kassis et al. | |
| 2014/0156202 A1 | 6/2014 | Floridia et al. | |
| 2019/0018019 A1 | 1/2019 | Shan et al. | |
| 2019/0113520 A1 | 4/2019 | Blume et al. | |
| 2019/0267222 A1 | 8/2019 | Izumi et al. | |
| 2020/0033360 A1 | 1/2020 | Freinkman et al. | |
| 2020/0041487 A1 | 2/2020 | Stults et al. | |
| 2020/0074269 A1 | 3/2020 | Trygg et al. | |
| 2020/0194126 A1 | 6/2020 | Lim et al. | |
| 2020/0365237 A1 | 11/2020 | Madden et al. | |
| 2021/0116461 A1 | 4/2021 | De Carvalho Lains et al. | |
| 2021/0116467 A1 | 4/2021 | Jia | |
| 2021/0148924 A1 | 5/2021 | Ford et al. | |
| 2021/0174958 A1 | 6/2021 | Drake et al. | |
| 2021/0192370 A1 | 6/2021 | Toubiana et al. | |
| 2021/0196168 A1 | 7/2021 | Mitra | |
| 2021/0383893 A1 | 12/2021 | Yau-Rose et al. | |
| 2022/0003726 A1 | 1/2022 | Hankemeier et al. | |
| 2022/0013197 A1 | 1/2022 | Walsh et al. | |
| 2022/0050090 A1 | 2/2022 | Adam et al. | |
| 2022/0102000 A1 | 3/2022 | Segal et al. | |
| 2022/0137579 A1 | 5/2022 | Grimm et al. | |
| 2022/0196615 A1 | 6/2022 | Yamada et al. | |
| 2022/0214319 A1 | 7/2022 | Schwellenbach et al. | |
| 2022/0221433 A1 | 7/2022 | Robinson et al. | |
| 2022/0229029 A1 | 7/2022 | Stein et al. | |
| 2022/0237264 A1 | 7/2022 | Johansson et al. | |
| 2023/0133615 A1 | 5/2023 | Kassis et al. | |
| 2023/0137741 A1 | 5/2023 | Kassis et al. | |
| 2023/0170049 A1 | 6/2023 | Kassis et al. | |

FOREIGN PATENT DOCUMENTS

| | | |
|---|---|---|
| WO | WO-2015010097 A2 | 1/2015 |
| WO | WO-2016142691 A1 | 9/2016 |
| WO | WO-2021146401 A1 | 7/2021 |
| WO | WO-2021150598 A1 | 7/2021 |
| WO | WO-2021202620 A1 | 10/2021 |
| WO | WO-2021247527 A1 | 12/2021 |
| WO | WO-2022027118 A1 | 2/2022 |
| WO | WO-2022069180 A1 | 4/2022 |
| WO | WO-2023077166 A1 | 5/2023 |

OTHER PUBLICATIONS

Alexandrov. Spatial Metabolomics and Imaging Mass Spectrometry in the Age of Artificial Intelligence. Annu Rev Biomed Data Sci. Jul. 2020;3: 61-87.

Baek et al. Replacing the internal standard to estimate micropollutants using deep and machine learning. Water Research 188 (2021) 116535. Available online Oct. 19, 2020. 13 pages.

Blondeel et al. Tuning a MAb glycan profile in cell culture: Supplementing N-acetylglucosamine to favour G0 glycans without compromising productivity and cell growth. Journal of Biotechnology 214 (2015) 105-112. Available online Sep. 18, 2015.

Boysen et al. Best-Matched Internal Standard Normalization in Liquid Chromatography-Mass Spectrometry Metabolomics Applied to Environmental Samples. Anal Chem 90, 1363-1369 (Dec. 14, 2017).

Calderón-Celis et al. Standardization approaches in absolute quantitative proteomics with mass spectrometry. Mass Spec Rev. 2018;37:715-737.

Dolan. When Should an Internal Standard Be Used? LCGC Europe, LCGC Europe-06-01-2012, vol. 25, Issue 6, pp. 316-322 (May 31, 2012). Retrieved Feb. 16, 2023 at URL: https://www.chromatographyonline.com/view/when-should-internal-standard-be-used. 6 pages.

González et al. Matrix Effect Compensation in Small-Molecule Profiling for an LC-TOF Platform Using Multicomponent Postcolumn Infusion. Anal. Chem. 87, 5921-5929 (May 12, 2015).

Gritti et al. Achieving quasi-adiabatic thermal environment to maximize resolution power in very high-pressure liquid chromatography: Theory, models, and experiments. Journal of Chromatography A, 1444 (2016) 86-98. Available online Mar. 28, 2016.

Kim et al. A hierarchical approach to removal of unwanted variation for large-scale metabolomics data. Nature Communications 12:4992 (2021). 10 pages.

Liebal et al. Machine Learning Applications for Mass Spectrometry-Based Metabolomics. Metabolites 2020, 10, 243. 25 pages.

Liigand et al. Quantification for non-targeted LC/MS screening without standard substances. Scientific Reports (2020) 10:5808. 10 pages.

Liu et al. Reference Standardization for Quantification and Harmonization of Large-Scale Metabolomics. Anal. Chem. 2020, 92, 8836-8844.

Ma. Novor: Real-Time Peptide de Novo Sequencing Software. J Am Soc Mass Spectrom (2015) 26:1885-1894. Published online Jun. 30, 2015.

Mahapatra. Why Deep Learning over Traditional Machine Learning? Published in Towards Data Science (Mar. 21, 2018). Retrieved from internet: https://towardsdatascience.com/why-deep-learning-is-needed-over-traditional-machine-learning-1b6a99177063. 8 pages.

(56) References Cited

OTHER PUBLICATIONS

Maruthamuthu et al. Process Analytical Technologies and Data Analytics for the Manufacture of Monoclonal Antibodies. Trends in Biotechnology, vol. 38, No. 10, pp. 1169-1186 (Oct. 2020).

Mayhew et al. New Approach Combining Molecular Fingerprints and Machine Learning to Estimate Relative Ionization Efficiency in Electrospray Ionization. ACS Omega 2020, 5, 9510-9516.

Palm et al. Machine Learning for Absolute Quantification of Unidentified Compounds in Non-Targeted LC/HRMS. Molecules 2022, 27, 1013. 17 pages.

PCT/US2022/079082 International Search Report and Written Opinion dated Feb. 15, 2023.

Rossmann et al. Post-column infusion of internal standard quantification for liquid chromatography-electrospray ionization-tandem mass spectrometry analysis—Pharmaceuticals in urine as example approach. Journal of Chromatography A, 1535 (2018) 80-87. Available online Jan. 2, 2018.

Skinnider et al. Chemical language models enable navigation in sparsely populated chemical space. Nat Mach Intell 3, 759-770 (2021). DOI: https://doi.org/10.1038/s42256-021-00368-1 .

Stahnke et al. Compensation of Matrix Effects by Postcolumn Infusion of a Monitor Substance in Multiresidue Analysis with LC-MS/MS. Analytical Chemistry, vol. 81, No. 6, pp. 2185-2192 (Mar. 15, 2009). Published online Feb. 16, 2009.

Star-Weinstock et al. LC-ESI-MS/MS Analysis of Testosterone at Sub-Picogram Levels Using a Novel Derivatization Reagent. Anal. Chem. 2012, 84, 9310-9317.

Tada et al. Creating a Reliable Mass Spectral-Retention Time Library for All Ion Fragmentation-Based Metabolomics. Metabolites 9, 251 (Oct. 26, 2019). 15 pages.

Tideman et al. Automated biomarker candidate discovery in imaging mass spectrometry data through spatially localized Shapley additive explanations. Analytica Chimica Acta 1177 (2021) 338522. Available online Apr. 26, 2021. 17 pages.

Timm et al. Peak intensity prediction in MALDI-TOF mass spectrometry: A machine learning study to support quantitative proteomics. BMC Bioinformatics 2008, 9:443. 18 pages.

U.S. Appl. No. 17/930,324 Office Action dated Apr. 27, 2023.

U.S. Appl. No. 17/930,340 Office Action dated Apr. 13, 2023.

Van Oosten et al. A novel high-throughput and label-free phenotypic drug screening approach: MALDI-TOF mass spectrometry combined with machine learning strategies. Dissertation. Ruperto Carola University, Heidelberg, Germany (2020). Retrieved Feb. 16, 2023 from URL: http://www.ub.uni-heidelberg.de/archiv/28395. 175 pages.

Vappiani et al. Exometabolome profiling reveals activation of the carnitine buffering pathway in fed-batch cultures of CHO cells co-fed with glucose and lactic acid. Biotechnol Progress. 2021;e3198. 16 pages.

Weindl et al. Non-targeted mass isotopolome analysis to gain insights into cancer cell metabolism. Dissertation. University of Luxembourg (2015). Retrieved Feb. 16, 2023 at URL: https://orbilu.uni.lu/bitstream/10993/21182/1/PhD-FSTC-2015-20-web.pdf. 201 pages.

Weis et al. Direct antimicrobial resistance prediction from clinical MALDI-TOF mass spectra using machine learning. Nat Med 28, 164-174 (2022). DOI: https://doi.org/10.1038/s41591-021-01619-9 .

U.S. Appl. No. 17/930,324 Office Action dated Jul. 27, 2023.

U.S. Appl. No. 17/930,338 Notice of Allowance dated Jun. 23, 2023.

U.S. Appl. No. 17/930,338 Office Action dated Mar. 30, 2023.

U.S. Appl. No. 17/930,340 Office Action dated Jul. 27, 2023.

U.S. Appl. No. 17/930,340 Office Action dated Mar. 5, 2024.

Wikipedia Liquid Chromatography-Mass Spectrometry. [Internet] Wikipedia. Retrieved from URL: https://web.archive.org/web/20201031031920/https://en.wikipedia.org/wiki/Liquid_chromatography%E2%80%93mass_spectrometry. Last edited Oct. 18, 2020. Web Page captured by web.archive.org Oct. 31, 2020. 12 pages.

U.S. Appl. No. 17/930,340 Notice of Allowance dated Jun. 26, 2024.

* cited by examiner

Signal processing module configured to process MS signals using a machine learning model ML training scheme

| Compounds | | | |
|---|---|---|---|
| Name | Heavy | Heavy Label | Biological Pathway |
| Glutathione | × | | Redox |
| Triphosphopyridine nucleotide | × | | Energy Carriers |
| Guanosine diphosphate mannose | × | | Glycosylation Precursors |
| Terephthalic acid | × | | Chemistry Compound |
| Glyphosate | × | | Chemistry Compound |
| 3-(3-Pyridyl)acrylic acid | × | | Chemistry Compound |
| Pantothenic acid | ☑ | 13C3 15N | Vitamins |
| L-Lysine | ☑ | 13C6 15N | Amino Acids |
| 4-Nitrophenol | ☑ | D4 | |
| Everolimus | × | | Chemistry Compound |

« ‹ [1] 2 3 4 5 › »

Detailed View

Triphosphopyridine nucleotide ×

- Monomass: 743.0755
- Formula: C21H28N7O17P3
- HMDB URL

Glutathione ×

- Monomass: 307.0838
- Formula: C10H17N3O6S
- HMDB URL

Guanosine diphosphate mannose ×

FIG. 14

| Purines | Redox | Urea Cycle |
|---|---|---|
| Adenine | L-Cystathionine | Argininosuccinate |
| Adenosine | Glutathione Disulfide (GSSG) | Citrulline |
| Adenosine 5'-diphosphate (ADP) | Glutathione Reduced (GSH) | D-Ornithine |
| Adenosine Triphosphate (ATP) | | homoccitrulline |
| Adenosine-monophosphate (AMP) | Sugars | Urea |
| Guanosine | D-Glucose (total hexose) | |
| Guanosine Diphosphate (GDP) | L-Fucose | Vitamins |
| Guanosine Monophosphate (GMP) | Glucoasmine | 4-Aminobenzoate |
| Guanosine Triphosphate (GTP) | Mannose | Ascorbate |
| Hypoxanthine | | Biotin |
| Inosine | TCA | Pantothenate |
| Inosinic Acid (IMP) | 2-Hydroxyglutarate (2HG) | Pyridoxal |
| Uric Acid | Acetyl-CoA | Pyridoxine |
| Xanthine | Citrate | Riboflavin |
| | D-Malic Acid | Tetramethylpyrazine |
| Pyrimidines | Fumaric acid | |
| Carbamoyl phosphate | Glyoxylic acid | |
| Cytidine Triphosphate | Isocitrate | |
| Cytidine-5'-diphosphate | Itaconic acid | |
| Cytidine-5'-monophosphate | Oxaloacetate | |
| Orotic acid | Oxoglutarate | |
| Orotidylic acid (OMP) | Succinate | |
| Thiamine | Succinyl CoA | |
| Thymidine | trans-Aconitic acid | |
| Thymidine 5'-diphosphate | | |
| Thymidine 5'-triphosphate | | |
| Ureidosuccinic acid | | |
| Uridine 5'-Diphosphate (UDP) | | |
| Uridine Triphosphate (UTP) | | |
| Uridine-5'-monophosphate (UMP) | | |

FIG. 23B

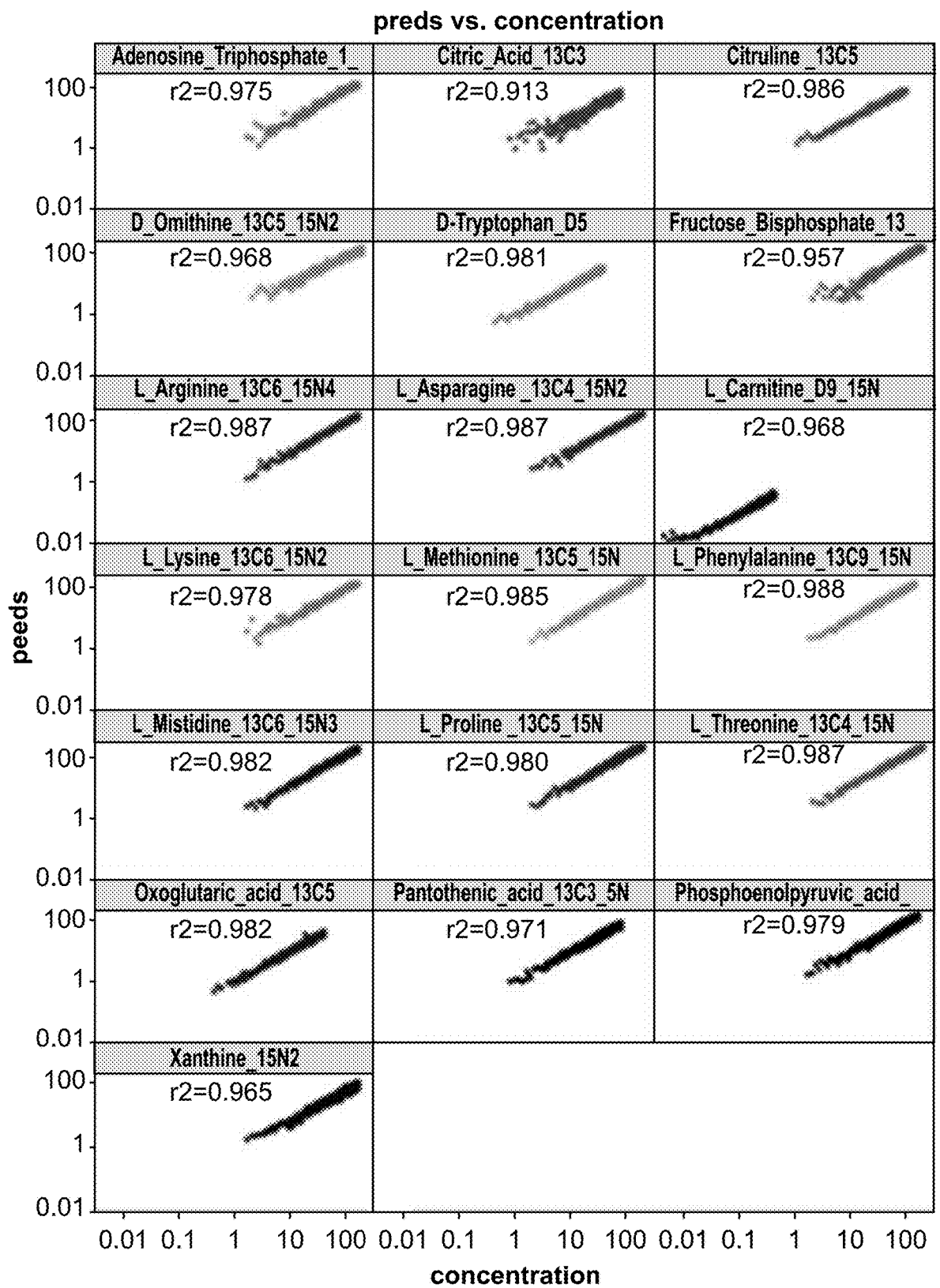
FIG. 31 (Cont. 1)

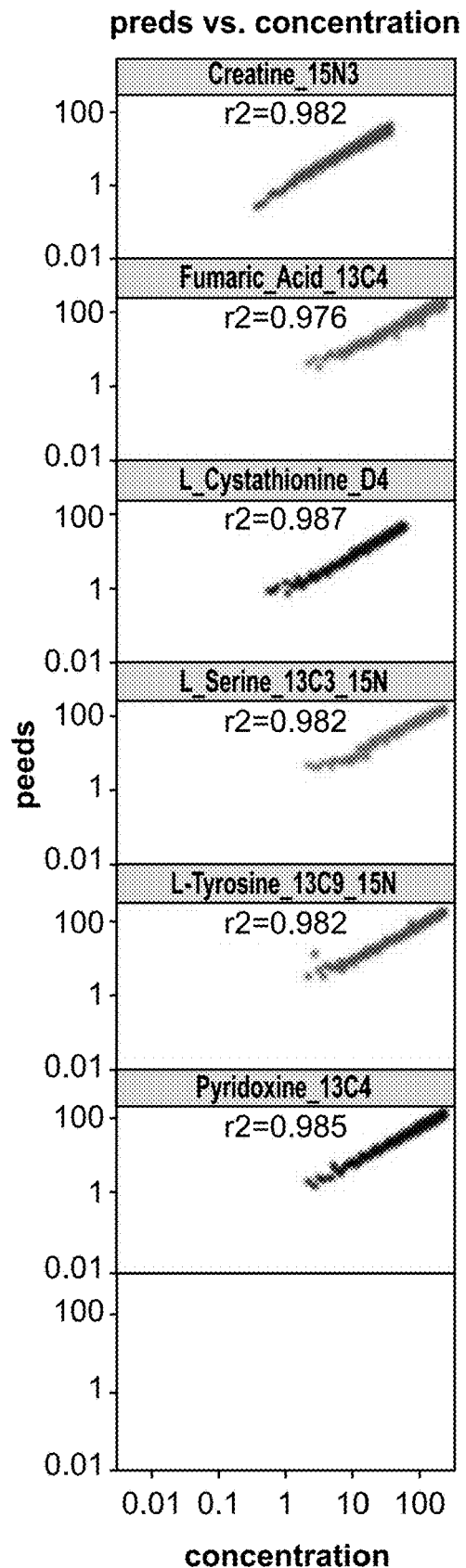
FIG. 31 (Cont. 2)

METHODS AND COMPOSITIONS FOR ANALYTE QUANTIFICATION

CROSS-REFERENCE TO RELATED APPLICATIONS

This application claims priority to U.S. patent application Ser. No. 17/930,338 filed Sep. 7, 2022 which claims priority to Provisional Patent Application No. 63/371,978, filed Aug. 19, 2022, and U.S. Provisional Patent Application No. 63/274,513, filed Nov. 1, 2021, which are hereby incorporated by reference in their entirety.

BACKGROUND

Metabolomics is the analytical science of determining the relative or absolute concentrations of one or more metabolites present in a biological sample. Metabolites can be primary metabolites, such as those produced from the central energy utilization pathways of aerobic and/or anaerobic biology. Or, metabolites can be secondary metabolites, produced for the purposes of cell signaling, immunoinflammatory regulation, taxonomic regulation of microbial communities, defense from predators, communication, species propagation, and many other essential functions of organisms, communities, and ecosystems.

Such metabolites may pertain to the various intermediates of glycolysis, short-chain fatty acid biosynthesis, the tricarboxylic acid (TCA) cycle, or other fermentative energy pathways. Metabolites may pertain to the synthesis and utilization of proteins, fatty acids, and complex carbohydrates. Metabolites may pertain to the intermediates and end products of secondary processes, such as degradation pathways, toxin elimination pathways, drug pharmacokinetics, and the general metabolic and catabolic processes of cells.

As such, metabolomics provides key insights into the health and functionality of a biological system. The tools of metabolomics have been employed to assess the health status of human or animal subjects, as select metabolites serve as biomarkers for various states of disease, malnutrition, or cellular dysfunction. For example, conditions such as diabetes mellitus, metabolic syndrome, renal failure, and hepatic failure present with recognized blood or urine metabolomic signals. Other cellular dysfunctions, such as various cancers, provide metabolomic signatures that enable early detection of disease. Thus, metabolomics is of key utility for the fields of medical and veterinary science.

In the field of synthetic biology, it is often desirable to insert new biochemical functionality into organisms, for example through the methods of recombinant DNA and organism engineering. Such engineered organisms are of interest for the commercial biomanufacturing of materials, such as sustainable plastics and fuels. During the engineering and optimization of such organisms, metabolomic analyses indicate whether the new biochemical functionality is performing efficiently, and to track the flux of unintended side-products that detract from the yield and productivity of the engineered fermentation host. Thus, metabolomics is of key utility to the field of synthetic biology.

In the fields of plant biology and crop science, metabolic signals provide insights into stress conditions, such as nitrogen, phosphorus, or water imbalances, as well as disease and/or infestation. In the developing field of microbiome science, metabolic signatures provide key insights into the metagenomic functions of microbiological communities, such as the sharing of chemical resources between distinct taxa. Thus, metabolomics is of key utility to the fields of plant biology and microbiome science.

In the field of food safety and environmental contamination, metabolomic signals provide measurements of the residual levels of pesticides, insecticides, and their biological degradation products in the food or drinking water supply. Thus, metabolomics is of key utility to the fields of food safety and environmental monitoring.

In short, metabolomics provides signals to assess the state of biological systems that expands upon what can be determined from other characterization methods, such as genomics, metagenomics, and transcriptomics. Typically, the larger the panel of metabolites that can be measured, the more comprehensive a picture of the metabolic state of the system that can be obtained, thus improved outcomes for the corresponding investigation.

Despite this opportunity, there are remarkable challenges to implementing metabolomic methods in practice. A typical biological sample may contain thousands of different biochemical species with concentrations that span orders of magnitude and molecular weights that span orders of magnitude. Complex metabolomic samples may contain different metabolites that are isomers of other metabolites or that are isobaric with other species in the sample. Traditional analytical chemistry approaches to metabolomics thus employ fractionation techniques such as chromatography to simplify the analysis of complex mixtures as a front-end to high-sensitivity detection systems, such as mass spectrometry.

Chromatography, however, introduces significant limitations to the practical application of metabolomic methods. Chromatographic separations are generally slow, adding tens of minutes or even hours to each sample analysis to obtain temporal separation of the various analytes (metabolites and standards) in the sample. Chromatography therefore reduces the sample analysis throughput, which dramatically increases the cost of the analysis. Furthermore, during chromatographic elution, analytes elute from the column over a period of time (chromatographic peaks) that is small compared to the total method run time. Thus, the detection equipment, e.g., high-resolution mass spectrometer, spends a large fraction of the method acquisition time detecting no signal, which is an inefficient utilization of detector capabilities.

Also, within a single sample, the various metabolites of interest are often chromatographically incompatible, meaning that different chromatographic methods must be employed for different classes of metabolites. For instance, lipids, amino acids, acyl-carnitines typically require different chromatographic equipment and methods, meaning that a joint metabolomic analysis of these species demands splitting the sample into aliquots and running a series of different methods on each, further reducing throughput and increasing analysis time and cost.

There is thus a need to develop metabolomic methods by which a broad panel of metabolites, including chromatographically incompatible species, can be determined with high throughput. It is known in the art that high-resolution mass spectrometry can be applied to complex mixtures using direct infusion, i.e., without performing front-end chromatographic separation. The high mass-resolution enables discrimination of analytes within the mixture. Tandem and fragmentation reaction methods can be used to discriminate between different equal exact-mass isomers.

With direct infusion methods, however, it is well-known in the art that interactions between the many different chemical species entering the mass-spectrometer at the same time complicate the determination of instrument response factors. Instrument response factors, such as the relationship between the ion current and the concentration of the corresponding metabolite species, are essential to performing quantification, that is determining the concentration of the analyte in the sample with known precision and accuracy. It is generally held in the art that effects such as ion suppression, induced fragmentation, in situ radical chemistry, and other such interaction effects preclude the ability to determine absolute, or even relative, concentrations of analytes in the sample. The response factor for each analyte is sample dependent.

Surprisingly, it is possible to perform quantification of large arrays of metabolites, including chromatographically incompatible species via direct infusion high-resolution mass spectrometry. The approach described herein overcomes sample interaction effects through the selection and optimization of various heavy internal standards combined with machine learning algorithms trained to control for sample-to-sample variation of analyte response factors in complex mixtures. The resulting methods dramatically increase the breath and throughput of metabolomic analytical methods for the fields of medicine, nutrition, food safety, impurity detection, and synthetic biology, among others.

Metabolomics provide key insights into the health and functionality of a biological system. The tools of metabolomics have been employed to assess the health status of human or animal subjects, as select metabolites serve as biomarkers for various states of disease, malnutrition, or cellular dysfunction. For example, conditions such as diabetes mellitus, metabolic syndrome, renal failure, and hepatic failure present with recognized blood or urine metabolomic signals. Other cellular dysfunctions, such as various cancers, provide metabolomic signatures that enable early detection of disease. Thus, metabolomics is of key utility for the fields of medical and veterinary science.

Despite this opportunity, there are challenges to implementing metabolomic methods in practice. A typical biological sample may contain thousands of different biochemical species with concentrations that span orders of magnitude and molecular weights that span orders of magnitude. Complex metabolomic samples may contain different metabolites that are isomers of other metabolites or that are isobaric with other species in the sample. Traditional analytical chemistry approaches to metabolomics thus employ fractionation techniques such as chromatography to simplify the analysis of complex mixtures as a front-end to high-sensitivity detection systems, such as mass spectrometry. However, chromatography may be generally slow, which reduces the sample analysis throughput. Additionally, within a single sample, various metabolites of interest are often chromatographically incompatible, meaning that different chromatographic methods must be employed for different classes of metabolites.

SUMMARY

The present disclosure relates to methods and compositions for analyte (e.g., metabolite) quantification, e.g., using mass spectrometry techniques. The present disclosure provides, systems, methods, software, platforms, kits, and compositions for analyte (e.g., metabolite) quantification, e.g., using mass spectrometry techniques. Metabolomics is the analytical science of determining the relative or absolute concentrations of one or more metabolites present in a biological sample. Metabolites can be primary metabolites, such as those produced from the central energy utilization pathways of aerobic and/or anaerobic biology. Metabolites can further be secondary metabolites, produced for the purposes of cell signaling, immunoinflammatory regulation, taxonomic regulation of microbial communities, defense from predators, communication, species propagation, and many other essential functions of organisms, communities, and ecosystems.

Such metabolites may pertain to the various intermediates of glycolysis, short-chain fatty acid biosynthesis, the tricarboxylic acid (TCA) cycle, or other fermentative energy pathways. Metabolites may pertain to the synthesis and utilization of proteins, fatty acids, and complex carbohydrates. Metabolites may pertain to the intermediates and end products of secondary processes, such as degradation pathways, toxin elimination pathways, drug pharmacokinetics, and the general metabolic and catabolic processes of cells.

Experiments in biological mass spectrometry can start with a neutral liquid sample and ends with the detection of a charged gas phase ion. The "ionization" process can be highly dynamic and in spite of decades of effort can be unpredictable, poorly understood, and can be difficult to effectively model using traditional techniques. The field of quantitative mass spectrometry has arisen from the need to determine the liquid phase abundance from the gas phase signal. Properties which affect efficiency of ionization comprise chemical properties of the analyte, "matrix" at the instant of ionization, such as other analytes or the solvent, and/or instrument parameters.

One aspect of the present disclosure provides a method comprising: a. adding one or more calibrators to a sample comprising one or more analytes to produce a sample mixture; b. applying mass spectrometry (MS) to the sample mixture; and c. using a trained machine learning model to determine an absolute concentration of the one or more analytes based on an output from the MS, wherein the output comprises at least (1) a first signal indicating an intensity value or a mass-to-charge ratio for the one or more analytes and (2) a second signal indicating an intensity value or a mass-to-charge ratio for the one or more calibrators.

In some embodiments, the one or more calibrators are molecular standards.

In some embodiments, the one or more calibrators are added to the sample after the one or more analytes of the sample are processed using liquid chromatography (LC).

In some embodiments, the one or more calibrators are added to the sample before the one or more analytes of the sample are processed using liquid chromatography (LC).

In some embodiments, the trained machine learning model is configured to determine the absolute concentration based on a relationship or a correlation between the first signal and the second signal.

In some embodiments, the trained machine learning model is configured to determine the absolute concentration of the one or more analytes based on a relationship or a correlation between the first signal and a known concentration of the one or more calibrators.

In some embodiments, in (a), a concentration of the one or more calibrators is known. In some embodiments, in (a), a concentration of the one or more analytes is unknown. In some embodiments, the absolute concentration of the one or more analytes is determined based on the known concentration of the one or more calibrators.

In some embodiments, the one or more calibrators do not comprise any isotopologue of the one or more analytes.

In some embodiments, the one or more analytes comprise a metabolite.

In some embodiments, the method further comprises, subsequent to (c), developing one or more cell lines based on the absolute concentration of the one or more analytes.

In some embodiments, the method further comprises, subsequent to (c), designing or optimizing a media or nutrient feed for one or more cells or cell lines.

In some embodiments, the method further comprises, subsequent to (c), developing or optimizing a development or production process based on the absolute concentration of the one or more analytes.

In some embodiments, the output from the MS comprises raw, unprocessed mass spec data.

In some embodiments, the machine learning model is trained using a data set comprising (i) a first set of intensity values for one or more reference analytes having a known concentration and (ii) a second set of intensity values for one or more reference calibrators having a known concentration. In some embodiments, the reference analytes and the one or more analytes in the sample mixture comprise a same analyte or a same type or class of analyte. In some embodiments, the reference calibrators and the one or more calibrators in the sample mixture comprise a same calibrator or a same type or class of calibrator.

In some embodiments, the one or more calibrators produce a signal that does not overlap a signal of the one or more analytes.

In some embodiments, at least one of the one or more calibrators comprises an alcohol, an amino acid, a nucleoside, a nucleotide, a nucleotide analogue, or an antimetabolite.

One aspect of the present disclosure provides a method comprising: a. providing a sample mixture comprising one or more analytes and one or more calibrators; and b. generating a MS output for the sample mixture, wherein the MS output comprises (1) a first MS signal for the one or more analytes and (2) a second MS signal for the one or more calibrators; and c. using a trained machine learning algorithm to determine an absolute concentration of the one or more analytes, based at least in part on a relationship or correlation between the first MS signal and the second MS signal.

In some embodiments, the trained machine learning model is configured to determine the absolute concentration of the one or more analytes based on a relationship or a correlation between the first MS signal and a known concentration of the one or more calibrators.

In some embodiments, in (a), a concentration of the one or more calibrators is known. In some embodiments, in (a), a concentration of the one or more analytes is unknown. In some embodiments, the absolute concentration of the one or more analytes is determined based on the known concentration of the one or more calibrators.

In some embodiments, the one or more calibrators do not comprise any isotopologue of the one or more analytes.

In some embodiments, the one or more analytes comprise a metabolite.

In some embodiments, the method further comprises, subsequent to (c), developing one or more cell lines based on the absolute concentration of the one or more analytes. In some embodiments, the method further comprises, subsequent to (c), designing or optimizing a media or nutrient feed for one or more cells or cell lines. In some embodiments, the method further comprises, subsequent to (c), developing or optimizing a development or production process based on the absolute concentration of the one or more analytes.

In some embodiments, the MS output comprises raw, unprocessed mass spec data.

In some embodiments, the machine learning model is trained using a data set comprising (i) a first set of intensity values for one or more reference analytes having a known concentration and (ii) a second set of intensity values for one or more reference calibrators having a known concentration. In some embodiments, the reference analytes and the one or more analytes in the sample mixture comprise a same analyte or a same type or class of analyte. In some embodiments, the reference calibrators and the one or more calibrators in the sample mixture comprise a same calibrator or a same type or class of calibrator.

In some embodiments, the one or more calibrators produce a signal that does not overlap a signal of the one or more analytes.

In some embodiments, at least one of the one or more calibrators comprises an alcohol, an amino acid, a nucleoside, a nucleotide, a nucleotide analogue, or an antimetabolite.

One aspect of the present disclosure provides a method comprising: using a trained machine learning model to determine an absolute concentration of one or more target analytes in a sample mixture comprising the target analytes and one or more calibrators, wherein the machine learning model is trained using a data set comprising (i) a first set of intensity values for one or more reference analytes having a known concentration and (ii) a second set of intensity values for one or more reference calibrators having a known concentration, and wherein the machine learning model is configured to determine the absolute concentration of the one or more target analytes based on (1) a first set of intensity values for the one or more target analytes in the sample mixture and (2) a second set of intensity values for the one or more calibrators in the sample mixture.

In some embodiments, the machine learning model is configured to determine the absolute concentration of the one or more target analytes based on (i) positive ionization information for the one or more target analytes, (ii) negative ionization information for the one or more target analytes, and (iii) a molecular representation of the one or more target analytes.

In some embodiments, the reference analytes and the target analytes in the sample mixture comprise a same analyte or a same type or class of analyte.

In some embodiments, the reference calibrators and the one or more calibrators in the sample mixture comprise a same calibrator or a same type or class of calibrator.

One aspect of the present disclosure provides a method comprising: (a) providing a sample mixture comprising a plurality of analytes and one or more calibrators, wherein a ratio between the analytes and the one or more calibrators is greater than 1:1; and (b) determining an absolute concentration of each of the plurality of analytes, based at least in part on a relationship or correlation between a first time series MS signal for the plurality of analytes and a second time series MS signal for the one or more calibrators.

In some embodiments, the one or more calibrators do not comprise any isotopologue of the plurality of analytes.

One aspect of the present disclosure provides a method comprising: (a) providing a sample mixture comprising a plurality of analytes and one or more calibrators; and (b) determining an absolute concentration of each of the plurality of analytes, based at least in part on a first time series MS signal for the plurality of analytes and a second time series MS signal for the one or more calibrators, wherein the one or more calibrators comprise a same set of calibrators usable to determine the absolute concentration of each of the plurality of analytes.

In some embodiments, the plurality of analytes comprise different analytes.

One aspect of the present disclosure provides a kit comprising: one or more calibrators representative of a chemical space or a chemical class for one or more analytes of interest in a sample, wherein the one or more calibrators comprise a nonbiologic that is usable to determine an absolute concentration of a plurality of different analytes comprising the one or more analytes of interest.

In some embodiments, the one or more calibrators do not comprise any isotopologue of the plurality of different analytes.

One aspect of the present disclosure provides a method comprising: (a) providing a media to one or more cells; (b) analyzing one or more outputs of the one or more cells after the one or more cells process the media to determine an absolute concentration of one or more analytes in (i) the one or more cells or (ii) the one or more outputs of the one or more cells; (c) characterizing a cell response or a cell behavior for the one or more cells based at least in part on the absolute concentration of the one or more analytes; and (d) optimizing the media based on the characterized cell response or cell behavior in order to promote or facilitate cell culturing or cell growth.

In some embodiments, the one or more analytes comprise one or more metabolites generated or produced by the one or more cells.

One aspect of the present disclosure provides a system comprising: a computing unit operably coupled to a mass spec (MS) machine, wherein the computing unit is configured to: (i) receive MS data from the MS machine, wherein the MS data is associated with a sample comprising one or more analytes and one or more calibrators, (ii) process the MS data using a trained ML algorithm to determine an absolute concentration of the analytes, and (iii) output one or more actionable biological insights based on the absolute concentration of the analytes, wherein the trained ML algorithm is configured to determine the absolute concentration of the analytes from the received MS data substantially in real time.

In some embodiments, the one or more calibrators comprise a nonendogenous molecule or compound. In some embodiments, the one or more calibrators comprise a nonbiologic.

In one aspect, the invention provides a method of quantifying a target analyte in a laboratory sample including the target analyte. The method includes the step of estimating the amount of the target analyte in the laboratory sample from mass spectrometric data including signal intensities for the target analyte and one or more internal standards, wherein the mass spectrometric data are an output of a mass spectrometric analysis of a target sample produced from the laboratory sample and a predetermined amount of the one or more internal standards. In general, the laboratory sample In some embodiments, the step of estimating the amount of the target analyte includes processing the mass spectrometric data using a pretrained machine learning model.

In some embodiments, the pretrained machine learning model is pretrained using a training data set including mass spectrometric data for a plurality of reference samples including the target analyte and known concentrations of the one or more internal standards. In some embodiments, the plurality of reference samples includes unknown concentrations of the target analyte spiked with a known quantity of the target analyte. In some embodiments, the plurality of reference samples includes known concentrations of the target analyte.

In some embodiments, the pretrained machine learning model is pretrained using a labeled training data set. In some embodiments, the pretrained machine learning model is pretrained using a partially labeled training data set. In some embodiments, the pretrained machine learning model is pretrained using an unlabeled training data set. In some embodiments, the plurality of reference samples includes unknown concentrations of the target analyte.

In some embodiments, the pretrained machine learning model is pretrained using deep learning. In some embodiments, the pretrained machine learning model is pretrained using a supervised learning method. In some embodiments, the pretrained machine learning model is pretrained using a semi-supervised learning method. In some embodiments, the pretrained machine learning model is pretrained using an unsupervised learning method. In some embodiments, the pretrained machine learning model is pretrained using a self-supervised learning method. In some embodiments, the pretrained machine learning model is pretrained using an automated hyperparameter tuning. In some embodiments, at least one hyperparameter used for the automated hyperparameter tuning is accuracy, precision, coefficient of determination, or dynamic range. In some embodiments, at least one hyperparameter used for the automated hyperparameter tuning is model performance.

In some embodiments, the step of estimating amount of the target analyte includes normalizing the signal intensities to produce normalized signal intensities. In some embodiments, the step of normalizing includes normalizing the signal intensities to reference signal intensities for one or more known samples including predetermined concentrations of the internal standards. In some embodiments, the one or more known samples are free of the target analyte. In some embodiments, the one or more known samples include a known concentration of the target analyte. In some embodiments, the one or more known samples are pooled samples including predetermined amounts of aliquots of samples including known concentrations of the internal standards and unknown concentrations of the target analyte.

In some embodiments, the method further includes the step of performing mass spectrometric analysis on the target sample to produce the mass spectrometric data. In some embodiments, the method further includes the step of producing the target sample from the laboratory sample including the target analyte. In some embodiments, the laboratory sample includes an unknown amount of the target analyte. In some embodiments, the step of producing includes addition of the predetermined amount of the one or more internal standards to the laboratory sample. In some embodiments, the step of producing includes eluting the laboratory sample with a mobile phase over a stationary phase. In some embodiments, the step of producing includes addition of the predetermined amount of the one or more internal standards to the laboratory sample, wherein the one or more internal standards are added to the laboratory sample in the mobile phase. In some embodiments, the step of producing does not result in a chromatographic isolation of the target analyte from other non-solvent components of the laboratory sample.

In some embodiments, each of the one or more internal standards produces a mass spectrometric signal that does not overlap the mass spectrometric signal of the target analyte. In some embodiments, the target sample includes one or more target analytes. In some embodiments, the method quantifies at least one of the one or more target analytes. In some embodiments, the method quantifies all of the target analytes.

In another aspect, the invention provides a method of identifying one or more internal standards for quantifying one or more target analytes in a laboratory sample, the method including selecting one or more internal standards producing mass spectrometric signals that do not overlap the mass spectrometric signals of the one or more target analytes to identify the one or more internal standards for quantifying one or more target analytes in a laboratory sample. In some embodiments, the one or more target analytes are 10, 100, 250, 500, 750, 1000, 2000, 3000, 4000, 5000, 10000, 250000, or 500000 different analytes.

In some embodiments, the one or more internal standards are 1 to 20 internal standards (e.g., 2 to 20 internal standards, 2 to 15 internal standards, 5 to 20 internal standards, 5 to 15 internal standards, 6 to 12 internal standards, 2 to 12 internal standards, or 5 to 8 internal standards).

In another aspect, the invention provides a non-transitory computer-readable storage medium comprising a set of instructions for executing the method described herein. In some embodiments, the machine learning model is selected from logistic regression, ada boost classifier, extra trees classifier, extreme gradient boosting, gaussian process classifier, gradient boosting classifier, K-nearest neighbor, light gradient boosting, linear discriminant analysis, multi-level perceptron, naïve Bayes, quadratic discriminant analysis, random forest classifier, ridge classifier, SVM (linear and radial kernels), fully connected neural network, or a deep neural network.

In some embodiments of any of the above aspects, the laboratory sample is a fermentation broth, a cell culture medium, a tissue culture medium, urine, fecal matter, blood, blood plasma, mucus, saliva, or soil.

In yet another aspect, the invention provides a library of 3000 or fewer internal standards for quantifying one or more target analytes, wherein each of the internal standards having a molecular weight of 18 to 5000 g/mol and having a permanently charged moiety or having at least one acidic proton with a pKa of <18 at 25° C. in water.

In still another aspect, the invention provides a sample including one or more target analytes and one or more internal standards, each of the internal standards having a molecular weight of 18 to 5000 g/mol and having a permanently charged moiety or having at least one acidic proton with a pKa of <18 at 25° C. in water.

In some embodiments of any aspect, each of the one or more internal standards is soluble in water and in 50% aqueous acetonitrile to at least 10 μM (e.g., 50 μM, 100 μM, 500 μM, or 1 mM) at 25° C. In some embodiments of any aspect, each of the one or more internal standards is a compound having a molecular weight of 18 to 5000 g/mol (e.g., 18 to 2500 g/mol, 50 to 2000 g/mol, or 50 to 1000 g/mol). In some embodiments of any aspect, one or more of the internal standards is isotopically enriched at least for one atomic position (e.g., at least one C, N, or O) in the internal standard. In some embodiments, one or more of the internal standards is halogenated. In some embodiments of any aspect, at least one of the one or more internal standards is an alcohol, an amino acid, a nucleoside, a nucleotide, a nucleotide analogue, a bile acid, or an antimetabolite. In some embodiments of any aspect, the target analyte is a metabolite.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 14 schematically illustrates a user interface with a compound database in accordance with embodiments described herein.

FIG. 23B schematically illustrates a metabolite list by biochemical pathway in accordance with embodiments described herein.

DETAILED DESCRIPTION

Figure 1:
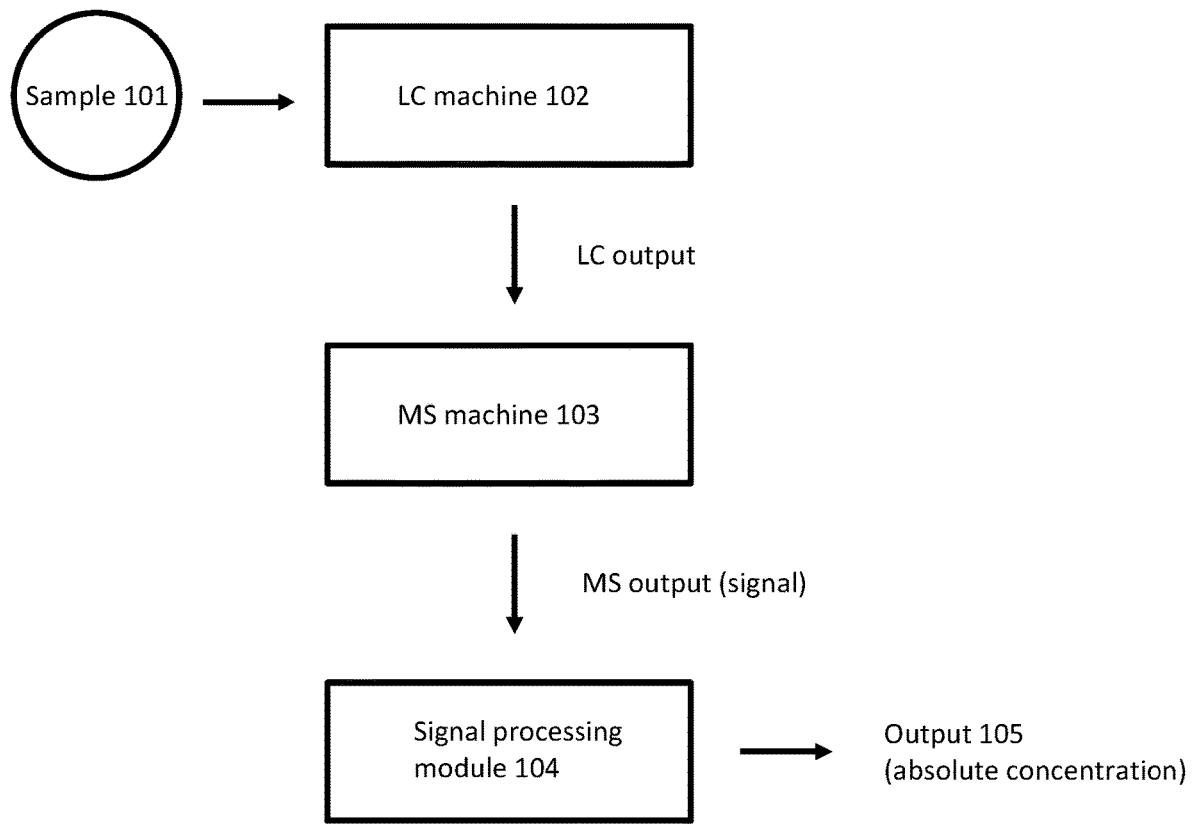
FIG. 1 schematically illustrates a method for sample processing in accordance with embodiments described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately or within a short enough time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

Provided herein are methods for determining a concentration of a target analyte. In some cases, the target analyte comprises one or more analytes. In some cases, the concentration comprises the absolute concentration. In some cases, the methods provide near instantaneous determination of the absolute concentration of critical intra and extra cellular metabolites in bioprocessing. In some cases, the concentration of a target analyte is determined via liquid chromatography (LC), mass spectrometry (MS), or a combination thereof (LC/MS). In some cases, the methods are enabled by a deep learning model, one or more candles (e.g., calibrators), and a platform to record expansive training data sets with high analytical fidelity. In some cases, the methods provide the power to bypass the efforts (and expertise) of traditional techniques and go directly from signal to concentration. In some instances, the method comprises little to no development time. In some instances, the method requires little to no expertise.

A first step in determining the abundance of a single analyte (e.g., mass-to-charge ratio (m/z)) from mass spectra data comprises extracting an intensity of a single m/z (e.g., exact m/z to +/−5 ppm) over the course of the LC run. The results curve is termed an extracted ion chromatogram (XIC) and the area under the curve (AUC) can be used as the signal in any computation of analyte concentration. AUC generally defines the necessary quality attributes of LC-MS data since there must be a well-defined curve to calculate area. Isomers may be well separated from each other, and each curve can contain a minimum of about 20 unique spectra (points across curve). The XIC is generally well defined enough to have a simply calculated area.

Absolute quantification can use extensive method development to link the AUC from the sample to an AUC from a standard in order to determine an accurate concentration (in moles/L or moles/cell count) of an identified analyte. In some cases, the advantage of absolute quantification is that it provides with an exact number that can be verified in an independent system. In some cases, the disadvantages are that substantial method development is required prior to samples being ready to quantify and only changes in identified analytes with a standard available can be determined. In some cases, in order to get from AUC to concentration, there is a needs to create matched conditions using either matched isotopologues and/or calibration curves.

The systems and methods provided herein may not involve XIC or AUCs. Rather, the systems and methods provided herein can use a fundamentally different input. The systems and methods provided herein can enable a user to bypass method development and get directly from MS signal to absolute concentration.

An method for sample processing to determine a concentration of an analyte is schematically illustrated in FIG. 1. A sample 101 can comprise one or more samples. A sample 101 may comprise one or more analytes (e.g., target analytes). In some cases, the one or more analytes comprises metabolites. In some instances, the sample is an aqueous solution comprising one or more metabolites. In some instances, the sample is an organic solution comprising one or more metabolites. In some instances, the sample comprises one or more metabolites that have been derivatized or functionalized prior to analysis.

Metabolites may comprise any known metabolite. The metabolite can be beneficial or detrimental from the perspective of a health status or disease biomarker, fermentation performance, microbiome function. Metabolites may be those involved in biological processes, such as glycolysis, TCA cycle, pentose phosphate path, purines/pyrimidines, amino acids, urea cycle, redox/energy carriers, fatty acid metabolism, vitamins, glycosylation precursors, etc.

Metabolites may comprise by way of non-limiting example, short chain fatty acids (SCFAs), bile acids, dipeptides, fatty alcohols, terpenoids, amino acids, peptides (e.g., dipeptides), polyphenols, hemiterpenoids, monoterpenoids, sesquiterpenoid, diterpenoids, sesterterpenoids, triterpenoids, tetraterpenoids, polyterpenoids, neurotransmitters (or precursors thereof), volatile fatty acids, alcohols, signaling factors, pro-inflammatory metabolites, nitrogenous metabolites. In some cases, the metabolites are amino acids, free fatty acids, acylcarnitines, or any combination thereof.

Exemplary metabolites include, but are not limited to, beta-nicotinamide adenine dinucleotide, glutamine, hypotaurine, n-methyl-alanine, citrate, threonine, purine, n-acetylneuraminate, n-acetylmannosamine, pyrimidine, trans-aconitate, urate, cytidine, serine, cysteine, citrulline, taurine, n-acetyltryptophan, nicotinate, inosine, gamma-aminobutyrate, cytosine, isoleucine, pyrazole, glutamate, ascorbate, p-hydroxyphenylacetate, n-acetylglucosamine, glycolate, sarcosine, creatinine, quinate, dihydroorotate, malonate, guanidinoacetate, formamide, glycine, methionine, tetrahydrofolate, 2-phosphoglycerate, methylthioadenosine, thymidine, cys-gly, aminoisobutanoate, glucose, xanthine, dihydrofolate, cystine, 1-alanine, diethanolamine, uridine monophosphate, proline, thymine, succinate semialdehyde, lactate, uridine, fructose bisphosphate, carnosine, nicotinamide, shikimate, succinate, phenylalanine, uracil, thiourea, aspartate, deoxycytidine monophosphate, hypoxanthine, creatine, L-dopa, guanosine, dihydrouracil, malate, isocitrate, tyrosine, glycerol, asparagine, valine, guanine, homoserine, pyridoxine, deoxyadenosine monophosphate, folate, nicotinamide mononucleotide, 3-methyl-L-histidine, diaminopimelate, aminoadipate, deoxycytidine, noradrenaline, glucosamine 6-phosphate, tartrate, 3-dehydroshikimate, caffeine, homocysteine, theophylline, leucine, trehalose, betaine, tryptophan, 3-sulfinoalanine, o-succinylhomoserine, allantoin, glyceraldehyde, d-glucuronolactone, (2-aminoethyl)phosphonate, 2,5-dihydrobenzoic acid, maleimide, threitol, glucosamine, paraxanthine, adenosine 5'-diphosphate, 2-deoxy-d-glucose, 1-methyl-1-histidine, galactitol, oxoproline, 4-pyridoxate, quinolinate, methylguanidine, deoxyguanosine-monophosphate, 3-hydroxy-3-methylglutaryl-coa, glucuronate, 1-methyladenosine, deoxypuridine, gluconate, urocanate, kynurenine, pyroglutamate, 4-acetamidobutanoate, trans-1,2-cyclohexanediol, melanin, dopamine, adenosine-monophosphate, lysine, citicoline, 1,3-diaminopropane, phosphoserine, 1-aminocyclopropanecarboxylate, glutarylcarnitine, cystathionine, norvaline, 3-hydroxymethylglutarate, phosphonoacetate, picolinate, ethanolamine, arginine, trans-4-hydroxy-L-proline, fucose, homocystine, n-methylglutamate, d-ornithine, xanthosine, 3-methylcrotonyl-coa, thyrotropin releasing hormone, cysteate, n-methylaspartate, galactarate, alpha-hydroxyisobutyrate, nicotinic acid adenine dinucleotide phosphate, n-acetylasparagine, pipecolate, glucose 6-phosphate, NADP, 6-phosphogluconate, isopentenyl pyrophosphate, guanosine triphosphate, dtdp-D-glucose, agmatine sulfate, glycolaldehyde, dgtp, n-acetylglycine, n-acetylaspartate, inosine 5'-diphosphate, palmitoylcarnitine, norspermidine, nicotinamide hypoxanthine dinucleotide, s-adenosylmethionine, erythritol, glucosaminate, uridine triphosphate, 2-keto-3-deoxy-d-gluconic acid, d-sedoheptulose, 1,4-diaminobutane dihydrocloride, deoxycarnitine, adenosine 2',3'-cyclic phosphate, mevalolactone, galactose 1-phosphate, dimethylallylpyrophosphate, deoxyuridine triphosphate, phosphorylcholine, o-acetylcarnitine, 6-hydroxydopamine, thiamine, 5-methylcytosine, glycerate, cytidine 2',3'-cyclic phosphate, n,n,n-trimethyllysine, riboflavin, uridine diphosphate glucose, methyl galactoside, pyridoxal-phosphate, dihydroxyacetone phosphate, phosphoenolpyruvate, mannose 6-phosphate, 3-phosphoglycerate, 1-carnitine, o-phosphoethanolamine, o-acetylserine, cytidine monophosphate, guanosine diphosphate mannose, adp-glucose, fructose 6-phosphate, adenosine 3',5'-diphosphate, 3-nitro-1-tyrosine, p-octopamine, n-alpha-acetyllysine, uridine diphosphategalactose, dihydroxyfumarate, pyridoxamine, 5-aminolevulinate, deoxyuridine-monophosphate, 5'-deoxyadenosine, ribose 1,5-bisphosphate, xanthosine-monophosphate, fad, deoxyguanosine, orotate, lauroylcarnitine, 1-methylnicotinamide, spermine, n-acetylmethionine, carbamoyl phosphate, phosphoribosyl pyrophosphate, aicar, uridine diphosphate-n-acetylgalactosamine, glyceraldehyde 3-phosphate, cyclic GMP, homocysteine thiolactone, o-phosphoserine, s-adenosylhomocysteine, 1-ornithine, adenine, normetanephrine, uridine diphosphate-n-acetylglucosamine, guanosine diphosphate, glutathione reduced, uridine diphosphate glucuronic acid, n,n-dimethylarginine, cytidine diphosphate, selenocystamine, histamine, indoxyl sulfate, ethyl 3-ureidopropionate, deoxyribose, phytate, thiamine monophosphate, uracil 5-carboxylate, s-hexyl-glutathione, glyoxylate, guanosine monophosphate, n-acetylalanine, 4-guanidinobutanoate, hydroxypyruvate, d-mannosamine, cytochrome c, deoxyadenosine, n-acetylputrescine, n-acetylgalactosamine, n-acetylglutamate, 2,4-dihydroxypteridine, 6-hydroxynicotinate, n-acetylcysteine, inosine-monophosphate, pantothenate, 2-aminoisobutyrate, aniline-2-sulfonate, s-carboxymethylcysteine, rhamnose, thiamine pyrophosphate, histidinol, thymidine-monophosphate, ureidopropionate, 5-aminopentanoate, norleucine, n-formylglycine, adenosine, raffinose, meso-tartrate, 2-acetamido-2-deoxy-beta-d-glucosylamine, saccharate, adenosine triphosphate, 3-methoxytyrosine, lactose, 3-hydroxybutanoate, 4-imidazoleacetate, galacturonate, cytidine triphosphate, cyclic amp, methionine sulfoximine, cis-4-hydroxy-d-proline, n1-acetylspermine, glucosamine 6-sulfate, NADPH, 3-methylhistamine, maleamate, choline, methyl 4-aminobutyrate, n-formyl-L-methionine, acetylcholine, oxalate, 5-hydroxytryptophan, d-alanine, theobromine, guanidinosuccinate, histidine, allothreonine, phosphocreatine, spermidine, adenosine diphosphate ribose, 2-methoxyethanol, citramalate, anserine, biliverdin, 5-hydroxylysine, cysteamine, ophthalmate, mesoxalate, trigonelline, epinephrine, 3,4-dihydroxyphenylglycol, cadaverine, 2-hydroxybutyrate, coenzyme a, oxalomalate, inosine triphosphate, cdp-ethanolamine, 2,5-dimethylpyrazine, stachyose, deoxycytidine-diphosphate, 2,3-butanediol, d-ribose 5-phosphate, hydroxykynurenine, galactosamine, deoxyadenosine triphosphate, glycerol 3-phosphate, cyanocobalamin, 4-hydroxy-L-phenylglycine, n-acetylserine, uridine 5'-diphosphate, methylglutarate, sorbate, monoethylmalonate, gluconolactone, 4-hydroxybenzoate, tyramine, cortisol, prenol, 3-hydroxybenzaldehyde, xanthurenate, 2-methylpropanal, indoxyl β-glucoside, trimethylamine, melatonin, maleate, pentanoate, propanoate, bilirubin, nicotine, pregnenolone sulfate, kynurenate, isobutyrate, 3-hydroxybenzyl alcohol, aniline, acetoin, 3,5-diiodo-L-tyrosine, mandelate, tryptamine, 4-aminobenzoate, glutarate, 5-valerolactone, caffeate, lumichrome, beta-alanine, n-acetylphenylalanine, n-acetylproline, L-tryptophanamide, phenol, n-methyltryptamine, oxaloacetate, 2,3-dihydroxybenzoate, 2-propenoate, indole-3-ethanol, ferulate, glycocholate, phenylethanolamine, thiopurine s-methylether, 2-hydroxy-4-(methylthio)butanoate, glycochenodeoxycholate, benzoate, 3-amino-5-hydroxybenzoate, pyrocatechol, 3,4-dihydroxybenzoate, cyclopentanone, pantolactone, guaiacol, 2-hydroxyphenylacetate, 10-hydroxydecanoate, didecanoyl-glycerophosphocholine, 2-hydroxypyridine, 3,4-dihydroxyphenylacetate, n6-(delta2-isopentenyl)-adenine, methyl vanillate, 2-oxobutanoate, lipoamide, 3-hydroxyanthranilate, 3-(4-hydroxyphenyl)pyruvate, hexanoate, methylmalonate, indole-3-acetate, cortisol 21-acetate, indole-3-acetamide, hippurate, ethylmalonate, 3,5-diiodo-l-thyronine, fumarate, benzaldehyde, 4-hydroxybenzaldehyde, 3-(2-hydroxyphenyl)propanoate, 3-methoxytyramine, benzylamine, 2-quinolinecarboxylate, serotonin, pterin, butanoate, 2-aminophenol, 6-carboxyhexanoate, indole-3-pyruvate, dehydroascorbate, 3-amino-4-hydroxybenzoate, 3,4 dihydroxymandelate, 2-methylcitrate, dihydrobiopterin, beta-glycerophosphate, glucose 1-phosphate, 2,3-diaminopropionate, 2,5-dihydroxybenzoate, 4-quinolinecarboxylate, hydroquinone, dethiobiotin, 3-hydroxybenzoate, 2-methylbutanal, n-acetylserotonin, hydrophenyllactic acid, itaconate, azelate, oxoadipate, 2-methylglutarate, phenylacetaldehyde, 3-methyl-2-oxovalerate, porphobilinogen, diacetyl, pyruvate, trans-cinnamaldehyde, 2,6-dihydroxypyridine, vanillin, methyl acetoacetate, suberate, adipate, geranyl-pp, n-acetylleucine, 2',4'-dihydroxyacetophenone, benzyl alcohol, monomethyl-glutarate, indole-3-methyl acetate, mevalonate, 3-methoxy-4-hydroxymandelate, homovanillate, 2-methylmaleate, 1-phenylethanol, salsolinol, salicylamide, oxoglutarate, ethyl 3-indoleacetate, 3-alpha, 11-beta, 17,21-tetrahydroxy-5-beta-pregnan-20-one, n,n-dimethyl-1,4-phenylenediamine, homogentisate, indoleacetaldehyde, 4-hydroxy-3-methoxyphenylglycol, 3-hydroxyphenylacetate, 4-methylcatechol, pyridoxal, salicylate, sebacate, 3-methyl-2-oxindole, 3-methyladenine, hydroxyphenyllactate, biotin, mercaptopyruvate, pyruvic aldehyde, pyrrole-2-carboxylate, 5-hydroxyindoleacetate, 3-methylglutaconate, resorcinol monoacetate, acetoacetate, acetylphosphate, sorbose, xylitol, ribitol, myoinositol, mannose, xylose, sucrose, galactose, alpha-d-glucose, allose, mannitol, melibiose, sorbitol, maltose, tagatose, 1-gulonolactone, arabinose, cellobiose, psicose, arabitol, lyxose, ribose, palatinose, d-pinitol, vitamin d2, squalene, 4-coumarate, nonanoate, estradiol-17alpha, caprylate, ursodeoxycholate, petroselinate, dipalmitoylglycerol, corticosterone, lithocholate, protoporphyrin, heptanoate, retinol, menaquinone, elaidate, chenodeoxycholate, myristate, cholesteryl oleate, rosmarinate, glyceryl tripalmitate, cortexolone, lithocholyltaurine, palmitoleate, palmitate, liothyronine, sphinganine, lanosterol, laurate, arachidate, erucate, deoxycholate, ketoleucine, eicosapentaenoate, heptadecanoate, glyceryl trimyristate, linoleate, sphingomyelin, 7-dehydrocholesterol, thyroxine, bis(2-ethylhexyl)phthalate, gamma-linolenate, omega-hydroxydodecanoate, methyl jasmonate, dipalmitoyl-phosphatidylcholine, hexadecanol, 5,6-dimethylbenzimidazole, retinoate, indole, cholate, phylloquinone, cholesteryl palmitate, quinoline, docosahexaenoate, diethyl 2-methyl-3-oxosuccinate, retinyl palmitate, 2-undecanone, 1-hydroxy-2-naphthoate, dipalmitoyl-phosphoethanolamine, phenylpyruvate, trans-cinnamate, oleate, stearate, beta-carotene, 25-hydroxycholesterol, nervonate, desmosterol, deoxycorticosterone acetate, oleoyl-glycerol, alpha-tocopherol, glycerol-myristate, tricosanoate, coenzyme q10, cortisone, decanoate, 6-diazo-5-oxo-L-norleucine, Acarbose, Aucubin, caffeine, Carbazochrome sodium sulfonate, Cefoselis Sulfate, Cellobiose, Ciprofloxacin hydrochloride hydrate, Cromolyn sodium, Cyclo (-RGDfK), Daminozide, Diminazene Aceturate, Fudosteine, Geniposidic acid, Gimeracil, Isoprinosine, Oseltamivir acid, Pidotimod, Puerarin, Sodium 4-amiroppa-raty Hyalrate, Telaglenastat, Tipiracil hydrochloride, Voglibose, Zanamivir.

The metabolite of interest may comprise a pesticide or pesticide residue. In some cases, the sample for metabolomic determination is a food product. In some cases, the food product is a produce product, a meat product, an agricultural product, or any combination thereof. Exemplary metabolites include but are not limited to Captan, Diuron, Triflumezopyrim, Acephate, Fenpicoxamid, Malathion, Ferbam, Ziram, S-Ethyl dipropylthiocarbamate, Inorganic bromide residues resulting from fumigation with methyl bromide, Inorganic bromide residues in peanut hay and peanut hulls, Methyl bromide, Piperonyl butoxide, Pyrethrins, o-Phenylphenol and its sodium salt, Hydrogen Cyanide, Thiram, 2,4-D, Fluorine compounds, Ethylene oxide, Diazinon, 1-Naphthaleneacetic acid, Dicofol, Carbaryl, Dodine, Maleic hydrazide, Mancozeb, Ethoxyquin, Chlorpropham, Endosulfan, Disulfoton, Linuron, DCPA, Coumaphos, Diphenylamine, Folpet, Trichlorfon, Dicloran, p-Chlorophenoxyacetic acid, Dimethoate, Paraquat, Phorate, Trifluralin, Benfluralin, Terbacil, Bromacil, Propachlor, S-Ethyl cyclohexylethylthiocarbamate, Simazine, Naled, Metiram, Atrazine, Prometryn, Phosphine, Diquat, Dicamba, Fluometuron, Dichlobenil, Dichlorvos, Triphenyltin hydroxide, Bensulide, Thiabendazole, Propazine, Streptomycin, Alachlor, Tetrachlorvinphos, Methomyl, Carbofuran, Ametryn, Propargite, Phosmet, Ethoprop, Aldicarb, Tribuphos, Propanil, Chlorothalonil, Formetanate hydrochloride, Phenmedipham, Zinc phosphide, Amitraz, 2-(Thiocyanomethylthio)benzothiazole, Methanearsonic acid, Pentachloronitrobenzene, Picloram, Endothall, N-1-Naphthyl phthalamic acid, Methidathion, Dicrotophos, Ethephon, Carboxin, Oxamyl, Oryzalin, Triallate, Pyrazon, Propyzamide, 4-(2-Methyl-4-chlorophenoxy) butyric acid, Interim tolerances, Bromoxynil, Napropamide, S-(2-(Ethylsulfinyl)ethyl) O,O-dimethyl phosphorothioate, 4-(2,4-Dichlorophenoxy) butyric acid, Metribuzin, Oxytetracycline, MCPA, 2,4-Dinitro-6-octylphenyl crotonate and 2,6-dinitro-4-octylphenyl crotonate, Chlorpyrifos, Ethofumesate, Fenamiphos, Nitrapyrin, Terbufos, Desmedipham, Bentazon, Norflurazon, Asulam, Pendimethalin, Fenbutatin-oxide, Glyphosate, n-Octyl bicycloheptenedicarboximide, Metolachlor, 5-Ethoxy-3-(trichloromethyl)-1,2,4-thiadiazole, Thiophanate-methyl, 2,6-Dimethyl-4-tridecylmorpholine, Diflubenzuron, Permethrin, Vinclozolin, Oxyfluorfen, Sodium salt of acifluorfen, Mepiquat (N,N-dimethylpiperidinium), Diclofop-methyl, Tebuthiuron, Hydramethylnon, Hexazinone, Iprodione, Thiobencarb, Thidiazuron, Profenofos, Chlorsulfuron, Thiodicarb, Metalaxyl, Pirimiphos-methyl, Triadimefon, Fluazifop-P-butyl, Sethoxydim, Imazalil, Cyromazine, Aluminum tris (O-ethylphosphonate), Ethalfluralin, Triclopyr, Cypermethrin and isomers alpha-cypermethrin and zeta-cypermethrin, Chlorpyrifos-methyl, Fluridone, Fenarimol, Clomazone, 2-[4,5-Dihydro-4-methyl-4-(1-methylethyl)-5-oxo-1H-imidazol-2-yl]-3-quinoline carboxylic acid, Tau-Fluvalinate, Metsulfuron methyl, Chlorimuron ethyl, Fenoxaprop-ethyl, Clopyralid, Lactofen, Fomesafen, Propiconazole, Deltamethrin, Cyfluthrin and the isomer beta-cyfluthrin, Imazamethabenz-methyl, Lambda-cyhalothrin and an isomer gamma-cyhalothrin, Thifensulfuron methyl, Tefluthrin, Quizalofop ethyl, Bifenthrin, Myclobutanil, Sulfur dioxide, Bensulfuron methyl, Clofentezine, Imazethapyr, Hexythiazox, Avermectin B1 and its delta-8,9-isomer, Beta-(4-Chlorophenoxy)-alpha-(1,1-dimethylethyl)-1H-1,2,4-triazole-1-ethanol, Tribenuron methyl, Primisulfuron-methyl, Nicosulfuron, Procymidone, Bitertanol, Clethodim, Triasulfuron, Benoxacor, Cadusafos, Pyridate, Quinclorac, Dimethenamid, 4-(Dichloroacetyl)-1-oxa-4-azaspiro[4.5]decane, Fenpropathrin, Carbon disulfide, Flumetsulam, Dichlormid, Acetochlor, Furilazole, Imidacloprid, Glufosinate ammonium, Tebuconazole, Difenoconazole, Triflumizole, Flumiclorac pentyl, Rimsulfuron, Halosulfuron-methyl, Fenbuconazole, Prosulfuron, Tebufenozide, Flutolanil, Cyproconazole, Chlorethoxyfos, Pyrithiobac sodium, Imazapic, Propylene oxide, Triflusulfuron-methyl, Dimethomorph, Pyridaben, Spinosad, Sulfentrazone, Propamocarb, Imazapyr, Hydroprene, Aminoethoxyvinylglycine hydrochloride (aviglycine HCl), Cymoxanil, Emamectin, Cyclanilide, Azoxystrobin, Mefenpyr-diethyl, Pyriproxyfen, Buprofezin, Chlorfenapyr, Cloransulam-methyl, Carfentrazone-ethyl, Fludioxonil, Fipronil, Pyrimethanil, Bromide ion and residual bromine, Fumigants for grain-mill machinery, Fumigants for processed grains used in production of fermented malt beverage, Metaldehyde, Resmethrin, Synthetic isoparaffinic petroleum hydrocarbons, Flufenacet, N-(4-fluorophenyl)-N-(1-methylethyl)-2-[[5-(trifluoromethyl)-1, 3, 4-thiadiazol-2-yl] oxy]acetamide and its metabolites containing the 4-fluoro-N-methylethyl benzenamine tolerances for residues, Cyprodinil, Esfenvalerate, Fluroxypyr 1-methylheptyl ester, Isoxaflutole, d-Limonene, Fenitrothion, Diclosulam, Methoxyfenozide, Prallethrin, Mefenoxam, Prohexadione calcium, Diflufenzopyr, Fluthiacet-methyl, Sulfosulfuron, Fenhexamid, Kresoxim-methyl, Trifloxystrobin, Pymetrozine, Tetraconazole, Clodinafop-propargyl, Cloquintocet-mexyl, Acibenzolar-S-methyl, Flucarbazone-sodium, Ethametsulfuron-methyl, Indoxacarb, Thiamethoxam, Fenpyroximate, Zoxamide, Flumioxazin, Forchlorfenuron, Isoxadifen-ethyl, Mesotrione, Bifenazate, Tepraloxydim, Fluazinam, Sulfuryl fluoride, Cyhalofop-butyl, Bispyribac-sodium, Acetamiprid, Fenamidone, Iodosulfuron-Methyl-Sodium, Iprovalicarb, Pyraclostrobin, Triticonazole, Tolylfluanid, Pyraflufen-ethyl, Clothianidin, Famoxadone, Quinoxyfen, Boscalid, 2, 6-Diisopropylnaphthalene (2, 6-DIPN), Trifloxysulfuron, Butafenacil, Etoxazole, Thiacloprid, Flufenpyr-ethyl, Fosthiazate, Mesosulfuron-methyl, Novaluron, Acequinocyl, Propoxycarbazone, Cyazofamid, Spiroxamine, Dinotefuran, Mepanipyrim, Penoxsulam, Spiromesifen, Spirodiclofen, Fluoxastrobin, Aminopyralid, Pinoxaden, Topramezone, Flonicamid, Kasugamycin, Amicarbazone, Fenpropimorph, Metconazole, Benthiavalicarb-isopropyl, Epoxiconazole, Etofenprox, Dithianon, Ethaboxam, Flufenoxuron, Metrafenone, Orthosulfamuron, Prothioconazole, Fluopicolide, Chlorantraniliprole, Flutriafol, Pyrasulfotole, Fenazaquin, Florasulam, Tembotrione, Spinetoram, 1,3-dichloropropene, Mandipropamid, Pyroxsulam, Flubendiamide, Pyridalyl, Spirotetramat, Uniconazole, Cyprosulfamide, Thiencarbazone-methyl, Ipconazole, d-Phenothrin, Meptyldinocap, Saflufenacil, Isoxaben, Imazosulfuron, Ethiprole, Indaziflam, Isopyrazam, Flazasulfuron, Amisulbrom, Metaflumizone, Penthiopyrad, Pyroxasulfone, Pyriofenone, Fluopyram, Trinexapac-ethyl, Ametoctradin, Penflufen, Sedaxane, Fluxapyroxad, Cyflufenamid, tolerance for residues, Sulfoxaflor, Picoxystrobin, Fenpyrazamine, Cyantraniliprole, Triforine, Proquinazid, Tolfenpyrad, Fenpropidin, Cyflumetofen, Tricyclazole, Flupyradifurone, Fluensulfone, Isofetamid, Bicyclopyrone, Benalaxyl-M, Oxathiapiprolin, Benzovindiflupyr, Teflubenzuron, Diethofencarb, Aminocyclopyrachlor, Mandestrobin, Halauxifen-methyl, Tioxazafen, Benzobicyclon, Cyclaniliprole, Tolpyralate, Flutianil, Chlormequat chloride, Pydiflumetofen, Afidopyropen, Pyrifluquinazon, Bixafen, 6-benzyladenine, Sulfometuron-methyl, Mefentrifluconazole, Valifenalate, Isotianil, Pethoxamid, and 1-Aminocyclopropane-1-carboxylic acid (ACC).

Metabolites may pertain to fermentation, fermentation pathway intermediates, and side products produced by a fermentation host. In some cases, the fermentation host is engineered. Exemplary metabolites include but are not limited to glutamine, citrate, threonine, serine, cysteine, citrulline, isoleucine, glutamate, glycine, methionine, 1-alanine, proline, shikimate, isocitrate, tyrosine, asparagine, valine, homoserine, diaminopimelate, aminoadipate, 3-dehydroshikimate, homocysteine, leucine, o-succinyl-homoserine, lysine, phosphoserine, cystathionine, arginine, s-adenosyl-methionine, dihydroxyacetone phosphate, phosphoenolpyruvate, o-acetylserine, carbamoyl phosphate, phosphoribosyl pyrophosphate, o-phosphoserine, s-adenosylhomocysteine, 1-ornithine, n-acetylglutamate, histidinol, histidine, d-ribose 5-phosphate, oxaloacetate, 2-oxobutanoate, 3-(4-hydroxyphenyl)pyruvate, oxoadipate, pyruvate, oxoglutarate, ketoleucine, and phenylpyruvate.

A sample 101 may further comprise one or more backgrounds or matrices. In some cases, the one or more matrices comprises a fermentation broth, a cell culture medium, a tissue culture medium, urine, fecal matter, blood, blood plasma, mucus, saliva, soil, or any combination thereof. In some cases, the one or more matrices is selected from the group consisting of a fermentation broth, a cell culture medium, a tissue culture medium, urine, fecal matter, blood, blood plasma, mucus, saliva, soil, or any combination thereof. In some cases, the one or more matrices comprises one or more salts. In some instances, the one or more salts comprise sodium ions, potassium ions, calcium ions, magnesium ions, ammonium cations, or any combination thereof. In some cases, the one or more salts comprise chloride, nitrate, sulfate, phosphate, formate, acetate, citrate anions, or any combination thereof. In some instances, the salt is sodium chloride. In some cases, the one or more matrices comprise one or more acids or bases. In some instances, the one or more matrices comprises hydrochloric acid, sulfuric acid, phosphoric acid, sodium hydroxide, potassium hydroxide, ammonium hydroxide, acetic acid, or any combination thereof. In some cases, the one or more matrices comprise a buffer. In some cases, the matrix comprises a citrate, phosphate, acetate buffer, or any combination thereof.

A sample 101 may be produced by a microbial community, such as a microbiome. In some cases, the microbiome samples are obtained from a human, an animal, a plant, a seed, a soil, an environment, or any combination thereof. In some instances, the microbiome sample is a sample of a gastrointestinal tract (e.g., stomach), skin, mammary glands, placenta, seminal fluid, uterus, ovarian follicles, lung, saliva, oral mucosa, conjunctiva, biliary tract, or any combination thereof. Methods of obtaining microbiome samples may be standard and/or known method to the skilled artisan.

A sample 101 may be produced by a fermentation process. In some cases, the fermentation process is an industrial fermentation for the production of an intended product. In some cases, the fermentation process produces one or more side products or by-products in addition to the intended product. In some cases, the presence or concentrations of the side products or by-products are used to determine the performance of the fermentation process. In some cases, the analytes in the fermentation broth are measured for the purpose of optimizing production parameters. In some instances, the analytes in the fermentation broth are measured for the purpose of fermentation strain engineering.

A sample 101 may be obtained from a human or animal subject. In some cases, the sample obtained from an animal or a human is for the purpose of evaluating the health or nutritional status of the animal or human. In some cases, the sample is a blood sample, a urine sample, a tissue sample, a tissue biopsy, or any combination thereof. In some cases, the sample is a clinical sample.

Methods may be employed to maintain the fidelity of the sample. A sample may be handled in a manner such that concentrations of the one or more metabolites in the sample are not significantly changed as a result of handling the sample. In some cases, the concentration of the one or more metabolites in the sample are changes by no more than 20%, 15%, 10%, 9%, 8%, 7%, 6%, 5%, 4%, 3%, 2%, 1%, 0.5%, 0.1%, 0.05%, or 0.01% as a result of handing of the sample. In some cases, handing comprises sterile handling, cold storage, light or dark storage, handling the sample under specific conditions, or any combination thereof. Methods of obtaining, preparing, storing, and shipping samples for analysis may be methods known to one of skill in the art.

Calibrators

A sample 101 may comprise one or more calibrators. In some cases, one or more calibrators are added to a sample comprising one or more analytes (e.g., metabolites) to produce a sample mixture. In some instances, the one or more analytes comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 300, 400, 500, 600, 700, 800, 900, 1000, 2000, 3000, 4000, or 5000 analytes. In some instances, about 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 calibrators are added to the sample. One or more calibrators may comprise, by way of non-limiting example, an alcohol, an amino acid, a nucleoside, a nucleotide, a nucleotide analogue, an antimetabolite, or any combination thereof. In some cases, the one or more calibrators comprise heavy calibrators comprising isotopically labeled species. In some cases, the one or more calibrators do not comprise any isotopologue of the one or more analytes. In some cases, the concentration of the one or more calibrators is known. In some cases, the concentration of the one or more analytes (e.g., metabolites) is unknown.

Examples of calibrators may comprise, but are not limited to, 1,4-Butanediamine (putrescine)·2HCl (13C4, 99%), L-Alanine (13C3, 99%; 15N, 99%), Ethanolamine HCl (1,1,2,2-D4, 98%), Sodium pyruvate (13C3, 99%), Creatinine (N-methyl-D3, 98%), Fumaric acid (13C4, 99%), Vitamin B3 (nicotinamide) (13C6, 99%), Thymine (1,3-15N2, 98%), L-Leucine (13C6, 99%), Hypoxanthine (13C5, 99%), L-Phenylalanine (ring-13C6, 99%), Indole-3-acetic acid (phenyl-13C6, 99%), L-Tyrosine (ring-13C6, 99%), a-Ketoglutaric acid, disodium salt (1,2,3,4-13C4, 99%) CP 97%, Citric acid (1,5,6-carboxyl-13C3, 99%), L-Tryptophan (13C11, 99%), Guanosine·2H2O (15N5, 96-98%), and Sodium palmitate (U-13C16, 98%).

In some cases, the one or more calibrators have a molecular weight of about 10 to 10,000 g/mol. In some cases, the one or more calibrators have a molecular weight of about 10 g/mol to about 50 g/mol, about 10 g/mol to about 100 g/mol, about 10 g/mol to about 500 g/mol, about 10 g/mol to about 1,000 g/mol, about 10 g/mol to about 5,000 g/mol, about 10 g/mol to about 10,000 g/mol, about 50 g/mol to about 100 g/mol, about 50 g/mol to about 500 g/mol, about 50 g/mol to about 1,000 g/mol, about 50 g/mol to about 5,000 g/mol, about 50 g/mol to about 10,000 g/mol, about 100 g/mol to about 500 g/mol, about 100 g/mol to about 1,000 g/mol, about 100 g/mol to about 5,000 g/mol, about 100 g/mol to about 10,000 g/mol, about 500 g/mol to about 1,000 g/mol, about 500 g/mol to about 5,000 g/mol, about 500 g/mol to about 10,000 g/mol, about 1,000 g/mol to about 5,000 g/mol, about 1,000 g/mol to about 10,000 g/mol, or about 5,000 g/mol to about 10,000 g/mol. In some cases, the one or more calibrators have a molecular weight of about 10 g/mol, about 18 g/mol, about 50 g/mol, about 100 g/mol, about 500 g/mol, about 1,000 g/mol, about 5,000 g/mol, or about 10,000 g/mol. In some cases, the one or more calibrators have a molecular weight of at least about 10 g/mol, about 18 g/mol, about 50 g/mol, about 100 g/mol, about 500 g/mol, about 1,000 g/mol, or about 5,000 g/mol. In some cases, the one or more calibrators have a molecular weight of at most about 18 g/mol, about 50 g/mol, about 100 g/mol, about 500 g/mol, about 1,000 g/mol, about 5,000 g/mol, or about 10,000 g/mol. In some cases, the one or more calibrators have a permanently charged moiety. In some cases, the one or more calibrators have at least one acidic proton with a pKa of <18 at 25° C. in water.

In some cases, the one or more calibrators is soluble in water and in 50% aqueous acetonitrile to at least 10 µM (e.g., 50 µM, 100 µM, 500 µM, or 1 mM) at 25° C. In some cases, each of the one or more calibrators is a compound having a molecular weight of 10 to 10,000 g/mol (e.g., 18 to 2500 g/mol, 50 to 2000 g/mol, or 50 to 1000 g/mol). In some cases, one or more calibrators is isotopically enriched at least for one atomic position (e.g., at least one C, N, or O) in the calibrator. In some cases, one or more of the calibrators is halogenated.

The one or more calibrators may be selected from a calibrator library. In some cases, the calibrator library comprises about 100 to about 10,000 calibrators. In some cases, the calibrator library comprises about 100 to about 500, about 100 to about 1,000, about 100 to about 5,000, about 100 to about 10,000, about 500 to about 1,000, about 500 to about 5,000, about 500 to about 10,000, about 1,000 to about 5,000, about 1,000 to about 10,000, or about 5,000 to about 10,000 calibrators. In some cases, the calibrator library comprises about 100, about 500, about 1,000, about 5,000, or about 10,000 calibrators. In some cases, the calibrator library comprises at least about 100, about 500, about 1,000, or about 5,000 calibrators. In some cases, the calibrator library comprises at most about 500, about 1,000, about 5,000, or about 10,000 calibrators.

Selection of Calibrators

The one or more calibrators may be selected based on convenience. For example, the one or more calibrators may be selected based on cost, stability, supply chain, etc. In some cases, the one or more calibrators cover a chemical space. A chemical space may generally represent species, compounds, or molecules that share one or more physical, chemical, analytical, structural, or biological properties, such as, but not limited to, those described herein. In some cases, the one or more calibrators do not comprise heavy calibrators for each of the one or more analytes.

The sample may be analyzed using chromatography. In some cases, the chromatography comprises gas chromatography (GC) or liquid chromatography (LC). As shown in FIG. 1, a sample 101 is analyzed using an LC machine 102. Chromatography generally comprises a laboratory technique for the separation of a mixture into its components. A mixture can be dissolves into a mobile phase, which can be carried through a system, such as a column, comprising a fixed stationary phase. The components within the mobile phase may have different affinities to the stationary phase, resulting in different retention times depending on these affinities. As a result, separation of components in the mixture is achieved.

Figure 11:
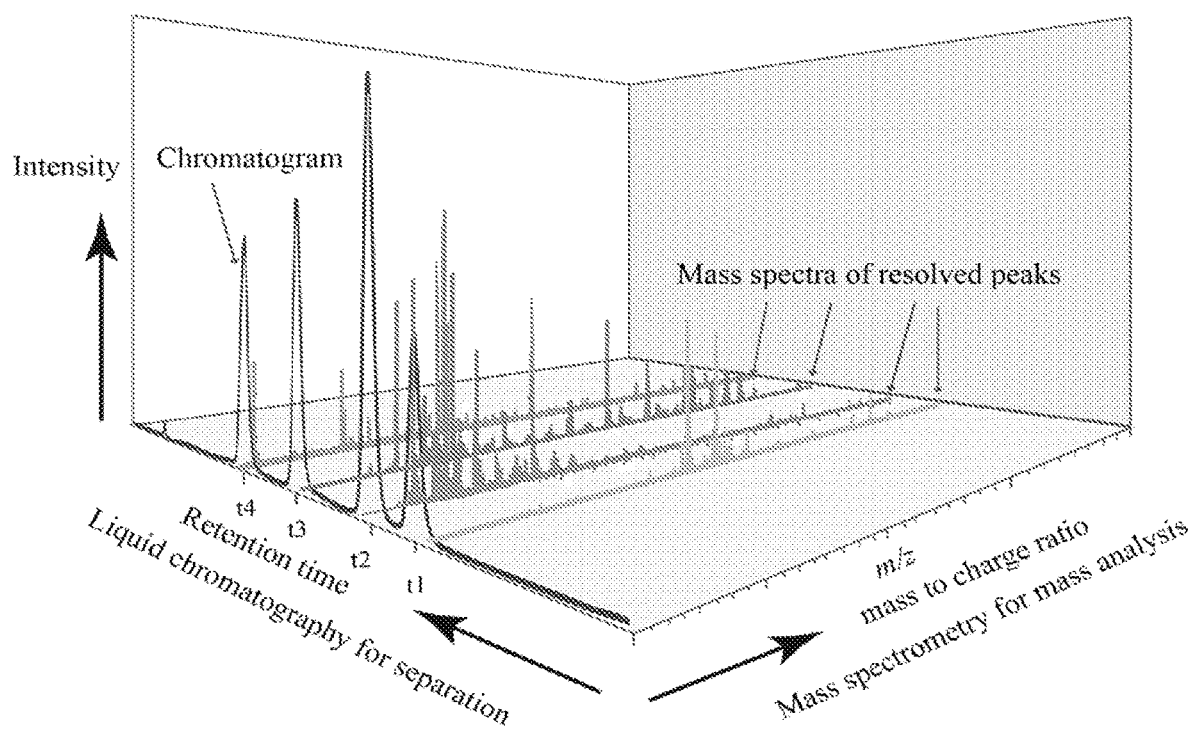
FIG. 11 schematically illustrates a readout and signals obtained from LC-MS in accordance with embodiments described herein.

The separated components from chromatography may be analyzed using mass spectrometry (MS). The combined analysis of MS with chromatography may be referred to as gas chromatography-mass spectrometry (GC-MS) or liquid-chromatography-mass spectrometry (LC-MS). As such, as shown in FIG. 1, the LC output from the LC machine 102 may be passed to a MS machine 103. MS analysis generally refers to measuring the mass-to-charge ratio of ions (e.g., m/z), resulting in a mass spectrum. The mass spectrum comprises a plot of intensity as a function of mass-to-charge ratio. The mass spectrum may be used to determine elemental or isotopic signatures in a sample, as well as the masses of the components (e.g., particles or molecules) in the mixture. This may be used to determine a chemical identity or structure of the components in the mixture. An exemplary read out or signal from an LC-MS is shown in FIG. 11. As shown, the retention time from LC and mass-to-charge ratio from MS are plotted against intensity values. The resulting readouts comprise a chromatograph as we as resolved peaks from the mass spectra obtained.

In some cases, one or more acquisition parameters is programmed in the MS machine 103. In some instances, the one or more acquisition parameters comprises, for example, the one or more mass acquisition windows, one or more acquisition times for the one or more mass acquisition windows, one or more resolutions for the one or more mass acquisition windows, one or more gain settings for the one or more acquisition windows, one or more ionization polarity settings for the one or more mass acquisition windows, one or more mass resolutions for the one or more mass acquisition windows, or any combination thereof. In some cases, the MS machine 103 comprises a high-resolution mass spectrometer. In some instances, the high-resolution mass spectrometer has a mass accuracy is less than or equal to 75 ppm, less than or equal to 30 ppm, less than or equal to 15 ppm, less than or equal to 10 ppm, or less than or equal to 5 ppm.

An exemplary protocol for derivatization of polar metabolites is provided. The protocol comprises formation of methoxime-tBDMS derivatives through incubation of the metabolites with 2% methoxylamine hydrochloride in pyridine followed by addition of N-tert-butyldimethylsilyl-N-methyltrifluoroacetamide (MTBSTFA) with 1% tert-butyldimethylchlorosilane (t-BDMCS). Non-polar fractions, including triacylglycerides and phospholipids, may be saponified to free fatty acids and esterified to form fatty acid methyl esters, for example, either by incubation with 2% $H_2SO_4$ in methanol or by using Methyl-8 reagent (Thermo Scientific). Derivatized samples may then be analyzed by GC-MS using standard GC-MS methods, for example, a DB-35MS column (30 m×0.25 mm i.d.×0.25 μm, Agilent J&W Scientific) installed on a gas chromatograph (GC) interfaced with a mass spectrometer (MS). Mass isotopomer distributions may be determined by integrating metabolite ion fragments and corrected for natural abundance using standard algorithms. In the case of liquid chromatography-mass spectrometry (LC-MS), polar metabolites may be analyzed using a standard benchtop LC-MS/MS equipped with a column, such as a SeQuant ZIC-Philic polymeric column (2.1×150 mm; EMD Millipore). Exemplary mobile phases used for separation could include buffers and organic solvents adjusted to a specific pH value.

The output signal from the MS machine 103 can comprise an intensity value, a mass-to-charge ratio, or a combination thereof. In some cases, the output signal from the MS comprises raw, unprocessed MS data. In some cases, the output signal comprises a first signal indicating an intensity value or a mass-to-charge ratio of one or more analytes. In some cases, the output signal comprises a second signal indicating an intensity value or a mass-to-charge ratio of one or more calibrators. In some cases, the output signal comprises the first signal and the second signal. In some instances, the output signal comprises the peak signal intensity obtained for an exact isotopic mass for each of the one or more analytes or one or more calibrators of known molecular weight. In some instances, the output signal comprises combined signals corresponding to one or more mass adducts for the one or more analytes. In some examples, the output signal for the one or more analytes is obtained by calculating the sum of the adduct signals for 1, 2, 3, 4, 5, 6, 7, 8, 9 or 10 analyte adducts. In some cases, the analyte adducts correspond to the proton, sodium, potassium, calcium, magnesium, ammonium, nitrate, sulfate, phosphate, acetate, citrate, or formate adducts. In one embodiment, the molecular weight of the adduct is calculated by subtracting or adding the mass of a proton and adding the mass of the corresponding adduct species.

In some cases, the LC-MS method provided herein is optimized for performance on a subset of cellular analytes. In some instances, the subset of cellular analytes are critical to bioprocessing. In some cases, the LC-MS method provided herein ionizes in both positive and negative modes. In some cases, the LC-MS method provided herein ionize analytes as molecular ions. In some cases, a single LC-MS method provided herein can be used to quantify a plurality of analytes, without a need to optimize chromatographic resolution.

The output signal from the MS machine 103 (e.g., mass spectrum, intensity value, mass-to-charge ratio, etc.) may be processed by a signal processing module 104. The input to the signal processing module 104 can comprise an input signal comprising an intensity value, a mass-to-charge ratio, or a combination thereof from the MS machine 103. In some cases, the input signal comprises a first signal indicating an intensity value or a mass-to-charge ratio of one or more analytes. In some cases, the input signal comprises a second signal indicating an intensity value or a mass-to-charge ratio of one or more calibrators. In some cases, the input signal comprises the first signal and the second signal from the MS machine 103. In some cases, the one or more calibrators produce a signal that does not overlap with a signal of the one or more analytes.

In some cases, the input to the signal processing module 104 comprises raw or unprocessed MS data. In some cases, the input comprises preprocessed MS data. Preprocessing MS data may comprise data cleaning, data transformation, data reduction, or any combination thereof. In some cases, data cleaning comprises cleaning missing data (e.g., fill in or ignore missing values), noisy data (e.g., binning, regression, clustering, etc.), or a combination thereof. In some cases, data transformation comprises standardization, normalization, attribute selection, discretization, hierarchy generation, or any combination thereof. In some cases, data reduction comprises data aggregation, attribute subset selection, numerosity reduction, dimensionality reduction, or any combination thereof. In some cases, the MS data is preprocessed prior to the signal processing module 104. In some cases, the MS data is preprocessed in the signal processing module 104.

In some cases, the signal processing module 104 comprises a machine learning model. In some instances, the machine learning model is a trained machine learning model. In some instances, the trained machine learning model determines an absolute concentration 105 of the one or more analytes based on the output signal from the MS machine 103. In some cases, the trained machine learning model is configured to determine the absolute concentration 105 of the one or more analytes based on a relationship or a correlation between the first signal and a known concentration of the one or more calibrators. In some instances, the trained machine learning model is configured to determine the absolute concentration 105 based on a relationship or a correlation between the first signal and the second signal. In some instances, the absolute concentration 105 of the one or more analytes is determined based on the known concentration of the one or more calibrators. In some examples, the absolute concentration comprises a molar concentration or a mass concentration. In some examples, the absolute concentration is determined based at least in part on a relationship or correlation between the MS signal of the one or more calibrators and the MS signal of the one or more analytes.

A method for sample processing to determine a concentration of an analyte can further comprise providing a sample mixture. The sample mixture can comprise one or more analytes and one or more calibrators, such as those described herein. In some cases, the concentration of the one or more calibrators is known. In some cases, the concentration of the one or more analytes is unknown. In some cases, the absolute concentration of the one or more analytes is determined based on the known concentration of the one or more calibrators.

Figure 2:
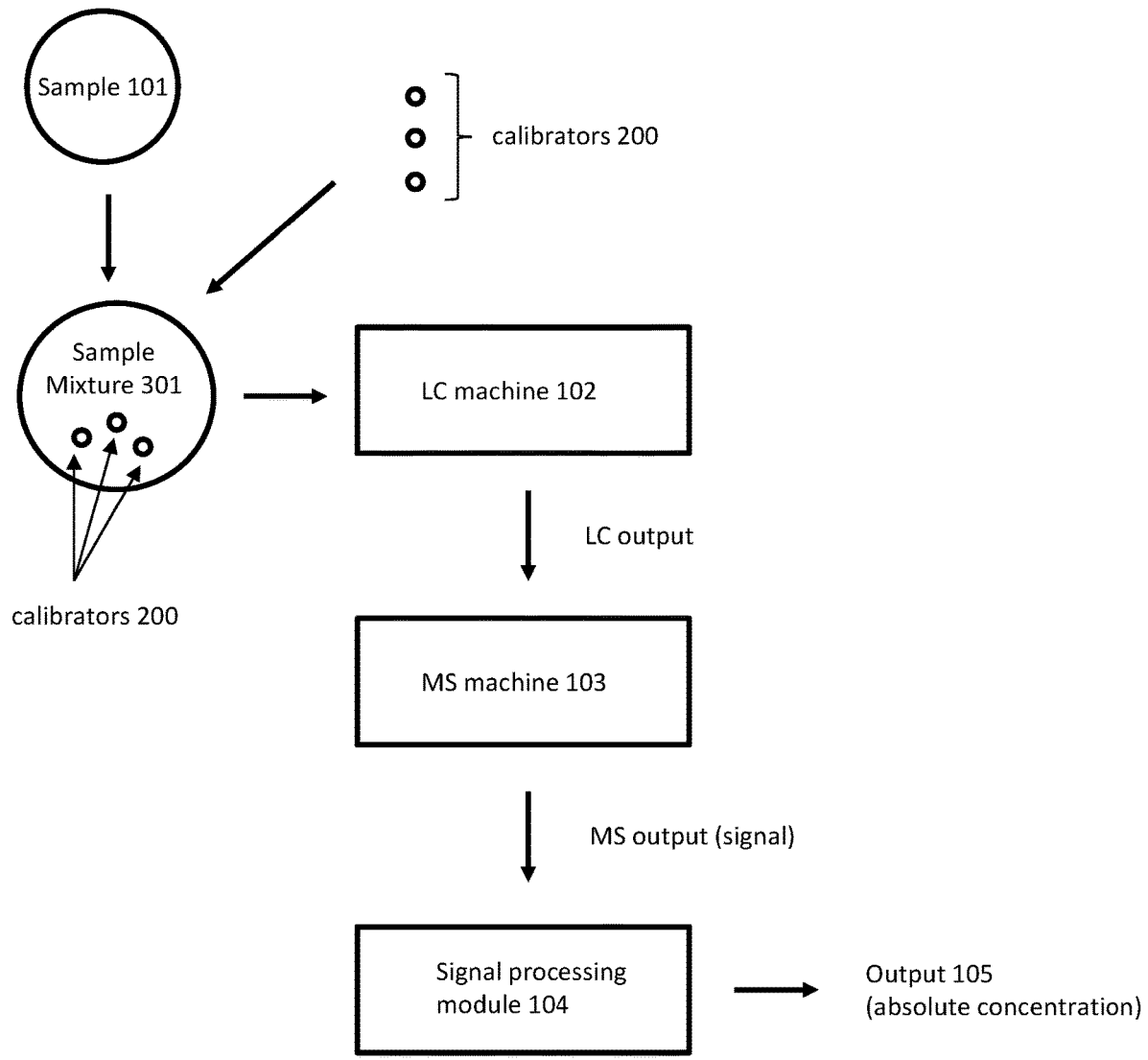
FIG. 2 schematically illustrates a method for sample processing with calibrators added before liquid chromatography (LC) in accordance with embodiments described herein.

In some cases, the one or more calibrators are added to the sample before the one or more analytes of the sample are processed using liquid chromatography (LC). This process is schematically illustrated in FIG. 2. As shown, the sample 101 and the calibrators 200 are combined in a sample mixture 301. The sample 101 comprises one or more analytes, as previously described herein. The one or more analytes and the calibrators 200 can comprise those previously described herein. The sample mixture 301 is then processed in the LC machine 102, followed by the MS machine 103, and finally the signal processing module 104 to output an absolute final concentration 105, as previously described herein.

Figure 3:
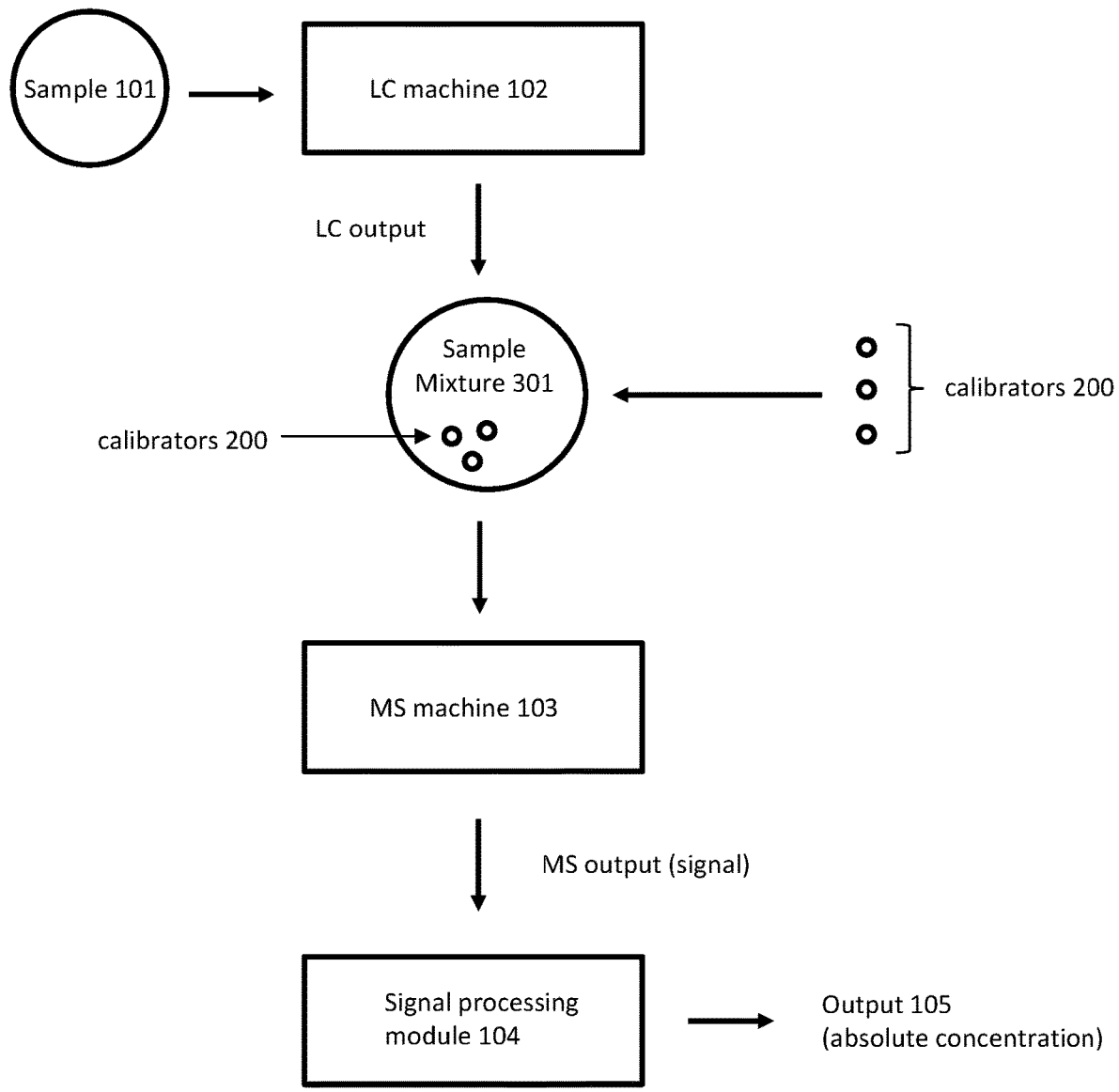
FIG. 3 schematically illustrates a method for sample processing with calibrators added after LC in accordance with embodiments described herein.

In some cases, the one or more calibrators are added to the sample after the one or more analytes of the sample are processed using liquid chromatography (LC). This process is schematically illustrated in FIG. 3. As shown, the sample 101 is first processed in the LC machine 102. The output from the LC machine and the calibrators 200 are combined in a sample mixture 301. The sample 101 comprises one or more analytes, as previously described herein. The one or more analytes and the calibrators 200 can comprise those previously described herein. The sample mixture 301 can then be processed by the MS machine 103, followed by the signal processing module 104 to output an absolute final concentration 105, as previously described herein.

Figure 4:
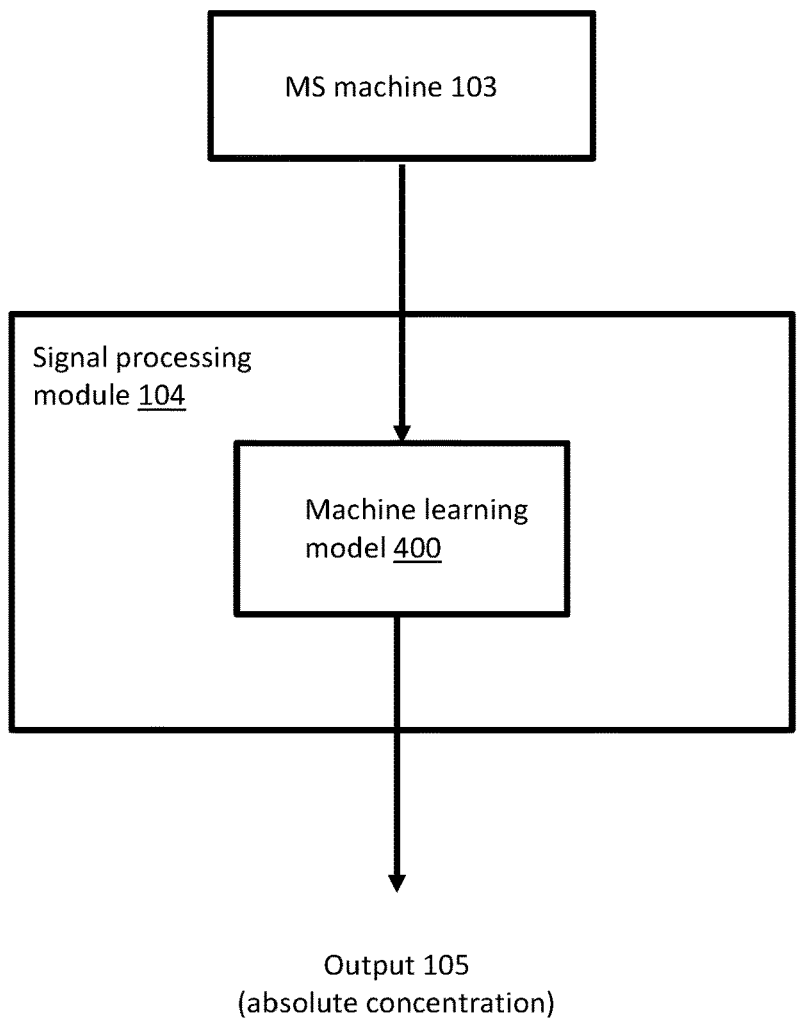
FIG. 4 schematically illustrates a signal processing module in accordance with embodiments described herein.

Referring to FIG. 4, the one or more analytes can be determined by generating a MS output for the sample mixture from a MS machine 103. In some cases, the MS output comprises (1) a first MS signal for the one or more analytes and (2) a second MS signal for the one or more calibrators. The MS signal can comprise raw, unprocessed data or processed data, as described herein. The MS signal can comprise a mass spectrum, an intensity value, a mass-to-charge ratio, or any combination thereof, as described herein.

The MS output can be processed by the signal processing module 104. The signal processing module 104 can comprise a machine learning model 400. The machine learning model may be a trained machine learning algorithm. The trained machine learning model may be used to determine an absolute concentration 105. In some cases, the trained machine learning model is used to determine an absolute concentration of the one or more analytes, based at least in part on a relationship or correlation between the first MS signal and the second MS signal. In some cases, the trained machine learning model is configured to determine the absolute concentration of the one or more analytes based on a relationship or a correlation between the first MS signal and a known concentration of the one or more calibrators.

The machine learning model can be trained on MS data. In some cases, the machine learning model is trained with one or more calibrators. The one or more calibrators may be referred to as candles. In some instances, the one or more calibrators are reference calibrators. In some cases, the machine learning model is trained with one or more reference analytes. In some instances, the concentration of the reference calibrators and reference analytes are known. In some cases, the machine learning model is trained using a data set comprising (i) a first set of intensity values for one or more reference analytes having a known concentration and (ii) a second set of intensity values for one or more reference calibrators having a known concentration.

In some cases, the reference analytes and the one or more analytes in the sample mixture comprise a same analyte or a same type or class of analyte. In some cases, the reference calibrators and the one or more calibrators in the sample mixture comprise a same calibrator or a same type or class of calibrator. The same type or class of analyte or calibrator can comprise the molecules that share one or more structural, physical, chemical, analytical, or biological properties. Structural properties can comprise, by way of non-limiting example, bonding angles, types of bonds, size of the molecules (e.g., mass), interactions between molecules, etc. Physical properties can comprise, by way of non-limiting example, boiling points, melting points, density, volume, mass, refractive indices, etc. Chemical properties can comprise, by way of non-limiting example, polarity, solubility, toxicity, pH value, stability, heat or combustion, flammability, oxidation states, solvent effects, free-radical polymerization, critical micelle concentrations, etc. Biological properties can comprise toxicity, biocompatibility, bioactivity, biodegradability, bioresobability, or any variation thereof. Analytical properties may comprise ionization modes or typical adducts formed.

The machine learning model may learn based on one or more features. In some cases, the number of features in a machine learning model is optimized. The machine learning model can be trained on MS data. In some cases, the machine learning model is trained with one or more calibrators. The one or more calibrators may be referred to as candles. In some instances, the one or more calibrators are reference calibrators. In some cases, the machine learning model is trained with one or more reference analytes. In some instances, the concentration of the reference calibrators and references analytes are known. In some cases, the machine learning model is trained using a data set comprising (i) a first set of intensity values for one or more reference analytes having a known concentration and (ii) a second set of intensity values for one or more reference calibrators having a known concentration.

In some cases, the one or more features of the machine learning model corresponds to signals obtained for one or more calibrators using one or more instrument acquisition parameters. In some cases, the one or more features of the machine learning model corresponds to information about the sample composition. In some cases, the one or more features of the machine learning model corresponds to the sample matrix. In some cases, the one or more features of the machine learning model corresponds to the concentrations of one or more salts in the sample. In some cases, the one or more features of the machine learning model corresponds to the source of the sample (e.g., fermentation medium, blood sample, plasma sample, urine sample, food sample). In some cases, the quality of machine learning models is measured by a fit statistic. In some cases, the fit statistic is R-squared. In some cases, the machine learning model is trained using a data set comprising impurities, such as 1%, 2%, 3%, 4%, 5%, 6%, 7%, 8%, 9%, 10%, 15%, or 20% impurities by mass.

In some cases, the machine learning model maps multiple factors affecting ionization. In some cases, the machine learning model enables instantaneous and/or accurate determination of an absolute concentration of one or more analytes. In some instances, the machine learning model is trained on the one or more analytes (e.g., trained analytes).

In some cases, the machine learning models enables scalability in metabolomics. In some cases, the machine learning model (e.g., deep learning) is scalable for new analytes and matrices. In some cases, the machine learning model (e.g., deep learning) provides absolute quantification.

In some cases, the control and calibration strategy (e.g., use of calibrators) allows for comparison between different runs. A run may generally refer to analyzing and processing one or more analytes using LC-MS and a signal processing module comprising a machine learning method, as described herein.

A machine learning model can comprise a supervised, semi-supervised, unsupervised, or self-supervised machine learning model. In some cases, the one or more ML approaches perform classification or clustering of the MS data. In some examples, the machine learning approach comprises a classical machine learning method, such as, but not limited to, support vector machine (SVM) (e.g., one-class SVM, linear or radial kernels, etc.), K-nearest neighbor (KNN), isolation forest, random forest, logistic regression, AdaBoost classifier, extra trees classifier, extreme gradient boosting, gaussian process classifier, gradient boosting classifier, light gradient boosting, linear discriminant analysis, naïve Bayes, quadratic discriminant analysis, ridge classifier, or any combination thereof. In some examples, the machine learning approach comprises a deep leaning method (e.g., deep neural network (DNN)), such as, but not limited to a fully-connected network, convolutional neural network (CNN) (e.g., one-class CNN), recurrent neural network (RNN), transformer, graph neural network (GNN), convolutional graph neural network (CGNN), multi-level perceptron (MLP), or any combination thereof.

In some embodiments, a classical ML method comprises one or more algorithms that learns from existing observations (i.e., known features) to predict outputs. In some embodiments, the one or more algorithms perform clustering of data. In some examples, the classical ML algorithms for clustering comprise K-means clustering, mean-shift clustering, density-based spatial clustering of applications with noise (DBSCAN), expectation-maximization (EM) clustering (e.g., using Gaussian mixture models (GMM)), agglomerative hierarchical clustering, or any combination thereof. In some embodiments, the one or more algorithms perform classification of data. In some examples, the classical ML algorithms for classification comprise logistic regression, naïve Bayes, KNN, random forest, isolation forest, decision trees, gradient boosting, support vector machine (SVM), or any combination thereof. In some examples, the SVM comprises a one-class SMV or a multi-class SVM.

Figure 5:
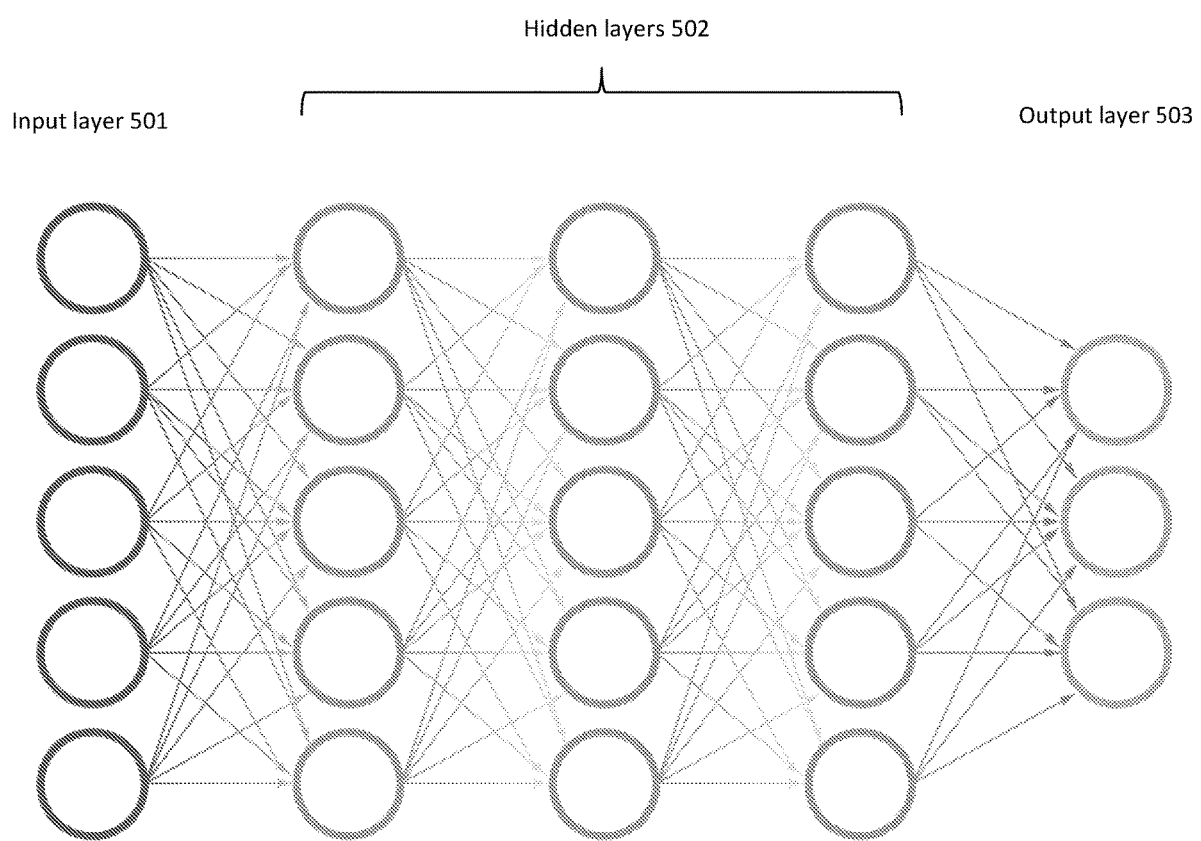
FIG. 5 schematically illustrates a deep neural network for signal processing in accordance with embodiments described herein.

In some embodiments, the deep learning method comprises one or more algorithms that learns by extracting new features to predict outputs. In some embodiments, the deep learning method comprises one or more layers, as illustrated in FIG. 5. In some embodiments, the deep learning method comprises a neural network (e.g., DNN comprising more than one layer). Neural networks generally comprise connected nodes in a network, which can perform functions, such as transforming or translating input data. In some embodiments, the output from a given node is passed on as input to another node. The nodes in the network generally comprise input units in an input layer 501, hidden units in one or more hidden layers 502, output units in an output layer 503, or a combination thereof. In some embodiments, an input node is connected to one or more hidden units. In some embodiments, one or more hidden units is connected to an output unit. The nodes can generally take in input through the input units and generate an output from the output units using an activation function. In some embodiments, the input or output comprises a tensor, a matrix, a vector, an array, or a scalar. In some embodiments, the activation function is a Rectified Linear Unit (ReLU) activation function, a sigmoid activation function, a hyperbolic tangent activation function, or a Softmax activation function.

The connections between nodes further comprise weights for adjusting input data to a given node (i.e., to activate input data or deactivate input data). In some embodiments, the weights are learned by the neural network. In some embodiments, the neural network is trained to learn weights using gradient-based optimizations. In some embodiments, the gradient-based optimization comprises one or more loss functions. In some embodiments, the gradient-based optimization is gradient descent, conjugate gradient descent, stochastic gradient descent, or any variation thereof (e.g., adaptive moment estimation (Adam)). In some further embodiments, the gradient in the gradient-based optimization is computed using backpropagation. In some embodiments, the nodes are organized into graphs to generate a network (e.g., graph neural networks). In some embodiments, the nodes are organized into one or more layers to generate a network (e.g., feed forward neural networks, convolutional neural networks (CNNs), recurrent neural networks (RNNs), etc.). In some embodiments, the CNN comprises a one-class CNN or a multi-class CNN.

In some embodiments, the neural network comprises one or more recurrent layers. In some embodiments, the one or more recurrent layers are one or more long short-term memory (LSTM) layers or gated recurrent units (GRUs). In some embodiments, the one or more recurrent layers perform sequential data classification and clustering in which the data ordering is considered (e.g., time series data). In such embodiments, future predictions are made by the one or more recurrent layers according to the sequence of past events. In some embodiments, the recurrent layer retains or "remembers" important information, while selectively "forgets" what is not essential to the classification.

In some embodiments, the neural network comprise one or more convolutional layers. In some embodiments, the input and the output are a tensor representing variables or attributes in a data set (e.g., features), which may be referred to as a feature map (or activation map). In such embodiments, the one or more convolutional layers are referred to as a feature extraction phase. In some embodiments, the convolutions are one dimensional (1D) convolutions, two dimensional (2D) convolutions, three dimensional (3D) convolutions, or any combination thereof. In further embodiments, the convolutions are 1D transpose convolutions, 2D transpose convolutions, 3D transpose convolutions, or any combination thereof.

The layers in a neural network can further comprise one or more pooling layers before or after a convolutional layer. In some embodiments, the one or more pooling layers reduces the dimensionality of a feature map using filters that summarize regions of a matrix. In some embodiments, this down samples the number of outputs, and thus reduces the parameters and computational resources needed for the neural network. In some embodiments, the one or more pooling layers comprises max pooling, min pooling, average pooling, global pooling, norm pooling, or a combination thereof. In some embodiments, max pooling reduces the dimensionality of the data by taking only the maximums values in the region of the matrix. In some embodiments, this helps capture the most significant one or more features. In some embodiments, the one or more pooling layers is one dimensional (1D), two dimensional (2D), three dimensional (3D), or any combination thereof.

The neural network can further comprise of one or more flattening layers, which can flatten the input to be passed on to the next layer. In some embodiments, a input (e.g., feature map) is flattened by reducing the input to a one-dimensional array. In some embodiments, the flattened inputs can be used to output a classification of an object. In some embodiments, the classification comprises a binary classification or multi-class classification of visual data (e.g., images, videos, etc.) or non-visual data (e.g., measurements, audio, text, etc.). In some embodiments, the classification comprises binary classification of an image (e.g., cat or dog). In some embodiments, the classification comprises multi-class classification of a text (e.g., identifying hand-written digits)). In some embodiments, the classification comprises binary classification of a measurement. In some examples, the binary classification of a measurement comprises a classification of a system's performance using the physical measurements described herein (e.g., normal or abnormal, normal or anormal).

The neural networks can further comprise of one or more dropout layers. In some embodiments, the dropout layers are used during training of the neural network (e.g., to perform binary or multi-class classifications). In some embodiments, the one or more dropout layers randomly set some weights as 0 (e.g., about 10%, 20%, 30%, 40%, 50%, 60%, 70%, 80% of weights). In some embodiments, the setting some weights as 0 also sets the corresponding elements in the feature map as 0. In some embodiments, the one or more dropout layers can be used to avoid the neural network from overfitting.

The neural network can further comprise one or more dense layers, which comprises a fully connected network. In some embodiments, information is passed through a fully connected network to generate a predicted classification of an object. In some embodiments, the error associated with the predicted classification of the object is also calculated. In some embodiments, the error is backpropagated to improve the prediction. In some embodiments, the one or more dense layers comprises a Softmax activation function. In some embodiments, the Softmax activation function converts a vector of numbers to a vector of probabilities. In some embodiments, these probabilities are subsequently used in classifications, such as classifications of a type or class of a molecule (e.g., calibrator or analyte) as described herein.

Figure 6:
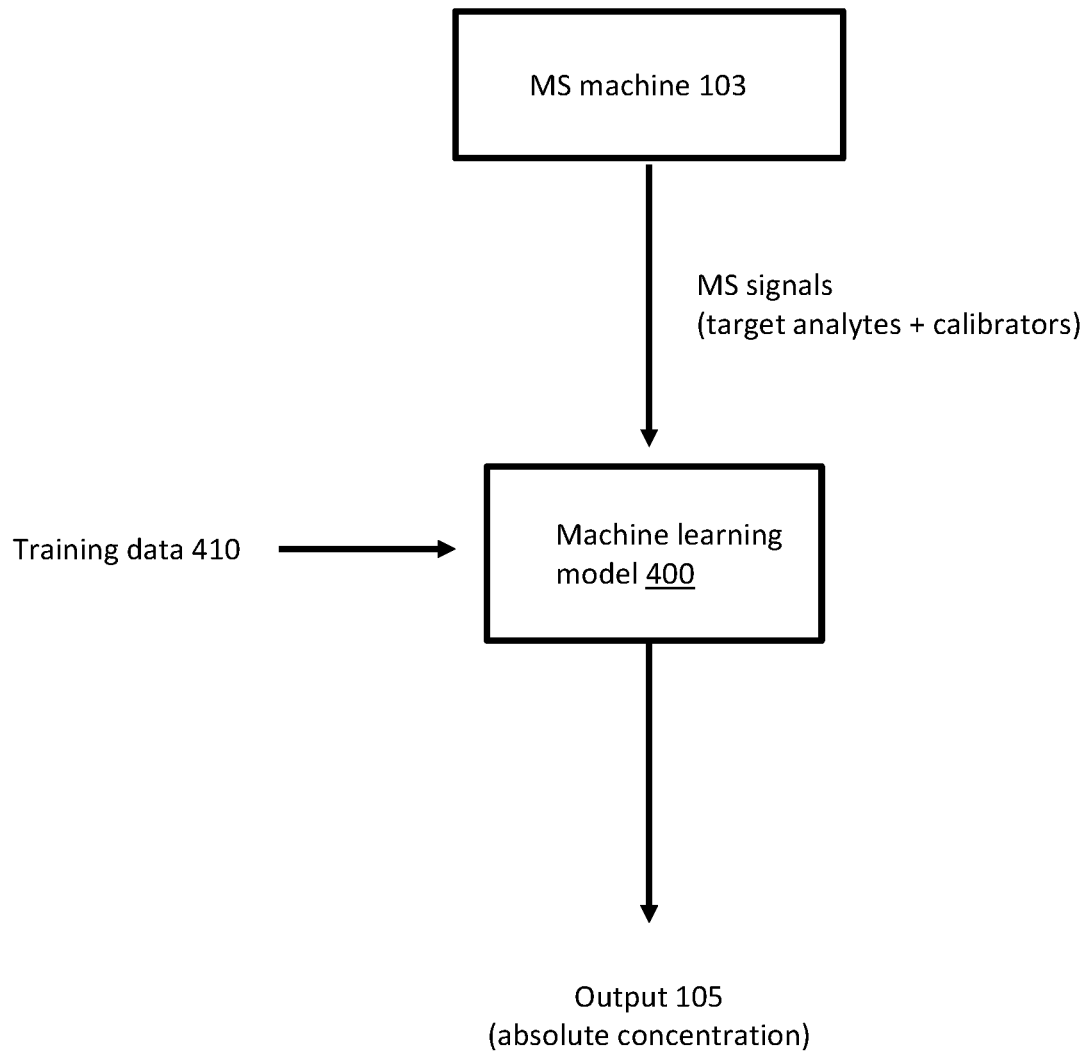
FIG. 6 schematically illustrates a machine learning (ML) training scheme in accordance with embodiments described herein.

The machine learning model, such as those described herein, are trained using training data, as illustrated in FIG. 6. As shown, the machine learning model 400 may be configured to determine an output 105 comprising an absolute concentration. The machine learning model 400 may be configured to determine an output 105 based on MS signals from the MS machine 103. The MS signals may comprise target analytes, calibrators, or a combination thereof.

The machine learning model 400 may be trained using training data 410. In some cases, the training of the machine learning model 400 is supervised. In some cases, the training of the machine learning model 400 is semi-supervised. In some cases, the training of the machine learning model 400 is unsupervised. In some cases, the training of the machine learning model 400 is self-supervised. In some cases, the machine learning model is trained using automated hyperparameter tuning. In some cases, at least one hyperparameter used for the automated hyperparameter tuning is accuracy, precision, coefficient of determination, or dynamic range. In some cases, at least one hyperparameter used for the automated hyperparameter tuning.

Figure 12:
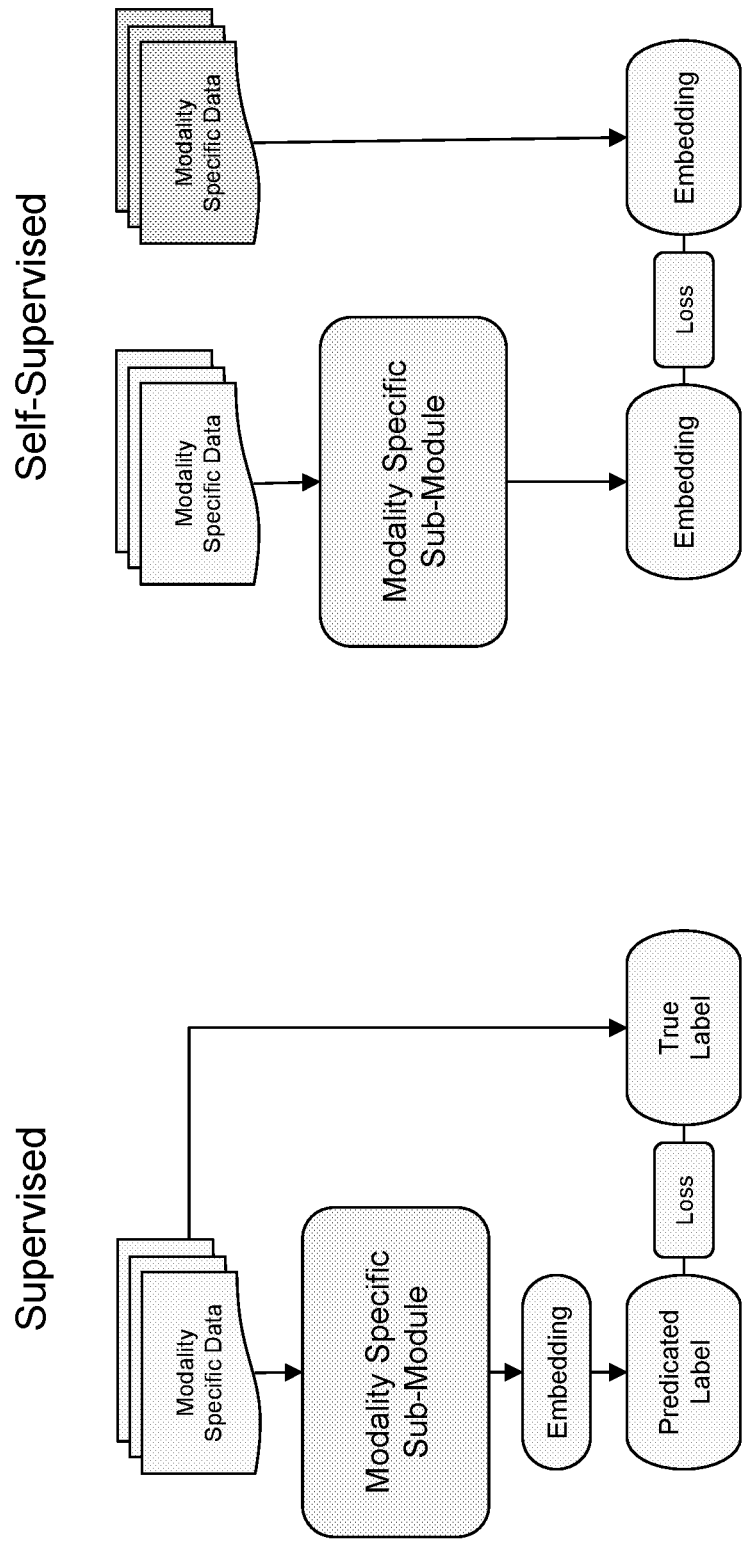
FIG. 12 schematically illustrates individual sub-models that can be trained in accordance with embodiments described herein.

The machine learning model can comprise one or more sub-models. In some cases, the one or more sub-models are trained individually. Individual sub-models and their training are schematically illustrated in FIG. 12. While multi-modality networks are extremely powerful, they typically require that training samples have all the associated modality data during training. In some cases, with scientific data this is not the case. The models described herein can comprise modularity by design, allowing flexibility by training individual modules based on available data. Depending on the module, this can allow for utilizing both in-house and external data. This can comprise both supervised and a variety of self-supervised training regimes. Modules can then be used as part of the foundation model or individually as part of another task specific dataset model.

Figure 13:
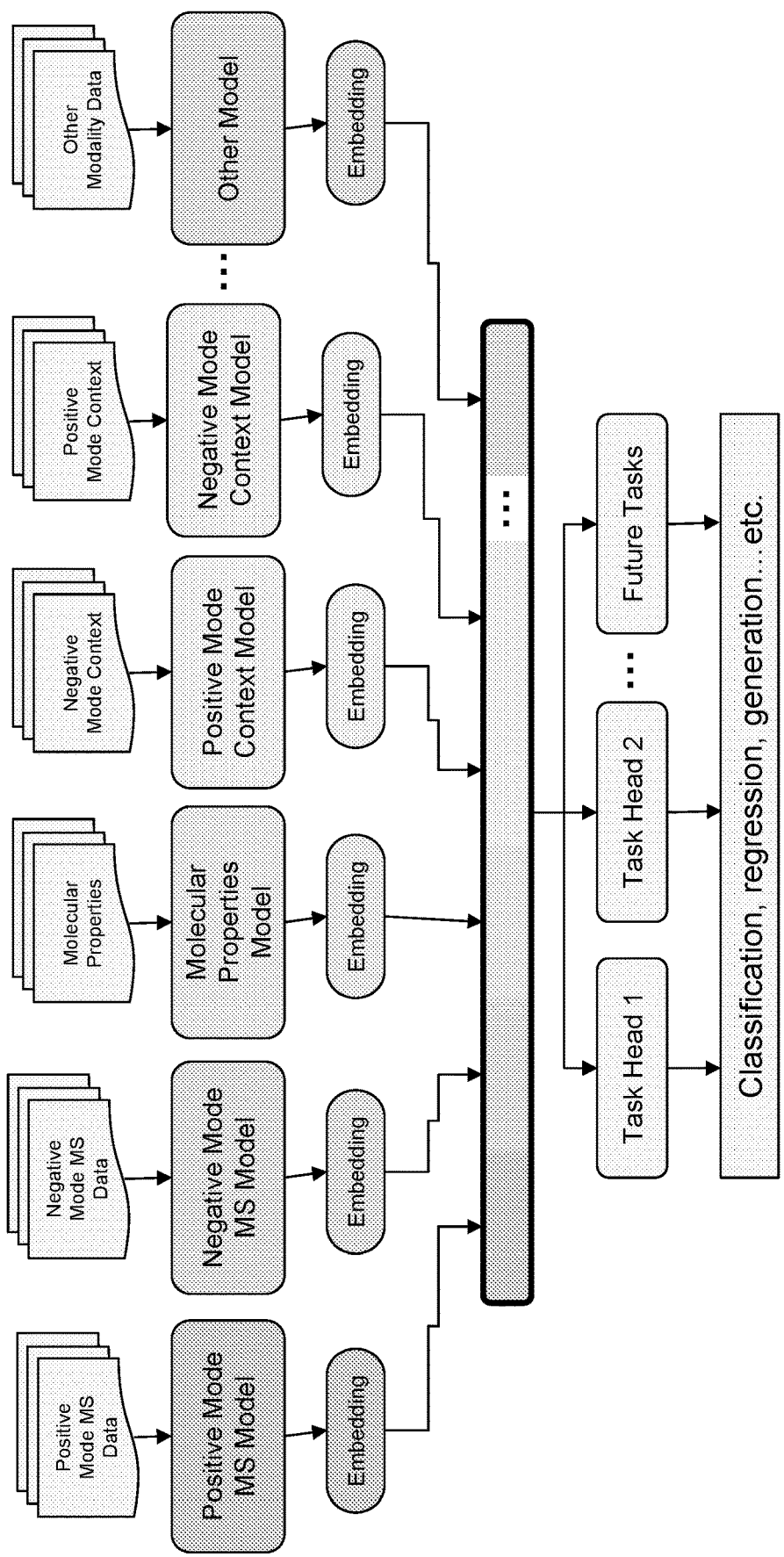
FIG. 13 schematically illustrates multi-modality models in accordance with embodiments described herein.

In some cases, the model comprises multi-modality models. An exemplary multi-modality model is shown in FIG. 13. In some cases, multi-modality models can be extremely powerful. Different modalities provide supportive, complementary or even completely orthogonal signals to the model. Multi-modality models allow the model to be use for a variety of downstream tasks that might benefit from some or all of the input modalities. Intermediate features and terminal embeddings from each model are fused. The fused representation is then used to train subsequent models for various tasks including regression, classification, generation and dimensionality reduction. The entire network and sub-models can be fine-tuned for specific tasks or the sub-models can be frozen and only the heads trained and/or finetuned. Future modalities can include not just mass spec related, but various omics signals, phenotypes, images, orthogonal measurement techniques, etc. Tasks can be as granular as predicting concentration to as abstract as classifying a high-level state. Additionally, the final fused embedding can be used by third parties for their own user-specific models The modularity offers the flexibility of interchanging a sub-model by higher performing models as they become available or designed. Sub-models can take any form, such as, but not limited to, CNN, Transformer, MLP, etc. Each module can then be used to generate embeddings for new unseen data that can then be used for downstream tasks.

In some cases, the training data comprises MS data. In some cases, the machine learning model is trained using a data set comprising a reference analyte, a calibrator, or a combination thereof. In some cases, the machine learning model is trained using a data set comprising (i) a first set of intensity values for one or more reference analytes having a known concentration and (ii) a second set of intensity values for one or more reference calibrators having a known concentration. In some instances, the reference analytes and the one or more analytes in the sample mixture comprise a same analyte or a same type or class of analyte. In some instances, the reference calibrators and the one or more calibrators in the sample mixture comprise a same calibrator or a same type or class of calibrator.

The training data may be designed based on one or more considerations. Considerations may comprise, by way of non-limiting example, effective LC separation of the broadest range of analytes, instrumental conditions for collective sensitivity of all analytes (ionization mode, RT, extracted ion chromatogram for each analyte), inherent range (high and low) of instrument detection (for each analyte), length of time between injections (acquisition and column equilibration), stability and reproducibility over long acquisition times, and/or use of spiked-in non-endogenous QC analytes to demarcate between sample issues and instrument issues.

For example, training data may comprise raw spectra comprising data on a plurality of analytes collected on a plurality of instruments. The instruments can comprise two or more different mass spectrometer types (e.g. ion trap, orbitrap, FT-ICR, time-of-flight (ToF), or QQQ-time-of-flight (QTOF) mass spectrometers) provided that each mass spectrometer has sufficient resolution to provide an exact mass of analyte ions. The instruments can comprise two or more different mass spectrometers of the same type. Training data may not require optimized or even effective chromatographic separation. Inclusion of the one or more design considerations in building the training set can produce a model which is capable of analyte quantitation independent of the particular design factor (e.g. a model built using a plurality of different mass spectrometer types can quantitate analytes using data collected from any mass spectrometer type included in the training set).

The methods described herein may not comprise an AUC (or similar construct). Since there is no AUC, the demands on the acquisition method are not a stringent as those in traditional LC-MS method development. Specifically, it can be possible for use to record a 5 minute method with high resolution and positive and negative switching because we do not need to record a specific number of "point" in each XIC. Further, the LC performance of each analyte does not have as stringent "appearance" requirements as traditional analytical method development (i.e., baseline separation and ideal peak shape are not as critical).

For example, models described herein are capable of providing absolute quantitation of two or more analytes of interest using chromatographic methods wherein the two or more analytes of interest overlap in time by at least 70%, 60%, 50%, 40%, or 30% (e.g. wherein the analyte peaks are only 30%, 40%, 50%, 60%, or 70% resolved). As a further example, models described herein are capable of providing absolute quantitation of analytes which produce chromatographic peaks with an asymmetric factor greater than 1.2 (e.g. 1.5, 2.0, 2.5, or greater than 3) or less than 0.9 (e.g. 0.8, 0.7, 0.6, 0.5, or less than 0.5).

The training data sets can be used as possible bioprocessing scenarios, such as those a user may detect in their workflow. In some cases, the training data sets are created to simulate a target bioprocessing event or scenario. In some cases, the training data sets created can aid a machine learning model to detect target analytes at a particular range. One challenges in training set creation may be to know and create a priori the concentration ranges at which the target analytes can and will be detected in.

The software infrastructure for the training data set may comprise a database and a platform for data collection. In some cases, the database comprises an internal compounds database which is used for adding, updating, searching, filtering and/or exploring compounds. Compounds comprise analytes currently offered, to be offered, candles, and heavy standards. The database can be a reference for both bench scientists who use it for examining molecular properties and biological pathway connectivity, as well as data scientists who use it for time-trackable metrics. The platform for data collection may comprise raw data and metadata collection and retrieval, conversion, quality control, storage and/or monitoring. In some cases, the platform designs the plates for training and creates the work lists to run in the lab. In some cases, the platform defines spotting patterns for stock solutions. In some cases, the platform automates partially or completely automates the laboratory workflows provided herein.

The compounds databased may comprise elements for distinguishing compounds. In some cases, the element comprises chemical properties, such as, but not limited to, chemical name, SMILES string, physiochemical properties. In some cases, the element comprises analytical properties, such as, but not limited to ionization mode(s) and typical adducts formed. In some cases, the element comprises biological information, such as a Human Metabolome Database (HMDB) link, Kyoto Encyclopedia of Genes and Genomes (KEGG) link, and pathway information. In some cases, the element comprises the training status.

An interface of a compound database is schematically illustrated in FIG. 14. As shown, the user interfaces with the compound database which shows the chemical name, formula, mass, structure, designation of a heavy label, the heavy label, and biological pathway.

The training set is created by obtaining data using techniques described herein. For example, samples are prepared and analyzed via LC-MS. The workflow for generating plates for training may comprise analyte stocks and plate layouts from a software being combined in a laboratory equipment. In some cases, sample preparation comprises distributing stock solutions (currently stable labelled standards (e.g., calibrators) in water) in varying concentrations. In some cases, a multi-drop system add an addition fixed volume of the selected matrix onto spotted wells. One or more candles (e.g., calibrators) or quality control metrics are then added to the LC-MS, and a run list may be created by a software to generate and process plates for training sets. In some cases, a MS run list is provided by a user interface. In some instances, the user interface comprises information such as sample plate positions, blank positions, calibration curve positions, number of drawers, number of slots per drawer, columns to run, blank plate number of wells, number of injections, plates between calibration curves, maximum blank well reuse, injection volume, blank frequency, etc. In some cases, prior to downloading instructions to an instrument, a user is provided with a visual quality control of the volume for each analyte to be spotted. In some instances, the visual quality control comprises a heat map key, for example, in unit volumes such as uL.

In some cases, an experimental browser is used to access training set data. For example, information may be downloadable as a CSV. In some examples, the format of the downloaded information is suitable for uploading for instrument acquisition. In some cases, the experimental browser comprises the source plate layout, a downloadable MS run list, concentrations spiked in each well, details on trained analytes, or a combination thereof.

The platforms generating training sets described herein may comprise highly scalable backend database storing chemical experiment entities. The platforms may further comprise frontend for creating new entities and combining existing to describe chemical protocols, frontend for uploading RAW files to cloud storage, automatic conversion and logging pipelines of RAW files to ML-friendly format, QC pipeline steps, large collection of visualizations, filtering and transformations which can be applied to ML-dataset samples, built-in logging of experimental metadata to backend database (e.g., known compound concentrations for training dataset), and/or MS automated workflow components, such as sample preparation (e.g., cherry pick list creation) or worklist creation for autosampler (e.g., highly configurable based on common workflow changes).

In some cases, prior to training, each analyte is screened to optimize detection and performance in training. The one or more analytes may be screened based on ionization mode(s), detected adducts, LC elution profile and retention time, limit of detection in water, limit of detection in cell lysate, and/or any observed issues with stability or solubility. The analytical information can then be captured and stored, for example in a database such as a compounds database.

Figure 15:
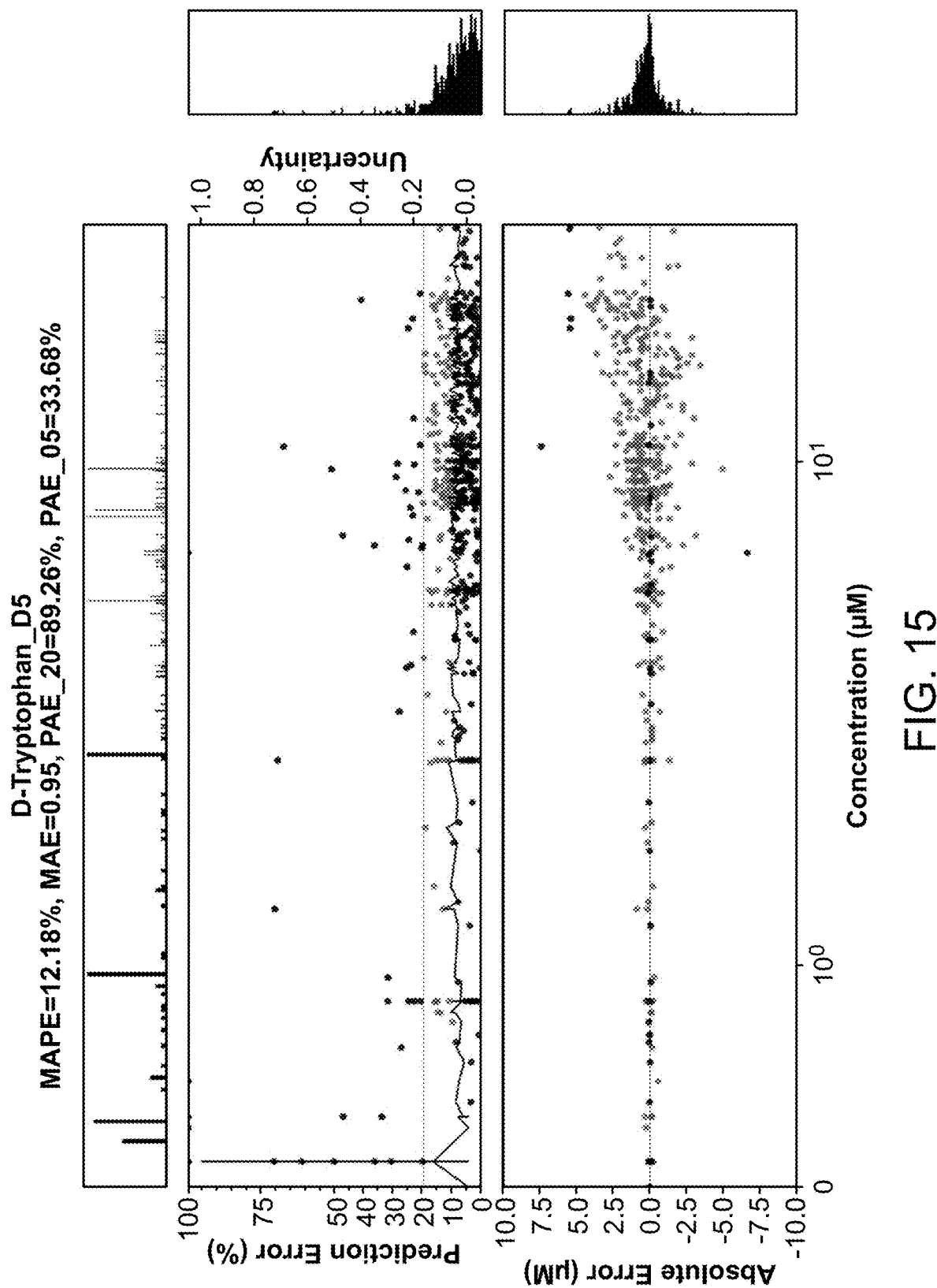
FIG. 15 schematically illustrates a model output comprising errors to quality control test data in accordance with embodiments described herein.
Figure 16:
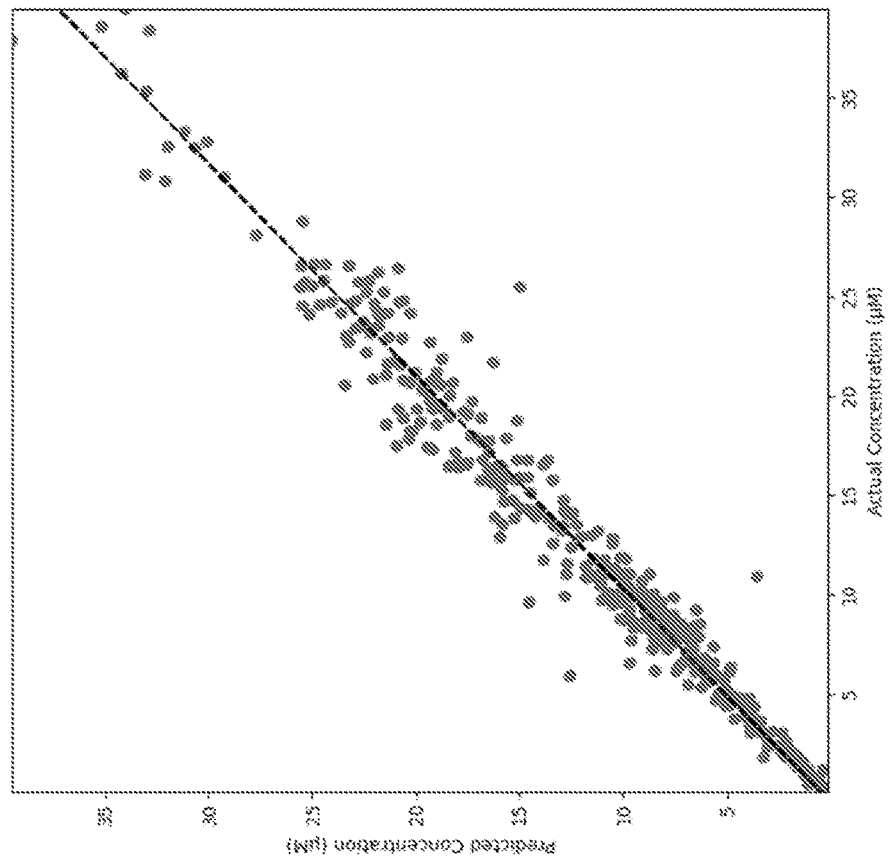
FIG. 16 schematically illustrates a model output comprising R-squared values to quality control test data in accordance with embodiments described herein.

The model quality may be dependent on data quality and training set acquisition. In some cases, the training set is analyzed using traditional MS analysis. In some cases, the data is used to assess traditional analytical performance of the methods to ensure quality control. For example, the concentration of trained analytes and MS data may be processed by a signal processing module comprising a machine learning model (e.g., deep learning model) to determine the concentration of trained analytes in a test set. In such an example, the MS data may also be used by a software that can enable control of a LC-MS system to output a values such as mass-to-charge ratio, retention time, AUC, etc., for each analyte. This can be used to assess analytical performance. There are several quality control data that can be used on analyze the training set. In some cases, known spikes in concentration of analytes is plotted against AUC to catch laboratory failures. In some cases, maintenance of low mass error can be critical for ensuring ability to identify targeted analytes in assay. The model workflows provided herein can enable internal calibration. In some cases, quality control comprises analyzing the retention stability. In some cases, stable retention time is critical for ensuring ability to identify targeted analytes in assay. In some instances, as secondary verification, model uses gatepost to monitor and correct for retention time drift. An exemplary model output to quality control test data is shown in FIG. 15. A model output can comprise concentration as a function of absolute error, prediction error, uncertainty, or a combination thereof. As shown in FIG. 15, value such as, the mean average percentage error (MAPE), the mean absolute error (MAE), percent average error <20% (PAE_20), and percent average error <5% (PAE_5) can also be provided. As shown in FIG. 16, a model output can further comprise the actual concentration vs the predicted concentration. An R-squared value can be determined to assess the accuracy of the predicted concentration by the model. In some cases, the model is assessed through correlation of positive and negative mode MS training data. In some instances, the positive and negative mode MS training data are trained separately.

Figure 17:
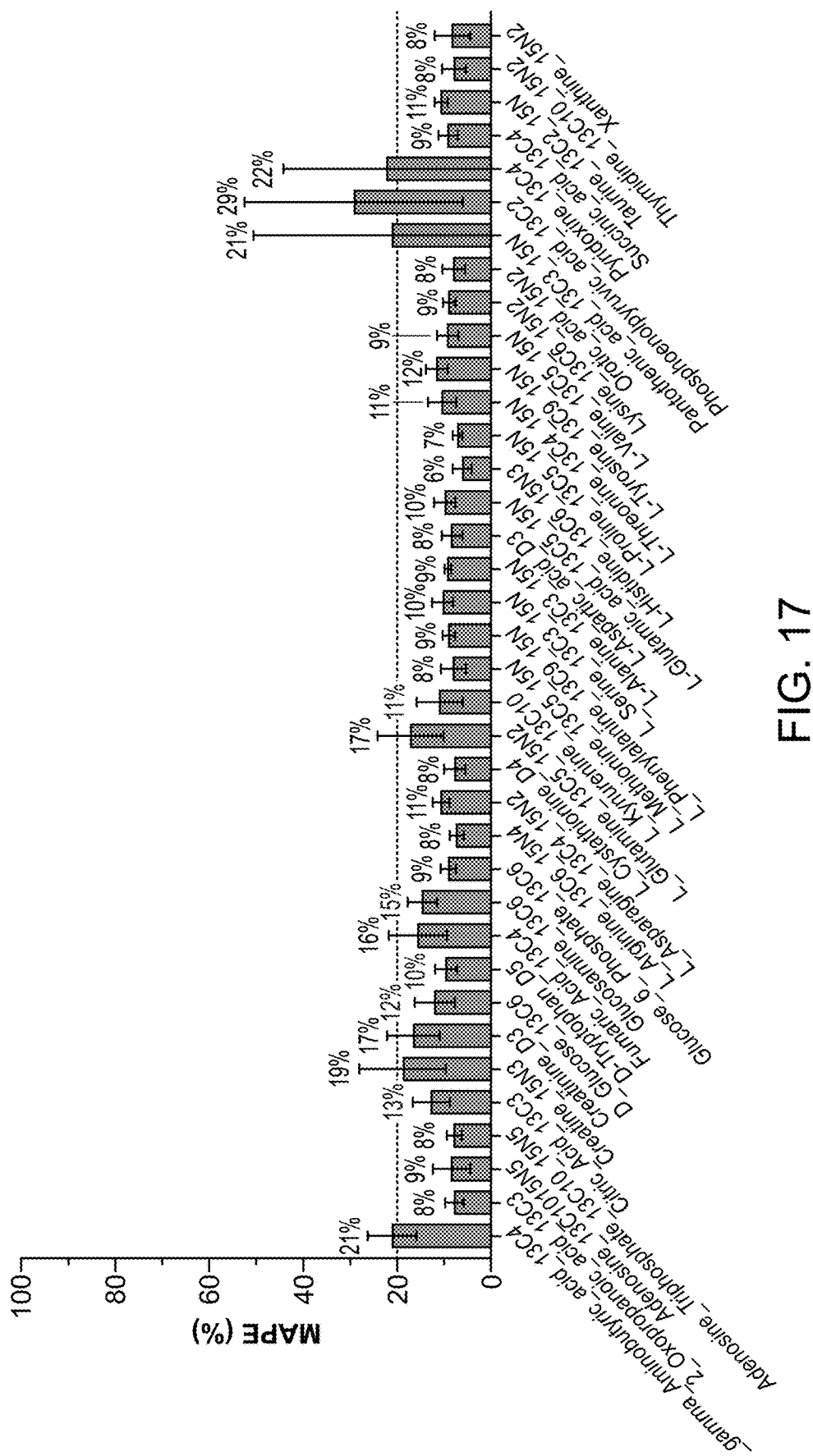
FIG. 17 schematically illustrates general model performance comprising mean average percent error (MAPE) for concentration prediction on random 10% of samples in accordance with embodiments described herein.
Figure 18:
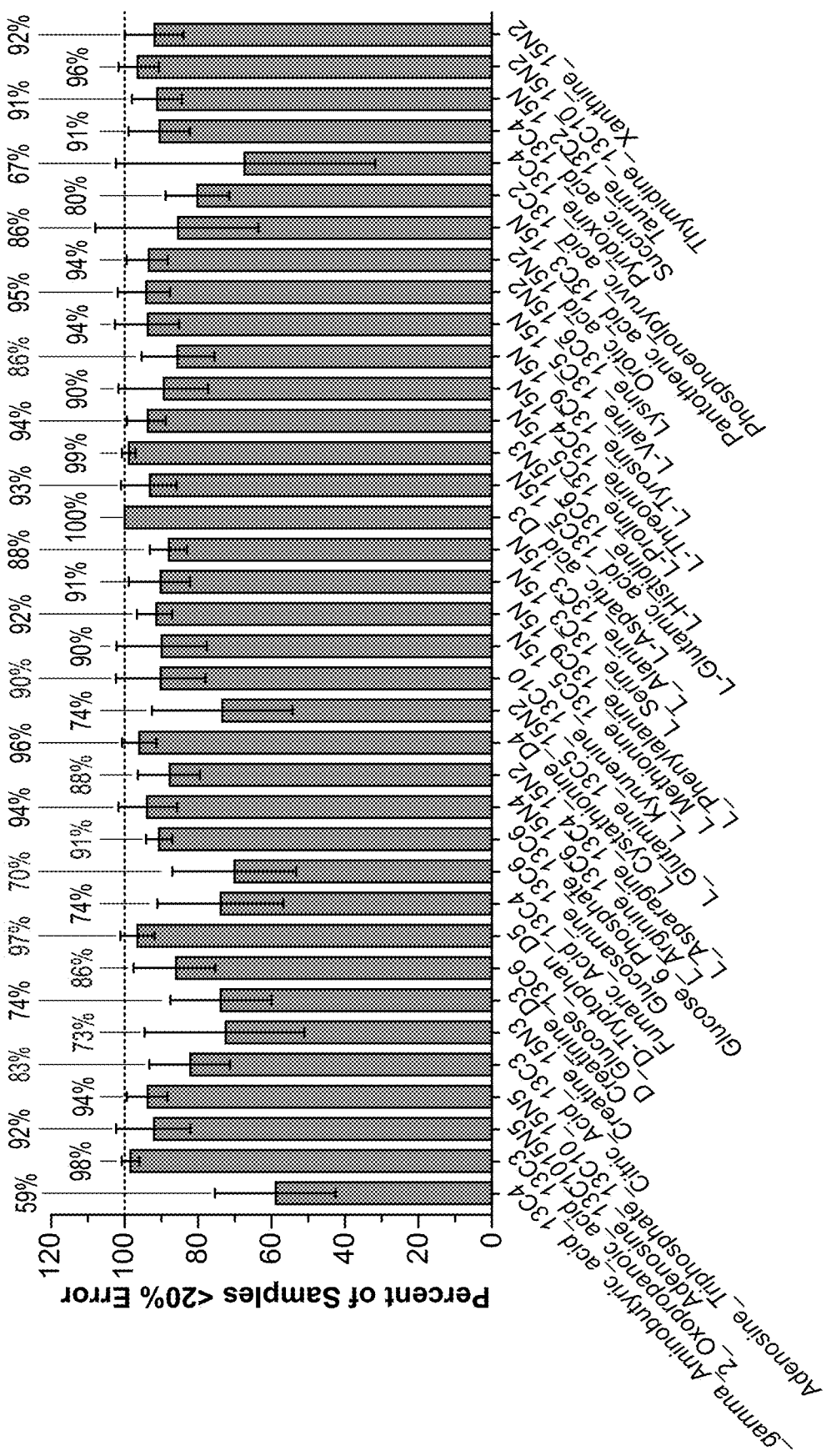
FIG. 18 schematically illustrates general model performance for concentration prediction on random of samples with less than 20% error in accordance with embodiments described herein.
Figure 19:
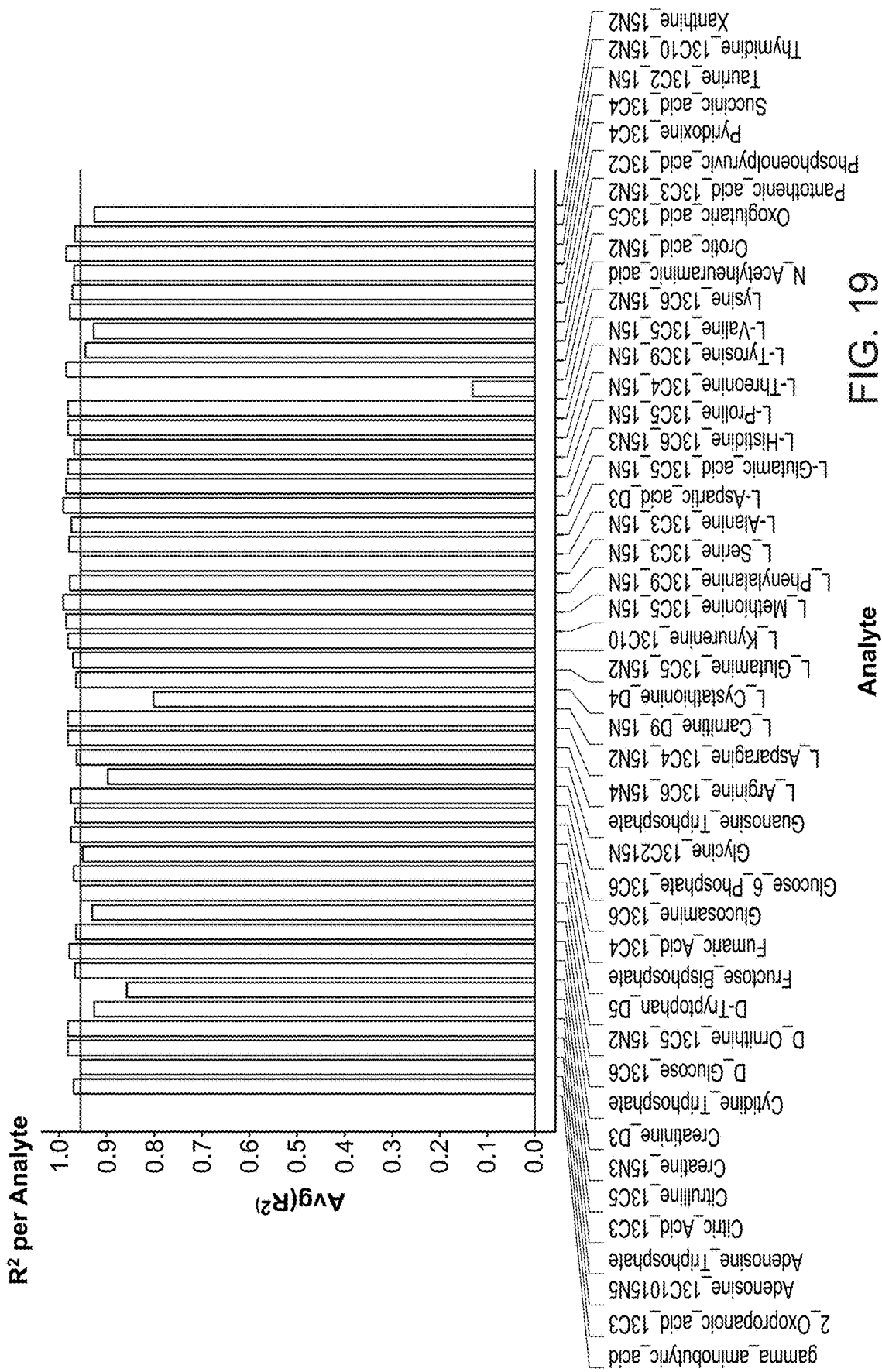
FIG. 19 schematically illustrates general model performance of R-squared values in accordance with embodiments described herein.

General model performance can be assessed by how accurately the model can impute concentrations and/or the R2 values. FIG. 17 illustrates examples of concentration predictions on a random 10% of samples, where the model is trained on many different plates. FIG. 17 shows the MAPE for various analyte, where lower performance is observed for analytes that ionize in only one mode, have a smaller number of training samples, or both. FIG. 18 further illustrates the concentration prediction of random samples for the same set of analytes, but shows the percent of samples with <20% error. FIG. 19 illustrates the general model performance based on R2 values for the same analytes in FIG. 17 and FIG. 18.

Figure 20:
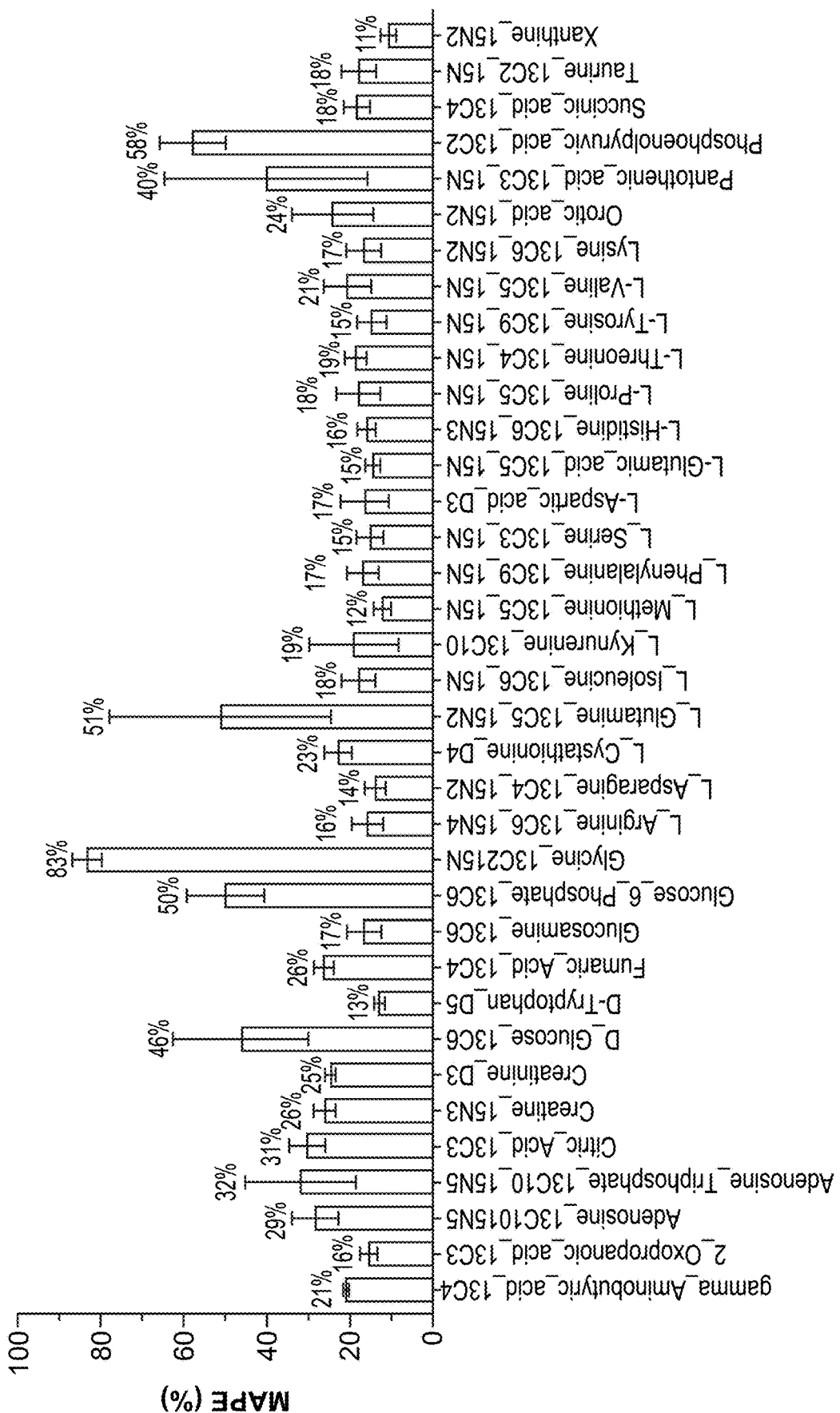
FIG. 20 schematically illustrates cross matrix model performance comprising MAPE in accordance with embodiments described herein.
Figure 21:
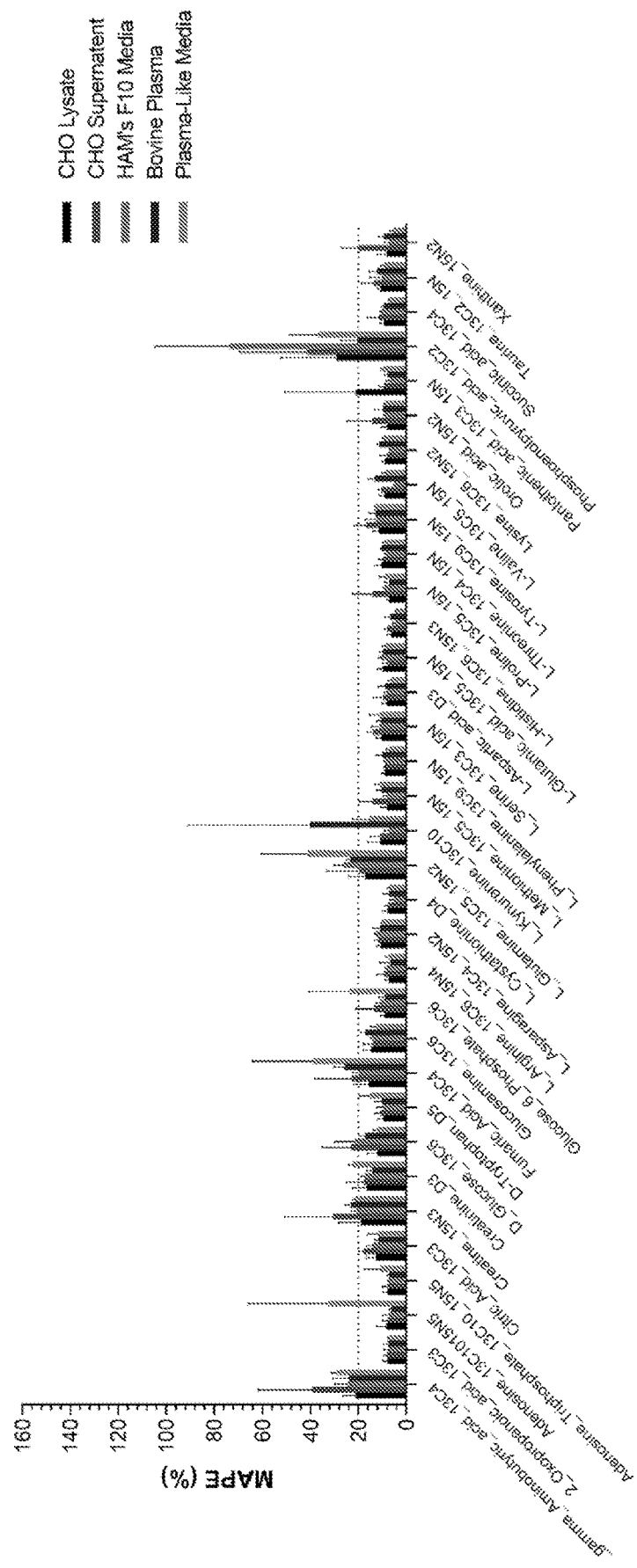
FIG. 21 schematically illustrates cross matrix model performance comprising MAPE with different matrices in accordance with embodiments described herein.
Figure 22:
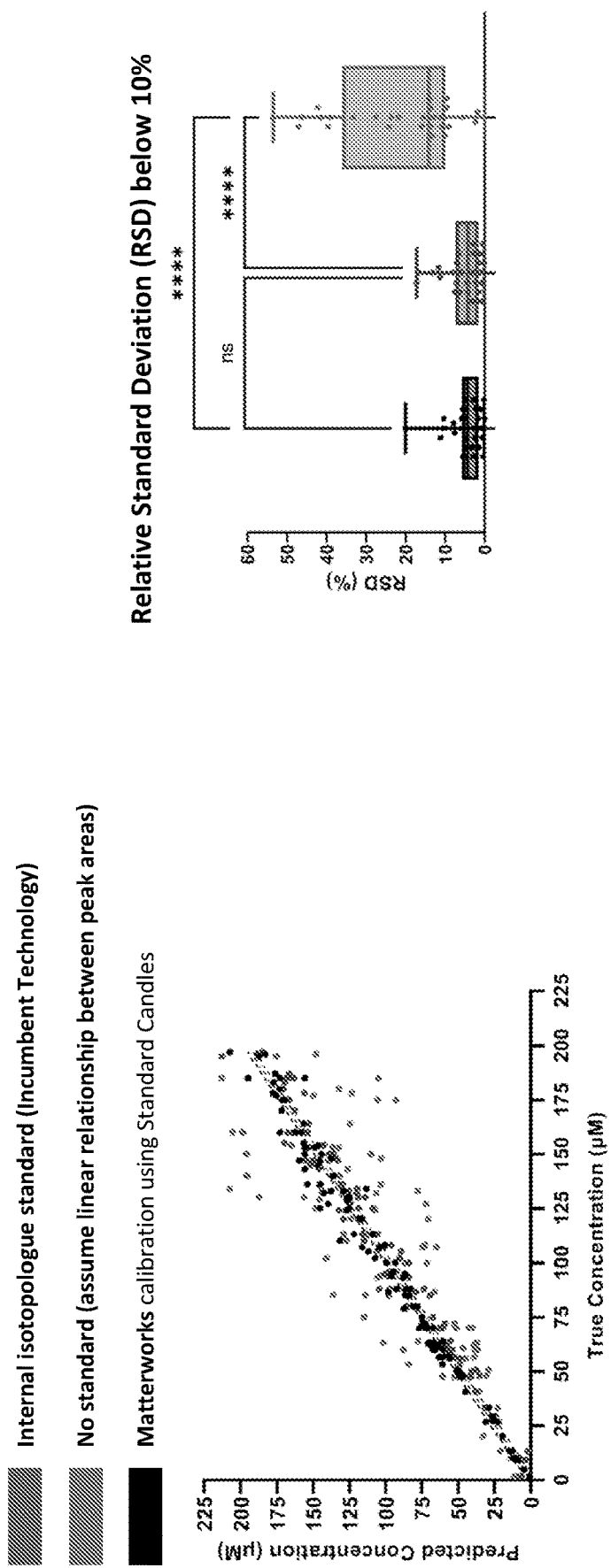
FIG. 22 schematically illustrates comparison data against in-sample isotopologues in accordance with embodiments described herein.

The model may further be assessed using cross matrix model performance. In some cases, the trained model is used to transform MS data from a variety of matrices. FIG. 20 shows the cross matrix model performance based on the MAPE of various analytes. FIG. 20 shows MAPE on 3 different dilutions of bovine plasma and show good results for the size of the training set. This model is trained on all data excluding Bovine Plasma and all 3 dilutions were excluded. FIG. 21 shows the cross matrix performance and the results are from the 10% of samples that were held out from the different matrices. The model is trained on 5 different backgrounds and the samples are split between 90% training data and 10% held-out test data. The training samples are around 1000 total matrices. In some cases, the performance increases significantly with about 10× to about 100× more training samples. In some cases, the performance is driven more by the analytes than by the matrix. Additional comparison data against in-sample isotopologues can be assessed (e.g., incumbent technology). FIG. 22 shows such comparison using gamma-aminobutyrate. As shown, the internal isotopologues and the calibrators results in similar predicted and true concentration values, and the relative standard deviation is below 10%.

In some cases, the machine learning model is configured to determine the absolute concentration of the one or more target analytes based on (1) a first set of intensity values for the one or more target analytes in the sample mixture and (2) a second set of intensity values for the one or more calibrators in the sample mixture. In some cases, the machine learning model is configured to determine the absolute concentration of the one or more target analytes based on (i) positive ionization information for the one or more target analytes, (ii) negative ionization information for the one or more target analytes, and (iii) a molecular representation of the one or more target analytes. In some instances, the positive ionization information comprises information of one or more target analytes with a positive charge. In some examples, the one or more target analytes with a positive charge comprises protonated and/or alkali adduct analyte molecules. In some instances, the negative ionization information comprises information of one or more target analytes with a negative charge. In some examples, the one or more target analytes with a negative charge comprises one or more target analytes comprising deprotonated analyte molecules. In some cases, a molecular representation comprises a representation of a chemical identity of a molecule in terms of its chemical composition and/or atomic configuration. In some instances, the molecular representation is two dimensional. In some instances, the molecular representation is three dimensional. A molecular representation may comprise, by way of non-limiting examples, a chemical formula, a SMILE string, a structural formula, a molecular graph, or any variations thereof.

The sample mixture comprising a plurality of analytes and the one or more calibrators can be provided to the MS device. In some cases, the sample mixture has a ratio between the analytes and the one or more calibrators is greater than 1:1. In some instances, the ratio between the analytes and the one or more calibrators is about 1:1, about 1:1.1, about 1:1.2, about 1:1.3, about 1:1.4, about 1:1.5, about 1:1.6, about 1:1.7, about 1:1.8, about 1:1.9, about 1:2, about 1:2.5, about 1:3, about 1:3.5, about 1:4, about 1:4.5, about 1:5, about 1:6, about 1:7, about 1:8, about 1:9, or about 1:10.

Figure 7:
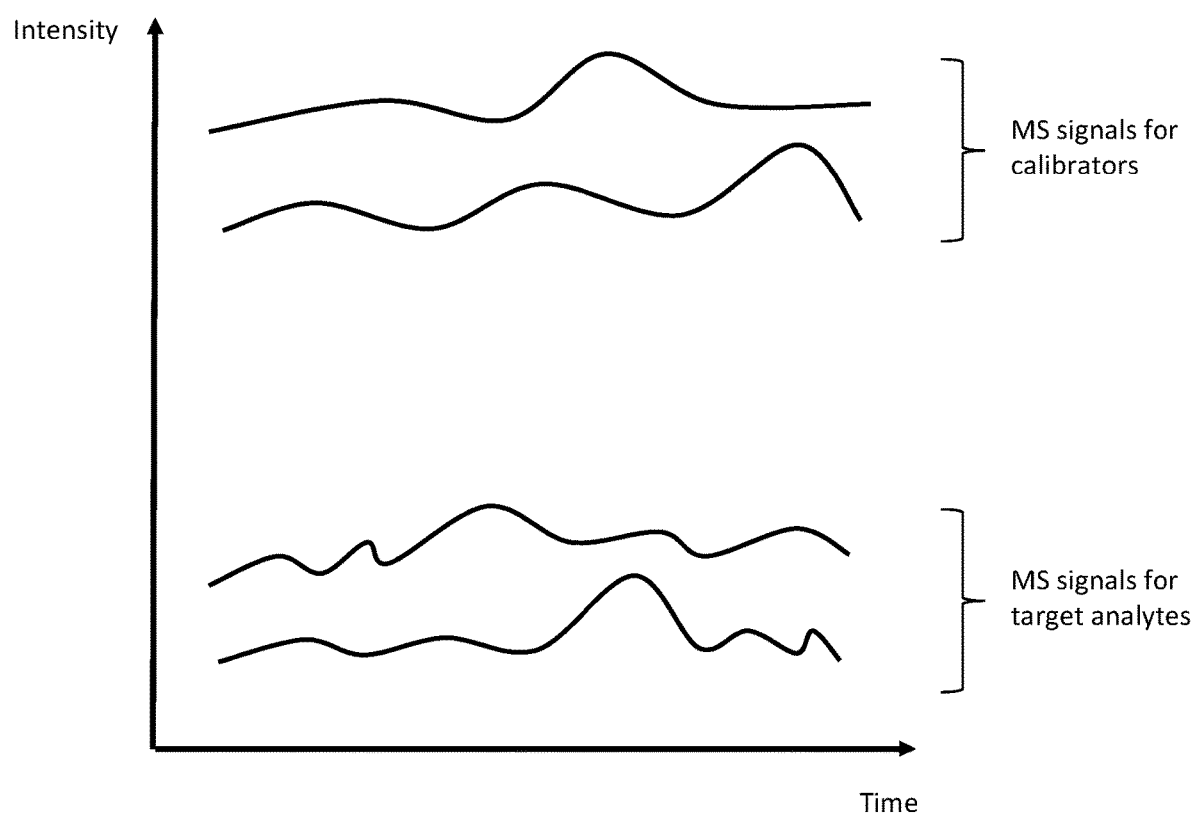
FIG. 7 schematically illustrates mass spectrometry (MS) signals analyzed by a signal processing module in accordance with embodiments described herein.

In some cases, the signal processing module determines an absolute concentration of each of the plurality of analytes based at least in part on time series data. MS signals analyzed by a signal processing module is schematically illustrated in FIG. 7. In some cases, the signal processing module analyzes the relationship between the calibrator MS signals and the target analyte signals to determine an absolute concentration of each of the target analytes. As shown, the MS signals may comprise intensity (y-axis) as a function of time (x-axis). In some cases, the MS signals comprise MS signals for one or more calibrators, one or more target analytes, or a combination thereof. In some cases, an absolute concentration of each of the plurality of analytes is determined based at least in part on a relationship or correlation between a first time series MS signal for the plurality of analytes and a second time series MS signal for the one or more calibrators. In some instances, the one or more calibrators do not comprise any isotopologue of the plurality of analytes.

In some cases, the one or more calibrators comprise a same set of calibrators usable to determine the absolute concentration of the plurality of analytes. In some instances, the plurality of analytes comprise different analytes. In some instances, the same set of calibrators comprises a set of universal calibrators. In some examples, the set of universal calibrators share one or more chemical, physical, structural, analytical, or biological properties described herein. In some examples, the set of universal calibrators differ by one or more chemical, physical, structural, analytical, or biological properties described herein. In some examples, the universal calibrators have the same concentrations. In some examples, the universal calibrators have different concentrations.

In some cases, the ratio of a number of the one ore more calibrators to the number of the plurality of analytes is at most about 1:2, 1:3, 1:5, 1:10, 1:25, 1:50, 1:100, 1:1000, or 1:5000.

The one or more calibrators may be in a kit. In some cases, the kit comprises a reagent kit. In some cases, the one or more calibrators comprises universal calibrators. In some cases, the one or more calibrators do not comprise any isotopologue of the plurality of different analytes. In some cases, the one or more calibrators are representative of one or more analytes of interest (e.g., target analytes). In some cases, the one or more calibrators comprise a nonbiologic that is usable to determine an absolute concentration of a plurality of different analytes comprising the one or more analytes of interest. In some cases, the kit enables a fast and transferable method of analyzing and processing one or more analytes. In some cases, the kit comprises MS compatible reagents (e.g., in a 96-well plate format), a sample preparation protocol, LC-MS run parameters, or any combination thereof.

Figure 8:
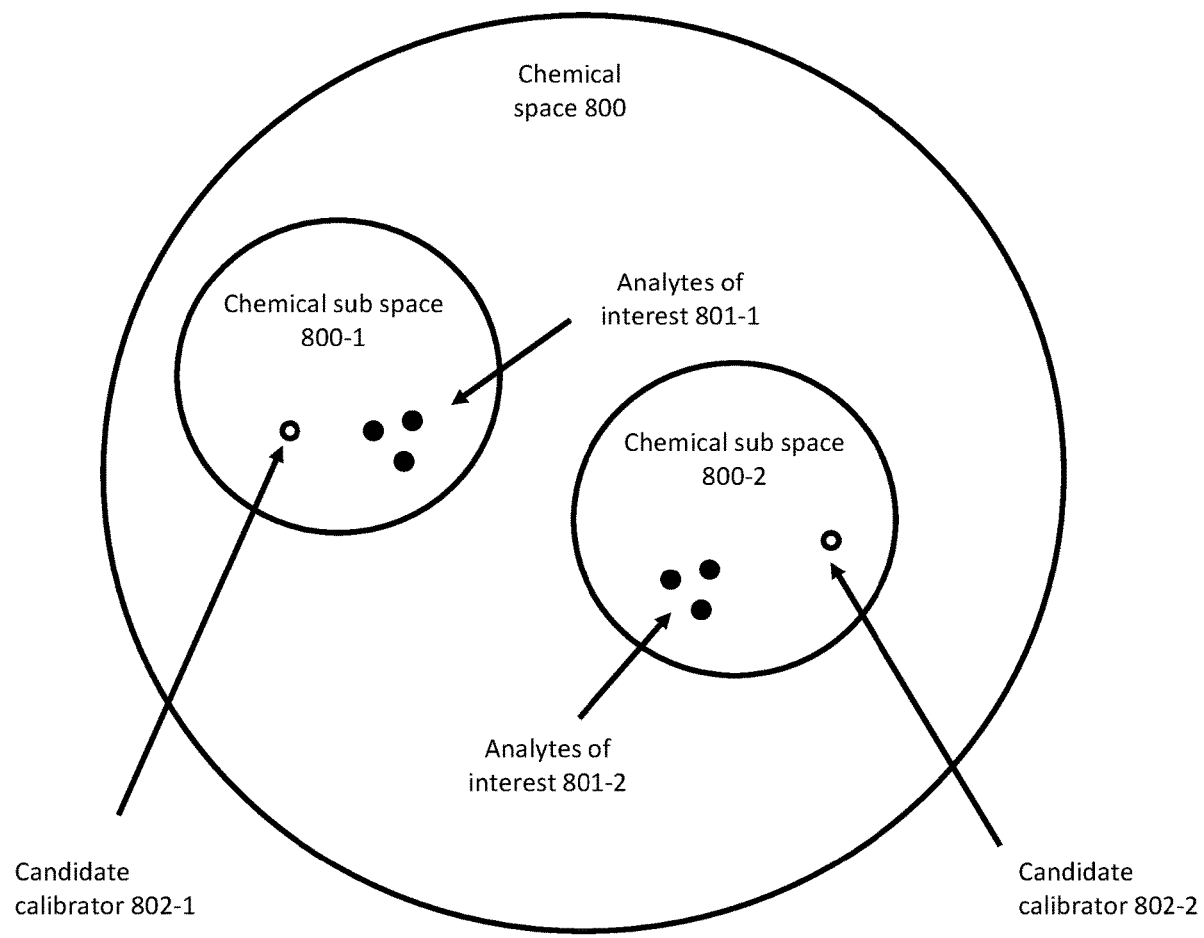
FIG. 8 schematically illustrates calibrators representative of a chemical space in accordance with embodiments described herein.

A kit may comprise one or more calibrators representative of a chemical space or a chemical class for one or more analytes of interest in a sample. For example, as illustrated in FIG. 8, a chemical space 800 may comprise one or more chemical sub spaces, e.g., 800-1 and 800-2. In some cases, species in a chemical space share one or more physical, chemical, and/or structural properties, such as, but not limited to, those described herein. In some cases, species in a chemical sub space may further share additional one or more physical, chemical, and/or structural properties, such as, but not limited to, those described herein.

Each chemical sub space may comprise one or more candidate calibrators, e.g., 802-1 and 802-2 as shown in FIG. 8. A candidate calibrator may comprise a calibrator representative of a chemical sub space. In some cases, a candidate calibrator comprises an alcohol, an amino acid, a nucleoside, a nucleotide, a nucleotide analogue, an antimetabolite, or any combination thereof. Each chemical subspace may further comprise analytes of interest, e.g., 801-1 and 801-2. In some cases, the analytes of interest comprise a metabolite, such as those described herein. In some cases, a candidate calibrator does not comprise any isotopologue of the analytes of interest.

The metabolomics analysis platforms provided by the systems and methods described herein comprise a kit comprising one or more product specifications. In some cases, the product specification comprises throughput (e.g., 5 min/sample for MS analysis), batch size (e.g., no minimum), data reported (e.g., absolute concentration), accuracy (e.g., <10% MAPE), reproducibility (e.g., 10% RDS), matrices supported (e.g., cell lysate+media), and/or data processing (e.g., fully automated).

Figure 23A:
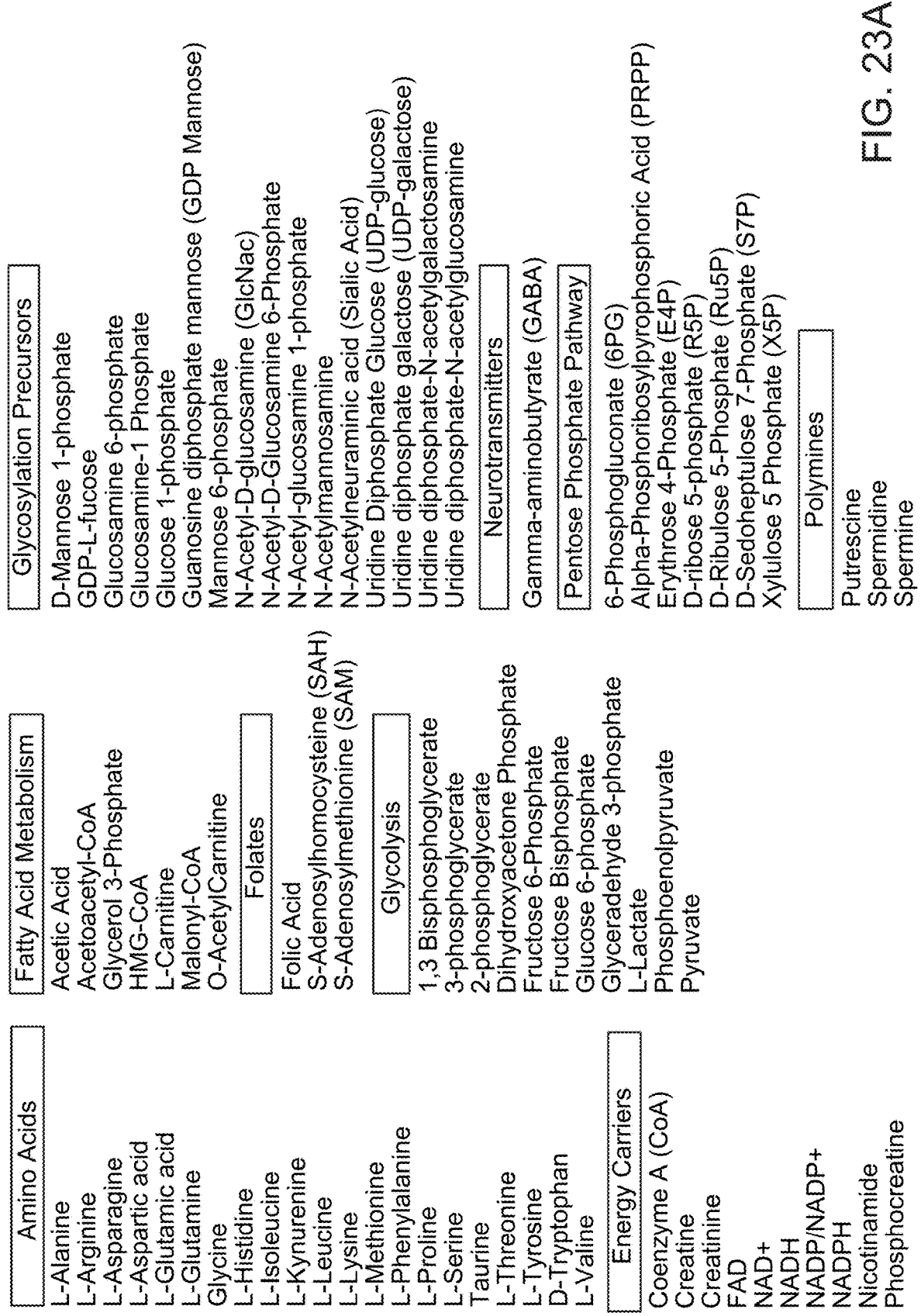
FIG. 23A schematically illustrates a metabolite list by biochemical pathway in accordance with embodiments described herein.

The metabolomics analysis platforms provided by the systems and methods described herein comprise a software and analysis package. In some cases, the software and analysis package comprises a cloud based software ecosystem. In some cases, the software and analysis package can design experiments, create MS run files, and/or provide full metabolomic data analysis insight. In some cases, the software and analysis package is used to analyze about at least 40, 60, 80, 100, 120, 140, or 150 metabolites across multiple pathways. The pathways can comprise, by way of non-limiting example, glycolysis, TCA cycle, pentose phosphate pathway, purines/pyrimidines, amino acids, urea cycle, redox/energy carriers, fatty acid metabolism, vitamins, or glycosylation precursors. Exemplary metabolites by biochemical pathways are provided in FIG. 23.

The product workflow enabled by the platform comprising systems and methods described herein can comprise the steps of, for example, onboarding, sample preparation, running samples, uploading raw data, and generating results. In some cases, the platform integrates into standard high resolution mass spec set ups. In some cases, access to a user portal can provide with both the methods for metabolite extraction but also the instrument methods, columns, and/or buffers. In some cases, the one or more calibrators can be added to sample preparation, which can allow for the data to be processed and analyzed using ML models. All raw mass spectra and results can be uploaded and accessed through this same user portal. From the time data is uploaded, the results can be viewed in strictly the time it takes to process the files (e.g., about 5 minutes per dataset). In some cases, this can eliminate the need for labor intensive peak picking and metabolite identification.

The methods provided herein may be used to gain biological insights. In some cases, an absolute concentration of an analyte (e.g., metabolite) is used to develop one or more cell lines based on the absolute concentration of the one or more analytes. In some cases, an absolute concentration of an analyte (e.g., metabolite) is used to design or optimize a media or nutrient feed for one or more cells or cell lines. In some cases, an absolute concentration of an analyte (e.g., metabolite) is used to develop or optimize a development or production process based on the absolute concentration of the one or more analytes.

Figure 9:
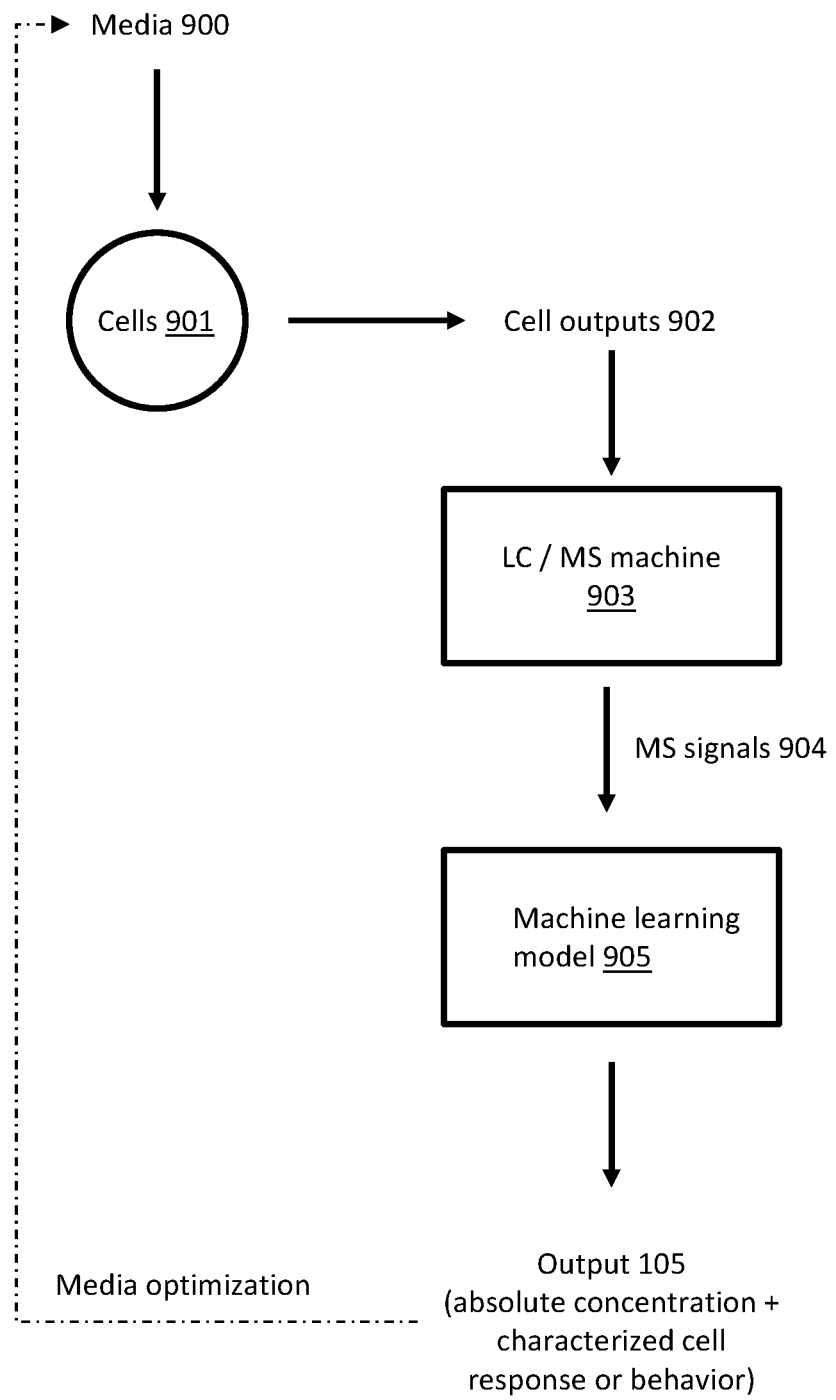
FIG. 9 schematically illustrates analysis and media optimization of cells in accordance with embodiments described herein.

An exemplary illustration of an analysis and media optimization of cells is shown in FIG. 9. As shown, a media 900 is provided to one or more cells 901. One or more cell outputs 902 of the one or more cells 901 can be analyzed. In some cases, the one or more cell outputs are analyzed after the one or more cells process the media. In some cases, the one or more cell outputs are analyzed before the one or more cells process the media. In some cases, the one or more cell outputs are analyzed periodically as the one or more cells process the media.

The cell outputs may be analyzed using chromatography and spectrometry. In some cases, the cell outputs 902 are analyzed by LC/MS machine 903, as previously described herein. In some cases, the MS signals 904 (e.g., mass spectrum, intensity, mass-to-charge ratio, etc.) are processed by a machine learning model 905. In some instances, the MS signals 904 are preprocessed, for example, using methods described herein. In some instances, the MS signals 904 comprise raw, unprocessed data. In some instances the machine learning model comprises neural networks, such as, for example, those described herein.

The cell outputs may be analyzed to determine an absolute concentration of one or more analytes. As shown in FIG. 9, the machine learning model 905 may process the MS signals 904 to generate an output 105. The output 105 may comprise an absolute concentration of the one or more analytes. In some cases, the one or more analytes comprise one or more metabolites generated or produced by the one or more cells. In some cases, the absolute concentrations of one or more analytes is determined in (i) the one or more cells or (ii) the one or more outputs of the one or more cells.

The output may further comprise a characterization of a cell response or cell behavior. In some cases, a cell response or a cell behavior is characterized for the one or more cells based at least in part on the absolute concentration of the one or more analytes. A cell behavior or response may generally comprise a change in a physical or chemical property in in the one or more cells. In some cases, the change in the physical or chemical property is characterized based at least in part on the absolute concentration of one or more analytes. In some cases, the change in the physical or chemical property comprises an increase or decrease in the absolute concentration of the one or more analytes. In some cases, the change in the physical or chemical property is characterized across more than one cell culture to optimize media or facilitate growth. In some cases, the change in the physical or chemical property of a cell culture is compared to a control culture comprising control media.

The media may further be optimized based on the characterized cell response or cell behavior. This process is illustrated in FIG. 9. In some cases, the media is optimized based on the characterized cell response or cell behavior in order to promote or facilitate cell culturing or cell growth.

The methods described herein may be utilized to insert new biochemical functionality into organisms, for example through the methods of recombinant DNA and organism engineering. Such engineered organisms can be of interest for the commercial biomanufacturing of materials, such as sustainable plastics and fuels. During the engineering and optimization of such organisms, metabolomic analyses can indicate whether the new biochemical functionality is performing efficiently, and to track the flux of unintended side-products that detract from the yield and productivity of the engineered fermentation host.

The methods can further be utilized in plant biology and crop science, where metabolic signals can provide insights into stress conditions, such as nitrogen, phosphorus, or water imbalances, as well as disease and/or infestation. In microbiome science, metabolic signatures can provide key insights into the metagenomic functions of microbiological communities, such as the sharing of chemical resources between distinct taxa.

The methods can further be utilized in food safety and environmental contamination, where metabolomic signals can provide measurements of the residual levels of pesticides, insecticides, and their biological degradation products in the food or drinking water supply.

The systems and methods described herein can be used to optimize or facilitate the use of metabolomics for biomanufacturing. The systems and methods may be used during process development and/or production. The systems and methods may be used during steps in biomanufacturing, including, but not limited to, during cell line development (e.g., clone selection, media formulation, etc.), process development, scale up (or scale down), lot release, or commercial process lock (e.g., continuous monitoring). In some cases, the quantitative metabolomics information in process can provide actionable data that drives biomanufacturing efficiency from cell line development to commercial process lock. In some cases, the systems and method provided herein can enable real-time in process metabolomic analysis. In some cases, the systems and method provided herein can shorten the time it takes to design, execute, and analyze experiments. In some cases, the systems and method provided herein can provide direct quantitative measurement of metabolic pathways. In some cases, the systems and method provided herein can provide datasets that enable predictive analytics.

Figure 24:
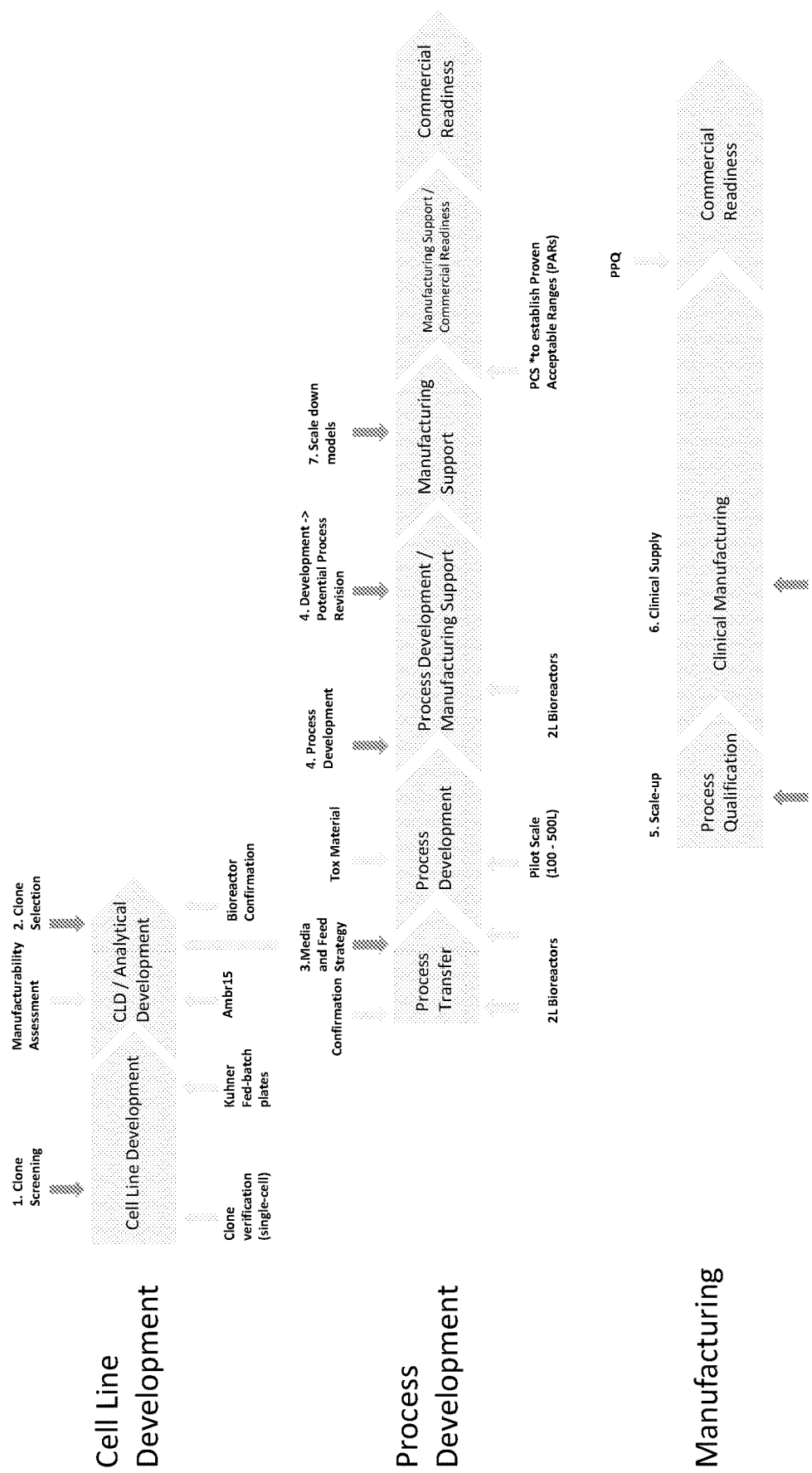
FIG. 24 schematically illustrates various utilities across aspects of a biopharmaceutical product lifecycle in accordance with embodiments described herein.

The systems and methods described herein can provide utilities across one or more aspects of a biopharmaceutical product lifecycle. A schematic of the utility across aspects of a biopharmaceutical product lifecycle is provided in FIG. 24. An example of a utility comprises analyzing clonal variation of mAB producing cells during cell line development. Observed metabolomic signatures can comprise a low mAB producer, such as truncated TCA produces less NADH due to higher efflux of malate via malic enzyme and/or higher dependence on glycolysis for ATP. Observed metabolomic signatures can comprise a high mAB producer, such as enhanced TCA cycle activity through pyruvate entry via PDH and PC and/or maintains a "healthy" ATP: ADP ratio through both glycolysis and OXPHOS. In some cases, the high-producer CHO cell clone maintains a more efficient metabolic state determined only by both intracellular and extracellular quantitative metabolic measurements. A further example of a utility comprises an 'omics approach to rational feed strategies during process development. For example, during experimental design, parental and CHO producing cultures are grown in 6 replicates for 8 days. The observed metabolic signatures can comprise metabolic pathways such as, TCA anaplerosis, Redox/NADPH, lipid synthesis, and/or folate metabolism, which may be transcriptionally upregulated as a result of Ab production. In some cases, is nutrient feed is designed based on metabolic systems under stress. In some instances, the nutrient feed results in a 75% increase in cell density. In some cases, scores are assigned to quantify the degree of upregulation. In some cases, media can be designed based on metabolic systems under stress during antibody production to improve cell density.

The methods described herein may be performed by a system. In some cases, the system comprises a computing unit operably coupled to a mass spec (MS) machine. In some cases, the computing system is configured to receive MS data from the MS machine. In some instances, the MS data is associated with a sample comprising one or more analytes and one or more calibrators. In some examples, the one or more calibrators comprises a nonendogenous molecule or compound. In some examples, the one or more calibrators comprise a nonbiologic. In some instances, the MS data received by the computing system comprises raw, unprocessed data. In some instances, the MS data received by the computing system comprises preprocessed data. In some instances, the MS data comprises mass spectrum data. In some instances, the MS data comprises intensity values. In some instances, the MS data comprises mass-to-charge ratios.

In some cases, the computing system is configured to process the MS data using a trained ML algorithm to determine an absolute concentration of the analytes. In some instances, the trained ML algorithm comprises a classical ML algorithm, a deep learning algorithm, or a combination thereof. In some examples, the ML algorithm comprises a neural network. In some examples, the neural network is a deep neural network. In some cases, the ML algorithm is configured to determine the absolute concentration of the one or more analytes based on (1) a first set of intensity values for the one or more analytes in the sample mixture and (2) a second set of intensity values for the one or more calibrators in the sample mixture. In some cases, the absolute concentration of the one or more analytes is based at least in part on a relationship or correlation between a first time series MS signal for the one or more analytes and a second time series MS signal for the one or more calibrators.

In some cases, the computing system is configured to output one or more actionable biological insights based on the absolute concentration of the analytes. In some instances, the trained ML algorithm is configured to determine the absolute concentration of the analytes from the received MS data substantially in real time. In some examples, the one or more actionable biological insight comprises a cell response or a cell behavior. In some examples, the cell response or the cell behavior is used to optimize a media in order to promote or facilitate cell culturing or cell growth. In some examples, the media is optimized in real time based on the cell response or the cell behavior.

In some cases, the analysis of the one or more analytes by the MS device and the computing system comprises a high-throughput analysis. In some instances, the total runtime comprises about 0.1 seconds, 0.5 seconds, 1 second, 2 seconds, 10 seconds, 30 seconds, 1 minute, 2 minutes, 3 minutes, 4 minutes, 5 minutes, 10 minutes, or 15 minutes. In particular embodiments, the total method run time is less than 1 minute, less than 2 minutes, less than 3 minutes, less than 5 minutes, less than 10 minutes, or less than about 12 minutes. In some cases, the total runtime comprises a data acquisition time and a data analysis time. In some cases, the data acquisition time and the data analysis time occur sequentially (e.g. they add together to make up the total analysis time). In some cases, the data acquisition time and the data analysis time occur in parallel, whereby the total analysis time per sample of the high-throughput system is limited by the longer of the data acquisition and data analysis time (e.g. the data acquisition can be determinative of the total runtime due to the time required for chromatographic separation). In some cases, the number of samples analyzed per hour is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, or 60.

Figure 10:
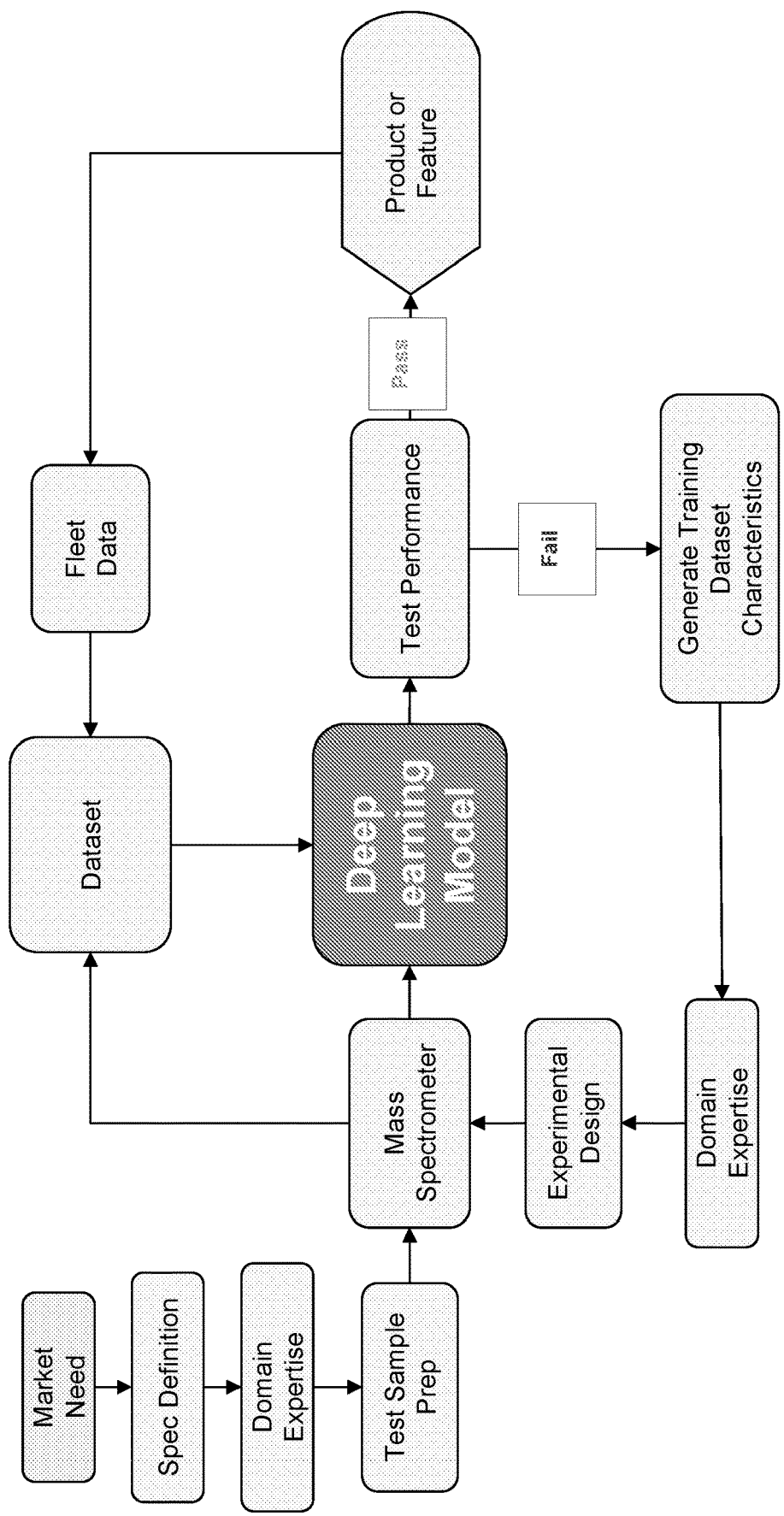
FIG. 10 schematically illustrates a data engine in accordance with embodiments described herein.

The methods described herein may be employed according to a data engine, as illustrated in FIG. 10. The date engine comprises a deep learning model which processes MS data and utilized datasets, as described herein. The deep learning model may output a performance (e.g., pass or fail). In some cases, the output results in a product or feature. In some cases, the output results in generating training dataset characteristics, which can be analyzed through domain expertise and improve experimental design. In some cases, test samples for MS analysis are prepared based on market need, spec definition, and/or domain expertise.

Computer Systems

Figure 25:
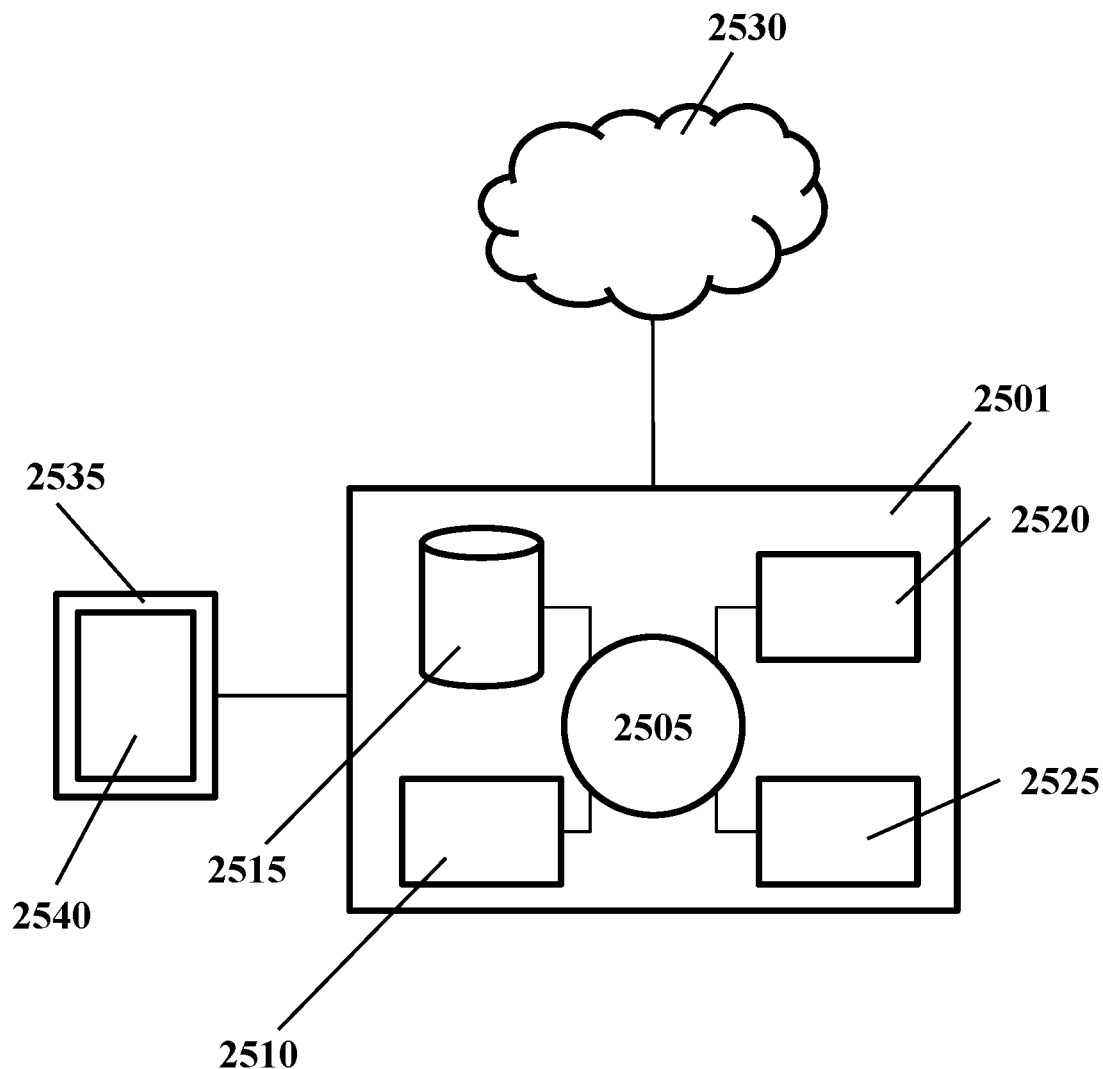
FIG. 25 schematically illustrates a computer system that is programmed or otherwise configured to implement methods provided herein.

In an aspect, the present disclosure provides computer systems that are programmed or otherwise configured to implement methods of the disclosure, e.g., a method or a system for determining or quantifying an absolute analyte concentration. FIG. 25 shows a computer system 1001 that is programmed or otherwise configured to implement a method for determining an absolute concentration of the analytes from mass-spectrometry (MS) data. The computer system 1001 may be configured to, for example, (i) receive MS data from the MS machine, wherein the MS data is associated with a sample comprising one or more analytes and one or more calibrators, (ii) process the MS data using a trained ML algorithm to determine an absolute concentration of the analytes, and (iii) output one or more actionable biological insights based on the absolute concentration of the analytes, wherein the trained ML algorithm is configured to determine the absolute concentration of the analytes from the received MS data substantially in real time. The computer system 2501 can be an electronic device of a user or a computer system that is remotely located with respect to the electronic device. The electronic device can be a mobile electronic device.

The computer system 2501 may include a central processing unit (CPU, also "processor" and "computer processor" herein) 2505, which can be a single core or multi core processor, or a plurality of processors for parallel processing. The computer system 2501 also includes memory or memory location 2510 (e.g., random-access memory, read-only memory, flash memory), electronic storage unit 2515 (e.g., hard disk), communication interface 2520 (e.g., network adapter) for communicating with one or more other systems, and peripheral devices 2525, such as cache, other memory, data storage and/or electronic display adapters. The memory 2510, storage unit 2515, interface 2520 and peripheral devices 2525 are in communication with the CPU 2505 through a communication bus (solid lines), such as a motherboard. The storage unit 2515 can be a data storage unit (or data repository) for storing data. The computer system 2501 can be operatively coupled to a computer network ("network") 2530 with the aid of the communication interface 2520. The network 2530 can be the Internet, an internet and/or extranet, or an intranet and/or extranet that is in communication with the Internet. The network 2530 in some cases is a telecommunication and/or data network. The network 2530 can include one or more computer servers, which can enable distributed computing, such as cloud computing. The network 2530, in some cases with the aid of the computer system 2501, can implement a peer-to-peer network, which may enable devices coupled to the computer system 2501 to behave as a client or a server.

The CPU 2505 can execute a sequence of machine-readable instructions, which can be embodied in a program or software. The instructions may be stored in a memory location, such as the memory 2510. The instructions can be directed to the CPU 2505, which can subsequently program or otherwise configure the CPU 2505 to implement methods of the present disclosure. Examples of operations performed by the CPU 2505 can include fetch, decode, execute, and writeback.

The CPU 2505 can be part of a circuit, such as an integrated circuit. One or more other components of the system 2501 can be included in the circuit. In some cases, the circuit is an application specific integrated circuit (ASIC).

The storage unit 2515 can store files, such as drivers, libraries and saved programs. The storage unit 2515 can store user data, e.g., user preferences and user programs. The computer system 2501 in some cases can include one or more additional data storage units that are located external to the computer system 2501 (e.g., on a remote server that is in communication with the computer system 2501 through an intranet or the Internet).

The computer system 2501 can communicate with one or more remote computer systems through the network 2530. For instance, the computer system 2501 can communicate with a remote computer system of a user. Examples of remote computer systems include personal computers (e.g., portable PC), slate or tablet PC's (e.g., Apple® iPad, Samsung® Gala3 Tab), telephones, Smart phones (e.g., Apple® iphone, Android-enabled device, Blackberry®), or personal digital assistants. The user can access the computer system 2501 via the network 2530.

Methods as described herein can be implemented by way of machine (e.g., computer processor) executable code stored on an electronic storage location of the computer system 2501, such as, for example, on the memory 2510 or electronic storage unit 2515. The machine executable or machine readable code can be provided in the form of software. During use, the code can be executed by the processor 2505. In some cases, the code can be retrieved from the storage unit 2515 and stored on the memory 2510 for ready access by the processor 2505. In some situations, the electronic storage unit 2515 can be precluded, and machine-executable instructions are stored on memory 2510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2501 can include or be in communication with an electronic display 2535 that comprises a user interface (UI) 2540 for providing, for example, a portal for a user to identify and/or view one or more MS data or ML algorithm. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2505. For example, the algorithm may determine an absolute concentration of one or more target analytes in a sample mixture comprising the one or more target analytes and one or more calibrators. The algorithm may be configured to determine the absolute concentration of the one or more target analytes based on (i) positive ionization information for the one or more target analytes, (ii) negative ionization information for the one or more target analytes, and/or (iii) a molecular representation of the one or more target analytes.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

[[*Original Spec Written By Clark & Elbing*]]

In general, provided are methods, libraries, and samples for quantifying a target analyte in a laboratory sample including the target analyte.

The invention disclosed herein includes compositions of standards for the quantification of analytes via liquid chromatography and mass spectrometry (LC/MS). Methods for quantitative determination of analytes by LC/MS using calibration standards is well-known in the art.

Typically, quantitation is performed by providing a calibration standard for each of the analytes of interest. One common approach to calibration is provided by external calibration standards, wherein a calibration curve between instrument signal and analyte concentration is determined by injecting a range of known analyte concentrations, measuring the instrument signal for each concentration, and fitting the concentration as a parameterized function of the instrument signal. In this case, the calibration standard is an authentic sample of the analyte to be determined. Typical fitting methods include least squares minimization using the calibration signal data. In such methods, a separate calibration standard must be provided for each of the target analytes and the calibration curve must be determined as a separate step in the method. That is to say, the range of calibration concentrations and instrument signals are measured in a distinct step from the analytical samples. Depending on the number of analytes of interest, external calibration is often prohibitive because the time and resources required to run a concentration range of many distinct analytes is prohibitive. In many circumstances, especially where fast determination is required, the time required to generate external calibration curves renders the method unusable. For example, real-time concentration tracking, samples with unstable analytes, etc.

Alternatively, internal calibration standards can be provided by combining the analytical sample with a mixture containing isotopologues of the target analytes. Isotopologues are otherwise chemically identical from the perspective of chromatography, but can be distinguished by a mass difference. Typical isotopologue standards are provided by substituting naturally abundant isotopes of carbon, nitrogen, oxygen, and/or hydrogen atoms with their isotopically enriched heavy analogs, e.g., 13C, 15N, 18O, and deuterium. Quantitation is then achieved by providing known concentrations of the isotopologues mixed with the analytical sample. For each target analyte, the instrument signal is corrected by reference to the isotopologue signal. This approach has the advantage that it is possible to run the calibration standards simultaneously with the analytes. It, however, faces the challenge that isotopically enriched analogs of complex analytes are often expensive. Furthermore, as the number of target analytes increase, adding an isotopologue standard for each becomes technically impractical due to solubility, chemical interactions, and other concentration limitations. For example, adding one thousand internal standards each at one millimolar concentration results in a sample with a molar concentration of standards, versus sample concentrations which might be in the micromolar range, or lower. Internal standard addition of isotopologues may be limited in practice to relatively small numbers of analytes, e.g., less than 1,000, less than 500, less than 400, less than 300, less than 200, less than 100, less than 50, or less than 25.

Samples

In some embodiments, the methods described herein are performed on one or more samples. In various embodiments, the one or more samples include one or more metabolites and one or more backgrounds or matrices. In certain embodiments, the sample is an aqueous solution including one or more metabolites for determination. In other embodiments, the sample is an organic solution including one or more metabolites for determination. In yet other embodiments, the sample includes one or more metabolites that have been derivatized or functionalized prior to analysis.

In some the one or more matrices may be selected from the group consisting of a fermentation broth, a cell culture medium, a tissue culture medium, urine, fecal matter, blood, blood plasma, mucus, saliva, or soil. In certain embodiments, the matrix includes one or more salts. In particular variations, the one or more salts include sodium ions, potassium ions, calcium ions, magnesium ions or ammonium cations. In other variations, the one or more salts include chloride, nitrate, sulfate, phosphate, formate, acetate, or citrate anions. In a particular embodiment, the salt is sodium chloride. In other variations, the matrix includes one or more acids or bases. In particular variations, the matrix includes hydrochloric acid, sulfuric acid, phosphoric acid, sodium hydroxide, potassium hydroxide, ammonium hydroxide, or acetic acid. In certain embodiments, the matrix includes a buffer. In a particular embodiment, the matrix includes a citrate, phosphate, or acetate buffer.

In some embodiments, the sample is produced by a microbial community, such as a microbiome. In various embodiments, the microbiome samples can be obtained from a human, an animal, a plant, a seed, a soil, or an environment. In some embodiments, the microbiome sample is a sample of a gastrointestinal tract (e.g., stomach), skin, mammary glands, placenta, seminal fluid, uterus, ovarian follicles, lung, saliva, oral mucosa, conjunctiva, or biliary tract. Methods of obtaining microbiome samples are standard and known to the skilled artisan.

In other embodiments, the sample is produced by a fermentation process. In particular embodiments, the fermentation process is an industrial fermentation for the production of an intended product. In particular embodiments, the fermentation process produces one or more side products or by-products in addition to the intended product. In certain embodiments, the presence or concentrations of the side products or by-products are used to determine the performance of the fermentation process. In other embodiments, the analytes in the fermentation broth are measured for the purpose of optimizing production parameters. In particular embodiments, the analytes in the fermentation broth are measured for the purpose of fermentation strain engineering.

In other embodiments, the sample is obtained from a human or animal subject. In particular embodiments, the sample obtained from an animal or a human is for the purpose of evaluating the health or nutritional status of the animal or human. In particular embodiments, the sample is a blood sample, a urine sample, a tissue sample, or a tissue biopsy. In certain embodiments, the sample is a clinical sample.

In various embodiments, methods are employed to maintain the fidelity of the sample, meaning that the sample is handled in a manner such that concentrations of the one or more metabolites in the sample are not significantly changed as a result of handling the sample. In certain variations, such handling might include sterile handling, cold storage, light or dark storage, or by handling the sample under specific conditions. Methods of obtaining, preparing, storing, and shipping samples for analysis are generally known to one of skill in the art.

Methods of Analyzing Samples

Provided herein are methods for analyzing samples to determine the absolute or relative concentration of one or more metabolites in one or more samples. In a particular embodiment, the method for analyzing samples includes the steps of:

preparing an analytical sample from said primary sample, said preparation including combining an aliquot of the primary sample with an aliquot of an internal standard solution, said internal standard solution including one or more internal standards of known concentration;

programming the acquisition parameters of a mass spectrometer;

providing the analytical sample to mass spectrometer;

obtaining one or more signals for the one or more metabolites and the one or more internal standards;

determining one or more predicted response factors for the one or more metabolites from the signals corresponding to one or more internal standards; and calculating the level of said one or more metabolites from said one or more instrument signals and said one or more predicted response factors.

In certain embodiments, the method includes accepting a primary sample for analysis and preparing an analytical sample for analysis by introducing one or more standard species of known concentration, optionally adjusting the overall concentration of the sample (e.g., by dilution or concentration), optionally cleaning the sample (e.g., desalting or extracting the sample), and optionally adding one or more chemical species to the sample to improve the detectability of the sample. In various embodiments, the method includes programming one or more acquisition parameters of a high-resolution mass spectrometer, including for example the one or more mass acquisition windows, one or more acquisition times for the one or more mass acquisition windows, one or more resolutions for the one or more mass acquisition windows, one or more gain settings for the one or more acquisition windows, one or more ionization polarity settings for the one or more mass acquisition windows, or one or more mass resolutions for the one or more mass acquisition windows.

In various embodiments, the method includes detecting the sample by direct infusion high-resolution mass spectrometry to obtain one or more signals for the one or more metabolites and one or more standards. In other embodiments, the method includes predicting one or more response factors for the one or more metabolites using a machine-learning model. In various embodiments, the method includes determining the concentrations of one of more metabolites from the one or more instrument signals and the one or more calculated response factors.

Instrumental Methods

Exemplary methods of determining the level of a metabolite in culture media include for example chromatography (e.g., gas (GC) or liquid chromatography (LC)) combined with mass spectrometry. The measurements may be validated by running metabolite standards through the same analytical systems.

In the case of gas chromatography-mass spectrometry (GC-MS) or liquid-chromatography-mass spectrometry (LC-MS) analysis, polar metabolites and fatty acids could be extracted using monophasic or biphasic systems of organic solvents and an aqueous sample and derivatized. An exemplary protocol for derivatization of polar metabolites involves formation of methoxime-tBDMS derivatives through incubation of the metabolites with 2% methoxylamine hydrochloride in pyridine followed by addition of N-tert-butyldimethylsilyl-N-methyltrifluoroacetamide (MTB-STFA) with 1% tert-butyldimethylchlorosilane (t-BDMCS). Non-polar fractions, including triacylglycerides and phospholipids, may be saponified to free fatty acids and esterified to form fatty acid methyl esters, for example, either by incubation with 2% $H_2SO_4$ in methanol or by using Methyl-8 reagent (Thermo Scientific). Derivatized samples may then be analyzed by GC-MS using standard GC-MS methods, for example, a DB-35MS column (30 m×0.25 mm i.d.×0.25 µm, Agilent J&W Scientific) installed on a gas chromatograph (GC) interfaced with a mass spectrometer (MS). Mass isotopomer distributions may be determined by integrating metabolite ion fragments and corrected for natural abundance using standard algorithms. In the case of liquid chromatography-mass spectrometry (LC-MS), polar metabolites may be analyzed using a standard benchtop LC-MS/MS equipped with a column, such as a SeQuant ZIC-Philic polymeric column (2.1×150 mm; EMD Millipore). Exemplary mobile phases used for separation could include buffers and organic solvents adjusted to a specific pH value.

Metabolites

Metabolites to be analyzed include any known metabolite. The metabolite can be beneficial or detrimental from the perspective of a health status or disease biomarker, fermentation performance, microbiome function. Exemplary metabolites include, but are not limited to, short chain fatty acids (SCFAs), bile acids, dipeptides, fatty alcohols, terpenoids, amino acids, peptides (e.g., dipeptides), polyphenols, hemiterpenoids, monoterpenoids, sesquiterpenoid, diterpenoids, sesterterpenoids, triterpenoids, tetraterpenoids, polyterpenoids, neurotransmitters (or precursors thereof), volatile fatty acids, alcohols, signaling factors, pro-inflammatory metabolites, nitrogenous metabolites. In particular embodiments, the metabolites are amino acids, free fatty acids, acylcarnitines, or any combination thereof.

Exemplary metabolites include, but are not limited to, BETA-NICOTINAMIDE ADENINE DINUCLEOTIDE, GLUTAMINE, HYPOTAURINE, N-METYL-ALANINE, CITRATE, THREONINE, PURINE, N-ACETYLNEURAMINATE, N-ACETYLMANNOSAMINE, PYRIMIDINE, TRANS-ACONITATE, URATE, CYTIDINE, SERINE, CYSTEINE, CITRULLINE, TAURINE, N-ACETYLTRYPTOPHAN, NICOTINATE, INOSINE, GAMMA-AMINOBUTYRATE, CYTOSINE, ISOLEUCINE, PYRAZOLE, GLUTAMATE, ASCORBATE, P-HYDROXYPHENYLACETATE, N-ACETYLGLUCOSAMINE, GLYCOLATE, SARCOSINE, CREATININE, QUINATE, DIHYDROOROTATE, MALONATE, GUANIDINOACETATE, FORMAMIDE, GLYCINE, METHIONINE, TETRAHYDROFOLATE, 2-PHOSPHOGLYCERATE, METHYLTHIOADENOSINE, THYMIDINE, CYS-GLY, AMINOISOBUTANOATE, GULOSE, XANTHINE, DIHYDROFOLATE, CYSTINE, L-ALANINE, DIETHANOLAMINE, URIDINE MONOPHOSPHATE, PROLINE, THYMINE, SUCCINATE SEMIALDEHYDE, LACTATE, URIDINE, FRUCTOSE BISPHOSPHATE, CARNOSINE, NICOTINAMIDE, SHIKIMATE, SUCCINATE, PHENYLALANINE, URACIL, THIOUREA, ASPARTATE, DEOXYCYTIDINE MONOPHOSPHATE, HYPOXANTHINE, CREATINE, L-DOPA, GUANOSINE, DIHYDROURACIL, MALATE, ISOCITRATE, TYROSINE, GLYCEROL, ASPARAGINE, VALINE, GUANINE, HOMOSERINE, PYRIDOXINE, DEOXYADENOSINE MONOPHOSPHATE, FOLATE, NICOTINAMIDE MONONUCLEOTIDE, 3-METHYL-L-HISTIDINE, DIAMINOPIMELATE, AMINOADIPATE, DEOXYCYTIDINE, NORADRENALINE, GLUCOSAMINE 6-PHOSPHATE, TARTRATE, 3-DEHYDROSHIKIMATE, CAFFEINE, HOMOCYSTEINE, THEOPHYLLINE, LEUCINE, TREHALOSE, BETAINE, TRYPTOPHAN, 3-SULFINOALANINE, O-SUCCINYLHOMOSERINE, ALLANTOIN, GLYCERALDEHYDE, D-GLUCURONOLACTONE, (2-AMINOETHYL)PHOSPHONATE, 2,5-DIHYDROBENZOIC ACID, MALEIMIDE, THREITOL, GLUCOSAMINE, PARAXANTHINE, ADENOSINE 5'-DIPHOSPHATE, 2-DEOXY-D-GLUCOSE, 1-METHYL-L-HISTIDINE, GALACTITOL, OXOPROLINE, 4-PYRIDOXATE, QUINOLINATE, METHYLGUANIDINE, DEOXYGUANOSINE-MONOPHOSPHATE, 3-HYDROXY-3-METHYLGLUTARYL-COA, GLUCURONATE, 1-METHYLADENOSINE, DEOXYURIDINE, GLUCONATE, UROCANATE, KYNURENINE, PYROGLUTAMATE, 4-ACETAMIDOBUTANOATE, TRANS-1,2-CYCLOHEXANEDIOL, MELANIN, DOPAMINE, ADENOSINE-MONOPHOSPHATE, LYSINE, CITICOLINE, 1,3-DIAMINOPROPANE, PHOSPHOSERINE, 1-AMINOCYCLOPROPANECARBOXYLATE, GLUTARYLCARNITINE, CYSTATHIONINE, NORVALINE, 3-HYDROXYMETHYLGLUTARATE, PHOSPHONOACETATE, PICOLINATE, ETHANOLAMINE, ARGININE, TRANS-4-HYDROXY-L-PROLINE, FUCOSE, HOMOCYSTINE, N-METHYLGLUTAMATE, D-ORNITHINE, XANTHOSINE, 3-METHYLCROTONYL-COA, THYROTROPIN RELEASING HORMONE, CYSTEATE, N-METHYLASPARTATE, GALACTARATE, ALPHA-HYDROXYISOBUTYRATE, NICOTINIC ACID ADENINE DINUCLEOTIDE PHOSPHATE, N-ACETYLASPARAGINE, PIPECOLATE, GLUCOSE 6-PHOSPHATE, NADP, 6-PHOSPHOGLUCONATE, ISOPENTENYL PYROPHOSPHATE, GUANOSINE TRIPHOSPHATE, DTDP-D-GLUCOSE, AGMATINE SULFATE, GLYCOLALDEHYDE, DGTP, N-ACETYLGLYCINE, N-ACETYLASPARTATE, INOSINE 5'-DIPHOSPHATE, PALMITOYLCARNITINE, NORSPERMIDINE, NICOTINAMIDE HYPOXANTHINE DINUCLEOTIDE, S-ADENOSYLMETHIONINE, ERYTHRITOL, GLUCOSAMINATE, URIDINE TRIPHOSPHATE, 2-KETO-3-DEOXY-D-GLUCONIC ACID, D-SEDOHEPTULOSE, 1,4-DIAMINOBUTANE DIHYDROCLORIDE, DEOXYCARNITINE, ADENOSINE 2',3'-CYCLIC PHOSPHATE, MEVALOLACTONE, GALACTOSE 1-PHOSPHATE, DIMETHYLALLYLPYROPHOSPHATE, DEOXYURIDINE TRIPHOSPHATE, PHOSPHORYLCHOLINE, O-ACETYLCARNITINE, 6-HYDROXYDOPAMINE, THIAMINE, DGDP, 5-METHYLCYTOSINE, GLYCERATE, CYTIDINE 2',3'-CYCLIC PHOSPHATE, N,N,N-TRIMETHYLLYSINE, RIBOFLAVIN, URIDINE DIPHOSPHATE GLUCOSE, METHYL GALACTOSIDE, PYRIDOXAL-PHOSPHATE, DIHYDROXYACETONE PHOSPHATE, PHOSPHOENOLPYRUVATE, MANNOSE 6-PHOSPHATE, 3-PHOSPHOGLYCERATE, L-CARNITINE, O-PHOSPHOETHANOLAMINE, O-ACETYLSERINE, CYTIDINE MONOPHOSPHATE, GUANOSINE DIPHOSPHATE MANNOSE, ADP-GLUCOSE, FRUCTOSE 6-PHOSPHATE, ADENOSINE 3',5'-DIPHOSPHATE, 3-NITRO-L-TYROSINE, P-OCTOPAMINE, N-ALPHA-ACETYLLYSINE, URIDINE DIPHOSPHATEGALACTOSE, DIHYDROXYFUMARATE, PYRIDOXAMINE, 5-AMINOLEVULINATE, DEOXYURIDINE-MONOPHOSPHATE, 5'-DEOXYADENOSINE, RIBOSE 1,5-BISPHOSPHATE, XANTHOSINE-MONOPHOSPHATE, FAD, DEOXYGUANOSINE, OROTATE, LAUROYLCARNITINE, 1-METHYLNICOTINAMIDE, SPERMINE, N-ACETYLMETHIONINE, CARBAMOYL PHOSPHATE, PHOSPHORIBOSYL PYROPHOSPHATE, AICAR, URIDINE DIPHOSPHATE-N-ACETYLGALACTOSAMINE, GLYCERALDEHYDE 3-PHOSPHATE, CYCLIC GMP, HOMOCYSTEINE THIOLACTONE, O-PHOSPHOSERINE, S-ADENOSYLHOMOCYSTEINE, L-ORNITHINE, ADENINE, NORMETANEPHRINE, URIDINE DIPHOSPHATE-N-ACETYLGLUCOSAMINE, GUANOSINE DIPHOSPHATE, GLUTATHIONE REDUCED, URIDINE DIPHOSPHATE GLUCURONIC ACID, N,N-DIMETHYLARGININE, CYTIDINE DIPHOSPHATE, SELENOCYSTAMINE, HISTAMINE, INDOXYL SULFATE, ETHYL 3-UREIDOPROPIONATE, DEOXYRIBOSE, PHYTATE, THIAMINE MONOPHOSPHATE, URACIL 5-CARBOXYLATE, S-HEXYL-GLUTATHIONE, GLYOXYLATE, GUANOSINE MONOPHOSPHATE, N-ACETYLALANINE, 4-GUANIDINOBUTANOATE, HYDROXYPYRUVATE, D-MANNOSAMINE, CYTOCHROME C, DEOXYADENOSINE, N-ACETYLPUTRESCINE, N-ACETYLGALACTOSAMINE, N-ACETYLGLUTAMATE, 2,4-DIHYDROXYPTERIDINE, 6-HYDROXYNICOTINATE, N-ACETYLCYSTEINE, INOSINE-MONOPHOSPHATE, PANTOTHENATE, 2-AMINOISOBUTYRATE, ANILINE-2-SULFONATE, S-CARBOXYMETHYLCYSTEINE, RHAMNOSE, THIAMINE PYROPHOSPHATE, HISTIDINOL, THYMIDINE-MONOPHOSPHATE, UREIDOPROPIONATE, 5-AMINOPENTANOATE, NORLEUCINE, N-FORMYLGLYCINE, ADENOSINE, RAFFINOSE, MESO-TARTRATE, 2-ACETAMIDO-2-DEOXY-BETA-D-GLUCOSYLAMINE, SACCHARATE, ADENOSINE TRIPHOSPHATE, 3-METHOXYTYROSINE, LACTOSE, 3-HYDROXYBUTANOATE, 4-IMIDAZOLEACETATE, GALACTURONATE, CYTIDINE TRIPHOSPHATE, CYCLIC AMP, METHIONINE SULFOXIMINE, CIS-4-HYDROXY-D-PROLINE, N1-ACETYLSPERMINE, GLUCOSAMINE 6-SULFATE, NADPH, 3-METHYLHISTAMINE, MALEAMATE, CHOLINE, METHYL 4-AMINOBUTYRATE, N-FORMYL-L-METHIONINE, ACETYLCHOLINE, OXALATE, 5-HYDROXYTRYPTOPHAN, D-ALANINE, THEOBROMINE, GUANIDINOSUCCINATE, HISTIDINE, ALLOTHREONINE, PHOSPHOCREATINE, SPERMIDINE, ADENOSINE DIPHOSPHATE RIBOSE, 2-METHOXYETHANOL, CITRAMALATE, ANSERINE, BILIVERDIN, 5-HYDROXYLYSINE, CYSTEAMINE, OPHTHALMATE, MESOXALATE, TRIGONELLINE, EPINEPHRINE, 3,4-DIHYDROXYPHENYLGLYCOL, CADAVERINE, 2-HYDROXYBUTYRATE, COENZYME A, OXALOMALATE, INOSINE TRIPHOSPHATE, CDP-ETHANOLAMINE, 2,5-DIMETHYLPYRAZINE, STACHYOSE, DEOXYCYTIDINE-DIPHOSPHATE, 2,3-BUTANEDIOL, D-RIBOSE 5-PHOSPHATE, HYDROXYKYNURENINE, GALACTOSAMINE, DEOXYADENOSINE TRIPHOSPHATE, GLYCEROL 3-PHOSPHATE, CYANOCOBALAMIN, 4-HYDROXY-L-PHENYLGLYCINE, N-ACETYLSERINE, URIDINE 5'-DIPHOSPHATE, METHYGLUTARATE, SORBATE, MONOETHYLMALONATE, GLUCONOLACTONE, 4-HYDROXYBENZOATE, TYRAMINE, CORTISOL, PRENOL, 3-HYDROXYBENZALDEHYDE, XANTHURENATE, 2-METHYLPROPANAL, INDOXYL β-GLUCOSIDE, TRIMETHYLAMINE, MELATONIN, MALEATE, PENTANOATE, PROPANOATE, BILIRUBIN, NICOTINE, PREGNENOLONE SULFATE, KYNURENATE, ISOBUTYRATE, 3-HYDROXYBENZYL ALCOHOL, ANILINE, ACETOIN, 3,5-DIIODO-L-TYROSINE, MANDELATE, TRYPTAMINE, 4-AMINOBENZOATE, GLUTARATE, 5-VALEROLACTONE, CAFFEATE, LUMICHROME, BETA-ALANINE, N-ACETYLPHENYLALANINE, N-ACETYLPROLINE, L-TRYPTOPHANAMIDE, PHENOL, N-METHYLTRYPTAMINE, OXALOACETATE, 2,3-DIHYDROXYBENZOATE, 2-PROPENOATE, INDOLE-3-ETHANOL, FERULATE, GLYCOCHOLATE, PHENYLETHANOLAMINE, THIOPURINE S-METHYLETHER, 2-HYDROXY-4-(METHYLTHIO)BUTANOATE, GLYCOCHENODEOXYCHOLATE, BENZOATE, 3-AMINO-5-HYDROXYBENZOATE, PYROCATECHOL, 3,4-DIHYDROXYBENZOATE, CYCLOPENTANONE, PANTOLACTONE, GUAIACOL, 2-HYDROXYPHENYLACETATE, 10-HYDROXYDECANOATE, DIDECANOYL-GLYCEROPHOSPHOCHOLINE, 2-HYDROXYPYRIDINE, 3,4-DIHYDROXYPHENYLACETATE, N6-(DELTA2-ISOPENTENYL)-ADENINE, METHYL VANILLATE, 2-OXOBUTANOATE, LIPOAMIDE, 3-HYDROXYANTHRANILATE, 3-(4-HYDROXYPHENYL)PYRUVATE, HEXANOATE, METHYLMALONATE, INDOLE-3-ACETATE, CORTISOL 21-ACETATE, INDOLE-3-ACETAMIDE, HIPPURATE, ETHYLMALONATE, 3,5-DIIODO-L-THYRONINE, FUMARATE, BENZALDEHYDE, 4-HYDROXYBENZALDEHYDE, 3-(2-HYDROXYPHENYL)PROPANOATE, 3-METHOXYTYRAMINE, BENZYLAMINE, 2-QUINOLINECARBOXYLATE, SEROTONIN, PTERIN, BUTANOATE, 2-AMINOPHENOL, 6-CARBOXYHEXANOATE, INDOLE-3-PYRUVATE, DEHYDROASCORBATE, 3-AMINO-4-HYDROXYBENZOATE, 3,4 DIHYDROXYMANDELATE, 2-METHYLCITRATE, DIHYDROBIOPTERIN, BETA-GLYCEROPHOSPHATE, GLUCOSE 1-PHOSPHATE, 2,3-DIAMINOPROPIONATE, 2,5-DIHYDROXYBENZOATE, 4-QUINOLINECARBOXYLATE, HYDROQUINONE, DETHIOBIOTIN, 3-HYDROXYBENZOATE, 2-METHYLBUTANAL, N-ACETYLSEROTONIN, HYDROPHENYLLACTIC ACID, ITACONATE, AZELATE, OXOADIPATE, 2-METHYLGLUTARATE, PHENYLACETALDEHYDE, 3-METHYL-2-OXOVALERATE, PORPHOBILINOGEN, DIACETYL, PYRUVATE, TRANS-CINNAMALDEHYDE, 2,6-DIHYDROXYPYRIDINE, VANILLIN, METHYL ACETOACETATE, SUBERATE, ADIPATE, GERANYL-PP, N-ACETYLLEUCINE, 2',4'-DIHYDROXYACETOPHENONE, BENZYL ALCOHOL, MONOMETHYLGLUTARATE, INDOLE-3-METHYL ACETATE, MEVALONATE, 3-METHOXY-4-HYDROXYMANDELATE, HOMOVANILLATE, 2-METHYLMALEATE, 1-PHENYLETHANOL, SALSOLINOL, SALICYLAMIDE, OXOGLUTARATE, ETHYL 3-INDOLEACETATE, 3-ALPHA, 11-BETA, 17,21-TETRAHYDROXY-5-BETA-PREGNAN-20-ONE, N,N-DIMETHYL-1,4-PHENYLENEDIAMINE, HOMOGENTISATE, INDOLEACETALDEHYDE, 4-HYDROXY-3-METHOXYPHENYLGLYCOL, 3-HYDROXYPHENYLACETATE, 4-METHYLCATECHOL, PYRIDOXAL, SALICYLATE, SEBACATE, 3-METHYL-2-OXINDOLE, 3-METHYLADENINE, HYDROXYPHENYLLACTATE, BIOTIN, MERCAPTOPYRUVATE, PYRUVIC ALDEHYDE, PYRROLE-2-CARBOXYLATE, 5-HYDROXYINDOLEACETATE, 3-METHYLGLUTACONATE, RESORCINOL MONOACETATE, ACETOACETATE, ACETYLPHOSPHATE, SORBOSE, XYLITOL, RIBITOL, MYOINOSITOL, MANNOSE, XYLOSE, SUCROSE, GALACTOSE, ALPHA-D-GLUCOSE, ALLOSE, MANNITOL, MELIBIOSE, SORBITOL, MALTOSE, TAGATOSE, L-GULONOLACTONE, ARABINOSE, CELLOBIOSE, PSICOSE, ARABITOL, LYXOSE, RIBOSE, PALATINOSE, D-PINITOL, VITAMIN D2, SQUALENE, 4-COUMARATE, NONANOATE, ESTRADIOL-17ALPHA, CAPRYLATE, URSODEOXYCHOLATE, PETROSELINATE, DIPALMITOYLGLYCEROL, CORTICOSTERONE, LITHOCHOLATE, PROTOPORPHYRIN, HEPTANOATE, RETINOL, MENAQUINONE, ELAIDATE, CHENODEOXYCHOLATE, MYRISTATE, CHOLESTERYL OLEATE, ROSMARINATE, GLYCERYL TRIPALMITATE, CORTEXOLONE, LITHOCHOLYLTAURINE, PALMITOLEATE, PALMITATE, LIOTHYRONINE, SPHINGANINE, LANOSTEROL, LAURATE, ARACHIDATE, ERUCATE, DEOXYCHOLATE, KETOLEUCINE, EICOSAPENTAENOATE, HEPTADECANOATE, GLYCERYL TRIMYRISTATE, LINOLEATE, SPHINGOMYELIN, 7-DEHYDROCHOLESTEROL, THYROXINE, BIS(2-ETHYLHEXYL) PHTHALATE, GAMMA-LINOLENATE, OMEGA-HYDROXYDODECANOATE, METHYL JASMONATE, DIPALMITOYL-PHOSPHATIDYLCHOLINE, HEXADECANOL, 5,6-DIMETHYLBENZIMIDAZOLE, RETINOATE, INDOLE, CHOLATE, PHYLLOQUINONE, CHOLESTERYL PALMITATE, QUINOLINE, DOCOSAHEXAENOATE, DIETHYL 2-METHYL-3-OXOSUCCINATE, RETINYL PALMITATE, 2-UNDECANONE, 1-HYDROXY-2-NAPHTHOATE, DIPALMITOYL-PHOSPHOETHANOLAMINE, PHENYLPYRUVATE, TRANS-CINNAMATE, OLEATE, STEARATE, BETA-CAROTENE, 25-HYDROXYCHOLESTEROL, NERVONATE, DESMOSTEROL, DEOXYCORTICOSTERONE ACETATE, OLEOYL-GLYCEROL, ALPHA-TOCOPHEROL,GLYCEROL-MYRISTATE, TRICOSANOATE, COENZYME Q10, CORTISONE, DECANOATE.

In some embodiments, the metabolite of interest is a pesticide or pesticide residue. In particular embodiments, the sample for metabolomic determination is a food product. In certain embodiments, the food product is a produce product, a meat product, an agricultural product, or any combination thereof. Exemplary metabolites include but are not limited to Captan, Diuron, Triflumezopyrim, Acephate, Fenpicoxamid, Malathion, Ferbam, Ziram, S-Ethyl dipropylthiocarbamate, Inorganic bromide residues resulting from fumigation with methyl bromide, Inorganic bromide residues in peanut hay and peanut hulls, Methyl bromide, Piperonyl butoxide, Pyrethrins, o-Phenylphenol and its sodium salt, Hydrogen Cyanide, Thiram, 2,4-D, Fluorine compounds, Ethylene oxide, Diazinon, 1-Naphthaleneacetic acid, Dicofol, Carbaryl, Dodine, Maleic hydrazide, Mancozeb, Ethoxyquin, Chlorpropham, Endosulfan, Disulfoton, Linuron, DCPA, Coumaphos, Diphenylamine, Folpet, Trichlorfon, Dicloran, p-Chlorophenoxyacetic acid, Dimethoate, Paraquat, Phorate, Trifluralin, Benfluralin, Terbacil, Bromacil, Propachlor, S-Ethyl cyclohexylethylthiocarbamate, Simazine, Naled, Metiram, Atrazine, Prometryn, Phosphine, Diquat, Dicamba, Fluometuron, Dichlobenil, Dichlorvos, Triphenyltin hydroxide, Bensulide, Thiabendazole, Propazine, Streptomycin, Alachlor, Tetrachlorvinphos, Methomyl, Carbofuran, Ametryn, Propargite, Phosmet, Ethoprop, Aldicarb, Tribuphos, Propanil, Chlorothalonil, Formetanate hydrochloride, Phenmedipham, Zinc phosphide, Amitraz, 2-(Thiocyanomethylthio)benzothiazole, Methanearsonic acid, Pentachloronitrobenzene, Picloram, Endothall, N-1-Naphthyl phthalamic acid, Methidathion, Dicrotophos, Ethephon, Carboxin, Oxamyl, Oryzalin, Triallate, Pyrazon, Propyzamide, 4-(2-Methyl-4-chlorophenoxy) butyric acid, Interim tolerances, Bromoxynil, Napropamide, S-(2-(Ethylsulfinyl)ethyl) O,O-dimethyl phosphorothioate, 4-(2,4-Dichlorophenoxy) butyric acid, Metribuzin, Oxytetracycline, MCPA, 2,4-Dinitro-6-octylphenyl crotonate and 2,6-dinitro-4-octylphenyl crotonate, Chlorpyrifos, Ethofumesate, Fenamiphos, Nitrapyrin, Terbufos, Desmedipham, Bentazon, Norflurazon, Asulam, Pendimethalin, Fenbutatin-oxide, Glyphosate, n-Octyl bicycloheptenedicarboximide, Metolachlor, 5-Ethoxy-3-(trichloromethyl)-1,2,4-thiadiazole, Thiophanate-methyl, 2,6-Dimethyl-4-tridecylmorpholine, Diflubenzuron, Permethrin, Vinclozolin, Oxyfluorfen, Sodium salt of acifluorfen, Mepiquat (N,N-dimethylpiperidinium), Diclofop-methyl, Tebuthiuron, Hydramethylnon, Hexazinone, Iprodione, Thiobencarb, Thidiazuron, Profenofos, Chlorsulfuron, Thiodicarb, Metalaxyl, Pirimiphos-methyl, Triadimefon, Fluazifop-P-butyl, Sethoxydim, Imazalil, Cyromazine, Aluminum tris (O-ethylphosphonate), Ethalfluralin, Triclopyr, Cypermethrin and isomers alpha-cypermethrin and zeta-cypermethrin, Chlorpyrifos-methyl, Fluridone, Fenarimol, Clomazone, 2-[4,5-Dihydro-4-methyl-4-(1-methylethyl)-5-oxo-1H-imidazol-2-yl]-3-quinoline carboxylic acid, Tau-Fluvalinate, Metsulfuron methyl, Chlorimuron ethyl, Fenoxaprop-ethyl, Clopyralid, Lactofen, Fomesafen, Propiconazole, Deltamethrin, Cyfluthrin and the isomer beta-cyfluthrin, Imazamethabenz-methyl, Lambda-cyhalothrin and an isomer gamma-cyhalothrin, Thifensulfuron methyl, Tefluthrin, Quizalofop ethyl, Bifenthrin, Myclobutanil, Sulfur dioxide, Bensulfuron methyl, Clofentezine, Imazethapyr, Hexythiazox, Avermectin B1 and its delta-8,9-isomer, Beta-(4-Chlorophenoxy)-alpha-(1,1-dimethylethyl)-1H-1,2,4-triazole-1-ethanol, Tribenuron methyl, Primisulfuron-methyl, Nicosulfuron, Procymidone, Bitertanol, Clethodim, Triasulfuron, Benoxacor, Cadusafos, Pyridate, Quinclorac, Dimethenamid, 4-(Dichloroacetyl)-1-oxa-4-azaspiro[4.5]decane, Fenpropathrin, Carbon disulfide, Flumetsulam, Dichlormid, Acetochlor, Furilazole, Imidacloprid, Glufosinate ammonium, Tebuconazole, Difenoconazole, Triflumizole, Flumiclorac pentyl, Rimsulfuron, Halosulfuron-methyl, Fenbuconazole, Prosulfuron, Tebufenozide, Flutolanil, Cyproconazole, Chlorethoxyfos, Pyrithiobac sodium, Imazapic, Propylene oxide, Triflusulfuron-methyl, Dimethomorph, Pyridaben, Spinosad, Sulfentrazone, Propamocarb, Imazapyr, Hydroprene, Aminoethoxyvinylglycine hydrochloride (avigycline HCl), Cymoxanil, Emamectin, Cyclanilide, Azoxystrobin, Mefenpyr-diethyl, Pyriproxyfen, Buprofezin, Chlorfenapyr, Cloransulam-methyl, Carfentrazone-ethyl, Fludioxonil, Fipronil, Pyrimethanil, Bromide ion and residual bromine, Fumigants for grain-mill machinery, Fumigants for processed grains used in production of fermented malt beverage, Metaldehyde, Resmethrin, Synthetic isoparaffinic petroleum hydrocarbons, Flufenacet, N-(4-fluorophenyl)-N-(1-methylethyl)-2-[[5-(trifluoromethyl)-1, 3, 4-thiadiazol-2-yl] oxy]acetamide and its metabolites containing the 4-fluoro-N-methylethyl benzenamine tolerances for residues, Cyprodinil, Esfenvalerate, Fluroxypyr 1-methylheptyl ester, Isoxaflutole, d-Limonene, Fenitrothion, Diclosulam, Methoxyfenozide, Prallethrin, Mefenoxam, Prohexadione calcium, Diflufenzopyr, Fluthiacet-methyl, Sulfosulfuron, Fenhexamid, Kresoxim-methyl, Trifloxystrobin, Pymetrozine, Tetraconazole, Clodinafop-propargyl, Cloquintocet-mexyl, Acibenzolar-S-methyl, Flucarbazone-sodium, Ethametsulfuron-methyl, Indoxacarb, Thiamethoxam, Fenpyroximate, Zoxamide, Flumioxazin, Forchlorfenuron, Isoxadifen-ethyl, Mesotrione, Bifenazate, Tepraloxydim, Fluazinam, Sulfuryl fluoride, Cyhalofop-butyl, Bispyribac-sodium, Acetamiprid, Fenamidone, Iodosulfuron-Methyl-Sodium, Iprovalicarb, Pyraclostrobin, Triticonazole, Tolylfluanid, Pyraflufen-ethyl, Clothianidin, Famoxadone, Quinoxyfen, Boscalid, 2, 6-Diisopropylnaphthalene (2, 6-DIPN), Trifloxysulfuron, Butafenacil, Etoxazole, Thiacloprid, Flufenpyr-ethyl, Fosthiazate, Mesosulfuron-methyl, Novaluron, Acequinocyl, Propoxycarbazone, Cyazofamid, Spiroxamine, Dinotefuran, Mepanipyrim, Penoxsulam, Spiromesifen, Spirodiclofen, Fluoxastrobin, Aminopyralid, Pinoxaden, Topramezone, Flonicamid, Kasugamycin, Amicarbazone, Fenpropimorph, Metconazole, Benthiavalicarb-isopropyl, Epoxiconazole, Etofenprox, Dithianon, Ethaboxam, Flufenoxuron, Metrafenone, Orthosulfamuron, Prothioconazole, Fluopicolide, Chlorantraniliprole, Flutriafol, Pyrasulfotole, Fenazaquin, Florasulam, Tembotrione, Spinetoram, 1,3-dichloropropene, Mandipropamid, Pyroxsulam, Flubendiamide, Pyridalyl, Spirotetramat, Uniconazole, Cyprosulfamide, Thiencarbazone-methyl, Ipconazole, d-Phenothrin, Meptyldinocap, Saflufenacil, Isoxaben, Imazosulfuron, Ethiprole, Indaziflam, Isopyrazam, Flazasulfuron, Amisulbrom, Metaflumizone, Penthiopyrad, Pyroxasulfone, Pyriofenone, Fluopyram, Trinexapac-ethyl, Ametoctradin, Penflufen, Sedaxane, Fluxapyroxad, Cyflufenamid, tolerance for residues, Sulfoxaflor, Picoxystrobin, Fenpyrazamine, Cyantraniliprole, Triforine, Proquinazid, Tolfenpyrad, Fenpropidin, Cyflumetofen, Tricyclazole, Flupyradifurone, Fluensulfone, Isofetamid, Bicyclopyrone, Benalaxyl-M, Oxathiapiprolin, Benzovindiflupyr, Teflubenzuron, Diethofencarb, Aminocyclopyrachlor, Mandestrobin, Halauxifen-methyl, Tioxazafen, Benzobicyclon, Cyclaniliprole, Tolpyralate, Flutianil, Chlormequat chloride, Pydiflumetofen, Afidopyropen, Pyrifluquinazon, Bixafen, 6-benzyladenine, Sulfometuron-methyl, Mefentrifluconazole, Valifenalate, Isotianil, Pethoxamid, and 1-Aminocyclopropane-1-carboxylic acid (ACC).

In other embodiments, the metabolites pertain to fermentation, fermentation pathway intermediates, and side products produced by a fermentation host. In particular embodiments, the fermentation host is engineered. Exemplary metabolites include but are not limited to GLUTAMINE, CITRATE, THREONINE, SERINE, CYSTEINE, CITRUL- LINE, ISOLEUCINE, GLUTAMATE, GLYCINE, METHIONINE, L-ALANINE, PROLINE, SHIKIMATE, ISOCITRATE, TYROSINE, ASPARAGINE, VALINE, HOMOSERINE, DIAMINOPIMELATE, AMINOADIPATE, 3-DEHYDROSHIKIMATE, HOMOCYSTEINE, LEUCINE, O-SUCCINYL-HOMOSERINE, LYSINE, PHOSPHOSERINE, CYSTATHIONINE, ARGININE, S-ADENOSYLMETHIONINE, DIHYDROXYACETONE PHOSPHATE, PHOSPHOENOLPYRUVATE, O-ACETYLSERINE, CARBAMOYL PHOSPHATE, PHOSPHORIBOSYL PYROPHOSPHATE, O-PHOSPHOSERINE, S-ADENOSYLHOMOCYSTEINE, L-ORNITHINE, N-ACETYLGLUTAMATE, HISTIDINOL, HISTIDINE, D-RIBOSE 5-PHOSPHATE, OXALOACETATE, 2-OXOBUTANOATE, 3-(4-HYDROXYPHENYL)PYRUVATE, OXOADIPATE, PYRUVATE, OXOGLUTARATE, KETOLEUCINE, and PHENYLPYRUVATE.

Internal Standards

In various embodiments, the sample further includes a set of standards including chemical species of known identity and concentration. In preferred embodiments, the chemical species in the set of standards are distinct and from the set of metabolites to be determined, for example by virtue of having a different molecular weight from any of the metabolites. In various embodiments, the standard species are added to the sample such that the final concentration of the one or more of the standards is known. In particular embodiments, the final concentration of each standard in the sample is determined by add-mixing to a known volume of the sample a known volume of one or more solutions containing one or more of the standards in known concentration and then accounting for all volumetric dilution factors.

In particular embodiments, the set of standards are heavy standards including isotopically labeled species. In particular embodiments, the set of heavy standards for inclusion in the sample is selected to cover a range of molecular weights. In particular embodiments, the molecular weight range covered by the set of heavy standards is 18 to 5,000 g/mol, 20 to 2,000 g/mol, 50 to 1,000 g/mol, about 50 to 800 g/mol, or 50 to 600 g/mol. In certain embodiments, the number of heavy standards added to the sample at known concentration is 1, 2, 3, 4, 5, 6, 7, 8, 9, 10, 11, 12, 13, 14, 15, 16, 17, 18, 19, 20, 21, 22, 23, 24, 25, 30, 35, 40, 45, 50. In particular embodiments, the heavy standards added to the sample at known concentration are selected from 1,4-Butanediamine (putrescine)·2HCl (13C4, 99%), L-Alanine (13C3, 99%; 15N, 99%), Ethanolamine HCl (1,1,2,2-D4, 98%), Sodium pyruvate (13C3, 99%), Creatinine (N-methyl-D3, 98%), Fumaric acid (13C4, 99%), Vitamin B3 (nicotinamide) (13C6, 99%), Thymine (1,3-15N2, 98%), L-Leucine (13C6, 99%), Hypoxanthine (13C5, 99%), L-Phenylalanine (ring-13C6, 99%), Indole-3-acetic acid (phenyl-13C6, 99%), L-Tyrosine (ring-13C6, 99%), a-Ketoglutaric acid, disodium salt (1,2,3,4-13C4, 99%) CP 97%, Citric acid (1,5,6-carboxyl-13C3, 99%), L-Tryptophan (13C11, 99%), Guanosine·2H2O (15N5, 96-98%), and Sodium palmitate (U-13C16, 98%).

High-Resolution Mass Spectrometry

In various embodiments, the mass accuracy is less than or equal to 75 ppm, less than or equal to 30 ppm, less than or equal to 15 ppm, less than or equal to 10 ppm, or less than or equal to 5 ppm.

Instrument Signals & Adducts

In various embodiments, the signal for each of the one or more metabolites is a mass spectrometric signal corresponding to the known molecular weight for the parent ions corresponding to the one or more metabolites. In particular embodiments, the signal obtained from the mass spectrometer is the peak signal intensity obtained for the exact isotopic mass for each of the one or more metabolites of known molecular weight. In other embodiments, the signal obtained from the mass spectrometer is the signal area under the curve integrated within a MW range surrounding the exact isotopic mass for each of the one or more metabolites of known molecular weight.

In other embodiments, the signal obtained from the mass spectrometer for each of the one or more metabolites combines the signals corresponding to one or more mass adducts for the one or more metabolites. In particular embodiments, the one or more metabolite signals are obtained by calculating the sum of the adduct signals for 1, 2, 3, 4, 5, 6, 7, 8, 9 or 10 metabolite adducts. In particular variations, the metabolite adducts correspond to the proton, sodium, potassium, calcium, magnesium, ammonium, nitrate, sulfate, phosphate, acetate, citrate, or formate adducts. In one embodiment, the MW of the adduct is calculated by subtracting the mass of a proton and adding the mass of the corresponding adduct species. In another embodiment, the MW of the adduct is calculated by adding the mass of a proton.

Acquisition Parameters

In some embodiments, the acquisition parameters of the mass spectrometer are set based on the known set of one or more metabolites for analysis. In various embodiments, the acquisition parameters are programmed into the instrument to control the mass spectrometer operation. In some embodiments, the acquisition parameters are programmed into the mass spectrometer instrument in the form of a script read by the instrument or the software package that controls the instrument. In some embodiments, the acquisition parameters are programmed into the mass spectrometer in advance of the acquisition period. In other embodiments, the acquisition parameters are programmed into the instrument during the signal acquisition process. In particular embodiments, the acquisition parameters are programmed into the instrument during the signal acquisition process based on the value of the signal measured during the acquisition process.

In certain embodiments, the acquisition parameter programmed into the instrument is the acquisition mode. In particular embodiments, the acquisition mode is set to scan mode. In other embodiments, the acquisition mode is set to selected ion mode. In yet other embodiments, the acquisition mode is set to parallel reaction monitoring mode.

In certain embodiments, the acquisition parameter programmed into the instrument is the ionization mode. In particular embodiments, the ionization mode is positive ionization mode or negative ionization mode.

In certain embodiments, the acquisition parameter programmed into the instrument is the automatic gain control (AGC) setting. In particular embodiments, the AGC setting programmed into the instrument is 1%, 5%, 10%, 15%, 20%, 30%, 40%, 50%, 60%, 70%, 80%, 90%, 100%, 120%, 140%, 160%, 180%, 200%, 300%, 400%, 500%, 1000%, 5000%, 1000%, or unlimited.

In certain embodiments, the acquisition parameter programmed into the instrument is the acquisition time (also sometimes called the injection time). In particular embodiments, the acquisition time is set to 1 ms, 5 ms, 10 ms, 50 ms, 100 ms, 200 ms, 300 ms, 400 ms, 500 ms, 600 ms, 700 ms, 800 ms, 900 ms, 1000 ms, 1500 ms, 2000 ms, 2500 ms, 3000 ms, 4000 ms, 5000 ms, 10000 ms, 20000 ms, 50000 ms, 10s, 20s, 30s, 60s, 1 min, 2 min, 3 min, 4, min, 5, min, or 10 min.

In certain embodiments, the acquisition parameter programmed into the instrument is the molecular weight (MW) width. In particular embodiments, the MW width is 1 g/mol, 2 g/mol, 3 g/mol, 4 g/mol, 5 g/mol, 6 g/mol, 7 g/mol, 8 g/mol, 9 g/mol, 10 g/mol, 15 g/mol, 20 g/mol, 30 g/mol, 40 g/mol, 50 g/mol, 60 g/mol, 70 g/mol, 80 g/mol, 90 g/mol, 100 g/mol, 200 g/mol, 300 g/mol, 400 g/mol, 500 g/mol, 600 g/mol, 700 g/mol, 800 g/mol, 900 g/mol, 1000 g/mol, 1500 g/mol, 2000 g/mol, 3000 g/mol, 4000 g/mol, 5000 g/mol, 10000 g/mol, 20000 g/mol, 50000 g/mol. In other embodiments, the MW width is 1 m/z, 2 m/z, 3 m/z, 4 m/z, 5 m/z, 6 m/z, 7 m/z, 8 m/z, 9 m/z, 10 m/z, 15 m/z, 20 m/z, 30 m/z, 40 m/z, 50 m/z, 60 m/z, 70 m/z, 80 m/z, 90 m/z, 100 m/z, 200 m/z, 300 m/z, 400 m/z, 500 m/z, 600 m/z, 700 m/z, 800 m/z, 900 m/z, 1000 m/z, 1500 m/z, 2000 m/z, 3000 m/z, 4000 m/z, 5000 m/z, 10000 m/z, 20000 m/z, 50000 m/z.

In certain embodiments, the acquisition parameter programmed into the instrument is the molecular weight (MW) scan range. In particular embodiments, the scan range is set to 10-5000 m/z, 20-2000 m/z, 30-3000 m/z, 50-1000 m/z, 50-500 m/z, 60-325 m/z or 60-200 m/z. In other embodiments, the scan range is centered on or near the mass of a target metabolite and the scan width is used to set the minimum and maximum of the scan range. In particular embodiments, the scan range or scan width is chosen to account for variability in the detector response envelope function. In one embodiment, the scan range or scan width is chosen to extend the acquisition range to greater than that of the metabolite or standard molecular masses to increase the uniformity of the instrument response envelope function across the one or more metabolites or standards.

In some embodiments, the acquisition parameter programmed into the instrument is the instrument resolution.

Acquisition Windows and Programs

In some embodiments, the total instrument acquisition period is subdivided into one or more acquisition windows, each with its own corresponding set of instrument acquisition parameters. In various embodiments, one or more acquisition windows are combined into an instrument acquisition program including a sequence of one or more acquisition windows. In particular embodiments, one or more acquisition windows in the acquisition program correspond to different instrument acquisition parameter settings. In a particular embodiment, one or more acquisition windows corresponds to a choice of settings for the instrument acquisition mode, ionization mode, scan range, scan width, automatic gain control setting and acquisition time. In a particular embodiment, one or more acquisition windows in an acquisition program correspond to distinct instrument parameter settings. In a particular embodiment, the sequence of acquisition windows in the acquisition program contains at least 2, 3, 4, 5, 6, 7, 8, 9, 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 225, 250, 275, 300, 350, 400, 500, 600, 700, 800, 900, or 1000 windows.

In certain embodiments the acquisition windows are determined algorithmically based on the number and identity of the one or more metabolites to be determined in the sample. In particular embodiments, the acquisition program including the one or more acquisition windows is programmed into the instrument. In one embodiment, the acquisition program including the one or more acquisition windows is programmed into the instrument using a script read by the instrument or the software controlling the instrument.

In various embodiments, the acquisition program including two or more acquisition windows increases the number of detectable or quantifiable metabolites compared to an acquisition program including fewer acquisition windows. In a particular embodiment the acquisition program including two or more acquisition windows increases the number of detectable or quantifiable metabolites compared to an acquisition program with a static set of acquisition parameters. In various embodiments, the relative increase in the number of detectable or quantifiable metabolites compared to an acquisition program including a static set of acquisition parameters is at least 5%, 10%, 15%, 20%, 30%, 40%, 50%, 60%, 70%, 80%, 90%, 100%, 150%, 200%, 250%, 300%, 400%, 500%, 1000%, or 10000%.

In various embodiments the acquisition program including two or more acquisition windows decreases the signal interference between detectable or quantifiable metabolites compared to an acquisition program including fewer acquisition windows.

Calculated Response Factors

In some embodiments, the methods described herein include the determination of one or more response factors for one or more metabolites in the sample. In particular embodiments, the one or more response factors for the one or more metabolites in the sample are determined based on the detected signal for one or more standards. In various embodiments, the one or more response factors for the one or more metabolites in the sample are calculated from the signals detected for one or more standards using a model. In particular embodiments, the model for calculating the one or more response factors is a machine learning or regression mode. In various embodiments, the machine learning or regression models are selected from logistic regression, ada boost classifier, extra trees classifier, extreme gradient boosting, gaussian process classifier, gradient boosting classifier, K-nearest neighbor, light gradient boosting, linear discriminant analysis, multi-level perceptron, naïve Bayes, quadratic discriminant analysis, random forest classifier, ridge classifier, SVM (linear and radial kernels), fully-connected neural network, or a deep neural network.

In various embodiments, the features of the regression model or machine learning model correspond to the signals for one or more standards in the sample. In certain embodiments, the number of features in the regression model is optimized to maximize the predictive power of the regression or machine learning model. In particular embodiments, the number of features in the regression or machine learning model is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 200, 300, 400, or 500. In various embodiments, one or more features of the regression or machine learning model correspond to signals obtained for one or more standards using one or more distinct instrument acquisition parameters. In other embodiments, one or more features of the regression or machine learning model correspond to information about the sample composition. In particular embodiments, one or more features of the regression or machine learning model correspond to the sample matrix. In other embodiments, one or more features of the regression or machine learning model correspond to the concentrations of one or more salts in the sample. In yet other embodiments, one or more features of the regression or machine learning model correspond to the source of the sample (e.g., fermentation medium, blood sample, plasma sample, urine sample, food sample).

In certain embodiments, the quality of the regression or machine learning models is measured by a fit statistic. In particular embodiments, said fit statistic is R-squared.

In certain embodiments, the regression or machine learning models are generated by training the model using a set of training samples including known concentrations of one or more metabolites and known concentrations of one or more metabolites. In various embodiments, the training samples include various levels of impurities, such as 1%, 2%, 3%, 4%, 5%, 6%, 7%, 8%, 9%, 10%, 15%, or 20% impurities by mass.

Determination of the Level of One or More Metabolites

In some embodiments, the methods described herein include the determination of the level (e.g., concentration) of one or more metabolites in a sample. In some embodiments, the methods described herein include quantification of the level (e.g., molar concentration or mass concentration) of one or more metabolites in a sample. In various embodiments, the quantification is performed by multiplying the signal obtained from mass spectrometric detection for each of one or more metabolites by a calculated response factor for each of the one or more metabolites.

In particular embodiments, the methods described herein include the simultaneous determination of the levels of a plurality of metabolites. In various embodiments, the number of metabolites in the plurality of metabolites simultaneously determined by the method is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 300, 400, 500, 600, 700, 800, 900, 1000, 2000, 3000, 4000, or 5000.

Method Cycle Time and Throughput

In some embodiments, the methods described herein pertain to high-throughput analysis. In particular embodiments, the total method runtime is about 0.1 seconds, 0.5 seconds, 1 second, 2 seconds, 10 seconds, 30 seconds, 1 minute, 2 minutes, 3 minutes, 4 minutes or 5 minutes. In particular embodiments, the total method run time is less than 1 minute, less than 2 minutes, less than 3 minutes, less than 5 minutes, or less than 10 minutes. In certain embodiments, the number of samples analyzed per hour is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, or 60.

Performance Criteria

In some embodiments, the methods described herein include determining one or more performance criteria of each agent tested. Exemplary performance criteria include, but are not limited to, a) the production of a target level (e.g., concentration) (or range) of said at least one metabolite in each experimental culture; b) a decrease or increase in the level (e.g., concentration) of said at least one metabolite in each experimental culture, relative to the level (e.g., concentration) of said at least one metabolite produced by a corresponding control culture that did not include the agent (or combination of agents); c) a target level (e.g., concentration) (or range) of said at least one metabolite across the plurality of experimental cultures; and d) a decrease or increase in the level (e.g., concentration) of said at least one metabolite across the plurality of experimental cultures relative to the level (e.g., concentration) of said at least one metabolite produced by a plurality of corresponding control cultures that did not include the agent (or combination of agents).

In some embodiments, multiple performance criteria are determined for one or more agents tested (e.g., each agent of a plurality). In some embodiments, the at least two performance criteria include i) production of a target level (e.g., concentration) (or range) of said at least one metabolite in each experimental culture; and ii) production of a target level (e.g., concentration) (or range) of said at least one metabolite across the plurality of experimental cultures. In some embodiments, the at least two performance criteria include i) a decrease or increase in the level (e.g., concentration) of said at least one metabolite in each experimental culture, relative to the level (e.g., concentration) of said at least one metabolite produced by a corresponding control culture that did not include the agent (or combination of agents); and ii) a decrease or increase in the level (e.g., concentration) of said at least one metabolite across the plurality of experimental cultures relative to the level (e.g., concentration) of said at least one metabolite produced by a plurality of corresponding control cultures that did not include the agent (or combination of agents).

Compositions for Sample Analysis Kits

Provided herein are compositions for standards, reagents, and sample preparation kits for metabolomic analysis. In some embodiments, the compositions described herein include a solution including one or more internal standards at a known concentration. In various embodiments, said internal standards are chosen to optimize the quality of a regression or machine-learning model to predict the response factor for one or more metabolites based on the instrument signals measured for the standards.

Computer Implementation

Methods described herein, or portions of the methods described herein are, in some embodiments, performed on one or more computers. For example, portion of the methods for determining a level of one or more metabolites in a primary sample may be performed on one or more computers.

As a specific example, the training and deployment of a machine-learned model that predicts response factors corresponding to one or more internal standards and/or the calculation of levels of metabolites from instrument signals can be implemented in hardware or software, or a combination of both. In one embodiment of the invention, a machine-readable storage medium is provided, the medium including a data storage material encoded with machine readable data which, when using a machine programmed with instructions for using said data, is capable of displaying any of the datasets and execution and results of methods described herein. Methods disclosed herein can be implemented in computer programs executing on programmable computers, including a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture including a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

The following examples are meant to illustrate the invention. They are not meant to limit the invention in any way.

EXAMPLES

Example 1

The following species were dissolved in water: 13C6 15N2 Lysine, 13C5 15N Valine, 13C6 15N3 Histidine, 13C5 15N Proline, 13C4 15N Threonine, 13C5 15N Glutamic Acid, D5 Cholic Acid, 5-Fluoro Uracil, Cidifovir, and Adefovir with concentrations between 10-100 uM. The mixture was also prepared in 20% acetonitrile in water. The mixture was also prepared with at least one of the species at a concentration below one micromolar.

Example 2

The following species were dissolved in water:

| | Neutral Weight (g/mol) | Concentration (mM) |
|---|---|---|
| Ethanolamine•HCl (1,1,2,2-D4, 98%) | 65.0778 | 1.1E−01 |
| Sodium pyruvate (13C3, 99%) | 91.0261 | 1.1E+00 |
| 1,4-Butanediamine (putrescine)•2HCl (13C4, 99%) | 92.1134 | 1.5E−01 |
| L-Alanine (13C3, 99%; 15N, 99%) | 93.0547 | 1.1E+00 |
| Creatinine (N-methyl-D3, 98%) | 116.0777 | 8.6E−01 |
| Fumaric acid (13C4, 99%) | 120.0243 | 8.3E−01 |
| Thymine (1,3-15N2, 98%) | 128.0369 | 3.9E−02 |

-continued

| | Neutral Weight (g/mol) | Concentration (mM) |
|---|---|---|
| Vitamin B3 (nicotinamide) (13C6, 99%) | 128.0681 | 1.6E−01 |
| L-Leucine (13C6, 99%) | 137.1147 | 3.6E−02 |
| Hypoxanthine (13C5, 99%) | 141.0552 | 7.1E−02 |
| α-Ketoglutaric acid, disodium salt (1,2,3,4-13C4, 99%) CP 97% | 150.0349 | 5.8E−01 |
| L-Phenylalanine (ring-13C6, 99%) | 171.0991 | 2.8E−02 |
| Indole-3-acetic acid (phenyl-13C6, 99%) | 181.0834 | 5.3E−01 |
| L-Tyrosine (ring-13C6, 99%) | 187.0940 | 6.7E−01 |
| Citric acid (1,5,6-carboxyl-13C3, 99%) | 195.0370 | 5.1E−02 |
| L-Tryptophan (13C11, 99%) | 215.1267 | 4.6E−01 |
| Sodium palmitate (U-13C16, 98%) | 272.2939 | 6.9E−03 |
| Guanosine•2H2O (15N5, 96-98%) | 288.076 | 3.7E−02 |

Example 3

Figure 26:
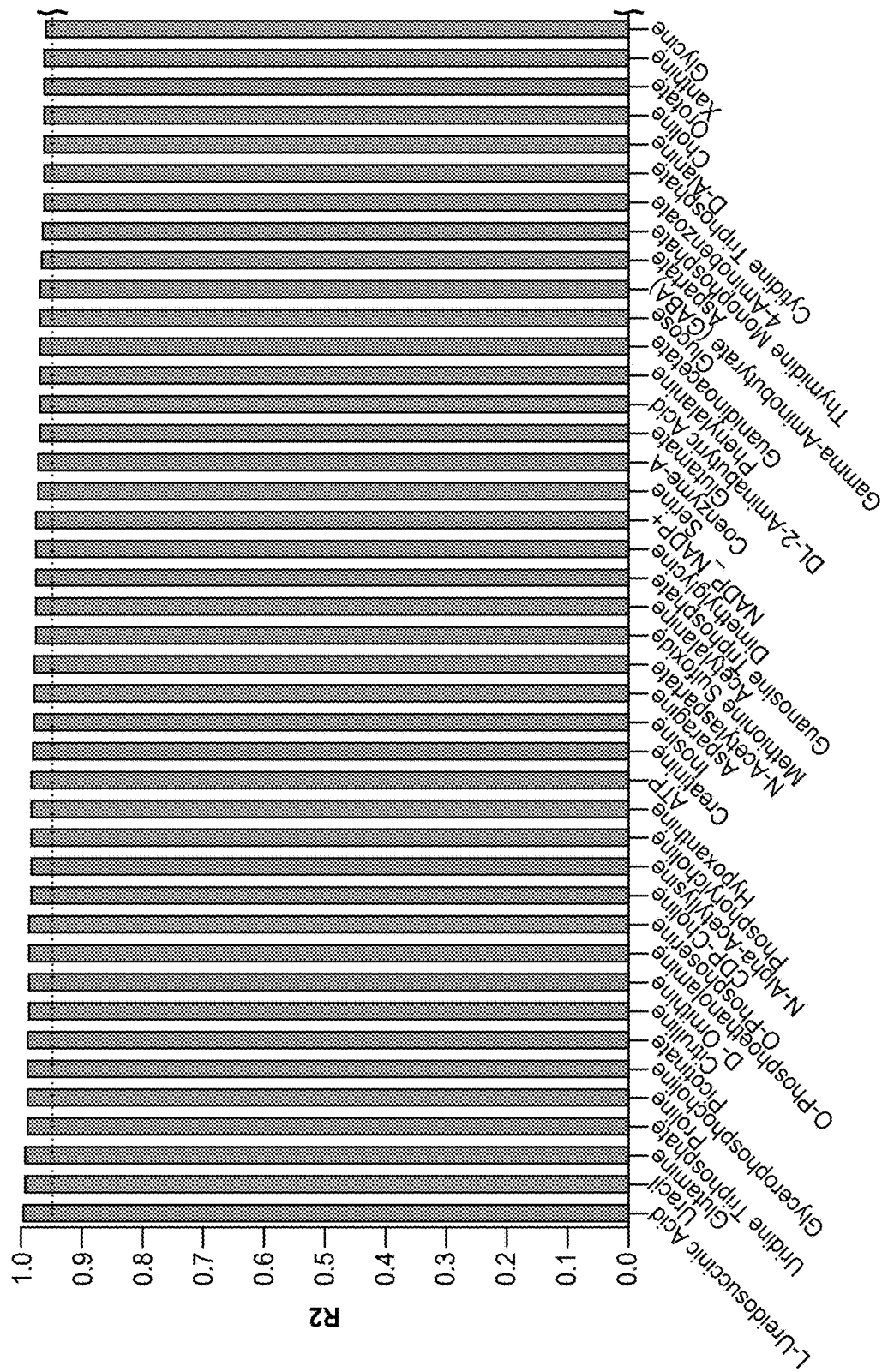
FIG. 26 schematically illustrates a chart showing the coefficients of determination ($R^2$) for measuring target analytes using exemplary internal standards according to the methods described herein.
Figure 26:
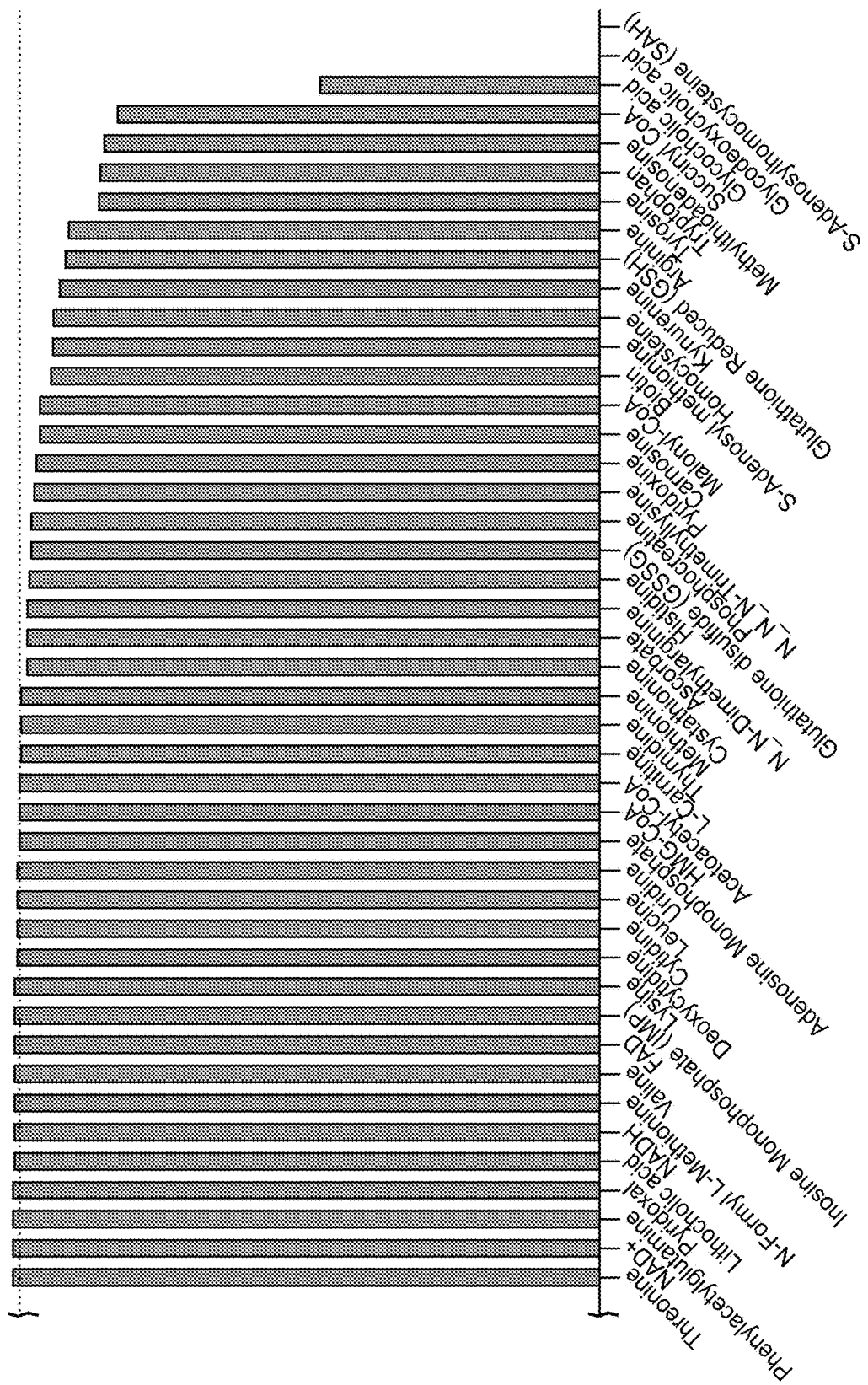

The following species were dissolved in water:
13C6 15N2 Lysine
13C5 15N Valine
13C6 15N3 Histidine
13C5 15N Proline
13C4 15N Threonine
13C5 15N Glutamic Acid
D5 Cholic Acid
5-Fluoro Uracil
Cidofovir
Adefovir The above-listed internal standards were used to quantify target analytes in one or more mixtures. The quantified target analytes and coefficient of determination (R2). The results are shown in FIG. 26.

Figure 27:
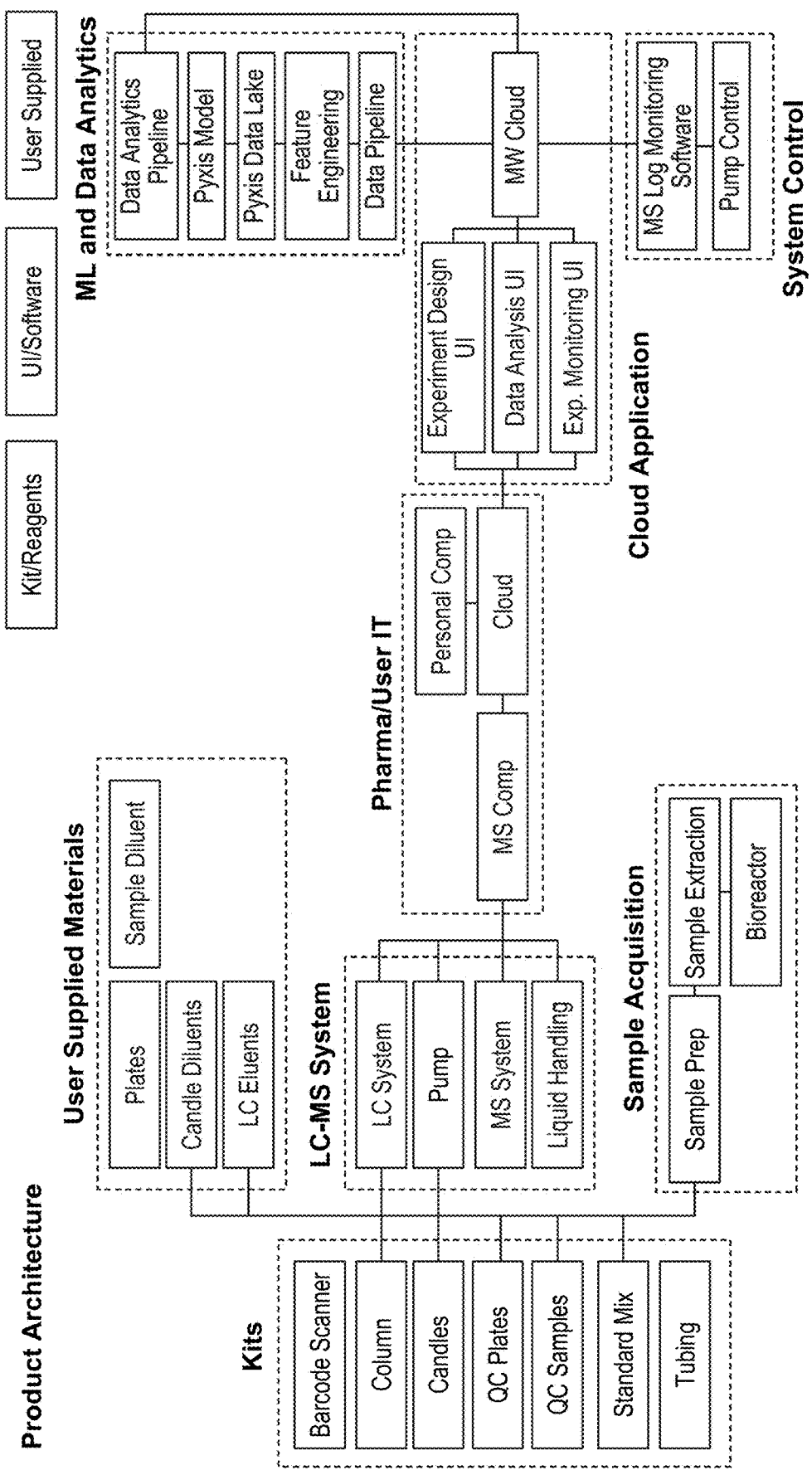
FIG. 27 schematically illustrates a diagram mapping an interrelationship and a compatibility between various kits, reagents, user interfaces, software applications, and supplies, equipment, or materials that can be used to perform or aid in a performance of a metabolomics analysis of one or more samples, in accordance with some embodiments.

FIG. 27 illustrates a diagram mapping an interrelationship and a compatibility between various kits, reagents, user interfaces, software applications, and supplies, equipment, or materials that can be used to perform or aid in a performance of a metabolomics analysis of one or more samples. The supplies, equipment, or materials can be provided or sourced from one or more users.

In some embodiments, the kit may comprise a kit for metabolomic analysis of a sample. The kit may comprise one or more calibrators that are usable in a mass spectrometer to quantify a plurality metabolites associated with one or more metabolic pathways. In some cases, a number of the plurality of metabolites can be greater than a number of the one or more calibrators. In some cases, one or more of the calibrators is used as a universal standard for quantitation of one or more analytes whose molecular structure is different from that of the calibrator. In some cases, each of the calibrators is used as a universal standard for quantitation of one or more analytes whose molecular structure is different from that of the calibrator.

In some embodiments, the one or more calibrators may comprise no more than 2, 4, 6, 8, 10, 12, 15, or 20 calibrators. In some embodiments, the plurality of metabolites may comprise at least about 40, 60, 80, 100, 120, or 150 metabolites. In some embodiments, the one or more calibrators may comprise at least two calibrators from different chemical classes. In some embodiments, the different chemical classes may be selected from the group consisting of nucleic acids, small molecules, proteins, amino acids, ethers, and sugars.

In some embodiments, the one or more calibrators are non-endogenous. In some embodiments, the one or more calibrators are non-isotopologues. In some embodiments, the one or more calibrators comprise a nonbiologic.

In some embodiments, the one or more calibrators have an ionization efficiency or an ionization potential that spans a plurality of metabolic pathways. The metabolic pathways may comprise any of the pathways shown in FIG. 23 or any pathways that are associated with any of the metabolites shown in FIG. 23. In some embodiments, at least two of the one or more calibrators may be configured to ionize both positively and negatively. In some embodiments, the ions utilized are molecular ions.

In some embodiments, the one or more calibrators may be soluble in water. In some embodiments, the one or more calibrators may be stable at room temperature. In some embodiments, the one or more calibrators may be stable in acidic and basic conditions or matrices. In some embodiments, the one or more calibrators may be non-volatile. In some embodiments, the one or more calibrators may comprise a plurality of calibrators that are non-reactive with each other and/or the one or more metabolites. In some embodiments, the one or more calibrators may comprise a plurality of calibrators that are non-reactive with a sample or one or more matrices in which the one or more metabolites are provided. In some embodiments, the one or more calibrators may be chemically inert. In some embodiments, the one or more calibrators may have a pH ranging from about 2 to about 10.

In some embodiments, the one or more calibrators may span one or more chemical spaces. In some embodiments, the one or more chemical spaces may comprise at least two analytes having a same or similar property. In some embodiments, the property may comprise a molecular mass or weight, a molecular structure, a chemical property, a physical property, or an ionization efficiency.

In some embodiments, the kit may further comprise a set of instructions for using the one or more calibrators to determine an absolute concentration of the one or more metabolites. In some embodiments, the set of instructions may comprise one or more run parameters for operating a mass spectrometer or a liquid chromatography machine. In some embodiments, the set of instructions may comprise one or more run parameters for operating a liquid chromatography (LC) system.

In some embodiments, the kit may comprise a liquid chromatography column for use with the chromatographic methods. In some embodiments, the column is a reverse phase column with a hydrophobic stationary phase. In some embodiments the column is a hydrophilic interaction chromatography (HILIC) column. In some embodiments, the column length is about 30, 50, 100, or 150 mm. In some embodiments, the column diameter is about 2.1 mm, 1 mm, or 0.5 mm. In some embodiments, the particle size of the column is about 1.7 μm to about 4 μm. In some embodiments, the particle size of the column is about 2.1 μm to about 2.5 μm.

In some embodiments, the set of instructions may comprise a standardized chromatographic gradient for use with a column included with or prescribed in the instructions. In some embodiments, the chromatographic gradient comprises a solvent gradient. In some embodiments, the gradient is isocratic. In some embodiments, the gradient is isothermal. In some embodiments the temperature is ambient temperature. In some embodiments, the temperature is about 30° C., 40° C., 45° C., or 50° C. In some embodiments, the chromatographic gradient comprises a temperature gradient. In some embodiments, the temperature gradient ranges from ambient temperature or about 30° C. to about 50° C.

In some embodiments, a first solvent of the mobile-phase of the liquid chromatographic gradient can comprise water, methanol, acetonitrile, and/or combinations thereof. In some embodiments, a second solvent of the mobile-phase of the liquid chromatographic gradient can comprise water, methanol, acetonitrile, and/or combinations thereof. In some embodiments, the first or second solvent can each independently comprise a buffer. In some embodiments, the buffer is formic acid, acetic acid, ammonium carbonate, or combinations thereof.

In some embodiments, the kit may further comprise one or more quality control samples for verifying or validating an absolute concentration of the one or more metabolites. In some embodiments, the kit may further comprise a column configured to interface with a liquid chromatography (LC) system that is coupled to the mass spectrometer. In some embodiments, the kit may further comprise a standard mixture for generating a sample mixture comprising the one or more calibrators and the one or more metabolites. In some embodiments, the kit may further comprise tubing for preparing, collecting, or delivering the sample to a LC or MS. In some embodiments, the kit may further comprise a barcode or a barcode scanner.

In some embodiments, the kit may be used to identify or detect one or more metabolic pathways. The one or more metabolic pathways may be selected from or associated with fatty acid metabolism, glycolysis, glycosylation, neurotransmission, a pentose phosphate pathway, redox, a tricarboxylic acid cycle, and a urea cycle.

In some embodiments, the kit may comprise one or more calibrators. The one or more calibrators may be selected from the group consisting of 1,4-Butanediamine (putrescine) ·2HCl (13C4, 99%), L-Alanine (13C3, 99%; 15N, 99%), Ethanolamine HCl (1,1,2,2-D4, 98%), Sodium pyruvate (13C3, 99%), Creatinine (N-methyl-D3, 98%), Fumaric acid (13C4, 99%), Vitamin B3 (nicotinamide) (13C6, 99%), Thymine (1,3-15N2, 98%), L-Leucine (13C6, 99%), Hypoxanthine (13C5, 99%), L-Phenylalanine (ring-13C6, 99%), Indole-3-acetic acid (phenyl-13C6, 99%), L-Tyrosine (ring-13C6, 99%), α-Ketoglutaric acid, disodium salt (1,2,3,4-13C4, 99%) CP 97%, Citric acid (1,5,6-carboxyl-13C3, 99%), L-Tryptophan (13C11, 99%), Guanosine·2H2O (15N5, 96-98%), and Sodium palmitate (U-13C16, 98%).

In some embodiments, the kit may be used to quantify a plurality of metabolites. The plurality of metabolites may be selected from the group consisting of beta-nicotinamide adenine dinucleotide, glutamine, hypotaurine, n-methyl-alanine, citrate, threonine, purine, n-acetylneuraminate, n-acetylmannosamine, pyrimidine, trans-aconitate, urate, cytidine, serine, cysteine, citrulline, taurine, n-acetyltryptophan, nicotinate, inosine, gamma-aminobutyrate, cytosine, isoleucine, pyrazole, glutamate, ascorbate, p-hydroxyphenylacetate, n-acetylglucosamine, glycolate, sarcosine, creatinine, quinate, dihydroorotate, malonate, guanidinoacetate, formamide, glycine, methionine, tetrahydrofolate, 2-phosphoglycerate, methylthioadenosine, thymidine, cys-gly, aminoisobutanoate, gulose, xanthine, dihydrofolate, cystine, 1-alanine, diethanolamine, uridine monophosphate, proline, thymine, succinate semialdehyde, lactate, uridine, fructose bisphosphate, carnosine, nicotinamide, shikimate, succinate, phenylalanine, uracil, thiourea, aspartate, deoxycytidine monophosphate, hypoxanthine, creatine, 1-dopa, guanosine, dihydrouracil, malate, isocitrate, tyrosine, glycerol, asparagine, valine, guanine, homoserine, pyridoxine, deoxyadenosine monophosphate, folate, nicotinamide mononucleotide, 3-methyl-1-histidine, diaminopimelate, aminoadipate, deoxycytidine, noradrenaline, glucosamine 6-phosphate, tartrate, 3-dehydroshikimate, caffeine, homocysteine, theophylline, leucine, trehalose, betaine, tryptophan, 3-sulfinoalanine, o-succinyl-homoserine, allantoin, glyceraldehyde, d-glucuronolactone, (2-aminoethyl)phosphonate, 2,5-dihydrobenzoic acid, maleimide, threitol, glucosamine, paraxanthine, adenosine 5'-diphosphate, 2-deoxy-d-glucose, 1-methyl-1-histidine, galactitol, oxoproline, 4-pyridoxate, quinolinate, methylguanidine, deoxyguanosine-monophosphate, 3-hydroxy-3-methylglutaryl-coa, glucuronate, 1-methyladenosine, deoxyuridine, gluconate, urocanate, kynurenine, pyroglutamate, 4-acetamidobutanoate, trans-1,2-cyclohexanediol, melanin, dopamine, adenosine-monophosphate, lysine, citicoline, 1,3-diaminopropane, phosphoserine, 1-aminocyclopropanecarboxylate, glutarylcarnitine, cystathionine, norvaline, 3-hydroxymethylglutarate, phosphonoacetate, picolinate, ethanolamine, arginine, trans-4-hydroxy-1-proline, fucose, homocystine, n-methylglutamate, d-ornithine, xanthosine, 3-methylcrotonyl-coa, thyrotropin releasing hormone, cysteate, n-methylaspartate, galactarate, alpha-hydroxyisobutyrate, nicotinic acid adenine dinucleotide phosphate, n-acetylasparagine, pipecolate, glucose 6-phosphate, nadp, 6-phosphogluconate, isopentenyl pyrophosphate, guanosine triphosphate, dtdp-d-glucose, agmatine sulfate, glycolaldehyde, dgtp, n-acetylglycine, n-acetylaspartate, inosine 5'-diphosphate, palmitoylcarnitine, norspermidine, nicotinamide hypoxanthine dinucleotide, s-adenosylmethionine, erythritol, glucosaminate, uridine triphosphate, 2-keto-3-deoxy-d-gluconic acid, d-sedoheptulose, 1,4-diaminobutane dihydrochloride, deoxycarnitine, adenosine 2',3'-cyclic phosphate, mevalolactone, galactose 1-phosphate, dimethylallylpyrophosphate, deoxyuridine triphosphate, phosphorylcholine, o-acetylcarnitine, 6-hydroxydopamine, thiamine, dgdp, 5-methylcytosine, glycerate, cytidine 2',3'-cyclic phosphate, n,n,n-trimethyllysine, riboflavin, uridine diphosphate glucose, methyl galactoside, pyridoxal-phosphate, dihydroxyacetone phosphate, phosphoenolpyruvate, mannose 6-phosphate, 3-phosphoglycerate, 1-carnitine, o-phosphoethanolamine, o-acetylserine, cytidine monophosphate, guanosine diphosphate mannose, adp-glucose, fructose 6-phosphate, adenosine 3',5'-diphosphate, 3-nitro-1-tyrosine, p-octopamine, n-alpha-acetyllysine, uridine diphosphategalactose, dihydroxyfumarate, pyridoxamine, 5-aminolevulinate, deoxyuridine-monophosphate, 5'-deoxyadenosine, ribose 1,5-bisphosphate, xanthosine-monophosphate, fad, deoxyguanosine, orotate, lauroylcarnitine, 1-methylnicotinamide, spermine, n-acetylmethionine, carbamoyl phosphate, phosphoribosyl pyrophosphate, aicar, uridine diphosphate-n-acetylgalactosamine, glyceraldehyde 3-phosphate, cyclic gmp, homocysteine thiolactone, o-phosphoserine, s-adenosylhomocysteine, 1-ornithine, adenine, normetanephrine, uridine diphosphate-n-acetylglucosamine, guanosine diphosphate, glutathione reduced, uridine diphosphate glucuronic acid, n,n-dimethylarginine, cytidine diphosphate, selenocystamine, histamine, indoxyl sulfate, ethyl 3-ureidopropionate, deoxyribose, phytate, thiamine monophosphate, uracil 5-carboxylate, s-hexyl-glutathione, glyoxylate, guanosine monophosphate, n-acetylalanine, 4-guanidinobutanoate, hydroxypyruvate, d-mannosamine, cytochrome c, deoxyadenosine, n-acetylputrescine, n-acetylgalactosamine, n-acetylglutamate, 2,4-dihydroxypteridine, 6-hydroxynicotinate, n-acetylcysteine, inosine-monophosphate, pantothenate, 2-aminoisobutyrate, aniline-2-sulfonate, s-carboxymethylcysteine, rhamnose, thiamine pyrophosphate, histidinol, thymidine-monophosphate, ureidopropionate, 5-aminopentanoate, norleucine, n-formylglycine, adenosine, raffinose, meso-tartrate, 2-acetamido-2-deoxy-beta-d-glucosylamine, saccharate, adenosine triphosphate, 3-methoxytyrosine, lactose, 3-hydroxybutanoate, 4-imidazoleacetate, galacturonate, cytidine triphosphate, cyclic amp, methionine sulfoximine, cis-4-hydroxy-d-proline, n1-acetylspermine, glucosamine 6-sulfate, nadph, 3-methylhistamine, maleamate, choline, methyl 4-aminobutyrate, n-formyl-1-methionine, acetylcholine, oxalate, 5-hydroxytryptophan, d-alanine, theobromine, guanidinosuccinate, histidine, allothreonine, phosphocreatine, spermidine, adenosine diphosphate ribose, 2-methoxyethanol, citramalate, anserine, biliverdin, 5-hydroxylysine, cysteamine, ophthalmate, mesoxalate, trigonelline, epinephrine, 3,4-dihydroxyphenylglycol, cadaverine, 2-hydroxybutyrate, coenzyme a, oxalomalate, inosine triphosphate, cdp-ethanolamine, 2,5-dimethylpyrazine, stachyose, deoxycytidinediphosphate, 2,3-butanediol, d-ribose 5-phosphate, hydroxykynurenine, galactosamine, deoxyadenosine triphosphate, glycerol 3-phosphate, cyanocobalamin, 4-hydroxy-1-phenylglycine, n-acetylserine, uridine 5'-diphosphate, methyglutarate, sorbate, monoethylmalonate, gluconolactone, 4-hydroxybenzoate, tyramine, cortisol, prenol, 3-hydroxybenzaldehyde, xanthurenate, 2-methylpropanal, indoxyl β-glucoside, trimethylamine, melatonin, maleate, pentanoate, propanoate, bilirubin, nicotine, pregnenolone sulfate, kynurenate, isobutyrate, 3-hydroxybenzyl alcohol, aniline, acetoin, 3,5-diiodo-1-tyrosine, mandelate, tryptamine, 4-aminobenzoate, glutarate, 5-valerolactone, caffeate, lumichrome, beta-alanine, n-acetylphenylalanine, n-acetylproline, 1-tryptophanamide, phenol, n-methyltryptamine, oxaloacetate, 2,3-dihydroxybenzoate, 2-propenoate, indole-3-ethanol, ferulate, glycocholate, phenylethanolamine, thiopurine s-methylether, 2-hydroxy-4-(methylthio)butanoate, glycochenodeoxycholate, benzoate, 3-amino-5-hydroxybenzoate, pyrocatechol, 3,4-dihydroxybenzoate, cyclopentanone, pantolactone, guaiacol, 2-hydroxyphenylacetate, 10-hydroxydecanoate, didecanoylglycerophosphocholine, 2-hydroxypyridine, 3,4-dihydroxyphenylacetate, n6-(delta2-isopentenyl)-adenine, methyl vanillate, 2-oxobutanoate, lipoamide, 3-hydroxyanthranilate, 3-(4-hydroxyphenyl)pyruvate, hexanoate, methylmalonate, indole-3-acetate, cortisol 21-acetate, indole-3-acetamide, hippurate, ethylmalonate, 3,5-diiodo-1-thyronine, fumarate, benzaldehyde, 4-hydroxybenzaldehyde, 3-(2-hydroxyphenyl)propanoate, 3-methoxytyramine, benzylamine, 2-quinolinecarboxylate, serotonin, pterin, butanoate, 2-aminophenol, 6-carboxyhexanoate, indole-3-pyruvate, dehydroascorbate, 3-amino-4-hydroxybenzoate, 3,4 dihydroxymandelate, 2-methylcitrate, dihydrobiopterin, beta-glycerophosphate, glucose 1-phosphate, 2,3-diaminopropionate, 2,5-dihydroxybenzoate, 4-quinolinecarboxylate, hydroquinone, dethiobiotin, 3-hydroxybenzoate, 2-methylbutanal, n-acetylserotonin, hydrophenyllactic acid, itaconate, azelate, oxoadipate, 2-methylglutarate, phenylacetaldehyde, 3-methyl-2-oxovalerate, porphobilinogen, diacetyl, pyruvate, trans-cinnamaldehyde, 2,6-dihydroxypyridine, vanillin, methyl acetoacetate, suberate, adipate, geranyl-pp, n-acetylleucine, 2',4'-dihydroxyacetophenone, benzyl alcohol, monomethylglutarate, indole-3-methyl acetate, mevalonate, 3-methoxy-4-hydroxymandelate, homovanillate, 2-methylmaleate, 1-phenylethanol, salsolinol, salicylamide, oxoglutarate, ethyl 3-indoleacetate, 3-alpha, 11-beta, 17,21-tetrahydroxy-5-beta-pregnan-20-one, n,n-dimethyl-1,4-phenylenediamine, homogentisate, indoleacetaldehyde, 4-hydroxy-3-methoxyphenylglycol, 3-hydroxyphenylacetate, 4-methylcatechol, pyridoxal, salicylate, sebacate, 3-methyl-2-oxindole, 3-methyladenine, hydroxyphenyllactate, biotin, mercaptopyruvate, pyruvic aldehyde, pyrrole-2-carboxylate, 5-hydroxyindoleacetate, 3-methylglutaconate, resorcinol monoacetate, acetoacetate, acetylphosphate, sorbose, xylitol, ribitol, myoinositol, mannose, xylose, sucrose, galactose, alpha-d-glucose, allose, mannitol, melibiose, sorbitol, maltose, tagatose, 1-gulonolactone, arabinose, cellobiose, psicose, arabitol, lyxose, ribose, palatinose, d-pinitol, vitamin d2, squalene, 4-coumarate, nonanoate, estradiol-17alpha, caprylate, ursodeoxycholate, petroselinate, dipalmitoylglycerol, corticosterone, lithocholate, protoporphyrin, heptanoate, retinol, menaquinone, elaidate, chenodeoxycholate, myristate, cholesteryl oleate, rosmarinate, glyceryl tripalmitate, cortexolone, lithocholyltaurine, palmitoleate, palmitate, liothyronine, sphinganine, lanosterol, laurate, arachidate, erucate, deoxycholate, ketoleucine, eicosapentaenoate, heptadecanoate, glyceryl trimyristate, linoleate, sphingomyelin, 7-dehydrocholesterol, thyroxine, bis(2-ethylhexyl)phthalate, gamma-linolenate, omega-hydroxydodecanoate, methyl jasmonate, dipalmitoyl-phosphatidylcholine, hexadecanol, 5,6-dimethylbenzimidazole, retinoate, indole, cholate, phylloquinone, cholesteryl palmitate, quinoline, docosahexaenoate, diethyl 2-methyl-3-oxosuccinate, retinyl palmitate, 2-undecanone, 1-hydroxy-2-naphthoate, dipalmitoyl-phosphoethanolamine, phenylpyruvate, trans-cinnamate, oleate, stearate, beta-carotene, 25-hydroxycholesterol, nervonate, desmosterol, deoxycorticosterone acetate, oleoyl-glycerol, alpha-tocopherol, glycerol-myristate, tricosanoate, coenzyme q10, cortisone, and decanoate. The plurality of metabolites may comprise any of the metabolites listed in FIG. 23.

Methods

The present disclosure provides methods for analyte concentration detection. In one embodiment, the present disclosure provides a method comprising (a) training a machine learning model using a plurality of raw mass spectrometry (MS) datasets that are collected for a set of calibrators and a plurality of different analytes and a plurality of different matrices. In some embodiments, the method may comprise (b) providing the trained machine learning model for processing a MS dataset of a mixed sample that comprises at least one target analyte and the set of calibrators. In some embodiments, the trained machine learning model may be configured to determine an absolute concentration of the at least one target analyte in a manner that is agnostic to matrix type. In some embodiments, the plurality of different matrices may comprise CHO Lysate, CHO Supernatent, HAM's F10 Media, Bovine Plasma, or Plasma-like Media. In some embodiments, the at least one target analyte may be embedded in a sample matrix that is different from any of the matrices used for training the machine learning model. In some embodiments, the at least one target analyte may be embedded in a sample matrix that is the same as one of the matrices used for training the machine learning model.

In some embodiments, the trained machine learning model may be configured to interpolate across the plurality of different matrices to determine the absolute concentration of the at least one target analyte in a sample matrix. In some embodiments, the absolute concentration may be determined with a relative standard deviation (RSD) of less than about 20%. In some embodiments, the absolute concentration may be determined with a mean average percentage error (MAPE) of less than about 20%. In some embodiments, the trained machine learning model may be configured to determine absolute concentrations of at least about 80% of a plurality of metabolites with a MAPE of less than about 20%. In some embodiments, the trained machine learning model may be configured to directly determine the absolute concentration of the one or more analytes in less than about 5 minutes.

In some embodiments, the machine learning model may be trained using a MS training data set comprising (i) a first set of intensity values for one or more reference metabolites having a known concentration and (ii) a second set of intensity values for one or more reference calibrators having a known concentration. In some embodiments, the MS training data set may comprise raw, unprocessed mass spec data. In some embodiments, the MS training data set can be of a same data structure or format as an MS output for the mixed sample. In some embodiments, the reference metabolites and the one or more metabolites in the sample may comprise a same metabolite or a same type or class of metabolite. In some embodiments, the reference metabolites and the one or more metabolites in the sample may comprise different metabolites or different types or classes of metabolites. In some embodiments, the reference calibrators and the one or more calibrators in the sample may comprise a same calibrator or a same type or class of calibrator.

In some embodiments, the MS output for the mixed sample may comprise at least (1) a first signal indicating an intensity value or a mass-to-charge ratio for the one or more analytes and (2) a second signal indicating an intensity value or a mass-to-charge ratio for the one or more calibrators. In some embodiments, the trained machine learning model may be configured to determine an absolute concentration of the one or more analytes based on a relationship or a correlation between the first signal and the second signal. In some embodiments, the trained machine learning model may be configured to determine the absolute concentration of the one or more analytes based on a relationship or a correlation between the first signal and a known concentration of the one or more calibrators. In some embodiments, a concentration of the one or more calibrators is known. In some embodiments, the absolute concentration of the one or more analytes can be determined based on the known concentration of the one or more calibrators.

In some embodiments, the one or more calibrators are configured to produce a signal that does not overlap or interfere with a signal of the one or more analytes. In some embodiments, at least one calibrator of the one or more calibrators may comprise an alcohol, an amino acid, a nucleoside, a nucleotide, a nucleotide analogue, or an antimetabolite.

In some embodiments, the machine learning model may be trained using (1) a combinatorial library comprising a plurality of metabolites of interest and a plurality of metabolite concentrations for the metabolites of interest. In some embodiments, the machine learning model may be trained using (2) a training data set comprising MS signals for a plurality of samples comprising at least one metabolite of interest, at least one candidate calibrator, and a plurality of test sample matrices.

In another aspect, the present disclosure provides a method for enabling high-throughput quantitation of biomolecules. The method may comprise (a) providing a reagent that is to be added to a sample to form a mixed sample. In some embodiments, the reagent may comprise a set of calibrators that are selected such that at least one target analyte in the sample lies within a chemical space defined by or associated with one or more calibrators from the set of calibrators. In some embodiments, the method may comprise (b) providing a machine learning model for processing a raw mass spectrometry (MS) dataset of the mixed sample to directly determine in less than about 5 minutes an absolute concentration of the at least one target analyte.

In some embodiments, the method may further comprise using the absolute concentration of the at least one target analyte to perform a metabolomics analysis. In some embodiments, the metabolomics analysis may comprise identifying or characterizing a metabolic pathway. In some embodiments, the metabolomics analysis may comprise characterizing a cell response or a cell behavior for one or more cells based at least in part on the absolute concentration of the one or more analytes.

In some embodiments, the method may further comprise using the machine learning model to aid in identifying one or more options or solutions for optimizing a media provided to the one or more cells based on the absolute concentration of the one or more analytes and/or the characterized cell response or cell behavior, in order to promote or facilitate cell culturing or cell growth. In some embodiments, the method may further comprise using the characterized cell response or cell behavior to aid in a development of one or more cell lines. In some embodiments, the method may further comprise using the characterized cell response or cell behavior to aid in a development of one or more processes for cell line manufacturing. In some embodiments, the method may further comprise using the characterized cell response or cell behavior to aid in an analysis and/or comparison of clonal variations of the one or more cells and metabolic states or pathways associated with the clonal variations. In some embodiments, the method may further comprise using the characterized cell response or cell behavior to aid in a detection of one or more metabolic signatures or pathways for the one or more cells.

In some embodiments, the method may further comprise providing a run protocol comprising instructions for processing the mixed sample using a liquid chromatography (LC) or mass spectrometry (MS) machine to generate the raw MS dataset. In some embodiments, the run protocol may comprise a set of run parameters configured to control a processing of the sample by the liquid chromatography or mass spectrometry machine. In some embodiments, the set of run parameters may comprise one or more parameters for a sample flow rate, an eluent composition, a concentration gradient, or a rate of temperature ramping.

In some embodiments, (b) may further comprise determining in parallel or concurrently an absolute concentration of each of a plurality of target analytes within a total time of less than about 5 minutes. In some embodiments, the machine learning model may be configured to determine the absolute concentrations of at least 80% of the plurality of target analytes with a mean average percent error (MAPE) of less than 20%. In some embodiments, at least one target analyte may comprise a metabolite. The metabolite may be associated with one or more identifiable or detectable metabolic pathways that are previously known or previously unknown.

In some embodiments, the reagent may be provided within or as part of a metabolomics kit. In some embodiments, the set of calibrators may not or need not include an isotopologue or an isotopically labeled analogue of the at least one target analyte that is present in the sample.

In some embodiments, the machine learning model may be configured to determine the absolute concentration of the at least one target analyte without isotopologue matching. In some embodiments, the machine learning model may be configured to determine the absolute concentration of the at least one target analyte without constructing a calibration curve. In some embodiments, the machine learning model may be configured to determine the absolute concentration of the at least one target analyte without calculating an area under a curve (AUC). In some embodiments, the machine learning model may be configured to determine the absolute concentration of the at least one target analyte without computing a response factor. In some embodiments, the machine learning model may be configured to determine the absolute concentration of the at least one target analyte without performing extracted ion chromatography (XIC). In some embodiments, the machine learning model may be configured to directly determine the absolute concentration of the at least one target analyte without performing a peak integration for one or more MS signals from the MS dataset. In some embodiments, the machine learning model may be configured to detect absolute concentrations across a range of concentrations spanning at least two orders of magnitude.

In some embodiments, the methods or machine learning models of this disclosure can be used to monitor the activity within a bioreactor system. For example, metabolites sampled from the bioreactor may be quantified periodically over a period of hours or days (e.g. 1 hour, 2 hours, 4 hours, 6 hours, 12 hours, 1 day, 2 days, 3 days, 4 days, 5 days, 6 days, 7 days, 10 days, 14 days, or 30 days). The number of samples collected during the period of hours or days can vary depending on the processes involved in the bioreactor system. For example, 1, 2, 3, 5, 10, 100, 1000, or 10000 samples may be collected from a given process during the period of hours or days.

FURTHER EXAMPLES

Example 4 LC-MS Method for Quantitation of Metabolites Using Universal Standards

TABLE 1

| Mass Spectrometer Operating parameters | |
| --- | --- |
| Data Collection | 0-4.5 minutes |
| Dual Polarity Scanning | Positive mode 4 kV Negative mode 3 kV |
| Scanning | 70-1000 (m/z), 120000 res |
| RF Lens | 80% |
| Ion Transfer Tube | 350° C. |
| Vaporizer | 350° C. |

TABLE 2

| Liquid Chromatography System | |
| --- | --- |
| Column | 1.7 µm Acquity UPLC BEH Amide Column, 1.7 µm, 2.1 mm × 50 mm |
| Eluent A | 100% Water, 10 mM Ammonium Hydrogen Carbonate, pH 8 |
| Eluent B | 90% MeCN, 10% Water, 10 mM Ammonium Hydrogen Carbonate, pH 8 |

TABLE 3

| | | Liquid Chromatography Gradient | |
|---|---|---|---|
| Time | % B | Flow Rate (mL/min) | Slope |
| 0 | 100 | 0.6 | linear |
| 0.8 | 100 | 0.6 | linear |
| 2.2 | 70 | 0.6 | linear |
| 4.2 | 50 | 0.6 | linear |
| 4.7 | 30 | 0.7 | step |
| 6.2 | 100 | 0.7 | step |
| 9.2 | 100 | 0.6 | step |

Figure 28:
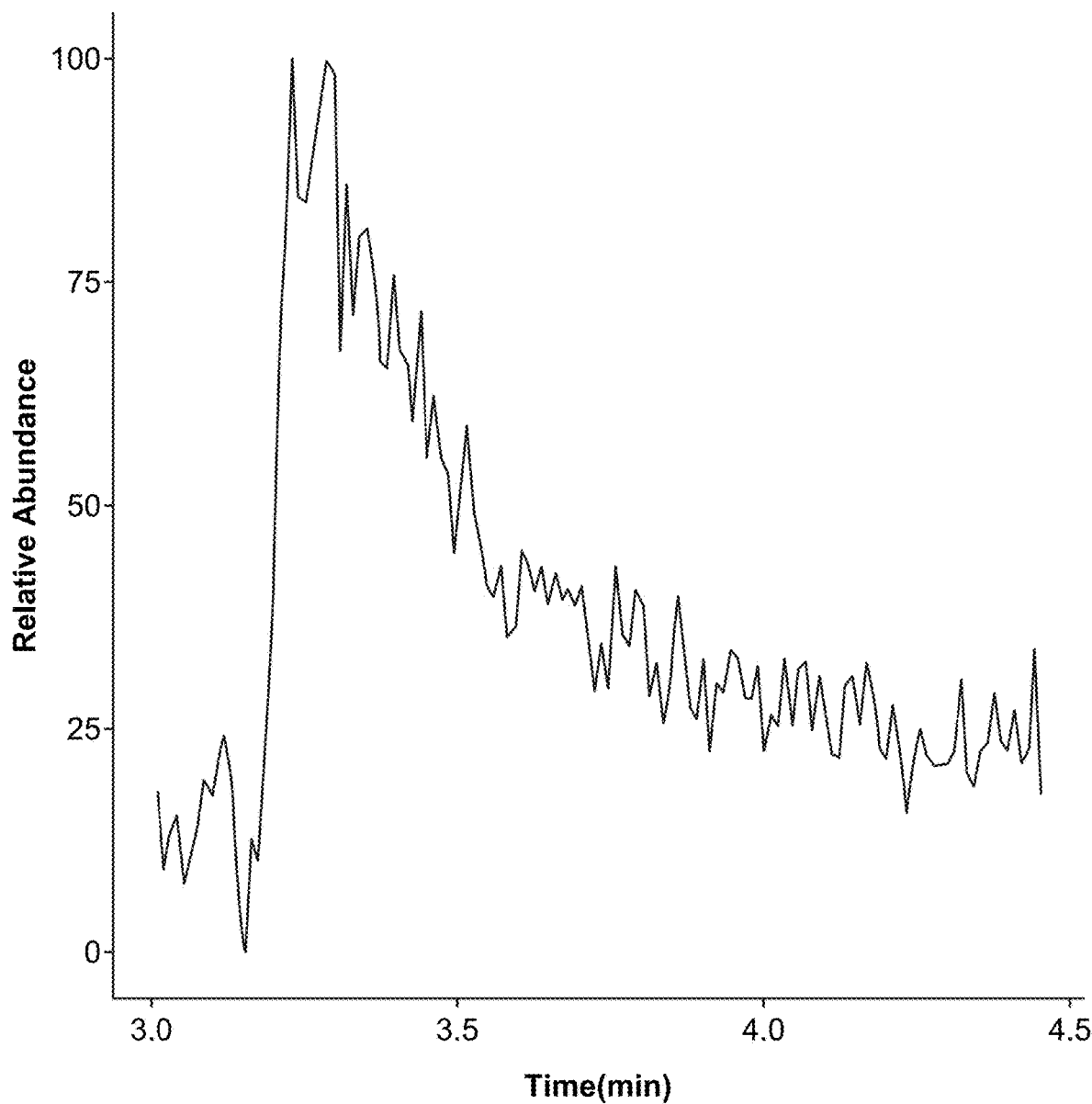
FIG. 28 illustrates an example extracted ion chromatogram of a sample analyte (Fructose-1-Biphosphate) separated using the chromatographic method of Example 4. In spite of the poor LC performance, excellent quantitative accuracy on this analyte is attained.

All data were recorded on two Thermo Orbitrap Exploris 120 mass spectrometers operated in accordance with the settings described in Table 1 and connected to Thermo Fisher Transcend LX-2/LX-4 with a Vanquish Flex, enabling parallel column equilibration and injection. Use of the chromatographic method described in Tables 2 and 3 allowed for rapid quantitation of analytes using a machine learning model with universal standards as described herein. Despite less-than-ideal chromatographic separation of the analytes (see FIG. 28 for a representative peak with an asymmetric factor worse than 1.8) accurate absolute quantitation was possible.

Example 5—Evaluation of the Analytical Performance

Figure 29:
FIG. 29 illustrates mean absolute percent errors (MAPE) for a test set of 46 metabolites—defined as a single plate (i.e., matrix-dilution combination) and incorporating 24,064 analyte-concentration data points into a machine learning model described herein. The dotted black line represents 20% error.
Figure 30:
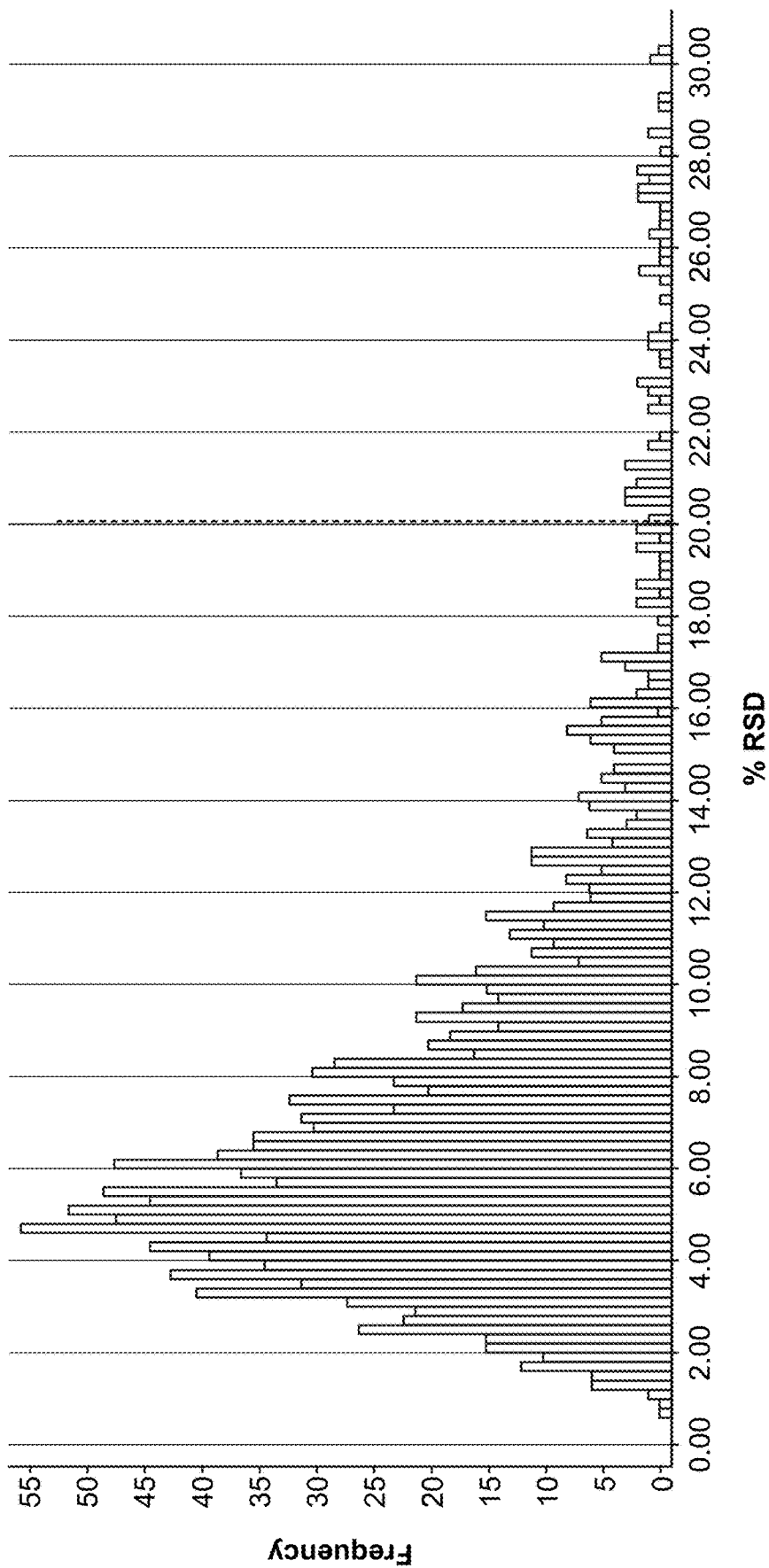
FIG. 30 illustrates the high precision of an example model through a frequency distribution of the percent residual standard deviations (% RSD) for 46 example analytes. The median % RSD across the collection of 46 analytes and the spiked in concentration range is 5%. Dotted red line represents 20% RSD.
Figure 31:
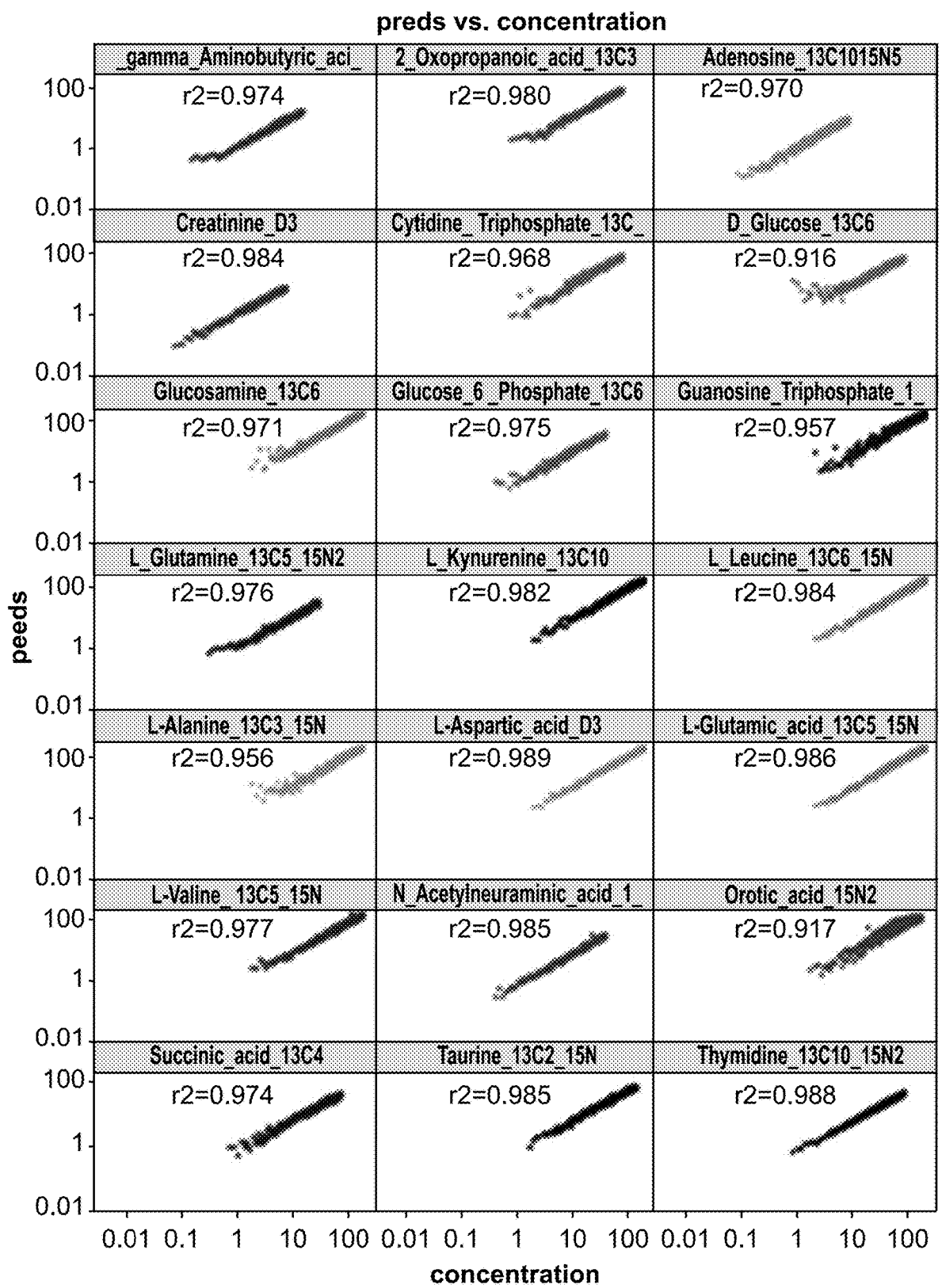
FIG. 31 illustrates an example linear regression of calculated concentration of 46 example analytes to actual concentrations, which yielded $R^2$ values between 0.913 to 0.989, indicating excellent linearity for the model in cell culture media for all measured metabolites. Matrices included in the model training set included CHO cell lysate, CHO spend media, Grace's media, HAMS media, and bovine plasma at different levels of incorporated matrix. The excellent agreement between the various matrices inherent to the model training regime and the tested sample matrix proves the model is robust to different sample types and variance within a given sample type.

A model according to this disclosure was evaluated after being trained with 24,064 training data points including samples from a variety of matrices. The quantitative performance 46 Analytes was then tested in a variety of matrices. The mean average percent error for 46 analytes was generally less than 20%, as shown in FIG. 29, the RSD was an average of approximately 5%, as shown in FIG. 30, and cross-matrix linearity showed $R^2$ values of at least 0.9 for all analytes evaluated (as shown in FIG. 31) demonstrating the robustness of the model.

Figure 32:
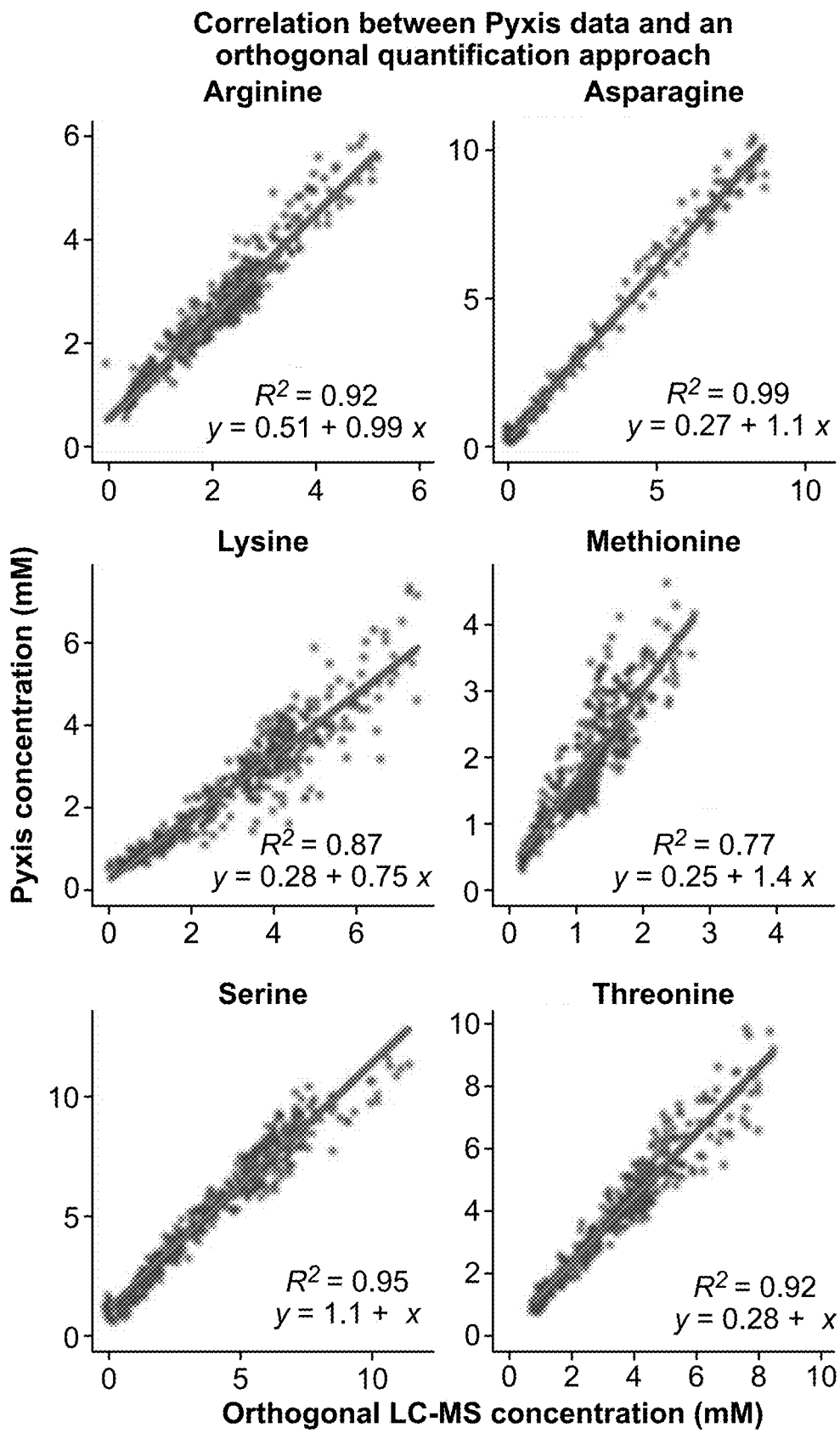
FIG. 32 illustrates post-hoc validation of model performance through high correlation (agreement) with LC-MS/MS Heavy Isotope Technique.
Figure 32:
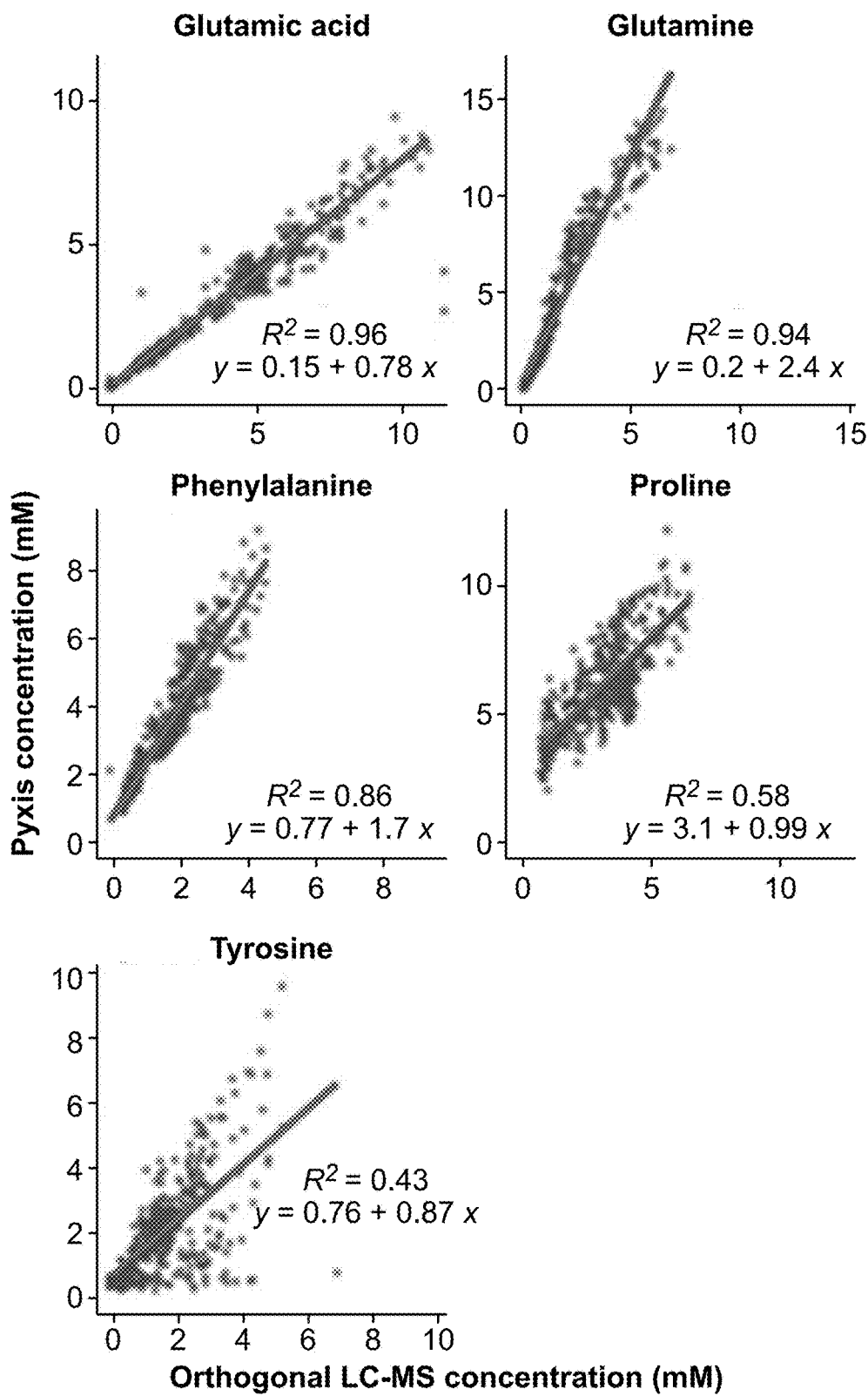

Example 6—Comparison of a Quantitative Machine Learning Model to Heavy Isotope LC-MS/MS A model according to this disclosure was evaluated against LC/MS-MS with a heavy-isotope standard for each analyte. The results of this comparison are plotted in FIG. 32. Analyte concentrations determined through the model were generally in close agreement with LC-MS/MS.

Example 7—Bioreactor Monitoring

Figure 33:
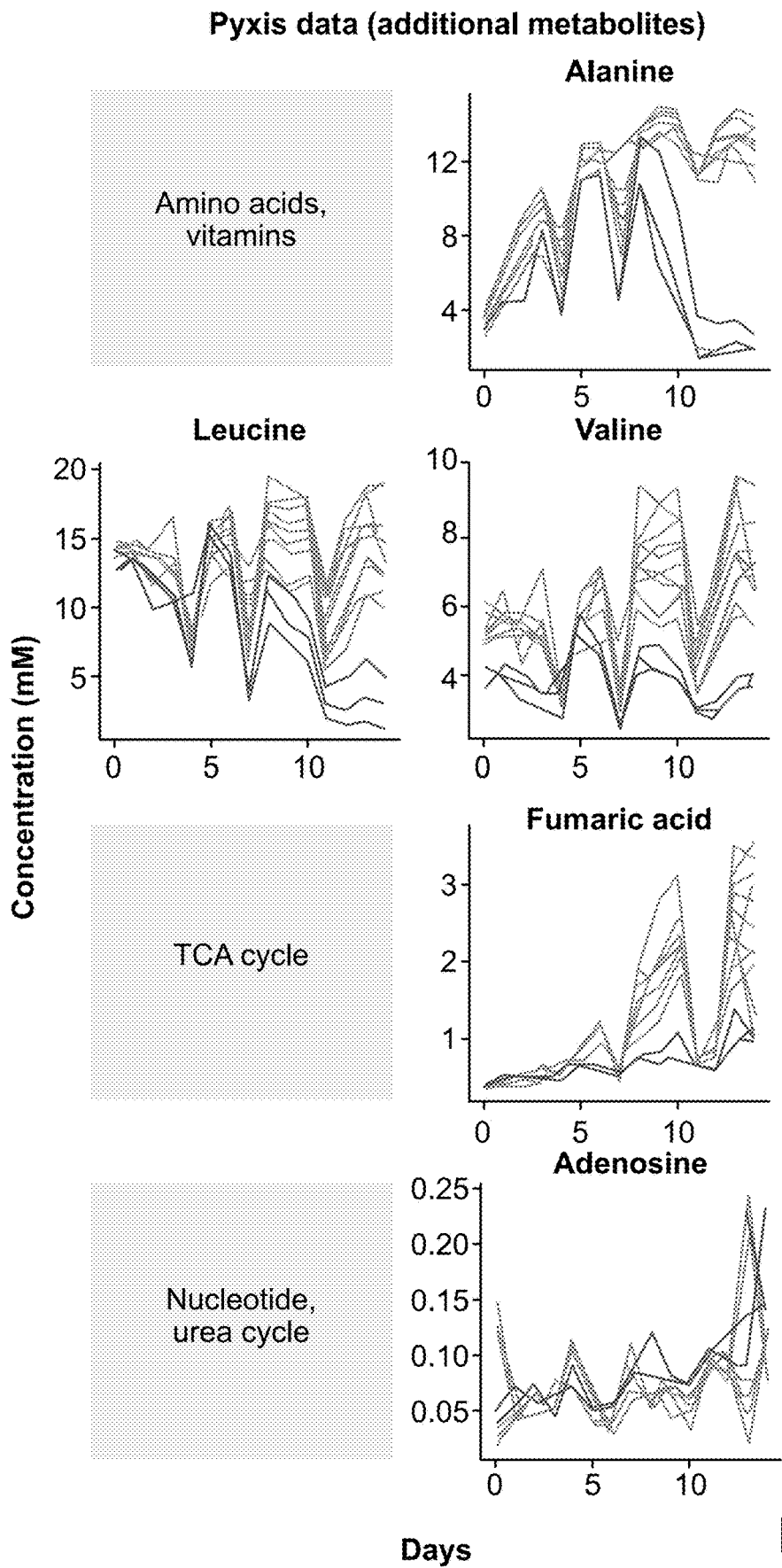
FIG. 33 illustrates example time series measurements of metabolites in a bioreactor by methods described herein. These methods offer high-throughput analysis and provide the ability to get quantitative results as samples are generated. They also provide experimental flexibility to measure on the spot rather than in relation to a treatment/control experiment and offer direct insight into intracellular activity of biological processes within the reactor.
Figure 33:
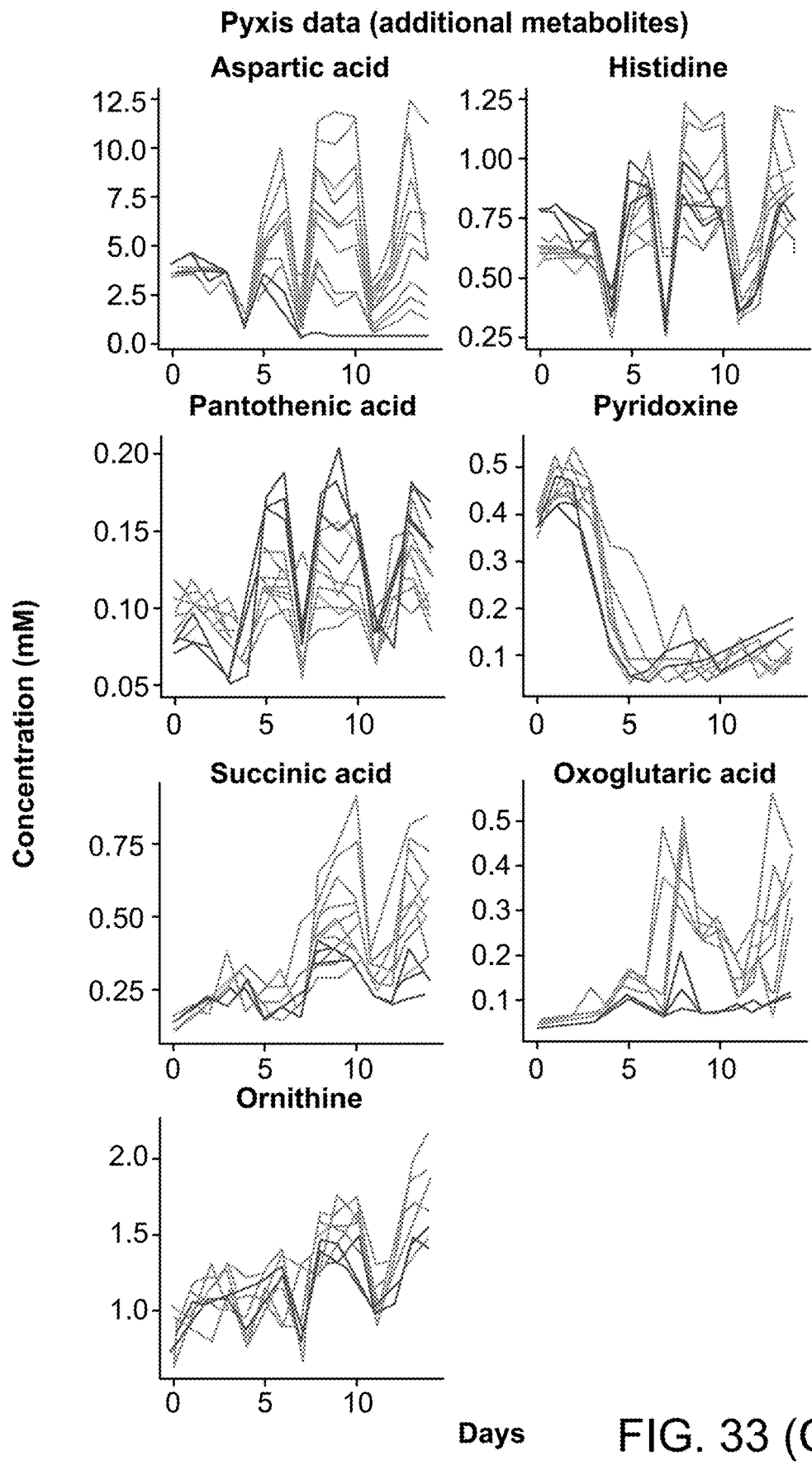
Figure 34:
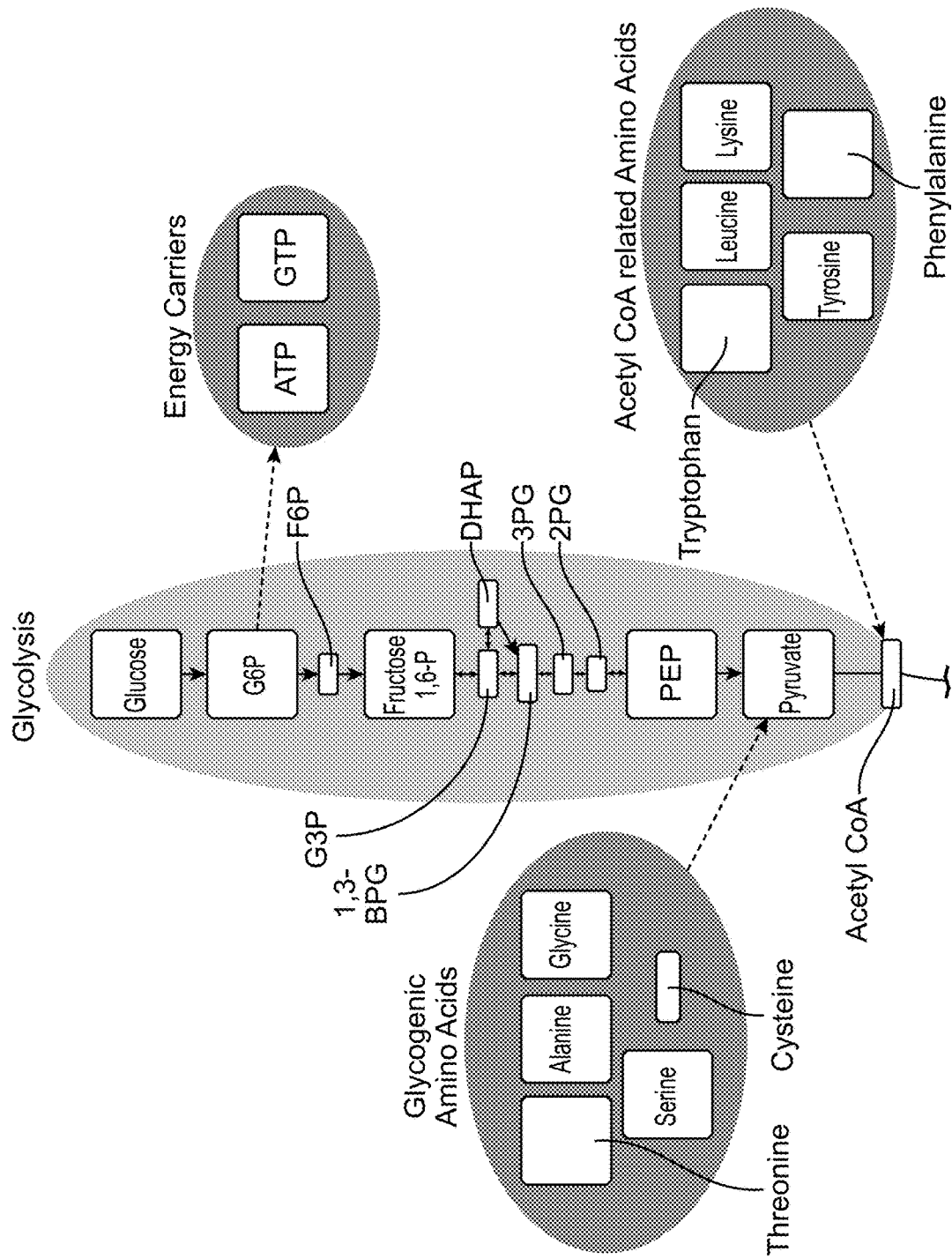
FIG. 34 illustrates metabolic pathway analysis which is possible using the models and methods described herein. Examples of using metabolomics data to assess glycosylation profiles and cellular energy metabolism (e.g. for use cases in biomanufacturing of biologics).
Figure 34:
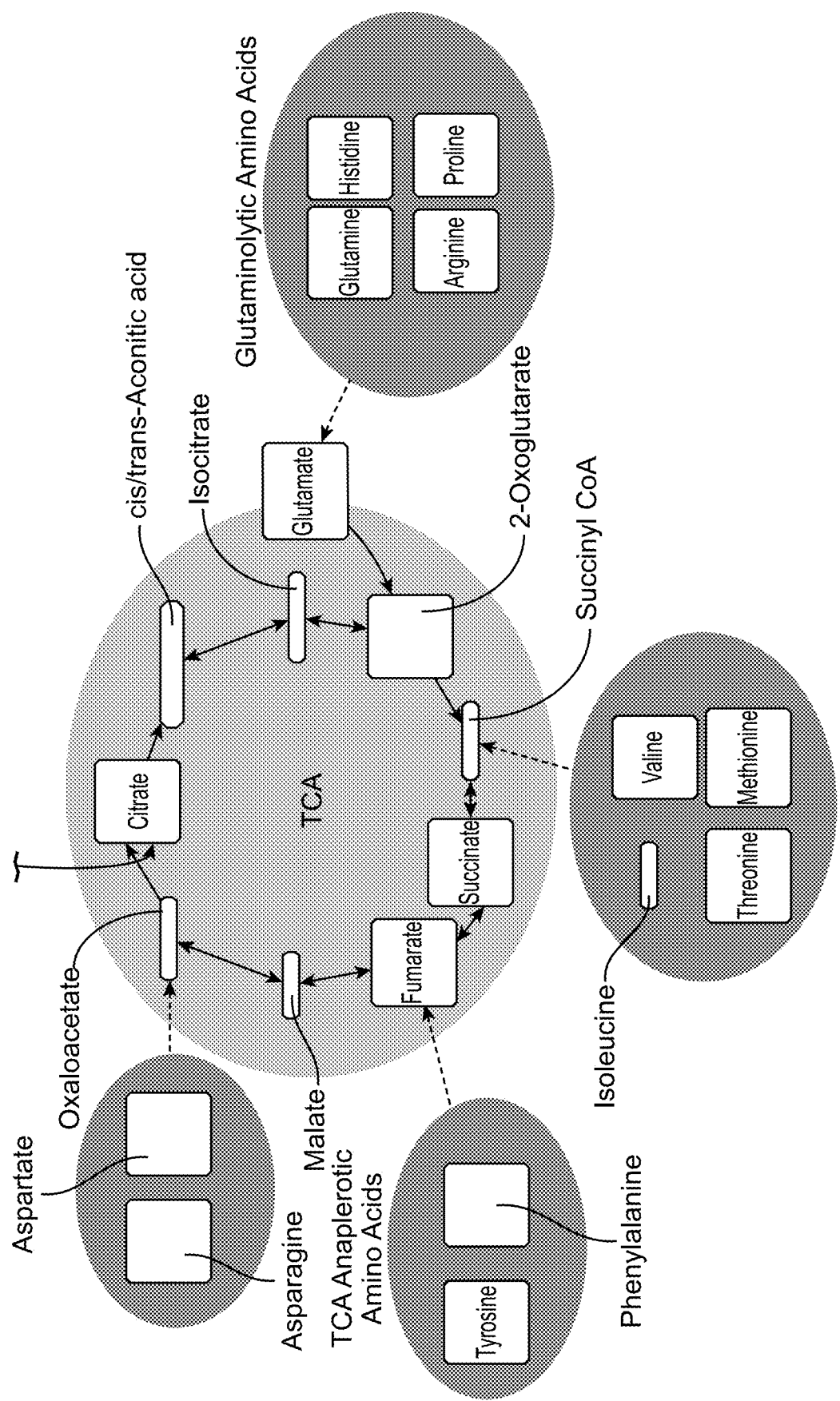
Figure 35:
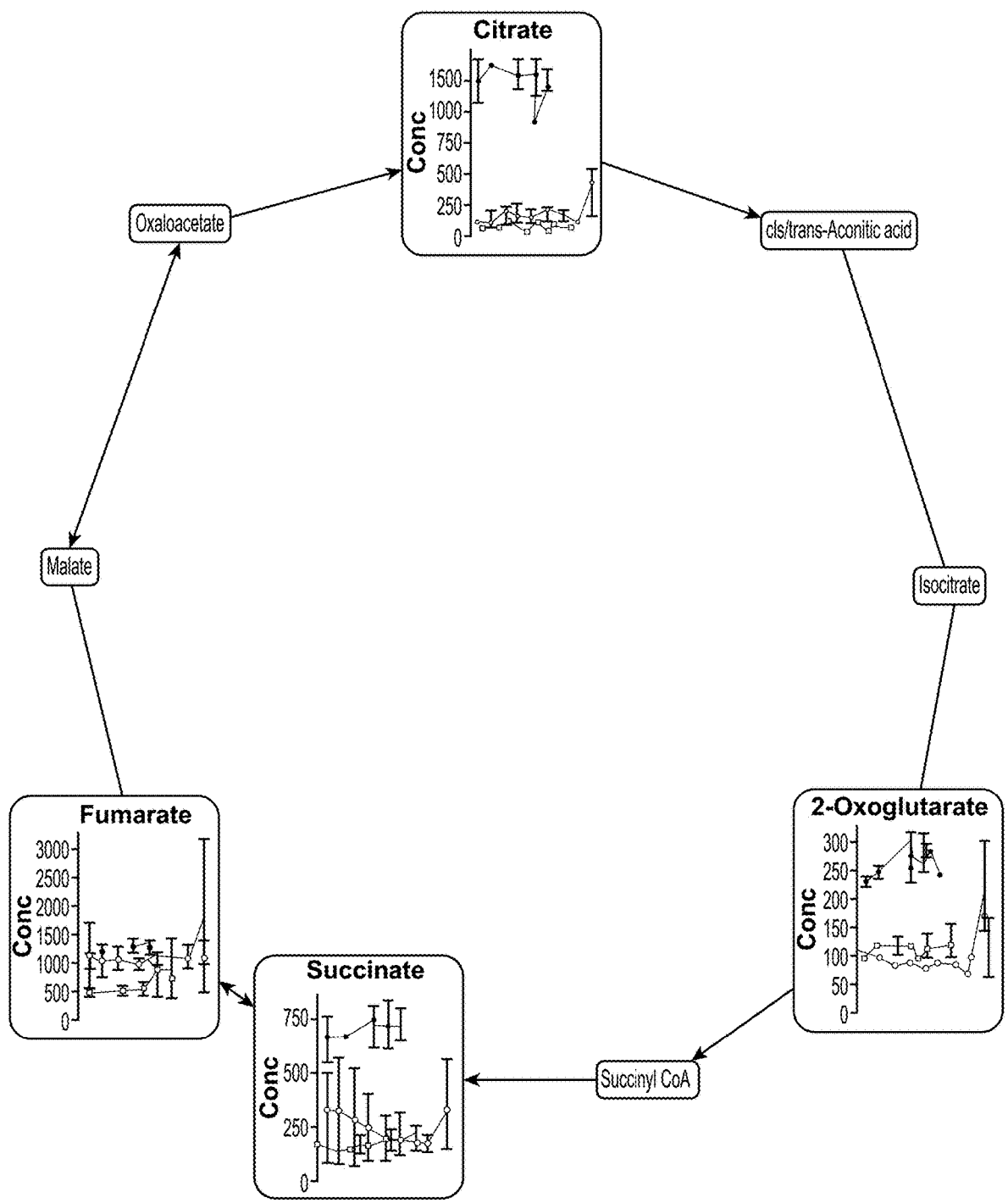
FIG. 35 illustrates analysis of protein production using methods described herein. Higher levels of citrate/2OG/succinate in the Glucose Fed Batch condition are consistent with the idea that keeping glucose constant allows the cell to continually feed the TCA with carbons in the form of Acetyl-CoA or from glutamine. An increased TCA cycle indicates more efficient energy production to drive protein synthesis.
Figure 36A:
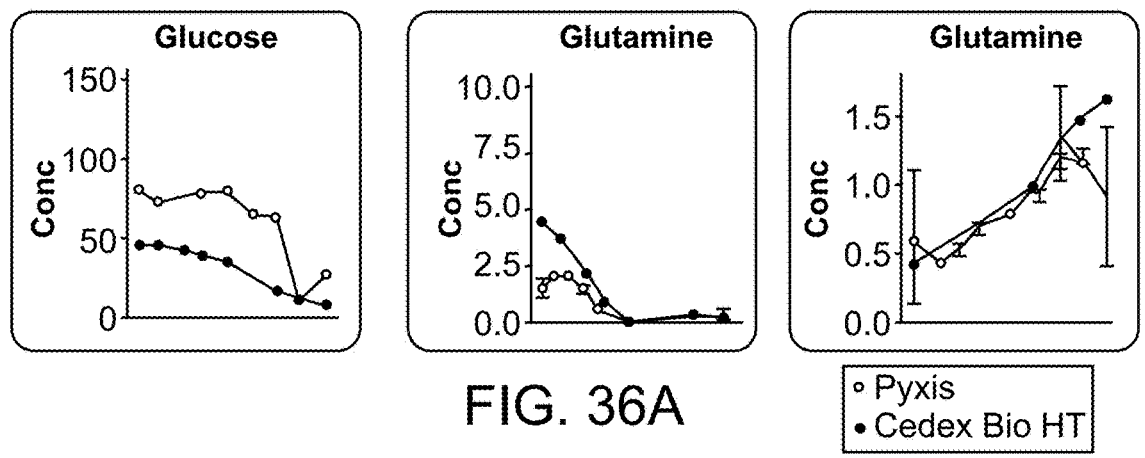
FIG. 36 illustrates important bioreactor metrics that can be probed using methods described herein. (a) Nutrient Analysis: Energy and carbon sources are important considerations for media formulation and feed strategy. Measurements of key nutrients by methods described herein correlated with measured concentrations from a Roche Cedex Bio HT at-line analyzer. This observation from the control condition saw both glucose and glutamine deplete over the course of culture. (b) Glycosylation Precursors: Availability of Acetyl-CoA and PEP directly affect the availability of N-Acetylneuraminic acid (Sialic Acid), a critical precursor for glycosylated proteins. Keeping glucose constant with a fed batch feeding strategy demonstrated a higher availability of these glycosylation precursors. (c) Energy Carrier Analysis: Higher levels of ATP/GTP were observed with the Glucose fed batch strategy as compared to the culture which allowed glucose to deplete. This suggests that this fed batch regime enables glycolysis to better meet the energy demands of the CHO cells over the course of culture.
Figure 36B:
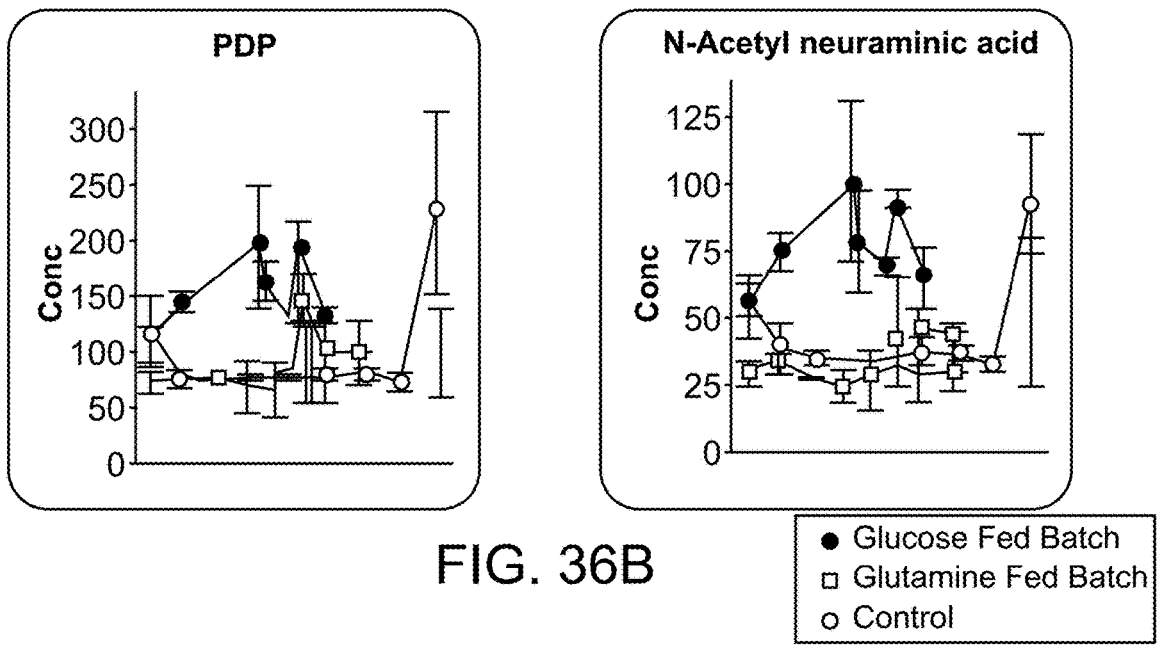
Figure 36C:
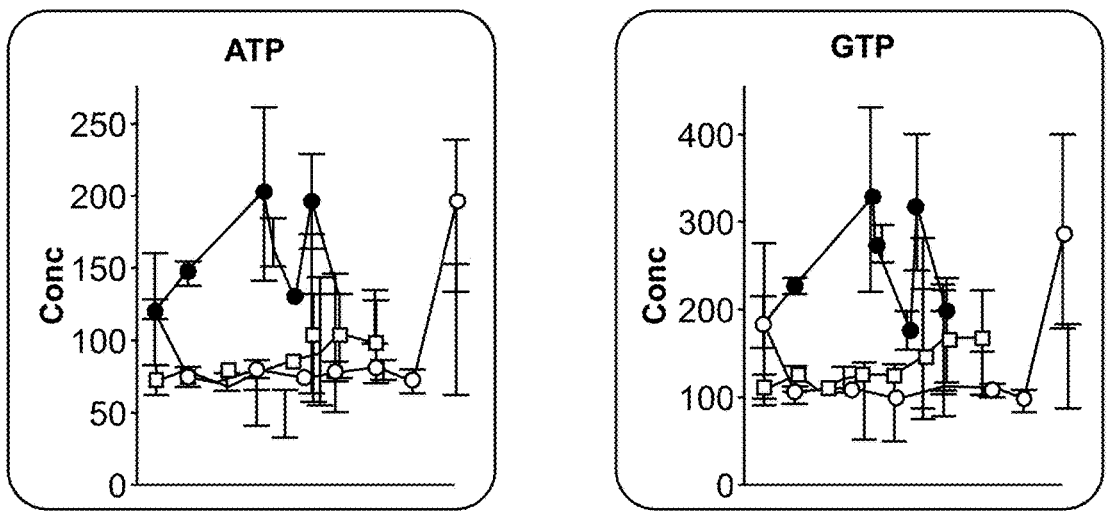

The speed, accuracy, and efficiency of the methods and models of this disclosure allow for rapid, quantitative monitoring of intracellular activity within a bioreactor. Measurements were performed using the LC method of Example 4 on samples collected from a bioreactor over a period of 15 days. Quantitative time series data for select monitored metabolites are show in FIG. 33. Monitoring metabolites over time provides insight into the activity of biological pathways within the reactor, such as the citric acid cycle, glycolysis, glycogenesis, protein production and others (for example, as detailed in FIGS. 34-35). Monitoring even a small number of the most crucial metabolites provides important detail on nutrients used to feed cells in a bioreactor (example measurements shown FIG. 36 row A), on glycosylation of proteins (example measurements shown FIG. 36 row B), and on energy carriers (example measurements shown FIG. 36 row C).

Example 8—Bioreactor Process Design

Figure 37:
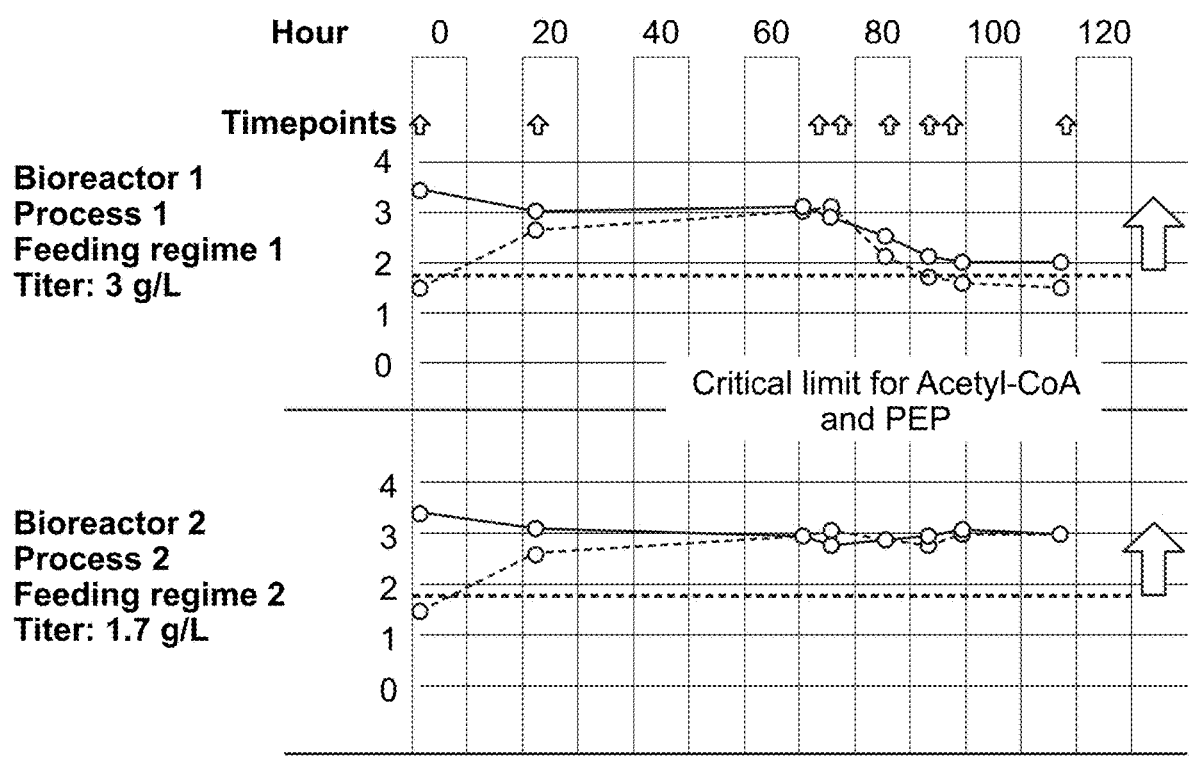
FIG. 37 illustrates use of methods described herein to guide biomanufacturing reactor process design considerations. Real-time metabolomic data enables determination of process parameters that maximize culture titer while maintaining CQAs—avoiding bridging clinical trials to re-qualify a mAb product. Comparison of two different media formulations to determine which increases titer AND maintains the correct glycoform structure allows informed refinement of reactor processes. Data produced by methods described herein provides improved insight compared to other methods which only analyze the final drug product (and would miss data that Bioreactor 1 is operating near the critical limit). Although Bioreactor 1 has a higher titer, it is more likely to produce drug with compromised product quality. Methods described herein can monitor critical market metabolites involved in glycosylation pathways that affect mAb quality. Methods described herein provide the scientific rationale to select Bioreactor 2 which has lower titer but will avoid the need for a clinical bridging study (which would require great expense and months to years delay in commercial launch). Levels below limit alter glycoform structure and change in CQA (process excursion).

Comparison of monitored bioreactor metabolites can also provide insight into process parameters, for example to allow culture titer to be maximized without requiring bridging studies in the case of a bioreactor process used for manufacturing a therapeutic. For example, as shown in FIG. 37, two experimental reactor processes are monitored. Process 1 shows a higher titer, however monitoring of critical metabolites indicate that one metabolite drops below a threshold limit (which would require a clinical bridging study). The operator can then choose either to use process 2 to avoid dropping below the limit and avoid a bridging study, or based on the timing information can modify process 1, for example by intervening at 60 hours to avoid this result and maintain higher yields.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Example 9. Alternate LC Gradients for Quantitation of Metabolites Using Universal Standards

TABLE 4

| | |
|---|---|
| Liquid Chromatography System | |
| Column | HILIC |
| Flow rate | 0.50 mL/min |
| Eluent A | 0.1% v/v formic acid in water |
| Eluent B | 0.1% v/v formic acid in acetonitrile |

TABLE 5

Liquid Chromatography Gradient

| Step Start Time (min) | Step Stop Time (min) | % B | Slope |
|---|---|---|---|
| 0 | 1 | 95 | step |
| 1 | 10 | 10 | linear |
| 10 | 11 | 10 | step |
| 11 | 12 | 95 | linear |
| 12 | 15 | 95 | step |

A HILIC column is selected with a diameter of 2.1 mm, a length of 50 mm, and a particle size of 2.1 to 2.5 μm is selected, and a liquid chromatography system is configured according to Tables 4 and 5. The solvent gradient of Table 5 is performed either isothermal at ambient temperature, or is configured with a temperature gradient which ramps from 40° C. to 45° C. Data are acquired using the mass spectrometer acquisition parameters shown in Table 1, except that the data collection time is extended to 15 minutes. Data are acquired using any high-resolution mass spectrometer connected to a liquid chromatography system configured as described above. Use of the chromatographic method described in Tables 4 and 5 allows for rapid quantitation of analytes using a machine learning model with universal standards as described herein. Accurate absolute quantitation is possible using a variety of mass spectrometers and/or liquid chromatography pairings.

EXEMPLARY EMBODIMENTS

Embodiments

1. A method of quantifying a target analyte in a laboratory sample comprising the target analyte, the method comprising the step of estimating the amount of the target analyte in the laboratory sample from mass spectrometric data comprising signal intensities for the target analyte and one or more internal standards, wherein the mass spectrometric data are an output of a mass spectrometric analysis of a target sample produced from the laboratory sample and a predetermined amount of the one or more internal standards.
2. The method of embodiment 1, wherein the step of estimating the amount of the target analyte comprises processing the mass spectrometric data using a pretrained machine learning model.
3. The method of embodiment 2, wherein the pretrained machine learning model is pretrained using a training data set comprising mass spectrometric data for a plurality of reference samples comprising the target analyte and known concentrations of the one or more internal standards.
4. The method of embodiment 3, wherein the plurality of reference samples comprises unknown concentrations of the target analyte spiked with a known quantity of the target analyte.
5. The method of embodiment 3, wherein the plurality of reference samples comprises known concentrations of the target analyte.
6. The method of embodiment 2, wherein the pretrained machine learning model is pretrained using a labeled training data set.
7. The method of embodiment 2, wherein the pretrained machine learning model is pretrained using a partially labeled training data set.
8. The method of embodiment 2, wherein the pretrained machine learning model is pretrained using an unlabeled training data set.
9. The method of embodiment 3, wherein the plurality of reference samples comprises unknown concentrations of the target analyte.
10. The method of any one of embodiments 2 to 9, wherein the pretrained machine learning model is pretrained using deep learning.
11. The method of any one of embodiments 2 to 10, wherein the pretrained machine learning model is pretrained using a supervised learning method.
12. The method of any one of embodiments 2 to 10, wherein the pretrained machine learning model is pretrained using a semi-supervised learning method.
13. The method of any one of embodiments 2 to 10, wherein the pretrained machine learning model is pretrained using an unsupervised learning method.
14. The method of any one of embodiments 2 to 10, wherein the pretrained machine learning model is pretrained using a self-supervised learning method.
15. The method of any one of embodiments 2 to 14, wherein the pretrained machine learning model is pretrained using an automated hyperparameter tuning.
16. The method of embodiment 15, wherein at least one hyperparameter used for the automated hyperparameter tuning is accuracy, precision, coefficient of determination, or dynamic range.
17. The method of embodiment 15 or 16, wherein least one hyperparameter used for the automated hyperparameter tuning is model performance.
18. The method of any one of embodiments 2 to 17, wherein the step of estimating amount of the target analyte comprises normalizing the signal intensities to produce normalized signal intensities.
19. The method of embodiment 18, wherein the step of normalizing comprises normalizing the signal intensities to reference signal intensities for one or more known samples comprising predetermined concentrations of the internal standards.
20. The method of embodiment 19, wherein the one or more known samples are free of the target analyte.
21. The method of embodiment 19, wherein the one or more known samples comprise a known concentration of the target analyte.
22. The method of embodiment 19, wherein the one or more known samples are pooled samples comprising predetermined amounts of aliquots of samples comprising known concentrations of the internal standards and unknown concentrations of the target analyte.
23. The method of any one of embodiments 1 to 22, wherein the method further comprises the step of performing mass spectrometric analysis on the target sample to produce the mass spectrometric data.
24. The method of embodiment 23, wherein the method further comprises the step of producing the target sample from the laboratory sample comprising the target analyte.
25. The method of embodiment 24, wherein the laboratory sample comprises an unknown amount of the target analyte.

26. The method of embodiment 24 or 25, wherein the step of producing comprises addition of the predetermined amount of the one or more internal standards to the laboratory sample.

27. The method of any one of embodiments 24 to 26, wherein the step of producing comprises eluting the laboratory sample with a mobile phase over a stationary phase.

28. The method of embodiment 27, wherein the step of producing comprises addition of the predetermined amount of the one or more internal standards to the laboratory sample, wherein the one or more internal standards are added to the laboratory sample in the mobile phase.

29. The method of embodiment 27 or 28, wherein the step of producing does not result in a chromatographic isolation of the target analyte from other non-solvent components of the laboratory sample.

30. The method of any one of embodiments 1 to 29, wherein each of the one or more internal standards produces a mass spectrometric signal that does not overlap the mass spectrometric signal of the target analyte.

31 The method of any one of embodiments 1 to 30, wherein the target sample comprises one or more target analytes.

32. The method of embodiment 31, wherein the method quantifies at least one of the one or more target analytes.

33. The method of embodiment 31 or 32, wherein the method quantifies all of the target analytes.

34. A method of identifying one or more internal standards for quantifying one or more target analytes in a laboratory sample, the method comprising selecting one or more internal standards producing mass spectrometric signals that do not overlap the mass spectrometric signals of the one or more target analytes to identify the one or more internal standards for quantifying one or more target analytes in a laboratory sample.

35. The method of any one of embodiments 31 to 34, wherein the one or more target analytes are 10, 100, 250, 500, 750, 1000, 2000, 3000, 4000, 5000, 10000, 250000, or 500000 different analytes.

36 The method of any one of embodiments 1 to 35, wherein the one or more internal standards are 1 to 20 internal standards.

37. The method of embodiment 36, wherein the one or more internal standards are 2 to 20 internal standards.

38. The method of embodiment 36, wherein the one or more internal standards are 2 to 15 internal standards.

39. The method of embodiment 36, wherein the one or more internal standards are 5 to 20 internal standards.

40. The method of embodiment 36, wherein the one or more internal standards are 5 to 15 internal standards.

41. The method of any one of embodiments 1 to 40, wherein each of the one or more internal standards is a compound having a molecular weight of 18 to 5000 g/mol.

42. The method of embodiment 41, wherein each of the one or more internal standards is a compound having a molecular weight of 18 to 2500 g/mol.

43. The method of any one of embodiments 1 to 42, wherein one or more of the internal standards is isotopically enriched at least for one atomic position in the internal standard.

44. The method of any one of embodiments 1 to 43, wherein one or more of the internal standards is halogenated.

45. The method of any one of embodiments 1 to 44, wherein at least one of the one or more internal standards is an alcohol, an amino acid, a nucleoside, a nucleotide, a nucleotide analogue, a bile acid, or an antimetabolite.

46. The method of any one of embodiments 1 to 45, wherein the target analyte is a metabolite.

47. The method of any one of embodiments 1 to 46, wherein the laboratory sample is a fermentation broth, a cell culture medium, a tissue culture medium, urine, fecal matter, blood, blood plasma, mucus, saliva, or soil.

48. A library of 3000 or fewer internal standards for quantifying one or more target analytes, wherein each of the internal standards having a molecular weight of 18 to 5000 g/mol and having a permanently charged moiety or having at least one acidic proton with a pKa of <18 at 25° C. in water.

49. A sample comprising one or more target analytes and one or more internal standards, each of the internal standards having a molecular weight of 18 to 5000 g/mol and having a permanently charged moiety or having at least one acidic proton with a pKa of <18 at 25° C. in water.

50. The library of embodiment 48 or the sample of embodiment 49, wherein each of the one or more internal standards is soluble in water and in 50% aqueous acetonitrile to at least 10 μM.

51. A non-transitory computer-readable storage medium comprising a set of instructions for executing the method of any one of embodiments 1 to 47.

52. The non-transitory computer-readable storage medium of embodiment 51, wherein the machine learning model is selected from logistic regression, ada boost classifier, extra trees classifier, extreme gradient boosting, gaussian process classifier, gradient boosting classifier, K-nearest neighbor, light gradient boosting, linear discriminant analysis, multi-level perceptron, naïve Bayes, quadratic discriminant analysis, random forest classifier, ridge classifier, SVM (linear and radial kernels), fully-connected neural network, or a deep neural network.

53. A method for metabolomic analysis of a sample, comprising:
  a. providing one or more calibrators that are selected based on a chemical space associated with the one or more calibrators and representative of one or more analytes that are quantifiable using the one or more calibrators, wherein the one or more analytes comprise one or more metabolites; and
  b. using a machine learning model to directly determine an absolute concentration of the one or more metabolites based on a mass spectrometry output for the sample, wherein the sample comprises the one or more analytes and the one or more calibrators,
    wherein the mass spectrometry output comprises at least (1) a first signal indicating an intensity value or a mass-to-charge ratio for the one or more analytes and (2) a second signal indicating an intensity value or a mass-to-charge ratio for the one or more calibrators,
    wherein the machine learning model is trained using a data set comprising (i) a first set of intensity values for one or more reference analytes having a known concentration and (ii) a second set of intensity values for one or more reference calibrators having a known concentration, wherein the reference analytes and the one or more analytes in the sample mixture comprise a same analyte or a same type or class of analyte, and wherein the reference calibrators and the one or more calibrators in the sample mixture comprise a same calibrator or a same type or class of calibrator.

54. The method of embodiment 53, wherein the one or more calibrators are non-endogenous.

55. The method of embodiment 53, wherein the one or more calibrators comprise a nonbiologic.

56. The method of embodiment 53, wherein the one or more calibrators are selected based on a comparison of or a degree of similarity between (i) a response or behavior of the one or more calibrators during mass spectrometry and (ii) a response or behavior of the one or more analytes during mass spectrometry.

57. The method of embodiment (53, wherein the one or more calibrators are selected based on an ionization efficiency of the one or more calibrators during mass spectrometry relative to the one or more analytes.

58 The method of embodiment 53, wherein the one or more calibrators are selected based on an ability of the one or more calibrators to ionize both positively and negatively.

59. The method of embodiment 53, wherein the one or more calibrators are selected based on a solubility of the one or more calibrators relative to the one or more analytes.

60 The method of embodiment 53, wherein the one or more calibrators are selected based on a stability of the one or more calibrators relative to the one or more analytes.

61. The method of embodiment 53, wherein the one or more calibrators are selected from a plurality of candidate calibrators that are encoded as one or more vectors comprising one or more features representing one or more properties of the one or more calibrators.

62. The method of embodiment 61, wherein the plurality of candidate calibrators are encoded as the one or more vectors using a nuclear representation encoding technique.

63. The method of embodiment 61, wherein the one or more properties comprise a molecular structure, a chemical property, a physical property, or an ionization efficiency of the one or more calibrators.

64. The method of embodiment 53, wherein a calibrator of the one or more calibrators is usable to quantify a plurality of analytes comprising a plurality of metabolites.

65. The method of embodiment 53, wherein (b) further comprises using the machine learning model to directly determine the absolute concentration of the one or more metabolites in less than about 5 minutes.

66. The method of embodiment 53, wherein the absolute concentration of the one or more metabolites is determined with an accuracy of at least about 80%.

67. A method comprising:
adding one or more calibrators to a sample comprising one or more analytes to produce a sample mixture;
applying mass spectrometry (MS) to the sample mixture; and
using a trained machine learning model to determine an absolute concentration of the one or more analytes based on an output from the MS, wherein the output comprises at least (1) a first signal indicating an intensity value or a mass-to-charge ratio for the one or more analytes and (2) a second signal indicating an intensity value or a mass-to-charge ratio for the one or more calibrators.

68 The method of embodiment 67, wherein the one or more calibrators are added to the sample after the one or more analytes of the sample are processed using liquid chromatography (LC).

69. The method of embodiment 67, wherein the one or more calibrators are added to the sample before the one or more analytes of the sample are processed using liquid chromatography (LC).

70. The method of embodiment 67, wherein the trained machine learning model is configured to determine the absolute concentration based on a relationship or a correlation between the first signal and the second signal.

71. The method of embodiment 67, wherein the trained machine learning model is configured to determine the absolute concentration of the one or more analytes based on a relationship or a correlation between the first signal and a known concentration of the one or more calibrators.

72. The method of embodiment 67, wherein in (a), a concentration of the one or more calibrators is known.

73. The method of embodiment 72, wherein in (a), a concentration of the one or more analytes is unknown.

74. The method of embodiment 73, wherein the absolute concentration of the one or more analytes is determined based on the known concentration of the one or more calibrators.

75. The method of embodiment 67, wherein the one or more calibrators do not comprise any isotopologue of the one or more analytes.

76. The method of embodiment 67, wherein the one or more analytes comprise a metabolite.

77. The method of embodiment 67, further comprising, subsequent to (c), developing one or more cell lines based on the absolute concentration of the one or more analytes.

78. The method of embodiment 67, further comprising, subsequent to (c), designing or optimizing a media or nutrient feed for one or more cells or cell lines.

79. The method of embodiment 67, further comprising, subsequent to (c), developing or optimizing a development or production process based on the absolute concentration of the one or more analytes.

80. The method of embodiment 67, wherein the output from the MS comprises raw, unprocessed mass spec data.

81. The method of embodiment 67, wherein the machine learning model is trained using a data set comprising (i) a first set of intensity values for one or more reference analytes having a known concentration and (ii) a second set of intensity values for one or more reference calibrators having a known concentration.

82. The method of embodiment 81, wherein the reference analytes and the one or more analytes in the sample mixture comprise a same analyte or a same type or class of analyte.

83. The method of embodiment 81, wherein the reference calibrators and the one or more calibrators in the sample mixture comprise a same calibrator or a same type or class of calibrator.

84. The method of embodiment 67, wherein the one or more calibrators produce a signal that does not overlap a signal of the one or more analytes.

85. The method of embodiment 67, wherein at least one of the one or more calibrators comprises an alcohol, an amino acid, a nucleoside, a nucleotide, a nucleotide analogue, or an antimetabolite.

86. A method comprising:
(a) providing a sample mixture comprising one or more analytes and one or more calibrators;
(b) generating a MS output for the sample mixture, wherein the MS output comprises (1) a first MS signal for the one or more analytes and (2) a second MS signal for the one or more calibrators; and
(c) using a trained machine learning algorithm to determine an absolute concentration of the one or more analytes, based at least in part on a relationship or correlation between the first MS signal and the second MS signal.

87. The method of embodiment 86, wherein the trained machine learning model is configured to determine the absolute concentration of the one or more analytes based on a relationship or a correlation between the first MS signal and a known concentration of the one or more calibrators.

88. The method of embodiment 87, wherein in (a), a concentration of the one or more calibrators is known.

89. The method of embodiment 88, wherein in (a), a concentration of the one or more analytes is unknown.

90. The method of embodiment 89, wherein the absolute concentration of the one or more analytes is determined based on the known concentration of the one or more calibrators.

91. The method of embodiment 86, wherein the one or more calibrators do not comprise any isotopologue of the one or more analytes.

92. The method of embodiment 86, wherein the one or more analytes comprise a metabolite.

93. The method of embodiment 86, further comprising, subsequent to (c), developing one or more cell lines based on the absolute concentration of the one or more analytes.

94. The method of embodiment 86, further comprising, subsequent to (c), designing or optimizing a media or nutrient feed for one or more cells or cell lines.

95. The method of embodiment 86, further comprising, subsequent to (c), developing or optimizing a development or production process based on the absolute concentration of the one or more analytes.

96. The method of embodiment 86, wherein the MS output comprises raw, unprocessed mass spec data.

97. The method of embodiment 86, wherein the machine learning model is trained using a data set comprising (i) a first set of intensity values for one or more reference analytes having a known concentration and (ii) a second set of intensity values for one or more reference calibrators having a known concentration.

98. The method of embodiment 97, wherein the reference analytes and the one or more analytes in the sample mixture comprise a same analyte or a same type or class of analyte.

99. The method of embodiment 97, wherein the reference calibrators and the one or more calibrators in the sample mixture comprise a same calibrator or a same type or class of calibrator.

100. The method of embodiment 86, wherein the one or more calibrators produce a signal that does not overlap a signal of the one or more analytes.

101. The method of embodiment 86, wherein at least one of the one or more calibrators comprises an alcohol, an amino acid, a nucleoside, a nucleotide, a nucleotide analogue, or an antimetabolite.

102. A method comprising:
using a trained machine learning model to determine an absolute concentration of one or more target analytes in a sample mixture comprising the target analytes and one or more calibrators,
wherein the machine learning model is trained using a data set comprising (i) a first set of intensity values for one or more reference analytes having a known concentration and (ii) a second set of intensity values for one or more reference calibrators having a known concentration, and
wherein the machine learning model is configured to determine the absolute concentration of the one or more target analytes based on (1) a first set of intensity values for the one or more target analytes in the sample mixture and (2) a second set of intensity values for the one or more calibrators in the sample mixture.

103. The method of embodiment 102, wherein the machine learning model is configured to determine the absolute concentration of the one or more target analytes based on (i) positive ionization information for the one or more target analytes, (ii) negative ionization information for the one or more target analytes, and (iii) a molecular representation of the one or more target analytes.

104. The method of embodiment 102, wherein the reference analytes and the target analytes in the sample mixture comprise a same analyte or a same type or class of analyte.

105. The method of embodiment 102, wherein the reference calibrators and the one or more calibrators in the sample mixture comprise a same calibrator or a same type or class of calibrator.

106. A method comprising:
(a) providing a sample mixture comprising a plurality of analytes and one or more calibrators, wherein a ratio between the analytes and the one or more calibrators is greater than 1:1; and
(b) determining an absolute concentration of each of the plurality of analytes, based at least in part on a relationship or correlation between a first time series MS signal for the plurality of analytes and a second time series MS signal for the one or more calibrators.

107. The method of embodiment 106, wherein the one or more calibrators do not comprise any isotopologue of the plurality of analytes.

108. A method comprising:
(a) providing a sample mixture comprising a plurality of analytes and one or more calibrators; and
(b) determining an absolute concentration of each of the plurality of analytes, based at least in part on a first time series MS signal for the plurality of analytes and a second time series MS signal for the one or more calibrators,
wherein the one or more calibrators comprise a same set of calibrators usable to determine the absolute concentration of each of the plurality of analytes.

109. The method of embodiment 108, wherein the plurality of analytes comprise different analytes.

110. A kit comprising:
one or more calibrators representative of a chemical space or a chemical class for one or more analytes of interest in a sample,
wherein the one or more calibrators comprise a nonbiologic that is usable to determine an absolute concentration of a plurality of different analytes comprising the one or more analytes of interest.

111. The kit of embodiment 110, wherein the one or more calibrators do not comprise any isotopologue of the plurality of different analytes.

112. A method comprising:
(a) providing a media to one or more cells;
(b) analyzing one or more outputs of the one or more cells after the one or more cells process the media to determine an absolute concentration of one or more analytes in (i) the one or more cells or (ii) the one or more outputs of the one or more cells;
(c) characterizing a cell response or a cell behavior for the one or more cells based at least in part on the absolute concentration of the one or more analytes; and
(d) optimizing the media based on the characterized cell response or cell behavior in order to promote or facilitate cell culturing or cell growth.

113. The method of embodiment 112, wherein the one or more analytes comprise one or more metabolites generated or produced by the one or more cells 114. A system comprising:
a computing unit operably coupled to a mass spec (MS) machine, wherein the computing unit is configured to:
(i) receive MS data from the MS machine, wherein the MS data is associated with a sample comprising one or more analytes and one or more calibrators,
(ii) process the MS data using a trained ML algorithm to determine an absolute concentration of the analytes, and
(iii) output one or more actionable biological insights based on the absolute concentration of the analytes, wherein the trained ML algorithm is configured to determine the absolute concentration of the analytes from the received MS data substantially in real time.

115. The system of embodiment 114, wherein the one or more calibrators comprise a nonendogenous molecule or compound.

116. The system of embodiment 114, wherein the one or more calibrators comprise a nonbiologic.

117. A kit for metabolomic analysis of a sample, comprising:
one or more calibrators that are usable in a mass spec to quantify a plurality metabolites associated with one or more metabolic pathways, wherein a number of the plurality of metabolites is greater than a number of the one or more calibrators.

118. The kit of embodiment 117, wherein the one or more calibrators comprise no more than 12 (e.g. no more than 10, 8, or 6) calibrators.

119. The kit of embodiment 117, wherein the plurality of metabolites comprise at least about 150 metabolites.

120. The kit of embodiment 117, wherein the one or more calibrators comprise at least two calibrators from different chemical classes.

121. The kit of embodiment 120, wherein the different chemical classes are selected from the group consisting of: nucleic acids, small molecules, proteins, amino acids, ethers, and sugars.

122. The kit of embodiment 117, wherein the one or more calibrators are non-endogenous.

123. The kit of embodiment 117, wherein the one or more calibrators are non-isotopologues.

124. The kit of embodiment 117, wherein the one or more calibrators comprise a nonbiologic.

125. The kit of embodiment 117, wherein the one or more calibrators have an ionization efficiency or an ionization potential that spans a plurality of metabolic pathways.

126. The kit of embodiment 117, wherein at least two of the one or more calibrators are configured to ionize both positively and negatively.

127. The kit of embodiment 117, wherein the one or more calibrators are soluble in water.

128. The kit of embodiment 117, wherein the one or more calibrators are stable at room temperature.

129. The kit of embodiment 117, wherein the one or more calibrators are stable in acidic and basic conditions or matrices.

130. The kit of embodiment 117, wherein the one or more calibrators are non-volatile.

131. The kit of embodiment 117, wherein the one or more calibrators comprise a plurality of calibrators that are non-reactive with each other and/or the one or more metabolites.

132. The kit of embodiment 117, wherein the one or more calibrators are chemically inert.

133. The kit of embodiment 117, wherein the one or more calibrators have a pH ranging from about 2 to about 10.

134. The kit of embodiment 117, wherein the one or more calibrators span one or more chemical spaces.

135. The kit of embodiment 134, wherein the one or more chemical spaces comprise at least two analytes having a same or similar property.

136. The kit of embodiment 135, wherein the property comprises a molecular mass or weight, a molecular structure, a chemical property, a physical property, or an ionization efficiency.

137. The kit of embodiment 117, further comprising a set of instructions for using the one or more calibrators to determine an absolute concentration of the one or more metabolites.

138. The kit of embodiment 117, wherein the set of instructions comprise one or more run parameters for operating the mass spec.

139. The kit of embodiment 117, wherein the set of instructions comprise one or more run parameters for operating a liquid chromatography (LC) system.

140. The kit of embodiment 117, further comprising one or more quality control samples for verifying or validating an absolute concentration of the one or more metabolites.

141. The kit of embodiment 117, further comprising a column configured to interface with a liquid chromatography (LC) system that is coupled to the mass spectrometer.

142. The kit of embodiment 117, further comprising a standard mixture for generating a sample mixture comprising the one or more calibrators and the one or more metabolites.

143. The kit of embodiment 117, further comprising tubing for preparing, collecting, or delivering the sample to a LC or MS.

144. The kit of embodiment 117, further comprising a barcode or a barcode scanner.

145. The kit of embodiment 117, wherein the one or more metabolic pathways are selected from or associated with fatty acid metabolism, glycolysis, glycosylation, neurotransmission, a pentose phosphate pathway, redox, a tricarboxylic acid cycle, and a urea cycle.

146. The kit of embodiment 117, wherein the one or more calibrators are selected from the group consisting of 1,4-Butanediamine (putrescine)·2HCl (13C4, 99%), L-Alanine (13C3, 99%; 15N, 99%), Ethanolamine HCl (1,1,2,2-D4, 98%), Sodium pyruvate (13C3, 99%), Creatinine (N-methyl-D3, 98%), Fumaric acid (13C4, 99%), Vitamin B3 (nicotinamide) (13C6, 99%), Thymine (1,3-15N2, 98%), L-Leucine (13C6, 99%), Hypoxanthine (13C5, 99%), L-Phenylalanine (ring-13C6, 99%), Indole-3-acetic acid (phenyl-13C6, 99%), L-Tyrosine (ring-13C6, 99%), a-Ketoglutaric acid, disodium salt (1,2,3,4-13C4, 99%) CP 97%, Citric acid (1,5,6-carboxyl-13C3, 99%), L-Tryptophan (13C11, 99%), Guanosine·2H2O (15N5, 96-98%), and Sodium palmitate (U-13C16, 98%).

147. The kit of embodiment 117, wherein the plurality of metabolites are selected from the group consisting of beta-nicotinamide adenine dinucleotide, glutamine, hypotaurine, n-methyl-alanine, citrate, threonine, purine, n-acetylneuraminate, n-acetylmannosamine, pyrimidine, trans-aconitate, urate, cytidine, serine, cysteine, citrulline, taurine, n-acetyltryptophan, nicotinate, inosine, gamma-aminobutyrate, cytosine, isoleucine, pyrazole, glutamate, ascorbate, p-hydroxyphenylacetate, n-acetylglucosamine, glycolate, sarcosine, creatinine, quinate, dihydroorotate, malonate, guanidinoacetate, formamide, glycine, methionine, tetrahydrofolate, 2-phosphoglycerate, methylthioadenosine, thymidine, cys-gly, aminoisobutanoate, gulose, xanthine, dihydrofolate, cystine, 1-alanine, diethanolamine, uridine monophosphate, proline, thymine, succinate semialdehyde, lactate, uridine, fructose bisphosphate, carnosine, nicotinamide, shikimate, succinate, phenylalanine, uracil, thiourea, aspartate, deoxycytidine monophosphate, hypoxanthine, creatine, l-dopa, guanosine, dihydrouracil, malate, isocitrate, tyrosine, glycerol, asparagine, valine, guanine, homoserine, pyridoxine, deoxyadenosine monophosphate, folate, nicotinamide mononucleotide, 3-methyl-1-histidine, diaminopimelate, aminoadipate, deoxycytidine, noradrenaline, glucosamine 6-phosphate, tartrate, 3-dehydroshikimate, caffeine, homocysteine, theophylline, leucine, trehalose, betaine, tryptophan, 3-sulfinoalanine, o-succinyl-homoserine, allantoin, glyceraldehyde, d-glucuronolactone, (2-aminoethyl)phosphonate, 2,5-dihydrobenzoic acid, maleimide, threitol, glucosamine, paraxanthine, adenosine 5'-diphosphate, 2-deoxy-d-glucose, 1-methyl-1-histidine, galactitol, oxoproline, 4-pyridoxate, quinolinate, methylguanidine, deoxyguanosine-monophosphate, 3-hydroxy-3-methylglutaryl-coa, glucuronate, 1-methyladenosine, deoxyuridine, gluconate, urocanate, kynurenine, pyroglutamate, 4-acetamidobutanoate, trans-1,2-cyclohexanediol, melanin, dopamine, adenosine-monophosphate, lysine, citicoline, 1,3-diaminopropane, phosphoserine, 1-aminocyclopropanecarboxylate, glutarylcarnitine, cystathionine, norvaline, 3-hydroxymethylglutarate, phosphonoacetate, picolinate, ethanolamine, arginine, trans-4-hydroxy-1-proline, fucose, homocystine, n-methylglutamate, d-ornithine, xanthosine, 3-methylcrotonyl-coa, thyrotropin releasing hormone, cysteate, n-methylaspartate, galactarate, alpha-hydroxyisobutyrate, nicotinic acid adenine dinucleotide phosphate, n-acetylasparagine, pipecolate, glucose 6-phosphate, nadp, 6-phosphogluconate, isopentenyl pyrophosphate, guanosine triphosphate, dtdp-d-glucose, agmatine sulfate, glycolaldehyde, dgtp, n-acetylglycine, n-acetylaspartate, inosine 5'-diphosphate, palmitoylcarnitine, norspermidine, nicotinamide hypoxanthine dinucleotide, s-adenosylmethionine, erythritol, glucosaminate, uridine triphosphate, 2-keto-3-deoxy-d-gluconic acid, d-sedoheptulose, 1,4-diaminobutane dihydrocloride, deoxycarnitine, adenosine 2',3'-cyclic phosphate, mevalolactone, galactose 1-phosphate, dimethylallylpyrophosphate, deoxyuridine triphosphate, phosphorylcholine, o-acetylcarnitine, 6-hydroxydopamine, thiamine, dgdp, 5-methylcytosine, glycerate, cytidine 2',3'-cyclic phosphate, n,n,n-trimethyllysine, riboflavin, uridine diphosphate glucose, methyl galactoside, pyridoxal-phosphate, dihydroxyacetone phosphate, phosphoenolpyruvate, mannose 6-phosphate, 3-phosphoglycerate, 1-carnitine, o-phosphoethanolamine, o-acetylserine, cytidine monophosphate, guanosine diphosphate mannose, adp-glucose, fructose 6-phosphate, adenosine 3',5'-diphosphate, 3-nitro-1-tyrosine, p-octopamine, n-alpha-acetyllysine, uridine diphosphategalactose, dihydroxyfumarate, pyridoxamine, 5-aminolevulinate, deoxyuridine-monophosphate, 5'-deoxyadenosine, ribose 1,5-bisphosphate, xanthosine-monophosphate, fad, deoxyguanosine, orotate, lauroylcarnitine, 1-methylnicotinamide, spermine, n-acetylmethionine, carbamoyl phosphate, phosphoribosyl pyrophosphate, aicar, uridine diphosphate-n-acetylgalactosamine, glyceraldehyde 3-phosphate, cyclic gmp, homocysteine thiolactone, o-phosphoserine, s-adenosylhomocysteine, 1-ornithine, adenine, normetanephrine, uridine diphosphate-n-acetylglucosamine, guanosine diphosphate, glutathione reduced, uridine diphosphate glucuronic acid, n,n-dimethylarginine, cytidine diphosphate, selenocystamine, histamine, indoxyl sulfate, ethyl 3-ureidopropionate, deoxyribose, phytate, thiamine monophosphate, uracil 5-carboxylate, s-hexyl-glutathione, glyoxylate, guanosine monophosphate, n-acetylalanine, 4-guanidinobutanoate, hydroxypyruvate, d-mannosamine, cytochrome c, deoxyadenosine, n-acetylputrescine, n-acetylgalactosamine, n-acetylglutamate, 2,4-dihydroxypteridine, 6-hydroxynicotinate, n-acetylcysteine, inosine-monophosphate, pantothenate, 2-aminoisobutyrate, aniline-2-sulfonate, s-carboxymethylcysteine, rhamnose, thiamine pyrophosphate, histidinol, thymidine-monophosphate, ureidopropionate, 5-aminopentanoate, norleucine, n-formylglycine, adenosine, raffinose, meso-tartrate, 2-acetamido-2-deoxy-beta-d-glucosylamine, saccharate, adenosine triphosphate, 3-methoxytyrosine, lactose, 3-hydroxybutanoate, 4-imidazoleacetate, galacturonate, cytidine triphosphate, cyclic amp, methionine sulfoximine, cis-4-hydroxy-d-proline, n1-acetylspermine, glucosamine 6-sulfate, nadph, 3-methylhistamine, maleamate, choline, methyl 4-aminobutyrate, n-formyl-1-methionine, acetylcholine, oxalate, 5-hydroxytryptophan, d-alanine, theobromine, guanidinosuccinate, histidine, allothreonine, phosphocreatine, spermidine, adenosine diphosphate ribose, 2-methoxyethanol, citramalate, anserine, biliverdin, 5-hydroxylysine, cysteamine, ophthalmate, mesoxalate, trigonelline, epinephrine, 3,4-dihydroxyphenylglycol, cadaverine, 2-hydroxybutyrate, coenzyme a, oxalomalate, inosine triphosphate, cdp-ethanolamine, 2,5-dimethylpyrazine, stachyose, deoxycytidine-diphosphate, 2,3-butanediol, d-ribose 5-phosphate, hydroxykynurenine, galactosamine, deoxyadenosine triphosphate, glycerol 3-phosphate, cyanocobalamin, 4-hydroxy-1-phenylglycine, n-acetylserine, uridine 5'-diphosphate, methyglutarate, sorbate, monoethylmalonate, gluconolactone, 4-hydroxybenzoate, tyramine, cortisol, prenol, 3-hydroxybenzaldehyde, xanthurenate, 2-methylpropanal, indoxyl β-glucoside, trimethylamine, melatonin, maleate, pentanoate, propanoate, bilirubin, nicotine, pregnenolone sulfate, kynurenate, isobutyrate, 3-hydroxybenzyl alcohol, aniline, acetoin, 3,5-diiodo-1-tyrosine, mandelate, tryptamine, 4-aminobenzoate, glutarate, 5-valerolactone, caffeate, lumichrome, beta-alanine, n-acetylphenylalanine, n-acetylproline, l-tryptophanamide, phenol, n-methyltryptamine, oxaloacetate, 2,3-dihydroxybenzoate, 2-propenoate, indole-3-ethanol, ferulate, glycocholate, phenylethanolamine, thiopurine s-methylether, 2-hydroxy-4-(methylthio)butanoate, glycochenodeoxycholate, benzoate, 3-amino-5-hydroxybenzoate, pyrocatechol, 3,4-dihydroxybenzoate, cyclopentanone, pantolactone, guaiacol, 2-hydroxyphenylacetate, 10-hydroxydecanoate, didecanoyl-glycerophosphocholine, 2-hydroxypyridine, 3,4-dihydroxyphenylacetate, n6-(delta2-isopentenyl)-adenine, methyl vanillate, 2-oxobutanoate, lipoamide, 3-hydroxyanthranilate, 3-(4-hydroxyphenyl)pyruvate, hexanoate, methylmalonate, indole-3-acetate, cortisol 21-acetate, indole-3-acetamide, hippurate, ethylmalonate, 3,5-diiodo-1-thyronine, fumarate, benzaldehyde, 4-hydroxybenzaldehyde, 3-(2-hydroxyphenyl)propanoate, 3-methoxytyramine, benzylamine, 2-quinolinecarboxylate, serotonin, pterin, butanoate, 2-aminophenol, 6-carboxyhexanoate, indole-3-pyruvate, dehydroascorbate, 3-amino-4-hydroxybenzoate, 3,4 dihydroxymandelate, 2-methylcitrate, dihydrobiopterin, beta-glycerophosphate, glucose 1-phosphate, 2,3-diaminopropionate, 2,5-dihydroxybenzoate, 4-quinolinecarboxylate, hydroquinone, dethiobiotin, 3-hydroxybenzoate, 2-methylbutanal, n-acetylserotonin, hydrophenyllactic acid, itaconate, azelate, oxoadipate, 2-methylglutarate, phenylacetaldehyde, 3-methyl-2-oxovalerate, porphobilinogen, diacetyl, pyruvate, trans-cinnamaldehyde, 2,6-dihydroxypyridine, vanillin, methyl acetoacetate, suberate, adipate, geranyl-pp, n-acetylleucine, 2',4'-dihydroxyacetophenone, benzyl alcohol, monomethylglutarate, indole-3-methyl acetate, mevalonate, 3-methoxy-4-hydroxymandelate, homovanillate, 2-methylmaleate, 1-phenylethanol, salsolinol, salicylamide, oxoglutarate, ethyl 3-indoleacetate, 3-alpha, 11-beta, 17,21-tetrahydroxy-5-beta-pregnan-20-one, n,n-dimethyl-1,4-phenylenediamine, homogentisate, indoleacetaldehyde, 4-hydroxy-3-methoxyphenylglycol, 3-hydroxyphenylacetate, 4-methylcatechol, pyridoxal, salicylate, sebacate, 3-methyl-2-oxindole, 3-methyladenine, hydroxyphenyllactate, biotin, mercaptopyruvate, pyruvic aldehyde, pyrrole-2-carboxylate, 5-hydroxyindoleacetate, 3-methylglutaconate, resorcinol monoacetate, acetoacetate, acetylphosphate, sorbose, xylitol, ribitol, myoinositol, mannose, xylose, sucrose, galactose, alpha-d-glucose, allose, mannitol, melibiose, sorbitol, maltose, tagatose, 1-gulonolactone, arabinose, cellobiose, psicose, arabitol, lyxose, ribose, palatinose, d-pinitol, vitamin d2, squalene, 4-coumarate, nonanoate, estradiol-17alpha, caprylate, ursodeoxycholate, petroselinate, dipalmitoylglycerol, corticosterone, lithocholate, protoporphyrin, heptanoate, retinol, menaquinone, elaidate, chenodeoxycholate, myristate, cholesteryl oleate, rosmarinate, glyceryl tripalmitate, cortexolone, lithocholyltaurine, palmitoleate, palmitate, liothyronine, sphinganine, lanosterol, laurate, arachidate, erucate, deoxycholate, ketoleucine, eicosapentaenoate, heptadecanoate, glyceryl trimyristate, linoleate, sphingomyelin, 7-dehydrocholesterol, thyroxine, bis(2-ethylhexyl)phthalate, gamma-linolenate, omega-hydroxydodecanoate, methyl jasmonate, dipalmitoyl-phosphatidylcholine, hexadecanol, 5,6-dimethylbenzimidazole, retinoate, indole, cholate, phylloquinone, cholesteryl palmitate, quinoline, docosahexaenoate, diethyl 2-methyl-3-oxosuccinate, retinyl palmitate, 2-undecanone, 1-hydroxy-2-naphthoate, dipalmitoyl-phosphoethanolamine, phenylpyruvate, trans-cinnamate, oleate, stearate, beta-carotene, 25-hydroxycholesterol, nervonate, desmosterol, deoxycorticosterone acetate, oleoyl-glycerol, alpha-tocopherol, glycerol-myristate, tricosanoate, coenzyme q10, cortisone, and decanoate.

148. A method for analyte concentration detection, comprising:
(a) training a machine learning model using a plurality of raw mass spectrometry (MS) datasets that are collected for a set of calibrators and a plurality of different analytes and a plurality of different matrices; and
(b) providing the trained machine learning model for processing a MS dataset of a mixed sample that comprises at least one target analyte and the set of calibrators, the trained machine learning model configured to determine an absolute concentration of the at least one target analyte in a manner that is agnostic to matrix type.

149. The method of embodiment 148, wherein the plurality of different matrices comprise CHO Lysate, CHO Supernatent, HAM's F10 Media, Bovine Plasma, or Plasma-like Media.

150. The method of embodiment 148, wherein the at least one target analyte is embedded in a sample matrix that is different from any of the matrices used for training the machine learning model.

151. The method of embodiment 148, wherein the at least one target analyte is embedded in a sample matrix that is the same as one of the matrices used for training the machine learning model.

152. The method of embodiment 148, wherein the trained machine learning model is configured to interpolate across the plurality of different matrices to determine the absolute concentration of the at least one target analyte in a sample matrix.

153. The method of embodiment 148, wherein the absolute concentration is determined with a relative standard deviation (RSD) of less than about 20%.

154. The method of embodiment 148, wherein the absolute concentration is determined with a mean average percentage error (MAPE) of less than about 20%.

155. The method of embodiment 154, wherein the trained machine learning model is configured to determine absolute concentrations of at least about 80% of a plurality of metabolites with a MAPE of less than about 20%.

156. The method of embodiment 148, wherein the trained machine learning model is configured to directly determine the absolute concentration of the one or more analytes in less than about 5 minutes.
157. The method of embodiment 148, wherein the machine learning model is trained using a MS training data set comprising (i) a first set of intensity values for one or more reference metabolites having a known concentration and (ii) a second set of intensity values for one or more reference calibrators having a known concentration.
158. The method of embodiment 157, wherein the MS training data set comprises raw, unprocessed mass spec data.
159. The method of embodiment 157, wherein the MS training data set is of a same data structure or format as an MS output for the mixed sample.
160. The method of embodiment 157, wherein the reference metabolites and the one or more metabolites in the sample comprise a same metabolite or a same type or class of metabolite.
161. The method of embodiment 157, wherein the reference metabolites and the one or more metabolites in the sample comprise different metabolites or different types or classes of metabolites.
162. The method of embodiment 157, wherein the reference calibrators and the one or more calibrators in the sample comprise a same calibrator or a same type or class of calibrator.
163. The method of embodiment 159, wherein the MS output for the mixed sample comprises at least (1) a first signal indicating an intensity value or a mass-to-charge ratio for the one or more analytes and (2) a second signal indicating an intensity value or a mass-to-charge ratio for the one or more calibrators.
164. The method of embodiment 163, wherein the trained machine learning model is configured to determine an absolute concentration of the one or more analytes based on a relationship or a correlation between the first signal and the second signal.
165. The method of embodiment 163, wherein the trained machine learning model is configured to determine the absolute concentration of the one or more analytes based on a relationship or a correlation between the first signal and a known concentration of the one or more calibrators.
166. The method of embodiment 148, wherein a concentration of the one or more calibrators is known.
167. The method of embodiment 166, wherein the absolute concentration of the one or more analytes is determined based on the known concentration of the one or more calibrators.
168. The method of embodiment 148, wherein the one or more calibrators are configured to produce a signal that does not overlap or interfere with a signal of the one or more analytes.
169. The method of embodiment 148, wherein at least one calibrator of the one or more calibrators comprises an alcohol, an amino acid, a nucleoside, a nucleotide, a nucleotide analogue, or an antimetabolite.
170. The method of embodiment 148, wherein the machine learning model is trained using (1) a combinatorial library comprising a plurality of metabolites of interest and a plurality of metabolite concentrations for the metabolites of interest, and (2) a training data set comprising MS signals for a plurality of samples comprising at least one metabolite of interest, at least one candidate calibrator, and a plurality of test sample matrices.
171. A method for enabling high-throughput quantitation of biomolecules, comprising:
(a) providing a reagent that is to be added to a sample to form a mixed sample, the reagent comprising a set of calibrators that are selected such that at least one target analyte in the sample lies within a chemical space defined by or associated with one or more calibrators from the set of calibrators; and
(b) providing a machine learning model for processing a raw mass spectrometry (MS) dataset of the mixed sample to directly determine in less than about 5 minutes an absolute concentration of the at least one target analyte.
172. The method of embodiment 171, further comprising using the absolute concentration of the at least one target analyte to perform a metabolomics analysis.
173. The method of embodiment 172, wherein the metabolomics analysis comprises identifying or characterizing a metabolic pathway.
174. The method of embodiment 172, wherein the metabolomics analysis comprises characterizing a cell response or a cell behavior for one or more cells based at least in part on the absolute concentration of the one or more analytes.
175. The method of embodiment 174, further comprising using the machine learning model to aid in identifying one or more options or solutions for optimizing a media provided to the one or more cells based on the absolute concentration of the one or more analytes and/or the characterized cell response or cell behavior, in order to promote or facilitate cell culturing or cell growth.
176. The method of embodiment 174, further comprising using the characterized cell response or cell behavior to aid in a development of one or more cell lines.
177. The method of embodiment 171, further comprising using the characterized cell response or cell behavior to aid in a development of one or more processes for cell line manufacturing.
178. The method of embodiment 171, further comprising using the characterized cell response or cell behavior to aid in an analysis and/or comparison of clonal variations of the one or more cells and metabolic states or pathways associated with the clonal variations.
179. The method of embodiment 171, further comprising using the characterized cell response or cell behavior to aid in a detection of one or more metabolic signatures or pathways for the one or more cells.
180. The method of embodiment 171, further comprising providing a run protocol comprising instructions for processing the mixed sample using a liquid chromatography (LC) or mass spectrometry (MS) machine to generate the raw MS dataset.
181. The method of embodiment 180, wherein the run protocol comprises a set of run parameters configured to control a processing of the sample by the liquid chromatography or mass spectrometry machine.
182. The method of embodiment 181, wherein the set of run parameters comprises one or more parameters for a sample flow rate, an eluent composition, a concentration gradient, or a rate of temperature ramping.
183. The method of embodiment 171, wherein (b) further comprises determining in parallel or concurrently an absolute concentration of each of a plurality of target analytes within a total time of less than about 5 minutes.
184. The method of embodiment 183, wherein the machine learning model is configured to determine the absolute concentrations of at least 80% of the plurality of target analytes with a mean average percent error (MAPE) of less than 20%.
185. The method of embodiment 171, wherein the at least one target analyte is a metabolite.
186. The method of embodiment 171, wherein the reagent is provided within or as part of a metabolomics kit.
187. The method of embodiment 171, wherein the set of calibrators does not include an isotopologue or an isotopically labeled analogue of the at least one target analyte that is present in the sample.
188. The method of embodiment 171, wherein the machine learning model is configured to determine the absolute concentration of the at least one target analyte without isotopologue matching.
189. The method of embodiment 171, wherein the machine learning model is configured to determine the absolute concentration of the at least one target analyte without constructing a calibration curve.
190. The method of embodiment 171, wherein the machine learning model is configured to determine the absolute concentration of the at least one target analyte without calculating an area under a curve (AUC).
191. The method of embodiment 171, wherein the machine learning model is configured to determine the absolute concentration of the at least one target analyte without computing a response factor.
192. The method of embodiment 171, wherein the machine learning model is configured to determine the absolute concentration of the at least one target analyte without performing extracted ion chromatography (XIC).
193. The method of embodiment 171, wherein the machine learning model is configured to directly determine the absolute concentration of the at least one target analyte without performing a peak integration for one or more MS signals from the MS dataset.
194. The method of embodiment 171, wherein the machine learning model is configured to detect absolute concentrations across a range of concentrations spanning at least two orders of magnitude.
195. The method of any one of embodiments 148-194, wherein a ratio of a number of the calibrators to a number of the plurality of analytes is about 1:2, 1:3, 1:5, 1:10, 1:25, 1:50, 1:100, 1:1000, or 1:5000.

What is claimed is:
1. A kit for metabolomic analysis of a sample, comprising: one or more calibrators configured to be used with a mass spectrometry (MS) machine equipped with a molecular ion source to quantify a plurality of metabolites associated with one or more metabolic pathways, wherein a number of the plurality of metabolites is greater than a number of the one or more calibrators, and the one or more calibrators comprise at least six calibrators selected from the group consisting of 1,4-Butanediamine (putrescine)·2HCl (13C4, 99%), LAlanine (13C3, 99%; 15N, 99%), Ethanolamine·HCl (1,1,2,2-D4, 98%), Sodium pyruvate (13C3, 99%), Creatinine (N-methyl-D3, 98%), Fumaric acid (13C4, 99%), Vitamin B3 (nicotinamide) (13C6, 99%), Thymine (1,3-15N2, 98%), L-Leucine (13C6, 99%), Hypoxanthine (13C5, 99%), LPhenylalanine (ring-13C6, 99%), Indole-3-acetic acid (phenyl-13C6, 99%), L-Tyrosine (ring-13C6, 99%), a-Ketoglutaric acid, disodium salt (1,2,3,4-13C4, 99%) CP 97%, Citric acid (1,5,6-carboxyl-13C3, 99%), L-Tryptophan (13Cl 1, 99%), Guanosine·2H20 (15N5, 96-98%), Sodium palmitate (U-13C 16, 98%), 6-diazo-5-oxo-L-norleucine, Acarbose, Aucubin, caffeine, Carbazochrome sodium sulfonate, Cefoselis Sulfate, Cellobiose, Ciprofloxacin hydrochloride hydrate, Cromolyn sodium, Cyclo (–RGDfK), Daminozide, Diminazene Aceturate, Fudosteine, Geniposidic acid, Gimeracil, Isoprinosine, Oseltamivir acid, Pidotimod, Puerarin, Sodium 4-amiropparaty Hyalrate, Telaglenastat, Tipiracil hydrochloride, Voglibose, and Zanamivir.

* * * * *